US010087225B2

(12) United States Patent
Lander et al.

(10) Patent No.: US 10,087,225 B2
(45) Date of Patent: Oct. 2, 2018

(54) FORMULATION OF MK2 INHIBITOR PEPTIDES

(71) Applicant: MOERAE MATRIX, INC., Morristown, NJ (US)

(72) Inventors: Cynthia Lander, Mendham, NJ (US); Colleen Brophy, Nashville, TN (US); Caryn Peterson, Encinitas, CA (US)

(73) Assignee: MOERAE MATRIX, INC., Morristown, NJ (US)

( * ) Notice: Subject to any disclaimer, the term of this patent is extended or adjusted under 35 U.S.C. 154(b) by 0 days.

(21) Appl. No.: 14/991,531

(22) Filed: Jan. 8, 2016

(65) Prior Publication Data

US 2016/0200782 A1 Jul. 14, 2016

Related U.S. Application Data

(60) Provisional application No. 62/101,190, filed on Jan. 8, 2015.

(51) Int. Cl.
| | |
|---|---|
| *A61K 38/00* | (2006.01) |
| *A61K 47/02* | (2006.01) |
| *A61K 47/26* | (2006.01) |
| *A61K 47/32* | (2006.01) |
| *C07K 14/47* | (2006.01) |
| *C07K 14/00* | (2006.01) |
| *A61K 9/00* | (2006.01) |
| *A61K 38/17* | (2006.01) |

(52) U.S. Cl.
CPC ........ *C07K 14/4703* (2013.01); *A61K 9/0019* (2013.01); *A61K 9/0075* (2013.01); *A61K 9/0078* (2013.01); *A61K 38/1709* (2013.01); *A61K 47/02* (2013.01); *A61K 47/26* (2013.01); *A61K 47/32* (2013.01); *A61K 38/00* (2013.01)

(58) Field of Classification Search
CPC .... A61K 38/00; A61K 38/1709; A61K 47/02; A61K 47/26; A61K 47/32; A61K 9/0019; A61K 9/0075; A61K 9/0078; C07K 14/4703; C07K 14/47; C07K 14/00
USPC ............... 514/21.4, 16.5; 530/326
See application file for complete search history.

(56) References Cited

U.S. PATENT DOCUMENTS

| | | | |
|---|---|---|---|
| 4,105,027 A | 8/1978 | Lundquist | |
| 4,192,309 A | 3/1980 | Poulsen | |
| 4,227,522 A | 10/1980 | Carris | |
| 4,627,432 A | 12/1986 | Newell | |
| 4,778,054 A | 10/1988 | Nowell | |
| 4,811,731 A | 3/1989 | Newell et al. | |
| 5,035,237 A | 7/1991 | Newell | |
| 6,921,527 B2 | 7/2005 | Platz et al. | |
| 8,536,303 B2 | 9/2013 | Panitch et al. | |
| 8,741,849 B2 | 6/2014 | Panitch et al. | |
| 9,034,815 B2 | 5/2015 | Panitch | |
| 9,493,508 B2 | 11/2016 | Panitch et al. | |
| 9,642,888 B2 | 5/2017 | Lander et al. | |
| 9,890,195 B2 | 2/2018 | Panitch et al. | |
| 2008/0176790 A1* | 7/2008 | DeFrees ................ | C07K 14/50 514/54 |
| 2009/0149389 A1 | 6/2009 | Panitch et al. | |
| 2009/0196927 A1 | 8/2009 | Panitch et al. | |
| 2010/0158968 A1 | 6/2010 | Panitch et al. | |
| 2011/0288036 A1 | 11/2011 | Lander et al. | |
| 2013/0101671 A9* | 4/2013 | Panitch ................ | C07K 14/00 424/484 |
| 2013/0115256 A1 | 5/2013 | Lander et al. | |
| 2014/0072613 A1 | 3/2014 | Lander et al. | |
| 2015/0064134 A1 | 3/2015 | Lander et al. | |
| 2016/0058876 A1* | 3/2016 | Duvall ................. | A61K 47/32 514/21.4 |

FOREIGN PATENT DOCUMENTS

| | | |
|---|---|---|
| WO | 1991016038 A1 | 10/1991 |
| WO | 2014169256 A2 | 10/2014 |

OTHER PUBLICATIONS

Sorkin A., et al., "Signal transduction and endocytosis: Close encounters of many kinds", Nature, 2002, vol. 3, pp. 600-614.
Stark V.K. et al., "Monocyte chemotactic protein-1 expression is associated with development of vein graft intimal hyperplasia", Arteriosclerosis, Thrombosis, and Vascular Biology, 1997, vol. 17, pp. 1614-1621.
Van ES J.H., et al., "You Wnt some, you lose some: oncogenes in the Wnt signaling pathway", Current Opinion in Genetics & Development, 2003, vol. 13, pp. 28-33.
Wootton J.C., et al., "Statistics of local complexity in amino acid sequences and sequence databases", Computers Chem. 1993, vol. 17, pp. 149-163, Pergamon Press Ltd.
Zarubin T., et al., "Activation and signaling of the p38 MAP kinase pathway", Cell Research, 2005, vol. 15, pp. 11-18.
Zwolak R.M., et al., "Kinetics of vein graft hyperplasi: Association with tangenital stress", Journal of Vascular Surgery, 1987, vol. 5, pp. 126-137.
Alstschul S.F., et al., "Gapped blast and PSI-BLAST: a new generation of protein database search programs", Nucleic Acids Research, 1997, vol. 25, pp. 3389-3402, Oxford University Press.
Bakin, A.V., et al., "p38 mitogen-activated protein kinase is required for TGF b-mediated fibroblastic transdifferentiation and cell migration", Journal of Cell Science, 2002, 3193-3206, The Company of Biologists Ltd.
Bode J.G., et al., "The macrophage response towards LPS and its control through the p38 MAPK-STAT3 axis", Cellular Signalling, 2012, vol. 24, pp. 1185-1194.

(Continued)

*Primary Examiner* — Julie Ha
(74) *Attorney, Agent, or Firm* — McCarter & English, LLP; Beverly W. Lubit

(57) ABSTRACT

A pharmaceutical formulation comprising a polypeptide of amino acid sequence YARAAARQARAKALARQLGVAA (SEQ ID NO: 1) or a functional equivalent thereof, up to 5% w/w solids before drying, a component selected from the group consisting of glycerin, lactose, and trehalose and excluding mannitol, and a pharmaceutically acceptable carrier, that preserves stability and bioavailability of the polypeptide is provided.

37 Claims, 83 Drawing Sheets

Specification includes a Sequence Listing.

(56) References Cited

OTHER PUBLICATIONS

Carpino L.A., et al., "The 9-flourenylmethoxycarbonyl amino-protecting group", J. Org. Chem., 1972, vol. 37, pp. 3404-3409.
Chen H-F, et al., "Role of heat shock protein 27 phosphorylation in migration of vascular smooth muscle cells", Mol Cell Biochem, 2009, vol. 327, pp. 1-6.
Claverie J-M, et al., "Information enhancement methods for large scale sequence analysis", Computers Chem., 1993, vol. 17, pp. 191-201, Pergamon Press Ltd.
Covertine A.J., et al., "Development of a novel endosomolytic diblock copolymer for siRNA delivery", J Control Release, 2009. vol. 133, pp. 221-229.
Corpet F., "Multiple sequence alignment with hierarchical clustering", Nucleic Acids Research, 1988, vol. 16, pp. 10881-10889.
Crownover E., et al., "Raft-synthesized graft copolymers that enhance ph-dependent membrane destablization and protein circulation times", J Control Release, 2011, vol. 155, pp. 167-174.
Ehlting C., et al., Distinct functions of the mitogen-activated protein kinase-activated protein (MAPKAP) kinases mk2 and mk3, The Journal of Biological Chemistry, 2011, vol. 286, pp. 24114-24124.
Eldar-Finkelman H., et al., "Substrate competitive gsk-3 inhibitors-strategy and implications", Biochmica et Biophysica Acta, 2010, vol. 1804, pp. 598-603.
Fields G.B., et al., "Solid phase peptide synthesis utilizing 9-fluorenylmethoxycarbonyl amino acids", Int. J. Peptide Protein Res., 1990, pp. 161-214.
Foster S., et al., "Intracellular delivery of a protein antigen with an endosomal-releasing polymer enhances CD8 t-cell production and prophylactic vaccine efficacy", Bioconjugate Chem., 2010, vol. 21, 2205-2212.
Fuchs L.C., et al., "Stress causes decrease in vascular relaxation linked with altered phosphorylation of heat shock proteins", Am J. Physiol Regulatory Integrative Comp Physiol, 2000, vol. 279, pp. 492-498.
Lopes L.B., et al., "A novel cell permean peptide inhibitor of MAPKAP kinase II inhibits intimal hyperplasia in a human saphenous vein organ culture model", Journal of Vascular Surgery, 2010, vol. 52, pp. 1596-1606.
Higgins D.G., et al., "Clustal: A package for performing multiple sequence alignment on a microcomputer", Gene, 1988, vol. 73, pp. 237-244.
Hitti E., et al., "Mitogen activated protein kinase-activated protein kinase 2 regulates tumor necrosis factor in mRNA stability and translation mainly by altering tristetraprolin expression, stability, and binding to adenine/uridine-rich element", Molecular and Cellular Biology, 2006, pp. 2399-2407.
Huang X., et al., "Parallelization of a local similarity algorithim", Cabios, 1992, vol. 8, pp. 155-165.
Humphries W.H., et al., "Imaging lysomal enzyme activity in live cells using self-quenched substrates", Anal Biochem, 2012, vol. 424, pp. 178-183.
Jalvey S., et al., "CREB mediates UTP-directed arterial smooth muscle cell migration and expression of the chemotactic protein osteopontin via its interaction with activator protein-1 sites", Molecular Medicine, 2007, vol. 100, pp. 1292-1299.
Jones R.A., et al., "Poly(2-alkylacrylic acid) polymers deliver molecules to the cytosol by pH-sensitive disruption of endosomal vesicles", Biochem, J. 2003, vol. 372, pp. 65-75.
Karlin S., et al., "Applications and statistics for multiple high-scoring segments in molecular sequences", Proc. Natl. Acad. Sci. USA, 1993, vol. 90, pp. 5873-5877.
Keatings V.M., et al., "Differences in interleukin-8 and tumor necrosis factor-a in induced sputum from patients with chronic obstructive pulmonary disease or asthman", A J. Respir Crit Care Med, 1996, vol. 153, pp. 530-534.
Lackey C.A., et al., "A biomimetic pH-responsive polymer directs endosomal release and intracellular delivery of an endocytosed antibody complex", Bioconjugate Chem., 2002, vol. 13, pp. 996-1001.

Lim S., et al., "Balance of matrix metalloprotease-9 and tissue inhibitor of metalloprotease-1 from alveolar macrophages in cigarette smokers", American Journal of Respiratory and Critical Care Medicine, 2000, vol. 162, pp. 1-18.
Merrifield R.B., "Solid phase peptide syhthesis. I. The synthesis of tetrapeptide", 1963, pp. 2149-2154.
Myers E.W., et al., "Optimal alignments in linear space", Computer Applic. Biol. Sci., 1988, vol. 4, pp. 11-17.
Mislick K.A., et al., "Evidence for the role of proteoglycans in cation-mediated", Proc. Natl. Acad. Sci. USA, 1996, vol. 93, pp. 12349-12354.
Mitchell R.N., et al., "Vascular remodeling in transplant vasculopathy", Circulation Reseach, 2007, vol. 100, pp. 367-978.
Molnar P., et al., "The cyclic AMP response element-binding protein (CREB) mediates smooth muscle cell proliferation in response to angiotensin II", J. Cell Commun. Signal, 2014, vol. 8, pp. 29-37.
Mueller L., et al., "TNF-a similarly induces IL-6 and MCP-1 in fibroblasts from colorectal liver metastases and formal liver fibroblasts", Biochemical and Biophysical Research Communicatins, 2010, vol. 397, pp. 586-591.
Murthy N., et al., "The design and synthesis of polymers for eukaryotic membrane disruption", Journal of Controlled Release, 1999, vol. 61, pp. 137-143.
Nakanishi K., et al., "Cyclic adenosine monophosphate response-element binding protein activation by mitogen-activated protein kinase-activated protein kinase 3 and four-and-a-half LIM domains 5 plays a key role for vein graft intimal hyperplasia", Journal of Vascular Surgery, 2013, vol. 57, pp. 183-191.
Needlman S.B., et al., "A general method applicable to the search for similarities in the amino acid sequence of two proteins", J. Mol. Biol., 1970, vol. 48, pp. 443-453.
Nelson C.E., et al., "Balancing cationic and hydrophobic content of PEGylated siRNA polyplexes enhances endosome escape, stability, blood circulation time, and bioactivity invivo", ACS NANO, 2013, vol. 7, pp. 8870-8880.
Ono H., et al., cAMP-response element-binding protein mediates tumor necrosis factor-a-induced vascular smooth muscle cell migration:, Arterioscler Thromb Vasc Biol., 2004, vol. 24, pp. 1634-1639.
Parcellier A., et al., "H5P27 is a ubiquitin-binding protein involved in I-kBa proteasomal degradation", Molecular and Cellular Biology, 2003, vol. 23, pp. 5790-5802.
Pearson W.R., et al., "Improved tools for biological sequence comparison", Proc. Natl. Acad. Sci. USA, 1988, vol. 35, pp. 2444-2448.
Richard J.P., et al., "Cellular uptake of unconjugated TAT peptide involves clathrin-dependendt endocytosis and heparan sulfate receptors", The Journal of Biological Chemistry, 2005, vol. 280, pp. 15300-15306.
Ronkina N., et al., "MAPKAP kinases MK2 and MK3 in inflammation: complex regulation of TNF biosynthesis via expression and phosphoroylation of tristetrapolin", Biochemical Pharmacology, 2010, vol. 80, pp. 1915-1920.
Rousseau S., et al., "Inhibition of SAPK2a/p38 prevents hnRNP A0 phosphorylation by MAPKAP-K2 and its interaction with cytokine mRNAs", The EMBO Journal, 2002, vol. 21, pp. 6505-6514.
Ruttekolk I.R., et al., "The intracellular pharmokinetics of terminally capped peptides", Molecular Pharmaceutics, 2012, vol. 9, pp. 1077-1086.
Schafmeister C.E., et al., "An all-hydrocarbon cross-linking system for enhancing the helicity and metabolic stability of peptides" J. Am. Chem. Soc., 2000, vol. 122, pp. 5891-5891.
Smith T.F., et al., "Comparison of Biosequences", Advances in Applied Mathematics, 1981, vol. 2, 482-489.
Snyder E.L., et al., "Cell penetrating peptides in drug delivery", Pharmaceutical Research, 2004, vol. 21, pp. 389-393.
Becker, et al., P-097 Aerosol Performance of Spray Dried MMI-0100 from the Microdose Inhaler for Treatment of Pulmonary Fibrosis, Journal of Aerosole Medicine and Pulmonary Drug Delivery, vol. 26, No. 2, 2013.

(56) References Cited

OTHER PUBLICATIONS

Beerens, AMJ, et al, Protein Transduction Domains and their Utility in Gene Therapy, Current Gene Therapy, 2003, 3, 486-494.

Duvall, C. L. et al, Intracellular Delivery of a Proapoptotic Peptide via Conjugation to a RAFT Synthesized Endosomolytic Polymer, Mol. Pharm 7, 468-476, (2010).

Evans, B.C., et al, Ex Vivo Red Blood Cell Hemolysis Assay for the Evaluation of pH-responsive Endosomolytic Agents for Cytosolic Delivery of Biomacromolecular Drugs, Journal of Visualized Experiments Mar. 2013, 73, e50166, 2013.

Evans, C., et al; MK2 inhibitory peptide delivered in nanopolyplexes prevents vascular graft intimal hyperplasia, Science Translational Medicine, Jun. 10, 2015, vol. 7, 1-11.

Healey, A.M., et al, Dry powders for oral inhalation free of lactose carrier particles, Advanced Drug Delivery Reviews vol. 75 (2014) 32-52.

Henikoff, S., et al; Amino Acid Substitution Matrices From Protein Blocks, Proc. Natl. Acad. Sci. USA 89:10915-10919, 1992.

Henry, S.M., et al, pH-Responsive Poly(styrene-alt-maleic anhydride) Alkylamide Copolymers for Intracellular Drug Delivery, Biomacromolecules 2006, 7, 2407-2414.

Jiang, Z., et al, A novel vein graft model: adaptation to differential flow environments, Am J Physiol Heart Circ Physiol 286: H240-H245, 2004.

Kalra, M, et al, Early Remodeling of Saphenous Vein Grafts: Proliferation, Migration and Apoptosis of Adventitial and Medial Cells Occur Simultaneously with Changes in Graft Diameter and Blood Flow, J Vasc Res, 2000; 37:576-584.

Lee G-L, et al., "TLR 2 induces vascular smooth muscle cell migration through cAMP response element-binding protein-mediated interleukin-6 production", Arteriolscler Thromb Vasc Biol, pp. 2751-2760, 2012.

Muto, A., et al, Inhibition of Mitogen Activated Protein Kinase Activated Protein Kinase II with MMI-0100 reduces intimal hyperplasia ex vivo and in vivo; Vascul Pharmacol. Jan. 2012 ; 56(1-2): 47-55. doi:10.1016/j. vph.2011.07.008.

PCT/US2016/012650; International Preliminary Report on Patentability, dated Jul. 11, 2017.

Pearson, W.R., Using the FASTA Program to Search Protein and DNA Sequence Databases, Methods in Molecular Biology 24:307-331 (1994) (abstract).

Rensen, S.S., et al, Regulation and characteristics of vascular smooth muscle cell phenotypic diversity, Netherlands Heart Journal, vol. 15, No. 3, Mar. 2007.

\* cited by examiner

FIG. 2

| | TECHNICAL DATA SHEET FORMPACK®-4 PLY | | ALCAN ALCAN PACKAGING PHARMA CENTER 6050 MIDLAND INDUSTRIAL DRIVE SHELBEYVILLE, KY 40965 |
|---|---|---|---|
| JUNE 15, 2004 | | PRODUCT CODE: 90256 | |

DESCRIPTION
PATENTED FORMPACK COLD-FORMABLE ALUMINUM-PLASTIC LAMINATES ARE SUITED FOR APPLICATIOS REQUIRING FORMING, WHILE MAINTAINING THE HIGHEST POSSIBLE BARRIER PROTECTION FORMPACKS 4-PLY COMBINES ALUMINUM FOIL FOR BARRIER PROTECTION WITH A PVC SEALENT ON BOTH SIDES FOR ADDED SUPPORT AND RIGIDITY

KEY PERFORMANCE CHARACTERISTICS
☐ COLD-FORMABLE
☐ RETAINS BARRIER PROPERTIES AT ICH CONDITIONS
☐ POST FORMING PINHOLE-FREE INTEGRITY
☐ HIGHEST BARRIER TO MOISTURE, UV, OXYGEN AND OTHER GASES, TOTAL BARRIER TO LIGHT
☐ ALLOWS USE OF COMMON LIDDING MATERIALS WITH STANDARD HEATSEAL COSTINGS
☐ HIGH RIGIDITY AFTER ACID FORMING;

PVC
ADHESIVE
oPA
ADHESIVO
PRIMER
ALUMINUM
ADHESIVE
PVC

STRUCTURE (FROM THE OUTSIDE TO THE INSIDE)

| MATERIAL | THICKNESS | | BASIS-WEIGHT | |
|---|---|---|---|---|
| | (mm) | (mils) | (xxxx) | (xxxx) |
| PVC | 60 | 2.4 | 18.00 | 47.80 |
| ADHESIVE | | | 4.00 | 2.46 |
| oPA | 75 | 1 | 28.75 | 17.85 |
| ADHESIVE | | | 3.50 | 2.15 |
| ALUMINUM PRIMED-MATTE SIDE | 60 | 2.36 | 164.00 | 100.68 |
| ADHESIVE | | | 4.00 | 2.48 |
| PVC | 60 | 2.4 | 78.00 | 47.80 |

| DESCRIPTIVE PROPERTY | VALUE | | |
|---|---|---|---|
| TOTAL BASIS WEIGHT | 380.25 XXXXX +/- 3.67 XXXXX | 221.16 | XXXXX |
| YIELD | 2.5 XXXXX +/- 0.28 XXXXX | 1061.6 | XXXXX |

PACKAGING DESIGN

IT IS CRITICAL THAT PROPER ATTENTION IS GIVEN TO THE DESIGN OF LOADING USED TO FORM THE LAMINATE IN ANY PACKAGING PROCESS. WHEN CONSIDERING A DESIGN, ALCAN PACKAGING PHARMA CENTER TECHNICAL SUPPORT WILL ASSIST THE CUSTOMER IN THE CAVITY (PACKAGE) DESIGN AND CAN OFFER TECHNICAL SERVICES WHICH WILL AID ALL CUSTOMERS IN MAINTENANCE OF A PINHOLE-FREE PACKAGE DURING FINAL PRODUCTION ON THE PACKAGING LINE

BY USING PROVEN COMPUTER ASSISTED MEASUREMENT TECHNOLOGIES, ALCAN PACKAGING PHARMA CENTER CAN ASSURE THE CUSTOMER THAT:

A PACKAGE CONCEPT IS FORMULATED INTO AN EFFICIENT PACKAGE DESIGN
A PACKAGE DESIGN DOES NOT COMPROMISE THE THEORETICAL LIMITATIONS OF THE MATERIAL

TGA

SEQUENCE LISTING

```
<160> NUMBER OF SEQ ID NOS: 27

<210> SEQ ID NO 1
<211> LENGTH: 22
<212> TYPE: PRT
<213> ORGANISM: Unknown
<220> FEATURE:
<223> OTHER INFORMATION: Mammalian

<400> SEQUENCE: 1

Tyr Ala Arg Ala Ala Ala Arg Gln Ala Arg Ala Lys Ala Leu Ala Arg
1               5                   10                  15

Gln Leu Gly Val Ala Ala
            20

<210> SEQ ID NO 2
<211> LENGTH: 11
<212> TYPE: PRT
<213> ORGANISM: Unknown
<220> FEATURE:
<223> OTHER INFORMATION: Mammalian

<400> SEQUENCE: 2

Lys Ala Leu Ala Arg Gln Leu Gly Val Ala Ala
1               5                   10

<210> SEQ ID NO 3
<211> LENGTH: 21
<212> TYPE: PRT
<213> ORGANISM: Unknown
<220> FEATURE:
<223> OTHER INFORMATION: Mammalian
```

```
<400> SEQUENCE: 3

Phe Ala Lys Leu Ala Ala Arg Leu Tyr Arg Lys Ala Leu Ala Arg Gln
1               5                   10                  15

Leu Gly Val Ala Ala
            20

<210> SEQ ID NO 4
<211> LENGTH: 23
<212> TYPE: PRT
<213> ORGANISM: Unknown
<220> FEATURE:
<223> OTHER INFORMATION: Mammalian

<400> SEQUENCE: 4

Lys Ala Phe Ala Lys Leu Ala Ala Arg Leu Tyr Arg Lys Ala Leu Ala
1               5                   10                  15

Arg Gln Leu Gly Val Ala Ala
            20

<210> SEQ ID NO 5
<211> LENGTH: 21
<212> TYPE: PRT
<213> ORGANISM: Unknown
<220> FEATURE:
<223> OTHER INFORMATION: Mammalian

<400> SEQUENCE: 5

Tyr Ala Arg Ala Ala Ala Arg Gln Ala Arg Ala Lys Ala Leu Ala Arg
1               5                   10                  15

Gln Leu Ala Val Ala
            20

<210> SEQ ID NO 6
<211> LENGTH: 21
<212> TYPE: PRT
<213> ORGANISM: Unknown
<220> FEATURE:
<223> OTHER INFORMATION: Mammalian

<400> SEQUENCE: 6

Tyr Ala Arg Ala Ala Ala Arg Gln Ala Arg Ala Lys Ala Leu Ala Arg
1               5                   10                  15

Gln Leu Gly Val Ala
            20

<210> SEQ ID NO 7
<211> LENGTH: 22
<212> TYPE: PRT
<213> ORGANISM: Unknown
<220> FEATURE:
<223> OTHER INFORMATION: Mammalian

<400> SEQUENCE: 7

His Arg Arg Ile Lys Ala Trp Leu Lys Lys Ile Lys Ala Leu Ala Arg
1               5                   10                  15

Gln Leu Gly Val Ala Ala
            20

<210> SEQ ID NO 8
<211> LENGTH: 10
<212> TYPE: PRT
<213> ORGANISM: Unknown
<220> FEATURE:
<223> OTHER INFORMATION: Mammalian
```

```
<400> SEQUENCE: 8

Lys Ala Leu Ala Arg Gln Leu Ala Val Ala
1               5                   10

<210> SEQ ID NO 9
<211> LENGTH: 10
<212> TYPE: PRT
<213> ORGANISM: Unknown
<220> FEATURE:
<223> OTHER INFORMATION: Mammalian

<400> SEQUENCE: 9

Lys Ala Leu Ala Arg Gln Leu Gly Val Ala
1               5                   10

<210> SEQ ID NO 10
<211> LENGTH: 11
<212> TYPE: PRT
<213> ORGANISM: Unknown
<220> FEATURE:
<223> OTHER INFORMATION: Mammalian

<400> SEQUENCE: 10

Lys Ala Leu Ala Arg Gln Leu Gly Val Ala Ala
1               5                   10

<210> SEQ ID NO 11
<211> LENGTH: 11
<212> TYPE: PRT
<213> ORGANISM: Unknown
<220> FEATURE:
<223> OTHER INFORMATION: Mammalian

<400> SEQUENCE: 11

Tyr Ala Arg Ala Ala Ala Arg Gln Ala Arg Ala
1               5                   10

<210> SEQ ID NO 12
<211> LENGTH: 14
<212> TYPE: PRT
<213> ORGANISM: Unknown
<220> FEATURE:
<223> OTHER INFORMATION: Mammalian

<400> SEQUENCE: 12

Trp Leu Arg Arg Ile Lys Ala Trp Leu Arg Arg Ile Lys Ala
1               5                   10

<210> SEQ ID NO 13
<211> LENGTH: 7
<212> TYPE: PRT
<213> ORGANISM: Unknown
<220> FEATURE:
<223> OTHER INFORMATION: Mammalian

<400> SEQUENCE: 13

Trp Leu Arg Arg Ile Lys Ala
1               5

<210> SEQ ID NO 14
<211> LENGTH: 11
<212> TYPE: PRT
<213> ORGANISM: Unknown
<220> FEATURE:
<223> OTHER INFORMATION: Mammalian
```

```
<400> SEQUENCE: 14

Tyr Gly Arg Lys Lys Arg Arg Gln Arg Arg
1               5                   10

<210> SEQ ID NO 15
<211> LENGTH: 12
<212> TYPE: PRT
<213> ORGANISM: Unknown
<220> FEATURE:
<223> OTHER INFORMATION: Mammalian

<400> SEQUENCE: 15

Trp Leu Arg Arg Ile Lys Ala Trp Leu Arg Arg Ile
1               5                   10

<210> SEQ ID NO 16
<211> LENGTH: 10
<212> TYPE: PRT
<213> ORGANISM: Unknown
<220> FEATURE:
<223> OTHER INFORMATION: Mammalian

<400> SEQUENCE: 16

Phe Ala Lys Leu Ala Ala Arg Leu Tyr Arg
1               5                   10

<210> SEQ ID NO 17
<211> LENGTH: 12
<212> TYPE: PRT
<213> ORGANISM: Unknown
<220> FEATURE:
<223> OTHER INFORMATION: Mammalian

<400> SEQUENCE: 17

Lys Ala Phe Ala Lys Leu Ala Ala Arg Leu Tyr Arg
1               5                   10

<210> SEQ ID NO 18
<211> LENGTH: 11
<212> TYPE: PRT
<213> ORGANISM: Unknown
<220> FEATURE:
<223> OTHER INFORMATION: Mammalian

<400> SEQUENCE: 18

His Arg Arg Ile Lys Ala Trp Leu Lys Lys Ile
1               5                   10

<210> SEQ ID NO 19
<211> LENGTH: 21
<212> TYPE: PRT
<213> ORGANISM: Unknown
<220> FEATURE:
<223> OTHER INFORMATION: Mammalian

<400> SEQUENCE: 19

Tyr Ala Arg Ala Ala Ala Arg Gln Ala Arg Ala Lys Ala Leu Asn Arg
1               5                   10                  15

Gln Leu Gly Val Ala
            20

<210> SEQ ID NO 20
<211> LENGTH: 9
<212> TYPE: PRT
<213> ORGANISM: Unknown
```

```
<220> FEATURE:
<223> OTHER INFORMATION: Mammalian

<400> SEQUENCE: 20

Arg Lys Lys Arg Arg Gln Arg Arg Arg
1               5

<210> SEQ ID NO 21
<211> LENGTH: 17
<212> TYPE: PRT
<213> ORGANISM: Unknown
<220> FEATURE:
<223> OTHER INFORMATION: Mammalian
<220> FEATURE:
<221> NAME/KEY: X
<222> LOCATION: (3)..(12)
<223> OTHER INFORMATION: Any amino acid

<400> SEQUENCE: 21

Lys Lys Xaa Xaa Xaa Xaa Xaa Xaa Xaa Xaa Xaa Lys Arg Arg Lys
1               5                   10                  15

Lys

<210> SEQ ID NO 22
<211> LENGTH: 7
<212> TYPE: PRT
<213> ORGANISM: Unknown
<220> FEATURE:
<223> OTHER INFORMATION: Mammalian

<400> SEQUENCE: 22

Leu Leu Lys Arg Arg Lys Lys
1               5

<210> SEQ ID NO 23
<211> LENGTH: 22
<212> TYPE: PRT
<213> ORGANISM: Unknown
<220> FEATURE:
<223> OTHER INFORMATION: Mammalian

<400> SEQUENCE: 23

Tyr Ala Arg Ala Ala Ala Arg Asp Ala Arg Ala Lys Ala Leu Asn Arg
1               5                   10                  15

Gln Leu Ala Val Ala Ala
            20

<210> SEQ ID NO 24
<211> LENGTH: 21
<212> TYPE: PRT
<213> ORGANISM: Unknown
<220> FEATURE:
<223> OTHER INFORMATION: Mammalian

<400> SEQUENCE: 24

Tyr Ala Arg Ala Ala Ala Arg Gln Ala Arg Ala Lys Ala Leu Asn Arg
1               5                   10                  15

Gln Leu Ala Val Ala
            20

<210> SEQ ID NO 25
<211> LENGTH: 11
<212> TYPE: PRT
<213> ORGANISM: Unknown
<220> FEATURE:
<223> OTHER INFORMATION: Mammalian
```

```
<400> SEQUENCE: 25

Lys Ala Leu Asn Arg Gln Leu Ala Val Ala Ala
1               5                   10

<210> SEQ ID NO 26
<211> LENGTH: 10
<212> TYPE: PRT
<213> ORGANISM: Unknown
<220> FEATURE:
<223> OTHER INFORMATION: Mammalian

<400> SEQUENCE: 26

Lys Ala Leu Asn Arg Gln Leu Ala Val Ala
1               5                   10

<210> SEQ ID NO 27
<211> LENGTH: 13
<212> TYPE: PRT
<213> ORGANISM: Unknown
<220> FEATURE:
<223> OTHER INFORMATION: Mammalian

<400> SEQUENCE: 27

Trp Leu Arg Arg Ala Ser Ala Pro Leu Pro Gly Leu Lys
1               5                   10
```

FORMULATION OF MK2 INHIBITOR PEPTIDES

CROSS-REFERENCE TO RELATED APPLICATIONS

This application claims the benefit of priority to U.S. provisional patent application Ser. No. 62/101,190, filed Jan. 8, 2015, entitled "FORMULATION OF MK2 INHIBITOR PEPTIDES", the content of which is incorporated by reference herein in its entirety.

FIELD OF INVENTION

The described invention relates to the fields of cell and molecular biology, polypeptides, pharmaceutical formulations and therapeutic methods of use.

BACKGROUND

Kinases

Kinases are a ubiquitous group of enzymes that catalyze the phosphoryl transfer reaction from a phosphate donor (usually adenosine-5'-triphosphate (ATP)) to a receptor substrate. Although all kinases catalyze essentially the same phosphoryl transfer reaction, they display remarkable diversity in their substrate specificity, structure, and the pathways in which they participate. A recent classification of all available kinase sequences (approximately 60,000 sequences) indicates kinases can be grouped into 25 families of homologous (meaning derived from a common ancestor) proteins. These kinase families are assembled into 12 fold groups based on similarity of structural fold. Further, 22 of the 25 families (approximately 98.8% of all sequences) belong to 10 fold groups for which the structural fold is known. Of the other 3 families, polyphosphate kinase forms a distinct fold group, and the 2 remaining families are both integral membrane kinases and comprise the final fold group. These fold groups not only include some of the most widely spread protein folds, such as Rossmann-like fold (three or more parallel β strands linked by two α helices in the topological order β-α-β-α-β), ferredoxin-like fold (a common α+β protein fold with a signature βαββαβ secondary structure along its backbone), TIM-barrel fold (meaning a conserved protein fold consisting of eight α-helices and eight parallel β-strands that alternate along the peptide backbone), and antiparallel β-barrel fold (a beta barrel is a large beta-sheet that twists and coils to form a closed structure in which the first strand is hydrogen bonded to the last), but also all major classes (all α, all β, α+β, α/β) of protein structures. Within a fold group, the core of the nucleotide-binding domain of each family has the same architecture, and the topology of the protein core is either identical or related by circular permutation. Homology between the families within a fold group is not implied.

Group I (23,124 sequences) kinases incorporate protein S/T-Y kinase, atypical protein kinase, lipid kinase, and ATP grasp enzymes and further comprise the protein S/T-Y kinase, and atypical protein kinase family (22,074 sequences). These kinases include: choline kinase (EC 2.7.1.32); protein kinase (EC 2.7.137); phosphorylase kinase (EC 2.7.1.38); homoserine kinase (EC 2.7.1.39); I-phosphatidylinositol 4-kinase (EC 2.7.1.67); streptomycin 6-kinase (EC 2.7.1.72); ethanolamine kinase (EC 2.7.1.82); streptomycin 3'-kinase (EC 2.7.1.87); kanamycin kinase (EC 2.7.1.95); 5-methylthioribose kinase (EC 2.7.1.100); viomycin kinase (EC 2.7.1.103); [hydroxymethylglutaryl-CoA reductase (NADPH2)] kinase (EC 2.7.1.109); protein-tyrosine kinase (EC 2.7.1.112); [isocitrate dehydrogenase (NADP+)] kinase (EC 2.7.1.116); [myosin light-chain] kinase (EC 2.7.1.117); hygromycin-B kinase (EC 2.7.1.119); calcium/calmodulin-dependent protein kinase (EC 2.7.1.123); rhodopsin kinase (EC 2.7.1.125); [beta-adrenergic-receptor]kinase (EC 2.7.1.126); [myosin heavy-chain] kinase (EC 2.7.1.129); [Tau protein] kinase (EC 2.7.1.135); macrolide 2'-kinase (EC 2.7.1.136); I-phosphatidylinositol 3-kinase (EC 2.7.1.137); [RNA-polymerase]-subunit kinase (EC 2.7.1.141); phosphatidylinositol-4,5-bisphosphate 3-kinase (EC 2.7.1.153); and phosphatidylinositol-4-phosphate 3-kinase (EC 2.7.1.154). Group I further comprises the lipid kinase family (321 sequences). These kinases include: I-phosphatidylinositol-4-phosphate 5-kinase (EC 2.7.1.68); I D-myo-inositol-triphosphate 3-kinase (EC 2.7.1.127); inositol-tetrakisphosphate 5-kinase (EC 2.7.1.140); I-phosphatidylinositol-5-phosphate 4-kinase (EC 2.7.1.149); I-phosphatidylinositol-3-phosphate 5-kinase (EC 2.7.1.150); inositol-polyphosphate multikinase (EC 2.7.1.151); and inositol-hexakiphosphate kinase (EC 2.7.4.21). Group I further comprises the ATP-grasp kinases (729 sequences) which include inositol-tetrakisphosphate I-kinase (EC 2.7.1.134); pyruvate, phosphate dikinase (EC 2.7.9.1); and pyruvate, water dikinase (EC 2.7.9.2).

Group II (17,071 sequences) kinases incorporate the Rossman-like kinases. Group II comprises the P-loop kinase family (7,732 sequences). These include gluconokinase (EC 2.7.1.12); phosphoribulokinase (EC 2.7.1.19); thymidine kinase (EC 2.7.1.21); ribosylnicotinamide kinase (EC 2.7.1.22); dephospho-CoA kinase (EC 2.7.1.24); adenylyl-sulfate kinase (EC 2.7.1.25); pantothenate kinase (EC 2.7.1.33); protein kinase (bacterial) (EC 2.7.1.37); uridine kinase (EC 2.7.1.48); shikimate kinase (EC 2.7.1.71); deoxycytidine kinase (EC 2.7.1.74); deoxyadenosine kinase (EC 2.7.1.76); polynucleotide 5'-hydroxyl-kinase (EC 2.7.1.78); 6-phosphofructo-2-kinase (EC 2.7.1.105); deoxyguanosine kinase (EC 2.7.1.113); tetraacyldisaccharide 4'-kinase (EC 2.7.1.130); deoxynucleoside kinase (EC 2.7.1.145); adenosylcobinamide kinase (EC 2.7.1.156); polyphosphate kinase (EC 2.7.4.1); phosphomevalonate kinase (EC 2.7.4.2); adenylate kinase (EC 2.7.4.3); nucleoside-phosphate kinase (EC 2.7.4.4); guanylate kinase (EC 2.7.4.8); thymidylate kinase (EC 2.7.4.9); nucleoside-triphosphate-adenylate kinase (EC 2.7.4.10); (deoxy)nucleoside-phosphate kinase (EC 2.7.4.13); cytidylate kinase (EC 2.7.4.14); and uridylate kinase (EC 2.7.4.22). Group II further comprises the phosphoenolpyruvate carboxykinase family (815 sequences). These enzymes include protein kinase (HPr kinase/phosphatase) (EC 2.7.1.37); phosphoenolpyruvate carboxykinase (GTP) (EC 4.1.1.32); and phosphoenolpyruvate carboxykinase (ATP) (EC 4.1.1.49). Group II further comprises the phosphoglycerate kinase (1,351 sequences) family. These enzymes include phosphoglycerate kinase (EC 2.7.2.3) and phosphoglycerate kinase (GTP) (EC 2.7.2.10). Group II further comprises the aspartokinase family (2,171 sequences). These enzymes include carbamate kinase (EC 2.7.2.2); aspartate kinase (EC 2.7.2.4); acetylglutamate kinase (EC 2.7.2.8 1); glutamate 5-kinase (EC 2.7.2.1) and uridylate kinase (EC 2.7.4.). Group II further comprises the phosphofructokinase-like kinase family (1,998 sequences). These enzymes include 6-phosphofructokinase (EC 2.7.1.1 1); NAD(+) kinase (EC 2.7.1.23); I-phosphofructokinase (EC 2.7.1.56); diphosphate-fructose-6-phosphate I-phosphotransferase (EC 2.7.1.90); sphinganine kinase (EC 2.7.1.91); diacylglycerol kinase (EC 2.7.1.107); and ceramide kinase (EC 2.7.1.138). Group II further comprises the ribokinase-like family (2,722 sequences). These enzymes include: glucokinase (EC 2.7.1.2); ketohexokinase (EC 2.7.1.3); fructokinase (EC 2.7.1.4); 6-phosphofructokinase (EC 2.7.1.11); ribokinase (EC 2.7.1.15); adenosine kinase (EC 2.7.1.20); pyridoxal kinase (EC 2.7.1.35); 2-dehydro-3-deoxygluconokinase (EC 2.7.1.45); hydroxymethylpyrimidine kinase (EC 2.7.1.49); hydroxyethylthiazole kinase (EC 2.7.1.50); I-phosphofructokinase (EC 2.7.1.56); inosine kinase (EC 2.7.1.73); 5-dehydro-2-deoxygluconokinase (EC 2.7.1.92); tagatose-6-phosphate kinase (EC 2.7.1.144); ADP-dependent phosphofructokinase (EC 2.7.1.146); ADP-dependent glucokinase (EC 2.7.1.147); and phosphomethylpyrimidine kinase (EC 2.7.4.7). Group II further comprises the thiamin pyrophosphokinase family (175 sequences) which includes thiamin pyrophosphokinase (EC 2.7.6.2). Group II further comprises the glycerate kinase family (107 sequences) which includes glycerate kinase (EC 2.7.1.31).

Group III kinases (10,973 sequences) comprise the ferredoxin-like fold kinases. Group III further comprises the nucleoside-diphosphate kinase family (923 sequences). These enzymes include nucleoside-diphosphate kinase (EC 2.7.4.6). Group III further comprises the HPPK kinase family (609 sequences). These enzymes include 2-amino-4-hydroxy-6-hydroxymethyldihydropteridine pyrophosphokinase (EC 2.7.6.3). Group III further comprises the guanido kinase family (324 sequences). These enzymes include guanidoacetate kinase (EC 2.7.3.1); creatine kinase (EC 2.7.3.2); arginine kinase (EC 2.7.3.3); and lombricine kinase (EC 2.7.3.5). Group III further comprises the histidine kinase family (9,117 sequences). These enzymes include protein kinase (histidine kinase) (EC 2.7.1.37); [pyruvate dehydrogenase (lipoamide)] kinase (EC 2.7.1.99); and [3-methyl-2-oxybutanoate dehydrogenase(lipoamide)] kinase (EC 2.7.1.115).

Group IV kinases (2,768 sequences) incorporate ribonuclease H-like kinases. These enzymes include hexokinase (EC 2.7.1.1); glucokinase (EC 2.7.1.2); fructokinase (EC 2.7.1.4); rhamnulokinase (EC 2.7.1.5); mannokinase (EC 2.7.1.7); gluconokinase (EC 2.7.1.12); L-ribulokinase (EC 2.7.1.16); xylulokinase (EC 2.7.1.17); erythritol kinase (EC 2.7.1.27); glycerol kinase (EC 2.7.1.30); pantothenate kinase (EC 2.7.1.33); D-ribulokinase (EC 2.7.1.47); L-fucolokinase (EC 2.7.1.51); L-xylulokinase (EC 2.7.1.53); allose kinase (EC 2.7.1.55); 2-dehydro-3-deoxygalactonokinase (EC 2.7.1.58); N-acetylglucosamine kinase (EC 2.7.1.59); N-acylmannosamine kinase (EC 2.7.1.60); polyphosphate-glucose phosphotransferase (EC 2.7.1.63); beta-glucoside kinase (EC 2.7.1.85); acetate kinase (EC 2.7.2.1); butyrate kinase (EC 2.7.2.7); branched-chain-fatty-acid kinase (EC 2.7.2.14); and propionate kinase (EC 2.7.2.15).

Group V kinases (1,119 sequences) incorporate TIM β-barrel kinases. These enzymes include pyruvate kinase (EC 2.7.1.40).

Group VI kinases (885 sequences) incorporate GHMP kinases. These enzymes include galactokinase (EC 2.7.1.6); mevalonate kinase (EC 2.7.1.36); homoserine kinase (EC 2.7.1.39); L-arabinokinase (EC 2.7.1.46); fucokinase (EC 2.7.1.52); shikimate kinase (EC 2.7.1.71); 4-(cytidine 5'-diphospho)-2-C-methyl-D-erythriol kinase (EC 2.7.1.148); and phosphomevalonate kinase (EC 2.7.4.2).

Group VII kinases (1,843 sequences) incorporate AIR synthetase-like kinases. These enzymes include thiamine-phosphate kinase (EC 2.7.4.16) and selenide, water dikinase (EC 2.7.9.3).

Group VIII kinases (565 sequences) incorporate riboflavin kinases (565 sequences). These enzymes include riboflavin kinase (EC 2.7.1.26).

Group IX kinases (197 sequences) incorporate dihydroxyacetone kinases. These enzymes include glycerone kinase (EC 2.7.1.29).

Group X kinases (148 sequences) incorporate putative glycerate kinases. These enzymes include glycerate kinase (EC 2.7.1.31).

Group XI kinases (446 sequences) incorporate polyphosphate kinases. These enzymes include polyphosphate kinases (EC 2.7.4.1).

Group XII kinases (263 sequences) incorporate integral membrane kinases. Group XII comprises the dolichol kinase family. These enzymes include dolichol kinases (EC 2.7.1.108). Group XII further comprises the undecaprenol kinase family. These enzymes include undecaprenol kinases (EC 2.7.1.66).

Kinases play indispensable roles in numerous cellular metabolic and signaling pathways, and are among the best-studied enzymes at the structural, biochemical, and cellular level. Despite the fact that all kinases use the same phosphate donor (in most cases, ATP) and catalyze apparently the same phosphoryl transfer reaction, they display remarkable diversity in their structural folds and substrate recognition mechanisms. This probably is due largely to the diverse nature of the structures and properties of their substrates.

Mitogen-Activated Protein Kinase (MAPK)-Activated Protein Kinases (MK2 and MK3)

Different groups of MAPK-activated protein kinases (MAP-KAPKs) have been defined downstream of mitogen-activated protein kinases (MAPKs). These enzymes transduce signals to target proteins that are not direct substrates of the MAPKs and, therefore, serve to relay phosphorylation-dependent signaling with MAPK cascades to diverse cellular functions. One of these groups is formed by the three MAPKAPKs: MK2, MK3 (also known as 3pK), and MK5 (also designated PRAK). Mitogen-activated protein kinase-activated protein kinase 2 (also referred to as "MAP-KAPK2", "MAPKAP-K2", "MK2") is a kinase of the serine/threonine (Ser/Thr) protein kinase family. MK2 is highly homologous to MK3 (approximately 75% amino acid identity). The kinase domains of MK2 and MK3 are most similar (approximately 35% to 40% identity) to calcium/calmodulin-dependent protein kinase (CaMK), phosphorylase b kinase, and the C-terminal kinase domain (CTKD) of the ribosomal S6 kinase (RSK) isoforms. The MK2 gene encodes two alternatively spliced transcripts of 370 amino acids (MK2A) and 400 amino acids (MK2B). The MK3 gene encodes one transcript of 382 amino acids. The MK2- and MK3 proteins are highly homologous, yet MK2A possesses a shorter C-terminal region. The C-terminus of MK2B contains a functional bipartite nuclear localization sequence (NLS) (Lys-Lys-Xaa-Xaa-Xaa-Xaa-Xaa-Xaa-Xaa-Xaa-Xaa-Xaa-Lys-Arg-Arg-Lys-Lys; SEQ ID NO: 21) that is not present in the shorter MK2A isoform, indicating that alternative splicing determines the cellular localization of the MK2 isoforms. MK3 possesses a similar nuclear localization sequence. The nuclear localization sequence found in both MK2B and MK3 encompasses a D domain (Leu-Leu-Lys-Arg-Arg-Lys-Lys; SEQ ID NO: 22), which was shown to mediate the specific interaction of MK2B and MK3 with p38α and p38β. MK2B and MK3 also possess a functional nuclear export signal (NES) located N-terminal to the NLS and D domain. The NES in MK2B is sufficient to trigger nuclear export following stimulation, a process which may be inhibited by leptomycin B. The sequence N-terminal to the catalytic domain in MK2 and MK3 is proline rich and contains one (MK3) or two (MK2) putative Src homology 3 (SH3) domain-binding sites, which studies have shown, for MK2, to mediate binding to the SH3 domain of c-Abl in vitro. Recent studies suggest that this domain is involved in MK2-mediated cell migration.

MK2B and MK3 are located predominantly in the nucleus of quiescent cells while MK2A is present in the cytoplasm. Both MK2B and MK3 are rapidly exported to the cytoplasm via a chromosome region maintenance protein (CRM1)-dependent mechanism upon stress stimulation. Nuclear export of MK2B appears to be mediated by kinase activation, as phosphomimetic mutation of Thr334 within the activation loop of the kinase enhances the cytoplasmic localization of MK2B. Without being limited by theory, it is thought that MK2B and MK3 may contain a constitutively active nuclear localization signal (NLS) and a phosphorylation-regulated nuclear export signal (NES).

MK2 and MK3 appear to be expressed ubiquitously, with increased relative expression in the heart, lungs, kidney, reproductive organs (mammary and testis), skin and skeletal muscle tissues, as well as in immune-related cells such as white blood cells/leukocytes and dendritic cells.

Activation

Various activators of p38α and p38β potently stimulate MK2 and MK3 activity. p38 mediates the in vitro and in vivo phosphorylation of MK2 on four proline-directed sites: Thr25, Thr222, Ser272, and Thr334. Of these sites, only Thr25 is not conserved in MK3. Without being limited by theory, while the function of phosphorylated Thr25 is unknown, its location between the two SH3 domain-binding sites suggests that it may regulate protein-protein interactions. Thr222 in MK2 (Thr201 in MK3) is located in the activation loop of the kinase domain and has been shown to be essential for MK2 and MK3 kinase activity. Thr334 in MK2 (Thr313 in MK3) is located C-terminal to the catalytic domain and is essential for kinase activity. The crystal structure of MK2 has been resolved and, without being limited by theory, suggests that Thr334 phosphorylation may serve as a switch for MK2 nuclear import and export. Phosphorylation of Thr334 also may weaken or interrupt binding of the C terminus of MK2 to the catalytic domain, exposing the NES and promoting nuclear export.

Studies have shown that while p38 is capable of activating MK2 and MK3 in the nucleus, experimental evidence suggests that activation and nuclear export of MK2 and MK3 are coupled by a phosphorylation-dependent conformational switch that also dictates p38 stabilization and localization, and the cellular location of p38 itself is controlled by MK2 and possibly MK3. Additional studies have shown that nuclear p38 is exported to the cytoplasm in a complex with MK2 following phosphorylation and activation of MK2. The interaction between p38 and MK2 may be important for p38 stabilization since studies indicate that p38 levels are low in MK2-deficient cells and expression of a catalytically inactive MK2 protein restores p38 levels.

Substrates and Functions

MK2 shares many substrates with MK3. Both enzymes have comparable substrate preferences and phosphorylate peptide substrates with similar kinetic constants. The minimum sequence required for efficient phosphorylation by MK2 was found to be Hyd-Xaa-Arg-Xaa-Xaa-pSer/pThr (SEQ ID NO: 22), where Hyd is a bulky, hydrophobic residue.

Accumulating studies have shown that MK2 phophorylates a variety of proteins, which include, but are not limited to, 5-Lipooxygenase (ALOX5), Cell Division Cycle 25 Homolog B (CDC25B), Cell Division Cycle 25 Homolog C (CDC25C), Embryonic Lethal, Abnormal Vision, *Drosophila*-Like 1 (ELAVL1), Heterogeneous Nuclear Ribonucleoprotein AO (HNRNPAO), Heat Shock Factor protein 1 (HSF1), Heat Shock Protein Beta-1 (HSPB1), Keratin 18 (KRT18), Keratin 20 (KRT20), LIM domain kinase 1 (LIMK1), Lymphocyte-specific protein 1 (LSP1), Polyadenylate-Binding Protein 1 (PABPC1), Poly(A)-specific Ribonuclease (PARN), CAMP-specific 3',5'-cyclic Phosphodiesterase 4A (PDE4A), RCSD domain containing 1 (RCSD1), Ribosomal protein S6 kinase, 90 kDa, polypeptide 3 (RPS6KA3), TGF-beta activated kinase 1/MAP3K7 binding protein 3 (TAB3), and Tristetraprolin (TTP/ZFP36).

Heat-Shock Protein Beta-1 (also termed HSPB1 or HSP27) is a stress-inducible cytosolic protein that is ubiquitously present in normal cells and is a member of the small heat-shock protein family. The synthesis of HSPB1 is induced by heat shock and other environmental or pathophysiologic stresses, such as UV radiation, hypoxia and ischemia. Besides its putative role in thermoresistance, HSPB1 is involved in the survival and recovery of cells exposed to stressful conditions.

Experimental evidence supports a role for p38 in the regulation of cytokine biosynthesis and cell migration. The targeted deletion of the mk2 gene in mice suggested that although p38 mediates the activation of many similar kinases, MK2 seems to be the key kinase responsible for these p38-dependent biological processes. Loss of MK2 leads (i) to a defect in lipopolysaccharide (LPS)-induced synthesis of cytokines such as tumor necrosis factor alpha (TNF-α), interleukin-6 (IL-6), and gamma interferon (IFN-γ) and (ii) to changes in the migration of mouse embryonic fibroblasts, smooth muscle cells, and neutrophils.

Consistent with a role for MK2 in inflammatory and immune responses, MK2-deficient mice showed increased susceptibility to *Listeria monocytogenes* infection and reduced inflammation-mediated neuronal death following focal ischemia. Since the levels of p38 protein also are reduced significantly in MK2-deficient cells, it was necessary to distinguish whether these phenotypes were due solely to the loss of MK2. To achieve this, MK2 mutants were expressed in MK2-deficient cells, and the results indicated that the catalytic activity of MK2 was not necessary to restore p38 levels but was required to regulate cytokine biosynthesis.

Knockout or knockdown studies of MK2 provide strong support that activated MK2 enhances stability of IL-6 mRNA through phosphorylation of proteins interacting with the AU-rich 3' untranslated region of IL-6 mRNA. In particular, it has been shown that MK2 is principally responsible for phosphorylation of hnRNPAO, an mRNA-binding protein that stabilizes IL-6 RNA. In addition, several additional studies investigating diverse inflammatory diseases have found that levels of pro-inflammatory cytokines, such as IL-6, IL-1β, TNF-α and IL-8, are increased in induced sputum from patients with stable chronic obstructive pulmonary disease (COPD) or from the alveolar macrophages of cigarette smokers (Keatings V. et al, Am J Resp Crit Care Med, 1996, 153:530-534; Lim, S. et al., J Respir Crit Care Med, 2000, 162:1355-1360).

Regulation of mRNA Translation.

Previous studies using MK2 knockout mice or MK2-deficient cells have shown that MK2 increases the production of inflammatory cytokines, including TNF-α, IL-1, and IL-6, by increasing the rate of translation of its mRNA. No significant reductions in the transcription, processing, and shedding of TNF-α could be detected in MK2-deficient mice. The p38 pathway is known to play an important role in regulating mRNA stability, and MK2 represents a likely target by which p38 mediates this function. Studies utilizing MK2-deficient mice indicated that the catalytic activity of MK2 is necessary for its effects on cytokine production and migration, suggesting that, without being limited by theory, MK2 phosphorylates targets involved in mRNA stability. Consistent with this, MK2 has been shown to bind and/or phosphorylate the heterogeneous nuclear ribonucleoprotein (hnRNP) A0, tristetraprolin (TTP), the poly(A)-binding protein PABP1, and HuR, a ubiquitously expressed member of the ELAV (Embryonic-Lethal Abnormal Visual in *Drosophila melanogaster*) family of RNA-binding protein. These substrates are known to bind or copurify with mRNAs that contain AU-rich elements in the 3' untranslated region, suggesting that MK2 may regulate the stability of AU-rich mRNAs such as TNF-α. It currently is unknown whether MK3 plays a similar role, but LPS treatment of MK2-deficient fibroblasts completely abolished hnRNP A0 phosphorylation, suggesting that MK3 is not able to compensate for the loss of MK2.

MK3 participates with MK2 in phosphorylation of the eukaryotic elongation factor 2 (eEF2) kinase. eEF2 kinase phosphorylates and inactivates eEF2. eEF2 activity is critical for the elongation of mRNA during translation, and phosphorylation of eEF2 on Thr56 results in the termination of mRNA translation. MK2 and MK3 phosphorylation of eEF2 kinase on Ser377 suggests that these enzymes may modulate eEF2 kinase activity and thereby regulate mRNA translation elongation.

Transcriptional Regulation by MK2 and MK3

Nuclear MK2, similar to many MKs, contributes to the phosphorylation of cAMP response element binding (CREB), Activating Transcription Factor-1 (ATF-1), serum response factor (SRF), and transcription factor ER81. Comparison of wild-type and MK2-deficient cells revealed that MK2 is the major SRF kinase induced by stress, suggesting a role for MK2 in the stress-mediated immediate-early response. Both MK2 and MK3 interact with basic helix-loop-helix transcription factor E47 in vivo and phosphorylate E47 in vitro. MK2-mediated phosphorylation of E47 was found to repress the transcriptional activity of E47 and thereby inhibit E47-dependent gene expression, suggesting that MK2 and MK3 may regulate tissue-specific gene expression and cell differentiation.

Other Targets of MK2 and MK3

Several other MK2 and MK3 substrates also have been identified, reflective of the diverse functions of MK2 and MK3 in several biological processes. The scaffolding protein 14-3-3 is a physiological MK2 substrate. Studies indicate that 14-3-3ζ interacts with a number of components of cell signaling pathways, including protein kinases, phosphatases, and transcription factors. Additional studies have shown that MK2-mediated phosphorylation of 14-3-3ζ on Ser58 compromises its binding activity, suggesting that MK2 may affect the regulation of several signaling molecules normally regulated by 14-3-3ζ.

Additional studies have shown that MK2 also interacts with and phosphorylates the p16 subunit of the seven-member Arp2 and Arp3 complex (p16-Arc) on Ser77. p16-Arc has roles in regulating the actin cytoskeleton, suggesting that MK2 may be involved in this process. Further studies have shown that the small heat shock protein HSPB1, lymphocyte-specific protein LSP-1, and vimentin are phosphorylated by MK2. HSPB1 is of particular interest because it forms large oligomers which may act as molecular chaperones and protect cells from heat shock and oxidative stress. Upon phosphorylation, HSPB1 loses its ability to form large oligomers and is unable to block actin polymerization, suggesting that MK2-mediated phosphorylation of HSPB1 serves a homeostatic function aimed at regulating actin dynamics that otherwise would be destabilized during stress. MK3 also was shown to phosphorylate HSPB1 in vitro and in vivo, but its role during stressful conditions has not yet been elucidated.

It was also shown that HSPB1 binds to polyubiquitin chains and to the 26S proteasome in vitro and in vivo. The ubiquitin-proteasome pathway is involved in the activation of transcription factor NF-kappa B (NF-κB) by degrading its main inhibitor, I kappa B-alpha (IκB-alpha), and it was shown that overexpression of HSPB1 increases NF-kappaB (NF-κB) nuclear relocalization, DNA binding, and transcriptional activity induced by etoposide, TNF-alpha, and Interleukin-1 beta (IL-1β). Additionally, previous studies have suggested that HSPB1, under stress conditions, favors the degradation of ubiquitinated proteins, such as phosphorylated I kappa B-alpha (IκB-alpha); and that this function of HSPB1 accounts for its anti-apoptotic properties through the enhancement of NF-kappa B (NF-κB) activity (Parcellier, A. et al., Mol Cell Biol, 23(16): 5790-5802, 2003).

MK2 and MK3 also may phosphorylate 5-lipoxygenase. 5-lipoxygenase catalyzes the initial steps in the formation of the inflammatory mediators, leukotrienes. Tyrosine hydroxylase, glycogen synthase, and Akt also were shown to be phosphorylated by MK2. Finally, MK2 phosphorylates the tumor suppressor protein tuberin on Ser1210, creating a docking site for 14-3-3ζ. Tuberin and hamartin normally form a functional complex that negatively regulates cell growth by antagonizing mTOR-dependent signaling, suggesting that p38-mediated activation of MK2 may regulate cell growth by increasing 14-3ζ binding to tuberin.

Accumulating studies have suggested that the reciprocal crosstalk between the p38 MAPK-pathway and signal transducer and activator of transcription 3 (STAT3)-mediated signal-transduction forms a critical axis successively activated in lipopolysaccharide (LPS) challenge models. It was shown that the balanced activation of this axis is essential for both induction and propagation of the inflammatory macrophage response as well as for the control of the resolution phase, which is largely driven by IL-10 and sustained STAT3 activation (Bode, J. et al., Cellular Signalling, 24: 1185-1194, 2012). In addition, another study has shown that MK2 controls LPS-inducible IFNβ gene expression and subsequent IFNβ-mediated activation of STAT3 by neutralizing negative regulatory effects of MK3 on LPS-induced p65 and IRF3-mediated signaling. The study further showed that in mk2/3 knockout macrophages, IFNβ-dependent STAT3 activation occurs independently from IL-10, because, in contrast to IFNβ-, impaired IL-10 expression is not restored upon additional deletion of MK3 in mk2/3 knockout macrophages (Ehlting, C. et al., J. Biol. Chem., 285(27): 24113-24124).

Kinase Inhibition

The eukaryotic protein kinases constitute one of the largest superfamilies of homologous proteins that are related by virtue of their catalytic domains. Most related protein kinases are specific for either serine/threonine or tyrosine phosphorylation. Protein kinases play an integral role in the cellular response to extracellular stimuli. Thus, stimulation of protein kinases is considered to be one of the most common activation mechanisms in signal transduction systems. Many substrates are known to undergo phosphorylation by multiple protein kinases, and a considerable amount of information on primary sequence of the catalytic domains of various protein kinases has been published.

These sequences share a large number of residues involved in ATP binding, catalysis, and maintenance of structural integrity. Most protein kinases possess a well conserved 30-32 kDa catalytic domain.

Studies have attempted to identify and utilize regulatory elements of protein kinases. These regulatory elements include inhibitors, antibodies, and blocking peptides.

Inhibitors

Enzyme inhibitors are molecules that bind to enzymes thereby decreasing enzyme activity. The binding of an inhibitor may stop a substrate from entering the active site of the enzyme and/or hinder the enzyme from catalyzing its reaction (as in inhibitors directed at the ATP biding site of the kinase). Inhibitor binding is either reversible or irreversible. Irreversible inhibitors usually react with the enzyme and change it chemically (e.g., by modifying key amino acid residues needed for enzymatic activity) so that it no longer is capable of catalyzing its reaction. In contrast, reversible inhibitors bind non-covalently and different types of inhibition are produced depending on whether these inhibitors bind the enzyme, the enzyme-substrate complex, or both.

Enzyme inhibitors often are evaluated by their specificity and potency. The term "specificity" as used in this context refers to the selective attachment of an inhibitor or its lack of binding to other proteins. The term "potency" as used herein refers to an inhibitor's dissociation constant, which indicates the concentration of inhibitor needed to inhibit an enzyme.

Inhibitors of protein kinases have been studied for use as a tool in protein kinase activity regulation. Inhibitors have been studied for use with, for example, cyclin-dependent (Cdk) kinase, MAP kinase, serine/threonine kinase, Src Family protein tyrosine kinase, tyrosine kinase, calmodulin (CaM) kinase, casein kinase, checkpoint kinase (Chk1), glycogen synthase kinase 3 (GSK-3), c-Jun N-terminal kinase (JNK), mitogen-activated protein kinase 1 (MEK), myosin light chain kinase (MLCK), protein kinase A, Akt (protein kinase B), protein kinase C, protein kinase G, protein tyrosine kinase, Raf kinase, and Rho kinase.

Small-Molecule MK2 Inhibitors

While individual inhibitors that target MK2 with at least modest selectivity with respect to other kinases have been designed, it has been difficult to create compounds with favorable solubility and permeability. As a result, there are relatively few biochemically efficient MK2 inhibitors that have advanced to in vivo pre-clinical studies (Edmunds, J. and Talanian, MAPKAP Kinase 2 (MK2) as a Target for Anti-inflammatory Drug Discovery. In Levin, J and Laufer, S (Ed.), RSC Drug Discovery Series No. 26, p 158-175, the Royal Society of Chemistry, 2012; incorporated by reference in its entirety).

The majority of disclosed MK2 inhibitors are classical type I inhibitors as revealed by crystallographic or biochemical studies. As such, they bind to the ATP site of the kinase and thus compete with intra-cellular ATP (estimated concentration 1 mM-5 mM) to inhibit phosphorylation and activation of the kinase. Representative examples of small-molecule MK2 inhibitors include, but are not limited to,

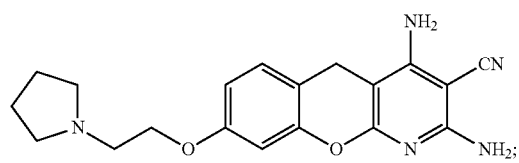

-continued

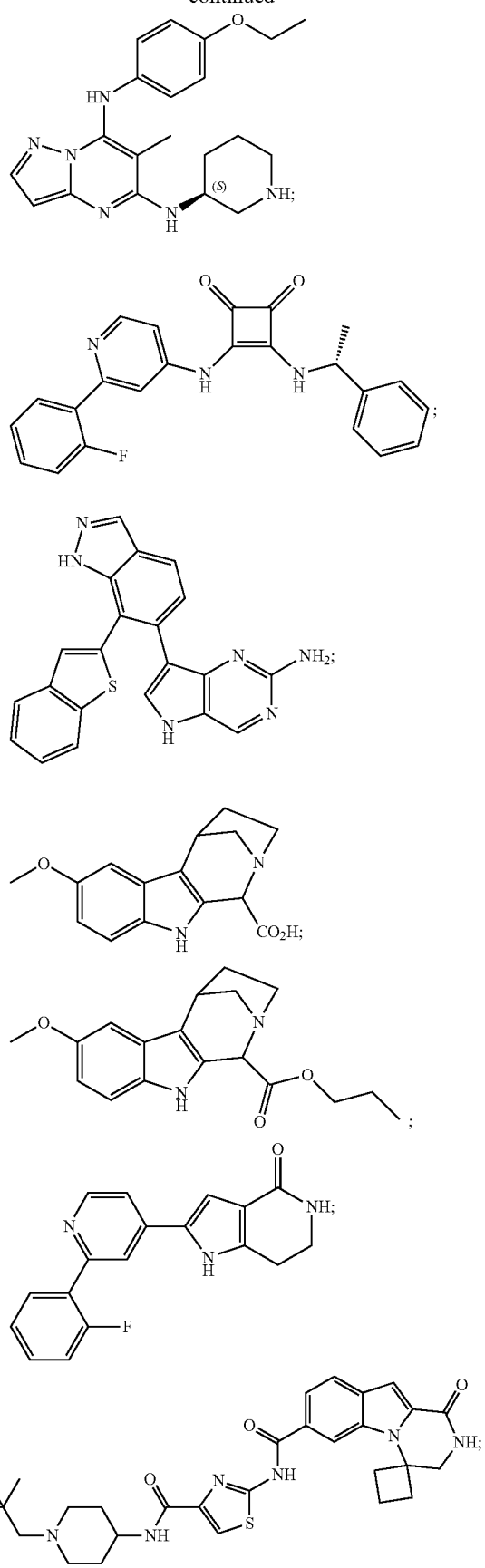

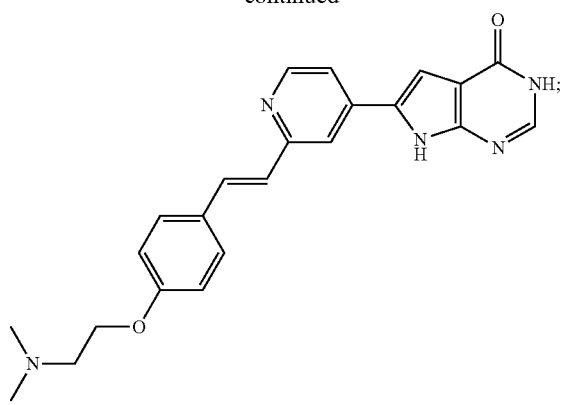
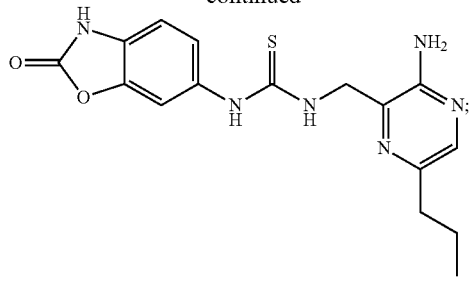
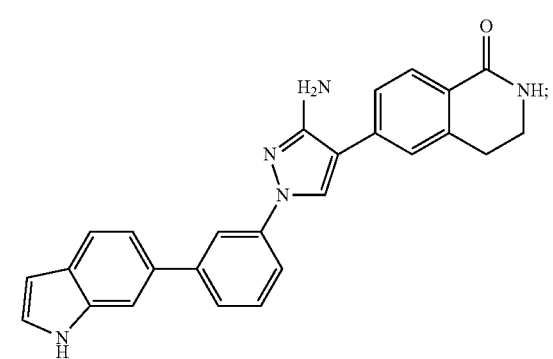
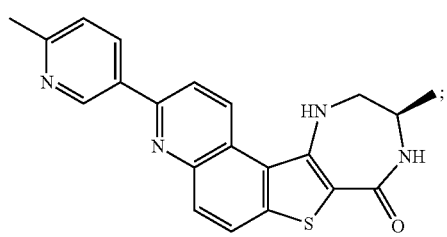
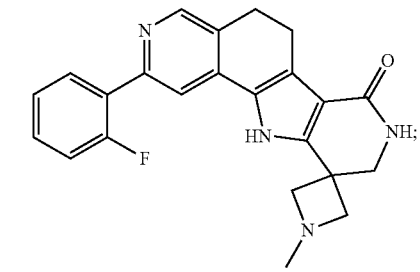
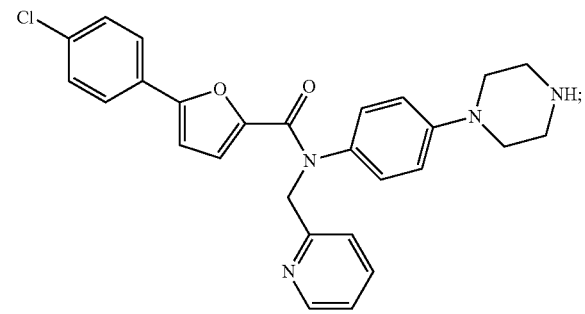
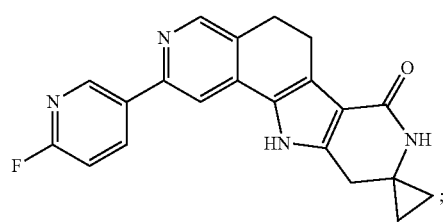
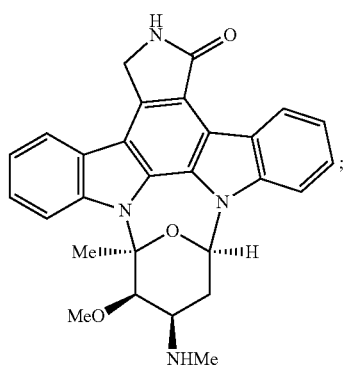
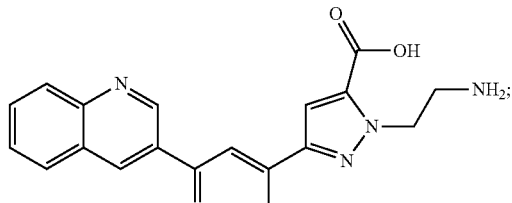
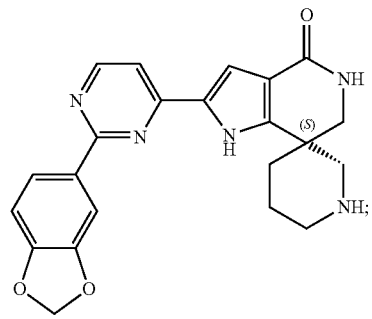
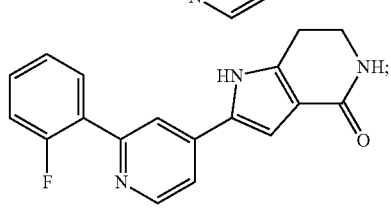

-continued

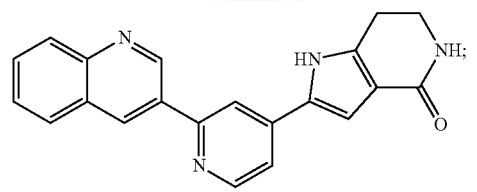

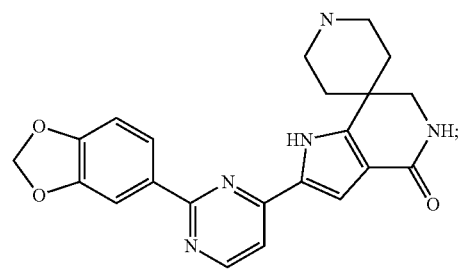

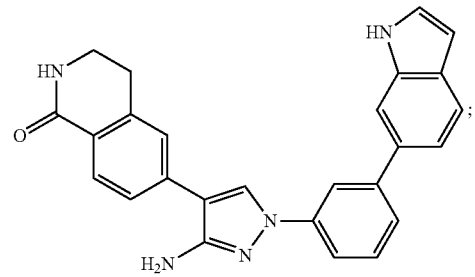

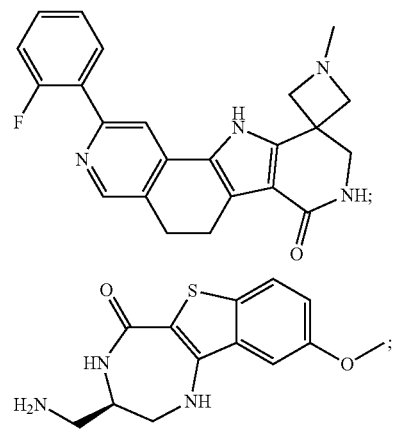

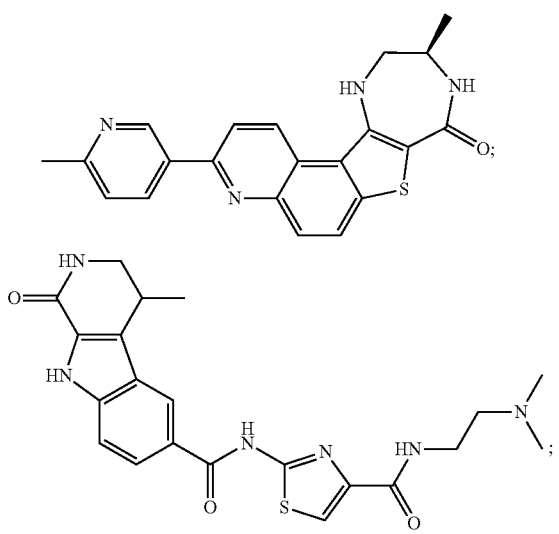

-continued

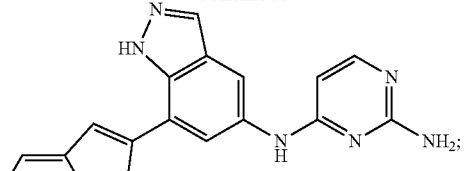

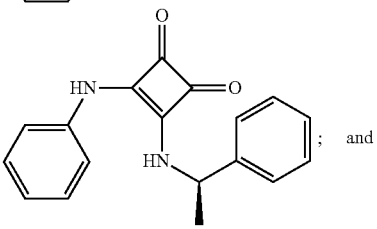

; and

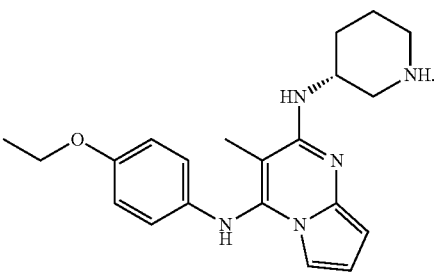 [SMILES: CCOc1ccc(Nc2c(C)c(N[C@@H]3CCCNC3)nc3cccn23)cc1]

Blocking Peptides

A peptide is a chemical compound that is composed of a chain of two or more amino acids whereby the carboxyl group of one amino acid in the chain is linked to the amino group of the other via a peptide bond. Peptides have been used inter alia in the study of protein structure and function. Synthetic peptides may be used inter alia as probes to see where protein-peptide interactions occur. Inhibitory peptides may be used inter alia in clinical research to examine the effects of peptides on the inhibition of protein kinases, cancer proteins and other disorders.

The use of several blocking peptides has been studied. For example, extracellular signal-regulated kinase (ERK), a MAPK protein kinase, is essential for cellular proliferation and differentiation. The activation of MAPKs requires a cascade mechanism whereby MAPK is phosphorylated by an upstream MAPKK (MEK) which then, in turn, is phosphorylated by a third kinase MAPKKK (MEKK). The ERK inhibitory peptide functions as a MEK decoy by binding to ERK.

Other blocking peptides include autocamtide-2 related inhibitory peptide (AIP). This synthetic peptide is a highly specific and potent inhibitor of $Ca^{2+}$/calmodulin-dependent protein kinase II (CaMKII). AIP is a non-phosphorylatable analog of autocamtide-2, a highly selective peptide substrate for CaMKII. AIP inhibits CaMKII with an IC50 of 100 nM (IC50 is the concentration of an inhibitor required to obtain 50% inhibition). The AIP inhibition is non-competitive with respect to syntide-2 (CaMKII peptide substrate) and ATP but competitive with respect to autocamtide-2. The inhibition is unaffected by the presence or absence of $Ca^{2+}$/calmodulin. CaMKII activity is inhibited completely by AIP (1 μM) while PKA, PKC and CaMKIV are not affected.

Other blocking peptides include cell division protein kinase 5 (Cdk5) inhibitory peptide (CIP). Cdk5 phosphorylates the microtubule protein tau at Alzheimer's Disease-specific phospho-epitopes when it associates with p25. p25 is a truncated activator, which is produced from the physiological Cdk5 activator p35 upon exposure to amyloid β peptides. Upon neuronal infections with CIP, CIPs selectively inhibit p25/Cdk5 activity and suppress the aberrant tau phosphorylation in cortical neurons. The reasons for the specificity demonstrated by CIP are not fully understood.

Additional blocking peptides have been studied for extracellular-regulated kinase 2 (ERK2), ERK3, p38/HOG1, protein kinase C, casein kinase II, $Ca^{2+}$/calmodulin kinase IV, casein kinase II, Cdk4, Cdk5, DNA-dependent protein kinase (DNA-PK), serine/threonine-protein kinase PAK3, phosphoinositide (PI)-3 kinase, PI-5 kinase, PSTAIRE (the cdk highly conserved sequence), ribosomal S6 kinase, GSK-4, germinal center kinase (GCK), SAPK (stress-activated protein kinase), SEK1 (stress signaling kinase), and focal adhesion kinase (FAK).

Protein Substrate-Competitive Inhibitors

Most of the protein kinase inhibitors developed to date are ATP competitors. This type of molecule competes for the ATP binding site of the kinase and often shows off-target effects due to serious limitations in its specificity. The low specificity of these inhibitors is due to the fact that the ATP binding site is highly conserved among diverse protein kinases. Non-ATP competitive inhibitors, on the other hand, such as substrate competitive inhibitors, are expected to be more specific as the substrate binding sites have a certain degree of variability among the various protein kinases.

Although substrate competitive inhibitors usually have a weak binding interaction with the target enzyme in vitro, studies have shown that chemical modifications can improve the specific biding affinity and the in vivo efficacy of substrate inhibitors (Eldar-Finkelman, H. et al., Biochim, Biophys. Acta, 1804(3):598-603, 2010). In addition, substrate competitive inhibitors show better efficacy in cells than in cell-free conditions in many cases (van Es, J. et al., Curr. Opin. Gent. Dev. 13:28-33, 2003).

In an effort to enhance specificity and potency in protein kinase inhibition, bisubstrate inhibitors also have been developed. Bisubstrate inhibitors, which consist of two conjugated fragments, each targeted to a different binding site of a bisubstrate enzyme, form a special group of protein kinase inhibitors that mimic two natural substrates/ligands and that simultaneously associate with two regions of given kinases. The principle advantage of bisubstrate inhibitors is their ability to generate more interactions with the target enzyme that could result in improved affinity and selectivity of the conjugates, when compared with single-site inhibitors. Examples of bisubstrate inhibitors include, but are not limited to, nucleotide-peptide conjugates, adenosine derivative-peptide conjugates, and conjugates of peptides with potent ATP-competitive inhibitors.

Protein Transduction Domains (PTD)/Cell Permeable Proteins (CPP)

The plasma membrane presents a formidable barrier to the introduction of macromolecules into cells. For nearly all therapeutics to exert their effects, at least one cellular membrane must be traversed. Traditional small molecule pharmaceutical development relies on the chance discovery of membrane permeable molecules with the ability to modulate protein function. Although small molecules remain the dominant therapeutic paradigm, many of these molecules suffer from lack of specificity, side effects, and toxicity. Information-rich macromolecules, which have protein modulatory functions far superior to those of small molecules, can be created using rational drug design based on molecular, cellular, and structural data. However, the plasma membrane is impermeable to most molecules of size greater than 500 Da. Therefore, the ability of cell penetrating peptides, such as the basic domain of Trans-Activator of Transcription (Tat), to cross the cell membrane and deliver macromolecular cargo in vivo, can greatly facilitate the rational design of therapeutic proteins, peptides, and nucleic acids.

Protein transduction domains (PTDs) are a class of peptides capable of penetrating the plasma membrane of mammalian cells and of transporting compounds of many types and molecular weights across the membrane. These compounds include effector molecules, such as proteins, DNA, conjugated peptides, oligonucleotides, and small particles such as liposomes. When PTDs are chemically linked or fused to other proteins, the resulting fusion peptides still are able to enter cells. Although the exact mechanism of transduction is unknown, internalization of these proteins is not believed to be receptor-mediated or transporter-mediated. PTDs are generally 10-16 amino acids in length and may be grouped according to their composition, such as, for example, peptides rich in arginine and/or lysine.

The use of PTDs capable of transporting effector molecules into cells has become increasingly attractive in the design of drugs as they promote the cellular uptake of cargo molecules. These cell-penetrating peptides, generally categorized as amphipathic (meaning having both a polar and a nonpolar end) or cationic (meaning of or relating to containing net positively charged atoms) depending on their sequence, provide a non-invasive delivery technology for macromolecules. PTDs often are referred to as "Trojan peptides", "membrane translocating sequences", or "cell permeable proteins" (CPPs). PTDs also may be used to assist novel HSPB1 kinase inhibitors to penetrate cell membranes. (see U.S. application Ser. No. 11/972,459, entitled "Polypeptide Inhibitors of HSPB1 Kinase and Uses Therefor," filed Jan. 10, 2008, and Ser. No. 12/188,109, entitled "Kinase Inhibitors and Uses Thereof," filed Aug. 7, 2008, the contents of each application are incorporated by reference in their entirety herein).

Viral PTD Containing Proteins

The first proteins to be described as having transduction properties were of viral origin. These proteins still are the most commonly accepted models for PTD action. The HIV-1 Transactivator of Transcription (Tat) and HSV-1 VP 22 protein are the best characterized viral PTD containing proteins.

Tat (HIV-1 trans-activator gene product) is an 86-amino acid polypeptide, which acts as a powerful transcription factor of the integrated HIV-1 genome. Tat acts on the viral genome, stimulating viral replication in latently infected cells. The translocation properties of the Tat protein enable it to activate quiescent infected cells, and it may be involved in priming of uninfected cells for subsequent infection by regulating many cellular genes, including cytokines. The minimal PTD of Tat is the 9 amino acid protein sequence RKKRRQRRR (TAT49-57; SEQ ID NO: 20). Studies utilizing a longer fragment of Tat demonstrated successful transduction of fusion proteins up to 120 kDa. The addition of multiple Tat-PTDs as well as synthetic Tat derivatives has been demonstrated to mediate membrane translocation. Tat PTD containing fusion proteins have been used as therapeutic moieties in experiments involving cancer, transporting a death-protein into cells, and disease models of neurodegenerative disorders.

The mechanism used by transducing peptides to permeate cell membranes has been the subject of considerable interest in recent years, as researchers have sought to understand the biology behind transduction. Early reports that Tat transduction occurred by a nonendocytic mechanism have largely been dismissed as artifactual though other cell-penetrating peptides might be taken up by way of direct membrane disruption. The recent findings that transduction of Tat and other PTDs occurs by way of macropinocytosis, a specialized form of endocytosis, has created a new paradigm in the study of these peptides. Enhanced knowledge of the mechanism of transduction helped improve transduction efficiency with the ultimate goal of clinical success (Snyder E. and Dowdy, S., Pharm Res., 21(3):389-393, 2004).

The current model for Tat-mediated protein transduction is a multistep process that involves binding of Tat to the cell surface, stimulation of macropinocytosis, uptake of Tat and cargo into macropinosomes, and endosomal escape into the cytoplasm. The first step, binding to the cell surface, is thought to be through ubiquitous glycan chains on the cell surface. Stimulation of macropinocytosis by Tat occurs by an unknown mechanism that might include binding to a cell surface protein or occur by way of proteoglycans or glycolipids. Uptake by way of macropinocytosis, a form of fluid phase endocytosis used by all cell types, is required for Tat and polyarginine transduction. The final step in Tat transduction is escape from macropinosomes into the cytoplasm; this process is likely to be dependent on the pH drop in endosomes that, along with other factors, facilitates a perturbation of the membrane by Tat and release of Tat and its cargo (i.e. peptide, protein or drug etc.) to the cytoplasm (Snyder E. and Dowdy, S., Pharm Res., 21(3):389-393, 2004).

VP22 is the HSV-1 tegument protein, a structural part of the HSV virion. VP22 is capable of receptor independent translocation and accumulates in the nucleus. This property of VP22 classifies the protein as a PTD containing peptide. Fusion proteins comprising full length VP22 have been translocated efficiently across the plasma membrane.

Homeoproteins with Intercellular Translocation Properties

Homeoproteins are highly conserved, transactivating transcription factors involved in morphological processes. They bind to DNA through a specific sequence of 60 amino acids. The DNA-binding homeodomain is the most highly conserved sequence of the homeoprotein. Several homeoproteins have been described as exhibiting PTD-like activity; they are capable of efficient translocation across cell membranes in an energy-independent and endocytosis-independent manner without cell type specificity.

The Antennapedia protein (Antp) is a trans-activating factor capable of translocation across cell membranes; the minimal sequence capable of translocation is a 16 amino acid peptide corresponding to the third helix of the protein's homeodomain (HD). The internalization of this helix occurs at 4° C., suggesting that this process is not endocytosis dependent. Peptides of up to 100 amino acids produced as fusion proteins with AntpHD penetrate cell membranes.

Other homeodomains capable of translocation include Fushi tarazu (Ftz) and Engrailed (En) homeodomain. Many homeodomains share a highly conserved third helix.

Human PTDs

Human PTDs may circumvent potential immunogenicity issues upon introduction into a human patient. Peptides with PTD sequences include: Hoxa-5, Hox-A4, Hox-B5, Hox-B6, Hox-B7, HOX-D3, GAX, MOX-2, and FtzPTD. These proteins all share the sequence found in AntpPTD. Other PTDs include Islet-1, Interleukin-1 (IL-1), Tumor Necrosis Factor (TNF), and the hydrophobic sequence from Kaposi-fibroblast growth factor or Fibroblast Growth Factor-4 (FGF-4) signal peptide, which is capable of energy-, receptor-, and endocytosis-independent translocation. Unconfirmed PTDs include members of the Fibroblast Growth Factor (FGF) family. FGFs are polypeptide growth factors that regulate proliferation and differentiation of a wide variety of cells. Several publications have reported that basic fibroblast growth factor (FGF-2) exhibits an unconventional internalization similar to that of VP-22, Tat, and homeodomains. It has also been reported that acidic FGF (FGF-1) translocated cell membranes at temperatures as low as 4° C. However, no conclusive evidence exists about the domain responsible for internalization or the translocation properties of fusion proteins (Beerens, A. et al., Curr Gene Ther., 3(5):486-494, 2003).

Synthetic PTDs

Several peptides have been synthesized in an attempt to create more potent PTDs and to elucidate the mechanisms by which PTDs transport proteins across cell membranes. Many of these synthetic PTDs are based on existing and well documented peptides, while others are selected for their basic residues and/or positive charges, which are thought to be crucial for PTD function. A few of these synthetic PTDs showed better translocation properties than the existing ones (Beerens, A. et al., Curr Gene Ther., 3(5):486-494, 2003). Exemplary Tat-derived synthetic PTDs include, for example, but are not limited to, WLRRIKAWLRRIKA (SEQ ID NO: 12); WLRRIKA (SEQ ID NO: 13); YGRK-KRRQRRR (SEQ ID NO: 14); WLRRIKAWLRRI (SEQ ID NO: 15); FAKLAARLYR (SEQ ID NO: 16); KAFAK-LAARLYR (SEQ ID NO: 17); and HRRIKAWLKKI (SEQ ID NO: 18).

Compositions Comprising PTDs Fused to MK2 Inhibitor Peptide Therapeutic Domains (TD)

Several MK2 inhibitor peptides (TD) have been synthesized, fused to synthetic PTDs and the use of compositions comprising these fused polypeptides has been studied. These polypeptides include, but are not limited to, YARAAAR-QARAKALARQLGVAA (SEQ ID NO: 1; MMI-0100), YARAAARQARAKALNRQLGVA (SEQ ID NO: 19; MMI-0200), FAKLAARLYRKALARQLGVAA (SEQ ID NO: 3; MMI-0300), KAFAKLAARLYRKALARQLGVAA (SEQ ID NO: 4; MMI-0400), HRRIKAWLKKIKALAR-QLGVAA (SEQ ID NO: 7; MMI-0500), YARAAARD-ARAKALNRQLAVAA (SEQ ID NO: 23; MMI-0600), and YARAAARQARAKALNRQLAVA (SEQ ID NO: 24; MMI-0600-2). Both in vitro and in vivo studies have shown that these polypeptides can be useful in the treatment of various diseases, disorders and conditions. These include, without limitation, hyperplasia and neoplasm (U.S. Pat. Nos. 8,536,303 and 8,741,849) inflammatory disorders (U.S. application Ser. No. 12/634,476 and U.S. application Ser. No. 13/934,933), adhesions (U.S. application Ser. No. 12/582,516), failure of a vascular graft due to neospasm (U.S. application Ser. No. 13/114,872), improving neurite outgrowth (U.S. application Ser. No. 12/844,815), a cutaneous scar (U.S. application Ser. No. 13/829,876), failure of a coronary artery bypass vascular graft (U.S. application Ser. No. 13/700,087) and interstitial lung disease and pulmonary fibrosis (U.S. application Ser. No. 13/445,759).

Peptide compositions present a number of particular challenges to formulation scientists (R. W. Payne and M. C. Manning, "Peptide formulation: challenges and strategies," Innovations in Pharmaceutical Technology, 64-68 (2009)). First, since peptides do not have a globular structure that can sequester reactive groups, the side chains of nearly all residues in a peptide are fully solvent exposed, and can exhibit chemical degradation through hydrolytic reactions, for example, oxidation and deamidation. Second, the conformation in aqueous solution may have little similarity to the structure found when bound to a receptor. Third, many peptides tend to be monomeric at very low concentration, but may self-assemble as the concentration is increased and behave as if in a highly associated state, but these structures are too transient or fluxional to provide any increase in long-term stability. Fourth, the propensity of peptides to self-associate is connected with their physical instablity, meaning their likelihood of forming aggregates. Moreover, excipients present in a peptide formulation can chemically degrade, interact with various surfaces during manufacturing, interact with the container or closure, or interact with the peptide itself, thereby negatively affecting critical properties of the preparation (Lars Hovgaard, and Sven Frokjaer, "Pharmacuetical Formulation Development of Peptides and Proteins, $2^{nd}$ Ed., CRC Press (2012) pp. 212-213).

The described invention provides effective formulations comprising a cell-penetrating peptide fused to a peptide-based inhibitor of MK2.

SUMMARY OF THE INVENTION

According to one aspect, the described invention provides a pharmaceutical formulation comprising a therapeutic amount of a polypeptide of amino acid sequence YARAAARQARAKALARQLGVAA; SEQ ID NO: 1 or a functional equivalent thereof, wherein the formulation is characterized by preservation of stability and bioavailability of the polypeptide.

According to one embodiment, the pharmaceutical formulation is a particulate pharmaceutical formulation. According to another embodiment, the pharmaceutical formulation is an aerosolized pharmaceutical formulation. According to another embodiment, the formulation is prepared by a process of spray drying. According to another embodiment, the pharmaceutical formulation comprises 1% w/w solids. According to another embodiment, the pharmaceutical formulation comprises 5% w/w solids. According to another embodiment, the pharmaceutical formulation further comprises trehalose. According to another embodiment, the polypeptide of amino acid sequence YARAAARQARAKALARQLGVAA; SEQ ID NO: 1 or the functional equivalent thereof and the trehalose are in a ratio of 80/20 respectively. According to another embodiment, the MMI-0100 (YARAAARQARAKALARQLGVAA; SEQ ID NO: 1) or the functional equivalent thereof and the trehalose are in a ratio of 92.5/7.5 respectively. According to another embodiment, the pharmaceutical formulation is delivered to a subject via a dry powder inhalation device (DPI).

According to one embodiment, the pharmaceutical formulation further comprises saline. According to another embodiment, the saline is NaCl. According to another embodiment, the polypeptide of amino acid sequence YARAAARQARAKALARQLGVAA; SEQ ID NO: 1 or the functional equivalent thereof is at a concentration of 0.7 mg/mL. According to another embodiment, the polypeptide of amino acid sequence YARAAARQARAKALARQLGVAA; SEQ ID NO: 1 or the functional equivalent thereof is at a concentration of 7.0 mg/mL. According to another embodiment, the pharmaceutical formulation is delivered to a subject via a nebulizer.

According to one embodiment, the pharmaceutical formulation comprises an ionic complex of a polypeptide of amino acid sequence YARAAARQARAKALARQLGVAA; SEQ ID NO: 1 or a functional equivalent thereof and a nano-polyplex polymer, the ionic complex being characterized by dissociation of the ionic complex in intracellular compartments selected by intracellular pH conditions such that bioactivity and stability of the peptide is preserved.

According to another aspect, the described invention provides a method for treating a vascular graft-induced intimal hyperplasia in a subject in need of such treatment, the method comprising administering the pharmaceutical formulation comprising an ionic complex of a polypeptide of amino acid sequence YARAAARQARAKALARQLGVAA; SEQ ID NO: 1 or a functional equivalent thereof and a nano-polyplex polymer, the ionic complex being characterized by dissociation of the ionic complex in intracellular compartments selected by intracellular pH conditions such that bioactivity and stability of the peptide is preserved, comprising a therapeutic amount of a polypeptide of amino acid sequence YARAAARQARAKALARQLGVAA (SEQ ID NO: 1) or a functional equivalent thereof, and a nano-polyplex polymer, wherein the therapeutic amount is effective to inhibit MK2; and to treat a vascular graft-induced intimal hyperplasia.

According to one embodiment, the nano-polyplex polymer is anionic and endosomolytic. According to another embodiment, the nano-polyplex polymer is poly(propylacrylic acid) (PPAA). According to another embodiment, the nano-polyplex polymer is poly(acrylic acid) (PAA). According to another embodiment, the pharmaceutical formulation comprises a charge ratio (CR) of the polypeptide of amino acid sequence YARAAARQARAKALARQLGVAA; SEQ ID NO: 1 or a functional equivalent thereof to PPAA selected from the group consisting of 10:1, 9:1, 8:1, 7:1, 6:1, 5:1, 4:1, 3:1, 2:1, 1:1, 1:1.5, 1:2, 1:3, 1:4, 1:5, 1:6, 1:7, 1:8, 1:9 and 1:10. According to another embodiment, the charge ratio (CR) is 1:3. According to another embodiment, the pharmaceutical formulation is delivered to a subject via an implantation device. According to another embodiment, the pharmaceutical formulation is delivered to a subject topically. According to another embodiment, the pharmaceutical formulation is delivered to a subject parenterally.

According to one embodiment, the functional equivalent is made from a fusion between a first polypeptide that is a protein transduction domain (PTD) and a second polypeptide that is a therapeutic domain (TD). According to another embodiment, the protein transduction domain (PTD) is selected from the group consisting of a polypeptide of amino acid sequence YARAAARQARA (SEQ ID NO: 11), FAK-LAARLYR (SEQ ID NO: 16), and KAFAKLAARLYR (SEQ ID NO: 17), and a second polypeptide that is a therapeutic domain (TD) of amino acid sequence KALAR-QLGVAA (SEQ ID NO: 2).

BRIEF DESCRIPTION OF THE DRAWINGS

FIG. 1 shows the technical characteristics of the blister lidding—push through.

FIG. 2 shows the technical characteristics of the Formpack®—4PLY.

DETAILED DESCRIPTION OF THE INVENTION

Glossary

Figure 1:

The term "active" as used herein refers to the ingredient, component or constituent of the compositions of the present invention responsible for the intended therapeutic effect. The term "active ingredient" ("AI", "active pharmaceutical ingredient", "API", or "bulk active") is the substance in a drug that is pharmaceutically active. As used herein, the phrase "additional active ingredient" refers to an agent, other than a compound of the described composition, that exerts a pharmacological, or any other beneficial activity.

The term "Actual Label Claim (ALC)" as used herein refers to the actual amount of drug substance present, based on the potency of the formulation and the target fill weight; equal to [(potency, in %)/100%]×(target fill weight, in mg)×(1,000 μg/mg).

The term "actuation" as used herein refers to the act of propelling; to put in motion or action.

The term "admixture" or "blend" as used herein generally refers to a physical combination of two or more different components.

The term "administer" or "administering" as used herein means to give or to apply, and includes in vivo administration, as well as administration directly to tissue ex vivo. Generally, administration may be systemic, e.g., orally, buccally, parenterally, topically, by inhalation or insufflation (i.e., through the mouth or through the nose), rectally in dosage unit formulations containing conventional nontoxic pharmaceutically acceptable carriers, adjuvants, and vehicles as desired, or locally by means such as, but not limited to, injection, implantation, grafting, topical application, or parenterally.

The term "agent" as used herein refers generally to compounds that are contained in or on the long-acting formulation. Agent may include an antibody or nucleic acid or an excipient or, more generally, any additive in the long-acting formulation. "Agent" includes a single such compound and is also intended to include a plurality of such compounds.

The term "agonist" as used herein refers to a chemical substance capable of activating a receptor to induce a pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus has an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The term "Andersen Cascade Impactor" (ACI) as used herein refers to an impactor used for the testing of inhaled products. Cascade impactors operate on the principle of inertial impaction. Each stage of the impactor comprises a series of nozzles or jets through which the sample laden air is drawn, directing any airborne sample towards the surface of the collection plate for that particular stage. Whether a particular particle impacts on that stage is dependent on its aerodynamic diameter. Particles having sufficient inertia will impact on that particular stage collection plate, while smaller particles will remain entrained in the air stream and pass to the next stage where the process is repeated. The stages are normally assembled in a stack or row in order of decreasing particle size. As the jets get smaller, the air velocity increases such that smaller particles are collected. At the end of the test, the particle mass relating to each stage is recovered using a suitable solvent and then analysed usually using HPLC to determine the amount of drug actually present.

The term "antagonist" as used herein refers to a substance that interferes with the effects of another substance. Functional or physiological antagonism occurs when two substances produce opposite effects on the same physiological function. Chemical antagonism or inactivation is a reaction between two substances to neutralize their effects. Dispositional antagonism is the alteration of the disposition of a substance (its absorption, biotransformation, distribution, or excretion) so that less of the agent reaches the target or its persistence there is reduced. Antagonism at the receptor for a substance entails the blockade of the effect of an antagonist with an appropriate antagonist that competes for the same site.

The term "bioactive agent" as used herein refers to a compound of interest contained in or on a pharmaceutical formulation or dosage form that is used for pharmaceutical or medicinal purposes to provide some form of therapeutic effect or elicit some type of biologic response or activity. "Bioactive agent" includes a single such agent and is also intended to include a plurality of bioactive agents including, for example, combinations of two or more bioactive agents.

The term "bioavailable" as used herein refers to the rate and extent to which an active ingredient is absorbed from a drug product and becomes available at the site of action.

The term "biocompatible" as used herein refers to a material that is generally non-toxic to the recipient and does not possess any significant untoward effects to the subject and, further, that any metabolites or degradation products of the material are non-toxic to the subject. Typically a substance that is "biocompatible" causes no clinically relevant tissue irritation, injury, toxic reaction, or immunological reaction to living tissue.

The term "biodegradable" as used herein refers to a material that will erode to soluble species or that will degrade under physiologic conditions to smaller units or chemical species that are, themselves, non-toxic (biocompatible) to the subject and capable of being metabolized, eliminated, or excreted by the subject.

The term "biomimetic" as used herein refers to materials, substances, devices, processes, or systems that imitate or "mimic" natural materials made by living organisms.

The term "blister" or "blister pack" as used herein refers to a unit dose package commonly constructed from a formed cavity containing one or more individual doses.

The term "% blister clearance" as used herein refers to the percentage of powder emitted from the blister during actuation, in %, equal to the [(Initial weight−Final Weight)/Fill Weight]*100%.

The term "carrier" as used herein refers to a material that does not cause significant irritation to an organism and does not abrogate the biological activity and properties of the peptide of the composition of the described invention. Carriers must be of sufficiently high purity and of sufficiently low toxicity to render them suitable for administration to the mammal being treated. The carrier can be inert, or it can possess pharmaceutical benefits. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "component" as used herein refers to a constituent part, element or ingredient.

The term "composition" as used herein refers to a product of the described invention that comprises all active and inert ingredients.

The term "condition", as used herein, refers to a variety of health states and is meant to include disorders or diseases caused by any underlying mechanism or disorder, injury, and the promotion of healthy tissues and organs.

The term "contact" and all its grammatical forms as used herein refers to a state or condition of touching or of immediate or local proximity.

The term "controlled release" as used herein refers to refer to any drug-containing formulation in which the manner and profile of drug release from the formulation are regulated. This refers to immediate as well as non-immediate release formulations, with non-immediate release formulations including, but not limited to, sustained release and delayed release formulations.

The term "delayed release" as used herein in its conventional sense refers to a formulation in which there is a time delay between administration of the formulation and the release of the therapeutic agent therefrom. "Delayed release" may or may not involve gradual release of the therapeutic agent over an extended period of time, and thus may or may not be "sustained release."

The term "Delivered Dose (DD)" as used herein refers to the amount of drug substance recovered from, for example, the extraction of the dose sampling apparatus (DSA), dose uniformity sampling apparatus (DUSA), Andersen Cascade Impactor (ACI), or Next Generation Pharmaceutical Impactor (NGI), in mg or µg. It is equivalent to the amount of drug substance ex-device (i.e., it does not include the amount of drug substance retained in a blister and/or flow channel).

The term "derived delivered dose (DDD)" as used herein refers to the amount of drug ex-device obtained from impactor testing, as opposed to the amount of drug ex-device obtained from Delivered Dose Uniformity (DDU) testing.

The term "% Delivered Dose" as used herein refers to a percentage of Actual Label Claim (ALC); equal to (DD/ALC)×100%.

The term "disease" or "disorder", as used herein, refers to an impairment of health or a condition of abnormal functioning.

The term "disposed", as used herein, refers to being placed, arranged or distributed in a particular fashion.

The term "drug" as used herein refers to a therapeutic agent or any substance, other than food, used in the prevention, diagnosis, alleviation, treatment, or cure of disease.

The term "dry powder inhaler" or "DPI" as used herein refers to a device similar to a metered-dose inhaler, but where the drug is in powder form. The patient exhales out a full breath, places the lips around the mouthpiece, and then quickly breathes in the powder. Dry powder inhalers do not require the timing and coordination that are necessary with MDIs.

The term "effective amount" refers to the amount necessary or sufficient to realize a desired biologic effect.

The term "excipient" is used herein to include any other agent or compound that may be contained in a long-acting formulation that is not the bioactive agent. As such, an excipient should be pharmaceutically or biologically acceptable or relevant (for example, an excipient should generally be non-toxic to the subject). "Excipient" includes a single such compound and is also intended to include a plurality of such compounds.

The term "fill weight" as used herein refers to the actual amount of powder (e.g., in mg or µg) weighed into each blister before actuation.

The term "final weight" as used herein refers to the weight of the sealed blister and powder after actuation.

The term "fine particle dose (FPD)" as used herein refers to the amount of drug substance (e.g., in mg or ug) recovered below a specified cut-off diameter of an impactor (e.g., ACI or NGI); equivalent to respirable dose.

The term "fine particle fraction (actual) as used herein refers to the FPD normalized to the theoretical amount of drug present in the blister(s) closed; equal to (FPD/[(fill weight)×(potency)]×100%.

The term "fine particle fraction (Nominal Label Claim) as used herein refers to the FPD normalized to the NLC; equal to [(FPD)/(NLC)×100%].

The term "fine particle fraction (Delivered Dose) as used herein refers to the FPD normalized to the DD; equal to [(FPD)/(DD)×100%].

The terms "formulation" as used herein refers to a mixture prepared according to a specific procedure, formula or rule.

The terms "functional equivalent" or "functionally equivalent" are used interchangeably herein to refer to substances, molecules, polynucleotides, proteins, peptides, or polypeptides having similar or identical effects or use. A polypeptide functionally equivalent to polypeptide YARAAARQARAKALARQLGVAA (SEQ ID NO: 1), for example, may have a biologic activity, e.g., an inhibitory activity, kinetic parameters, salt inhibition, a cofactor-dependent activity, and/or a functional unit size that is substantially similar or identical to the expressed polypeptide of SEQ ID NO: 1.

Examples of polypeptides functionally equivalent to YARAAARQARAKALARQLGVAA (SEQ ID NO: 1) include, but are not limited to, a polypeptide of amino acid sequence FAKLAARLYRKALARQLGVAA (SEQ ID NO: 3), a polypeptide of amino acid sequence KAFAKLAAR-LYRKALARQLGVAA (SEQ ID NO: 4), a polypeptide of amino acid sequence YARAAARQARAKALARQLAVA (SEQ ID NO: 5), a polypeptide of amino acid sequence YARAAARQARAKALARQLGVA (SEQ ID NO: 6), a polypeptide of amino acid sequence HRRIKAWLKKIKA-LARQLGVAA (SEQ ID NO: 7), a polypeptide of amino acid sequence YARAAARQARAKALNRQLGVA (SEQ ID NO: 19), a polypeptide of amino acid sequence YARAAARDARAKALNRQLAVAA (SEQ ID NO: 23) and a polypeptide of amino acid sequence YARAAAR-QARAKALNRQLAVA (SEQ ID NO: 24).

The MMI-0100 peptide of amino acid sequence YARAAARQARAKALARQLGVAA (SEQ ID NO: 1) described in the present invention comprises a fusion protein in which a protein transduction domain (PTD; YARAAAR-QARA; SEQ ID NO: 11) is operatively linked to a therapeutic domain (KALARQLGVAA; SEQ ID NO: 2) in order to enhance therapeutic efficacy.

Examples of polypeptides functionally equivalent to the therapeutic domain (TD; KALARQLGVAA; SEQ ID NO: 2) of the polypeptide YARAAARQARAKALARQLGVAA (SEQ ID NO: 1) include, but are not limited to, a polypeptide of amino acid sequence KALARQLAVA (SEQ ID NO: 8), a polypeptide of amino acid sequence KALARQLGVA (SEQ ID NO: 9), a polypeptide of amino acid sequence KALARQLGVAA (SEQ ID NO: 10), a polypeptide of amino acid sequence KALNRQLAVAA (SEQ ID NO: 25) and a polypeptide of amino acid sequence KALNRQLAVA (SEQ ID NO: 26).

Examples of polypeptides functionally equivalent to the protein transduction domain (PTD; YARAAARQARA; SEQ ID NO: 11) of the polypeptide YARAAARQARAKA-LARQLGVAA (SEQ ID NO: 1) include, but are not limited to, a polypeptide of amino acid sequence WLRRIKAWLR-RIKA (SEQ ID NO: 12), a polypeptide of amino acid sequence WLRRIKA (SEQ ID NO: 13), a polypeptide of amino acid sequence YGRKKRRQRRR (SEQ ID NO: 14), a polypeptide of amino acid sequence WLRRIKAWLRRI (SEQ ID NO: 15), a polypeptide of amino acid sequence FAKLAARLYR (SEQ ID NO: 16), a polypeptide of amino acid sequence KAFAKLAARLYR (SEQ ID NO: 17), and a polypeptide of amino acid sequence HRRIKAWLKKI (SEQ ID NO: 18).

The term "gene delivery vehicle" as used herein refers to a component that facilitates delivery to a cell of a coding sequence for expression of a polypeptide in the cell. The gene delivery vehicle can be any component or vehicle capable of accomplishing the delivery of a gene or cDNA to a cell, for example, a liposome, a virus particle, or an expression vector.

The term "Geometric Standard Deviation (GSD)" as used herein refers to a dimensionless number equal to the ratio between the mass median aerodynamic diameter (MMAD) and either 84% or 16% of the diameter size distribution (e.g., MMAD=2 pm; 84%=4 pm; GSD=4/2=2.0.) The MMAD, together with the GSD, describe the particle size distribution.

The term "granulation" as used herein refers to a process whereby small red, grain-like prominences form on a raw surface in the process of healing.

The term "hydrophilic" as used herein refers to a material or substance having an affinity for polar substances, such as water. The term "lipophilic" as used herein refers to a material or substance preferring or possessing an affinity for a non-polar environment compared to a polar or aqueous environment.

The term "inhalation" as used herein refers to the act of drawing in a medicated vapor with the breath.

The term "inhalation delivery device" as used herein refers to any device that produces small droplets or an aerosol from a liquid or dry powder aerosol formulation and is used for administration through the mouth in order to achieve pulmonary administration of a drug, e.g., in solution, powder, and the like. Examples of an inhalation delivery device include, but are not limited to, a nebulizer, a metered-dose inhaler, and a dry powder inhaler (DPI).

The term "insufflation" as used herein refers to the act of delivering air, a gas, or a powder under pressure to a cavity or chamber of the body. For example, nasal insufflation relates to the act of delivering air, a gas, or a powder under pressure through the nose.

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a second molecule that binds to a first molecule thereby decreasing the first molecule's activity. Enzyme inhibitors are molecules that bind to enzymes thereby decreasing enzyme activity. The binding of an inhibitor may stop substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "initial weight" as used herein refers to the weight of the scaled blister and powder before acuation (e.g., in mg).

The term "injury," as used herein, refers to damage or harm to a structure or function of the body caused by an outside agent or force, which may be physical or chemical.

The term "isolated" is used herein to refer to material, such as, but not limited to, a nucleic acid, peptide, polypeptide, or protein, which is: (1) substantially or essentially free from components that normally accompany or interact with it as found in its naturally occurring environment. The terms "substantially free" or "essentially free" are used herein to refer to considerably or significantly free of, or more than about 95% free of, or more than about 99% free of. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state.

The term "LPM" or "L/min" as used herein refers to liters per minute.

The term "mass balance" as used herein refers to the total amount of drug substance recovered from each component of an extraction, including the amount left in, for example, the inhaler. The mass balance can be expressed as a percentage of Actual Fill Weight equal to [(Metered Dose)/(Actual Fill Weight×Potency)]×100%.

The term "Mass Median Aerodynamic Diameter (MMAD)" as used herein refers to particle size distribution statistically, based on the weight and size of the particle. For example, 50% of particles by weight will be smaller than the median diameter (and 50% of particles will be larger than the median diameter).

The term "metered dose" as used herein refers to the delivery of a specific amount of a drug to a target. For example, delivery of an aerosolized drug to the lungs.

The term "metered-dose inhaler", "MDI", or "puffer" as used herein refers to a pressurized, hand-held device that uses propellants to deliver a specific amount of medicine ("metered dose") to the lungs of a patient. The term "propellant" as used herein refers to a material that is used to expel a substance usually by gas pressure through a convergent, divergent nozzle. The pressure may be from a compressed gas, or a gas produced by a chemical reaction. The exhaust material may be a gas, liquid, plasma, or, before the chemical reaction, a solid, liquid or gel. Propellants used in pressurized metered dose inhalers are liquified gases, traditionally chlorofluorocarbons (CFCs) and increasingly hydrofluoroalkanes (HFAs). Suitable propellants include, for example, a chlorofluorocarbon (CFC), such as trichlorofluoromethane (also referred to as propellant 11), dichlorodifluoromethane (also referred to as propellant 12), and 1,2-dichloro-1,1,2,2-tetrafluoroethane (also referred to as propellant 114), a hydrochlorofluorocarbon, a hydrofluorocarbon (HFC), such as 1,1,1,2-tetrafluoroethane (also referred to as propellant 134a, HFC-134a, or HFA-134a) and 1,1,1,2,3,3,3-heptafluoropropane (also referred to as propellant 227, HFC-227, or HFA-227), carbon dioxide, dimethyl ether, butane, propane, or mixtures thereof. In other embodiments, the propellant includes a chlorofluorocarbon, a hydrochlorofluorocarbon, a hydrofluorocarbon, or mixtures thereof. In other embodiments, a hydrofluorocarbon is used as the propellant. In other embodiments, HFC-227 and/or HFC-134a are used as the propellant.

The term "MK2 kinase" or "MK2" as used herein refers to mitogen-activated protein kinase-activated protein kinase 2 (also referred to as "MAPKAPK2", "MAPKAP-K2", "MK2"), which is a member of the serine/threonine (Ser/Thr) protein kinase family.

The terms "MMI-0100", "MMI-0100 peptide", "MMI-0100 polypeptide", "MK2 inhibitor", "MK2i", "MK2i peptide", "MK2i polypeptide" and the like, are used interchangeably herein to refer to amino acid sequence YARAAARQARAKALARQLGVAA (SEQ ID NO: 1).

The term "nebulizer" as used herein refers to a device used to administer liquid medication in the form of a mist inhaled into the lungs.

The term "Nominal Label Claim (NLC)" as used herein refers to the intended amount of drug substance present per actuation based upon target potency and target blister fill weight.

The term "nucleic acid" is used herein to refer to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" is used herein to refer to a chemical compound that consists of a heterocyclic base, a sugar, and one or more phosphate groups. In the most common nucleotides, the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. Purines include adenine (A), and guanine (G); pyrimidines include cytosine (C), thymine (T), and uracil (U).

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity."

(a) The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

(b) The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters may be employed alone or in combination.

(c) The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

(d) The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The term "operatively linked" as used herein refers to a linkage in which two or more protein domains or peptides are ligated or combined via recombinant DNA technology or chemical reaction such that each protein domain or polypeptide of the resulting fusion peptide retains its original function. For example, SEQ ID NO: 1 is constructed by operatively linking a protein transduction domain (SEQ ID NO: 26) with a therapeutic domain (SEQ ID NO: 2), thereby creating a fusion peptide that possesses both the cell penetrating function of SEQ ID NO: 26 and the MK2 kinase inhibitor function of SEQ ID NO: 2.

The term "particle" as used herein refers to an extremely small constituent, e.g., a nanoparticle or microparticle) that may contain in whole or in part at least one therapeutic agent as described herein. The term "microparticle" is used herein to refer generally to a variety of substantially structures having sizes from about 10 nm to 2000 microns (2 millimeters) and includes a microcapsule, microsphere, nanoparticle, nanocapsule, nanosphere as well as particles, in general, that are less than about 2000 microns (2 millimeters). The particles may contain therapeutic agent(s) in a core surrounded by a coating. Therapeutic agent(s) also may be dispersed throughout the particles. Therapeutic agent(s) also may be adsorbed into the particles. The particles may be of any order release kinetics, including zero order release, first order release, second order release, delayed release, sustained release, immediate release, etc., and any combination thereof. The particle may include, in addition to therapeutic agent(s), any of those materials routinely used in the art of pharmacy and medicine, including, but not limited to, erodible, nonerodible, biodegradable, or nonbiodegradable material or combinations thereof. The particles may be microcapsules that contain the active agent in a solution or in a semi-solid state. The particles may be of virtually any shape.

The term "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

The terms "pharmaceutical formulation" or "pharmaceutical composition" as used herein refer to a formulation or a composition that is employed to prevent, reduce in intensity, cure or otherwise treat a target condition or disease.

The term "prevent" as used herein refers to the keeping, hindering or averting of an event, act or action from happening, occurring, or arising.

The term "prodrug" as used herein means a peptide or derivative which is in an inactive form and which is converted to an active form by biological conversion following administration to a subject.

The term "recombinant" as used herein refers to a substance produced by genetic engineering.

The term "reduce", "reduced", "to reduce" or "reducing" as used herein refer to a diminution, a decrease, an attenuation or abatement of the degree, intensity, extent, size, amount, density or number.

The term "similar" is used interchangeably with the terms analogous, comparable, or resembling, meaning having traits or characteristics in common.

The term "stability" of a pharmaceutical product as used herein refers to the capability of a particular formulation to remain within its physical, chemical, microbiological, therapeutic and toxicological specifications.

The term "susceptible" as used herein refers to a member of a population at risk.

The terms "subject" or "individual" or "patient" are used interchangeably to refer to a member of an animal species of mammalian origin, including but not limited to, a mouse, a rat, a cat, a goat, a sheep, a horse, a hamster, a ferret, a platypus, a pig, a dog, a guinea pig, a rabbit and a primate, such as, for example, a monkey, an ape, or a human.

The phrase "subject in need thereof" as used herein refers to a patient that (i) will be administered a formulation containing at least one therapeutic peptide agent, (ii) is receiving a formulation containing at least one therapeutic peptide agent; or (iii) has received a formulation containing at least one therapeutic agent, unless the context and usage of the phrase indicates otherwise.

The term "sustained release" (also referred to as "extended release") is used herein in its conventional sense to refer to a drug formulation that provides for gradual release of a therapeutic agent over an extended period of time, and that preferably, although not necessarily, results in substantially constant levels of the agent over an extended time period.

The term "symptom" as used herein refers to a phenomenon that arises from and accompanies a particular disease or disorder and serves as an indication of it.

The term "syndrome," as used herein, refers to a pattern of symptoms indicative of some disease or condition.

The term "therapeutic agent" as used herein refers to a drug, molecule, nucleic acid, protein, composition or other substance that provides a therapeutic effect. The terms "therapeutic agent" and "active agent" are used interchangeably.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the $ED_{50}$ which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "therapeutically effective amount" or an "amount effective" of one or more of the active agents is an amount that is sufficient to provide the intended benefit of treatment. An effective amount of the active agents that can be employed ranges from generally 0.1 mg/kg body weight and about 50 mg/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a surgeon using standard methods.

The term "treat" or "treating" includes abrogating, substantially inhibiting, slowing or reversing the progression of a disease, condition, disorder or injury, substantially ameliorating clinical or esthetical symptoms of a disease, condition, disorder or injury, substantially preventing the appearance of clinical or esthetical symptoms of a disease, condition, disorder or injury, and protecting from harmful or annoying symptoms. The term "treat" or "treating" as used herein further refers to accomplishing one or more of the following: (a) reducing the severity of the disease, condition, disorder or injury; (b) limiting development of symptoms characteristic of the disease, condition, disorder or injury being treated; (c) limiting worsening of symptoms characteristic of the disease, condition, disorder or injury being treated; (d) limiting recurrence of the disease, condition, disorder or injury in patients that have previously had the disease, condition, disorder or injury; and (e) limiting recurrence of symptoms in patients that were previously symptomatic for the disease, condition, disorder or injury.

The terms "variants", "mutants", and "derivatives" are used herein to refer to nucleotide or polypeptide sequences with substantial identity to a reference nucleotide or polypeptide sequence. The differences in the sequences may be the result of changes, either naturally or by design, in sequence or structure. Natural changes may arise during the course of normal replication or duplication in nature of the particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants" or "derivatives" of the original sequence.

A skilled artisan likewise can produce polypeptide variants of polypeptide YARAAARQARAKALARQLGVAA (SEQ ID NO: 1) having single or multiple amino acid substitutions, deletions, additions or replacements, but functionally equivalent to SEQ ID NO: 1. These variants may include inter alia: (a) variants in which one or more amino acid residues are substituted with conservative or non-conservative amino acids; (b) variants in which one or more amino acids are added; (c) variants in which at least one amino acid includes a substituent group; (d) variants in which amino acid residues from one species are substituted for the corresponding residue in another species, either at conserved or non-conserved positions; and (d) variants in which a target protein is fused with another peptide or polypeptide such as a fusion partner, a protein tag or other chemical moiety, that may confer useful properties to the target protein, for example, an epitope for an antibody. The techniques for obtaining such variants, including, but not limited to, genetic (suppressions, deletions, mutations, etc.), chemical, and enzymatic techniques, are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "vehicle" as used herein refers to a substance that facilitates the use of a drug or other material that is mixed with it.

According to one embodiment, the described invention provides a pharmaceutical formulation comprising an inhibitor of MK2 kinase. According to another embodiment, the MK2 inhibitor is a polypeptide. According to another embodiment, the polypeptide includes, but is not limited to, MMI-0100 (YARAAARQARAKALARQLGVAA (SEQ ID NO: 1)) or its functional equivalents.

According to one embodiment, the pharmaceutical formulation comprises a neat spray dried dispersion comprising MMI-0100 (YARAAARQARAKALARQLGVAA; SEQ ID NO: 1) or a functional equivalent thereof, 5% w/w solids. According to another embodiment, the pharmaceutical formulation comprises a neat spray dried dispersion comprising MMI-0100 (YARAAARQARAKALARQLGVAA; SEQ ID NO: 1) or a functional equivalent thereof, 1% w/w solids. According to another embodiment, the pharmaceutical formulation comprises a spray dried dispersion comprising 80/20 MMI-0100 (YARAAARQARAKALARQLGVAA; SEQ ID NO: 1) or a functional equivalent thereof/trehalose. According to another embodiment, the pharmaceutical formulation comprises a spray dried dispersion comprising 92.5/7.5 MMI-0100 (YARAAARQARAKALARQLGVAA; SEQ ID NO: 1) or a functional equivalent thereof/trehalose.

A spray-dried dispersion (SDD) is a single-phase, amorphous molecular dispersion of a drug in a polymer matrix. It is a solid solution with a compound (e.g., drug) moleculary "dissolved" in a solid matrix. SDDs are obtained by dissolving drug and polymer in an organic solvent to obtain a solution and then spray-drying the solution. The use of spray drying for pharmaceutical applications results in amorphous dispersions with increased solubility of Biopharmaceutics Classification System (BCS) class II (high permeability, low solubility) and class IV (low permeability, low solubility) drugs. Formulation and process conditions are selected so that the solvent quickly evaporates from the droplets, thus allowing insufficient time for phase separation or crystallization. SDDs have demonstrated long-term stability and manufacturability. For example, shelf lives of more than 2 years have been consistently demonstrated with SDDs. Advantages of SDDs include, but are not limited to, enhanced oral bioavailabilty of poorly water-soluble compounds, delivery using traditional solid dosage forms (e.g., tablets and capsules), a reproducible, controllable and scalable manufacturing process and broad applicability to structurally diverse insoluble compounds with a wide range of physical properties.

According to one embodiment, the pharmaceutical formulation comprises MMI-0100 (YARAAARQARAKALARQLGVAA; SEQ ID NO: 1) or a functional equivalent thereof and 0.9% NaCl (saline). According to another embodiment, the pharmaceutical formulation comprises 7 mg/mL, 6 mg/mL, 5 mg/mL, 4 mg/mL, 3 mg/mL, 2 mg/mL, or 1 mg/mL MMI-0100 (YARAAARQARAKALARQLGVAA; SEQ ID NO: 1) or a functional equivalent thereof. According to anther embodiment, the pharmaceutical formulation comprises 0.9 mg/mL, 0.8 mg/mL, 0.7 mg/mL, 0.6 mg/mL, 0.5 mg/mL, 0.4 mg/mL, 0.3 mg/mL, 0.2 mg/mL, or 0.1 mg/mL MMI-0100 (YARAAARQARAKALARQL-GVAA; SEQ ID NO: 1) or a functional equivalent thereof. According to another embodiment, the formulation comparing MMI-0100 (YARAAARQARAKALARQLGVAA; SEQ ID NO: 1) or a functional equivalent thereof is a liquid formulation. According to another embodiment, the liquid formulation is aerosolized.

According to one embodiment, the pharmaceutical formulation comprises MMI-0100 (YARAAARQARAKA-LARQLGVAA; SEQ ID NO: 1) or a functional equivalent thereof and glycerin.

According to one embodiment, the pharmaceutical formulation comprises MMI-0100 (YARAAARQARAKA-LARQLGVAA; SEQ ID NO: 1) or a functional equivalent thereof and a nano-polyplex polymer. According to another embodiment, the nano-polyplex polymer is poly(acrylic acid) (PAA). According to another embodiment, the nano-polyplex polymer is poly(propylacrylic acid) (PPAA). According to another embodiment, the pharmaceutical formulation comprises a charge ratio (CR) of MMI-0100 (YARAAARQARAKALARQLGVAA; SEQ ID NO: 1) or a functional equivalent thereof to PPAA ($[NH_3^+]_{MK2i}$:$[COO^-]_{PPAA}$) selected from the group consisting of 10:1, 9:1, 8:1, 7:1, 6:1, 5:1, 4:1, 3:1, 2:1, 1:1, 1:1.5, 1:2, 1:3, 1:4, 1:5, 1:6, 1:7, 1:8, 1:9 and 1:10. According to another embodiment, the pharmaceutical formulation comprises a charge ratio of MMI-0100(YARAAARQARAKALARQLGVAA; SEQ ID NO: 1) or a functional equivalent thereof to PPAA ($[NH_3^+]_{MK2i}$:$[COO^-]_{PPAA}$) of 1:3.

According to another embodiment, the functional equivalent of the polypeptide YARAAARQARAKALARQL-GVAA (MMI-0100; SEQ ID NO: 1) has a substantial sequence identity to amino acid sequence YARAAAR-QARAKALARQLGVAA (SEQ ID NO: 1).

According to another embodiment, the functional equivalent of the polypeptide YARAAARQARAKALARQL-GVAA (MMI-0100; SEQ ID NO: 1) has at least 80 percent sequence identity to amino acid sequence YARAAAR-QARAKALARQLGVAA (SEQ ID NO: 1). According to another embodiment, the functional equivalent of the polypeptide YARAAARQARAKALARQLGVAA (MMI-0100; SEQ ID NO: 1) has at least 90 percent sequence identity to amino acid sequence YARAAARQARAKALARQLGVAA (SEQ ID NO: 1). According to another embodiment, the functional equivalent of the polypeptide YARAAAR-QARAKALARQLGVAA (MMI-0100; SEQ ID NO: 1) has at least 95 percent sequence identity to amino acid sequence YARAAARQARAKALARQLGVAA (SEQ ID NO: 1).

According to another embodiment, the functional equivalent of the polypeptide YARAAARQARAKALARQL-GVAA (MMI-0100; SEQ ID NO: 1) is a polypeptide of amino acid sequence YARAAARQARAKALNRQLGVA (MMI-0200; SEQ ID NO: 19)

According to another embodiment, the functional equivalent of the polypeptide YARAAARQARAKALARQL-GVAA (MMI-0100; SEQ ID NO: 1) is a polypeptide of amino acid sequence FAKLAARLYRKALARQLGVAA (MMI-0300; SEQ ID NO: 3).

According to another embodiment, the functional equivalent of the polypeptide YARAAARQARAKALARQL-GVAA (SEQ ID NO: 1) is a polypeptide of amino acid sequence KAFAKLAARLYRKALARQLGVAA (MMI-0400; SEQ ID NO: 4).

According to another embodiment, the functional equivalent of the polypeptide YARAAARQARAKALARQL-GVAA (SEQ ID NO: 1) is a polypeptide of amino acid sequence YARAAARQARAKALARQLAVA (SEQ ID NO: 5).

According to another embodiment, the functional equivalent of the polypeptide YARAAARQARAKALARQL-GVAA (SEQ ID NO: 1) is a polypeptide of amino acid sequence YARAAARQARAKALARQLGVA (SEQ ID NO: 6).

According to another embodiment, the functional equivalent of the polypeptide YARAAARQARAKALARQL-GVAA (SEQ ID NO: 1) is a polypeptide of amino acid sequence HRRIKAWLKKIKALARQLGVAA (MMI-0500; SEQ ID NO: 7).

According to another embodiment, the functional equivalent of the polypeptide YARAAARQARAKALARQL-GVAA (SEQ ID NO: 1) is a polypeptide of amino acid sequence YARAAARQARAKALNRQLAVAA (MMI0600, SEQ ID NO: 23)

According to another embodiment, the functional equivalent of the polypeptide YARAAARQARAKALARQL-GVAA (SEQ ID NO: 1) is a polypeptide of amino acid sequence YARAAARQARAKALNRQLAVA (MMI0600-2, SEQ ID NO: 24).

According to another embodiment, the functional equivalent of the polypeptide YARAAARQARAKALARQL-GVAA (SEQ ID NO: 1) is a fusion peptide comprising a first polypeptide operatively linked to a second polypeptide, wherein the first polypeptide is of amino acid sequence YARAAARQARA (SEQ ID NO: 11), and the second polypeptide comprises a therapeutic domain whose sequence has a substantial identity to amino acid sequence KALARQL-GVAA (SEQ ID NO: 2).

According to another embodiment, the second polypeptide has at least 70 percent sequence identity to amino acid sequence KALARQLGVAA (SEQ ID NO: 2), and the pharmaceutical formulation inhibits the kinase activity of Mitogen-Activated Protein Kinase-Activated Protein Kinase 2 (MK2). According to another embodiment, the second polypeptide has at least 80 percent sequence identity to amino acid sequence KALARQLGVAA (SEQ ID NO: 2), and the pharmaceutical formulation inhibits the kinase activity of Mitogen-Activated Protein Kinase-Activated Protein Kinase 2 (MK2). According to another embodiment, the second polypeptide has at least 90 percent sequence identity to amino acid sequence KALARQLGVAA (SEQ ID NO: 2), and the pharmaceutical formulation inhibits the kinase activity of Mitogen-Activated Protein Kinase-Activated Protein Kinase 2 (MK2). According to another embodiment, the second polypeptide has at least 95 percent sequence identity to amino acid sequence KALARQLGVAA (SEQ ID NO: 2), and the pharmaceutical formulation inhibits the kinase activity of Mitogen-Activated Protein Kinase-Activated Protein Kinase 2 (MK2).

According to another embodiment, the second polypeptide is a polypeptide of amino acid sequence KALAR-QLAVA (SEQ ID NO: 8).

According to another embodiment, the second polypeptide is a polypeptide of amino acid sequence KALARQL-GVA (SEQ ID NO: 9).

According to another embodiment, the second polypeptide is a polypeptide of amino acid sequence KALNRQLA-VAA (SEQ ID NO: 25)

According to another embodiment, the second polypeptide is a polypeptide of amino acid sequence KALN-RQLAVA (SEQ ID NO: 26).

According to another embodiment, the second polypeptide is a polypeptide of amino acid sequence KALARQL- GVAA (SEQ ID NO: 10); see, e.g., U.S. Published Application No. 2009-0196927, U.S. Published Application No. 2009-0149389, and U.S. Published Application No 2010-0158968, each of which is incorporated herein by reference in its entirety.

According to another embodiment, the functional equivalent of the polypeptide YARAAARQARAKALARQLGVAA (SEQ ID NO: 1) is a fusion peptide comprising a first polypeptide operatively linked to a second polypeptide, wherein the first polypeptide comprises a protein transduction domain functionally equivalent to YARAAARQARA (SEQ ID NO: 11), and the second polypeptide is of amino acid sequence KALARQLGVAA (SEQ ID NO: 2).

According to another embodiment, the first polypeptide is a polypeptide of amino acid sequence WLRRIKAWLRRIKA (SEQ ID NO: 12).

According to another embodiment, first polypeptide is a polypeptide of amino acid sequence WLRRIKA (SEQ ID NO: 13).

According to another embodiment, the first polypeptide is a polypeptide of amino acid sequence YGRKKRRQRRR (SEQ ID NO: 14).

According to another embodiment, the first polypeptide is a polypeptide of amino acid sequence WLRRIKAWLRRI (SEQ ID NO: 15).

According to another embodiment, the first polypeptide is a polypeptide of amino acid sequence FAKLAARLYR (SEQ ID NO: 16).

According to another embodiment, the first polypeptide is a polypeptide of amino acid sequence KAFAKLAARLYR (SEQ ID NO: 17).

According to another embodiment, the first polypeptide is a polypeptide of amino acid sequence HRRIKAWLKKI (SEQ ID NO: 18).

According to some embodiments, in order to enhance drug efficacy and to prevent accumulation of the polypeptide YARAAARQARAKALARQLGVAA (SEQ ID NO: 1) or its functional equivalent in non-target tissues, the polypeptide of the present invention of amino acid sequence YARAAARQARAKALARQLGVAA (SEQ ID NO: 1) or its functional equivalent can be linked or associated with a targeting moiety, which directs the polypeptide to a specific cell type or tissue. Examples of the targeting moiety include, but are not limited to, (i) a ligand for a known or unknown receptor or (ii) a compound, a peptide, or a monoclonal antibody that binds to a specific molecular target, e.g., a peptide or carbohydrate, expressed on the surface of a specific cell type.

According to some embodiments, the polypeptide of the described invention is chemically synthesized. Such a synthetic polypeptide, prepared using the well known techniques of solid phase, liquid phase, or peptide condensation techniques, or any combination thereof, may include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, *J. Am. Chem. Soc.* 85:2149-2154), or the base-labile N-α-amino protected 9-fluorenylmethoxycarbonyl (Fmoc) amino acids first described by Carpino and Han (1972, *J. Org. Chem.* 37:3403-3409). Both Fmoc and Boc N-α-amino protected amino acids can be obtained from Sigma, Cambridge Research Biochemical, or other chemical companies familiar to those skilled in the art. In addition, the polypeptide may be synthesized with other N-α-protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields and Noble, 1990, *Int. J. Pept. Protein Res.* 35:161-214, or using automated synthesizers, each incorporated by reference herein in its entirety.

According to some embodiments, the polypeptide of the invention comprises D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Examples of synthetic amino acid substitutions include ornithine for lysine, and norleucine for leucine or isoleucine.

According to some embodiments, the polypeptide may be linked to other compounds to promote an increased half-life in vivo, such as polyethylene glycol or dextran. Such linkage can be covalent or non-covalent as is understood by those of skill in the art. According to some other embodiments, the polypeptide may be encapsulated in a micelle, such as a micelle made of poly(ethyleneglycol)-block-poly(polypropylenglycol) or poly(ethyleneglycol)-block-polylactide. According to some other embodiments, the polypeptide may be encapsulated in degradable nano- or micro-particles composed of degradable polyesters including, but not limited to, polylactic acid, polyglycolide, and polycaprolactone.

According to one embodiment, the pharmaceutical formulation of the described invention may be administered by an inhalation device. Examples of the inhalation device that can be used for administering the pharmaceutical formulation includes, but is not limited to, a nebulizer, a metered-dose inhaler, a dry powder inhaler and an aqueous droplet inhaler.

Nebulizers, which actively aerosolize a liquid formulation and operate continuously once loaded, require either compressed air or an electrical supply. Exemplary nebulizers include, a vibrating mesh nebulizer, a jet nebulizer (also known as an atomizer) and an ultrasonic wave nebulizer. Exemplary vibrating mesh nebulizers include, but are not limited to, Respironics i-Neb, Omron MicroAir, Beurer Nebulizer IHSO and Aerogen Aeroneb. Acorn-I, Acorn-II, AquaTower, AVA-NEB, Cirrhus, Dart, DeVilbiss 646, Downdraft, Fan Jet, MB-5, Misty Neb, Salter Labs 8900, Sidestream, Updraft-II, and Whisper Jet are examples of a jet nebulizer. Exemplary ultrasonic nebulizers include, but are not limited to, an Omron NE-U17 nebulizer and a Beurer Nebulizer IH30.

Metered-dose inhalers (MDI) use a propellant to deliver a fixed volume of liquid solution or suspension to a patient in the form of a spray.

Dry powder inhalers (DPI) contain an active drug mixed with an excipient containing much larger particles (e.g., lactose) to which the drug attaches. During aerosolization, the active drug is stripped from the carrier and inhaled while the carrier particles impact on the mouth and throat and are ingested. DPIs synchronize drug delivery with inhalation.

According to one embodiment, the polypeptide of the described invention may be in the form of a dispersible dry powder for delivery by inhalation or insufflation (either through the mouth or through the nose, respectively). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the described invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition, such as gelatin or plastic capsules, with a removable portion that allows a stream of gas (e.g., air) to be directed into the container to disperse the dry powder composition. Such containers are exemplified by those shown in U.S. Pat. No. 4,227,522; U.S. Pat. No. 4,192,309; and U.S. Pat. No. 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). All of these references are incorporated herein by reference in their entireties.

Aqueous droplet inhalers (ADI) deliver a pre-metered dose of liquid formulation without using a propellant. ADIs actively aerosolize liquid producing a soft mist of fine particles. Berodual Respimat® (Boehringer Ingelheim Pharma Gmbh & Co.) is an exemplary aqueous droplet inhaler.

According to one embodiment, the polypeptide of the described invention may be in the form of a nebulization solution. According to another embodiment, the nebulization formulation does not contain mannitol. According to one embodiment, the nebulization solution is delivered by a nebulizer.

According to another embodiment, the polypeptide may be prepared in a solid form (including granules, powders or suppositories) or in a liquid form (e.g., solutions, suspensions, or emulsions).

According to another embodiment, the polypeptide of the described invention may be in the form of a nano-polyplex. According to one embodiment, the nan-polyplex polymer is anionic. According to another embodiment, the nano-polyplex polymer is an endosomolytic polymer. Exemplary nano-polyplex polymers include, but are not limited to, chitosan, polyethyleneimine (PEI), polyethylene oxide (PEO), poly(organophos-phazene), poly(acrylic acid) (PAA) and poly(propylacrylic acid) (PPAA).

According to one embodiment, the formulation of the described invention may be delivered by implanting a biomedical device. The biomedical device includes, but is not limited to, a graft. According to another embodiment, the formulation may be disposed on or in the graft. According to another embodiment, the graft includes, but is not limited to, a vascular graft. According to another embodiment, the formulation may be delivered parenterally. According to another embodiment, the formulation may be delivered topically.

According to another embodiment, the formulation of the described invention comprises a carrier. The carrier can include, but is not limited to, a release agent, such as a sustained release or delayed release carrier. According to such embodiments, the carrier can be any material capable of sustained or delayed release of the polypeptide to provide a more efficient administration, e.g., resulting in less frequent and/or decreased dosage of the polypeptide, improving ease of handling, and extending or delaying effects on diseases, disorders, conditions, syndromes, and the like. Non-limiting examples of such carriers include liposomes, microsponges, microspheres, or microcapsules of natural and synthetic polymers and the like. Liposomes may be formed from a variety of phospholipids, including, but not limited to, cholesterol, stearylamines or phosphatidylcholines.

According to another embodiment, the polypeptide of the invention may be applied in a variety of solutions. A suitable formulation is sterile, dissolves sufficient amounts of the therapeutic polypeptide, preserves stability of the therapeutic polypeptide, and is not harmful for the proposed application. For example, the compositions of the described invention may be formulated as aqueous suspensions wherein the active ingredient(s) is (are) in admixture with excipients suitable for the manufacture of aqueous suspensions.

Such excipients include, without limitation, suspending agents (e.g., sodium carboxymethylcellulose, methylcellulose, hydroxy-propylmethylcellulose, sodium alginate, polyvinylpyrrolidone, gum tragacanth, and gum acacia), dispersing or wetting agents including, a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., heptadecaethyl-eneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate).

Compositions of the described invention also may be formulated as oily suspensions by suspending the active ingredient in a vegetable oil (e.g., arachis oil, olive oil, sesame oil or coconut oil) or in a mineral oil (e.g., liquid paraffin). The oily suspensions may contain a thickening agent (e.g., beeswax, hard paraffin or cetyl alcohol).

Compositions of the described invention also may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients also may be present.

Compositions of the described invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate.

According to some embodiments, pharmaceutical formulations of the described invention are capable of inhibiting a kinase activity of Mitogen-Activated Protein Kinase-Activated Protein Kinase 2 (MK2). According to some embodiments, pharmaceutical formulations of the described invention inhibit at least 50% of the kinase activity of MK2 kinase. According to some embodiments, pharmaceutical formulations of the described invention inhibit at least 55% of the kinase activity of MK2 kinase. According to some embodiments, pharmaceutical formulations of the described invention inhibit at least 60% of the kinase activity of MK2 kinase. According to some embodiments, pharmaceutical formulations or the described invention inhibit at least 65% of the kinase activity of MK2 kinase. According to some embodiments, pharmaceutical formulations of the described invention inhibit at least 70% of the kinase activity of MK2 kinase. According to some embodiments, pharmaceutical formulations of the described invention inhibit at least 75% of the kinase activity of MK2 kinase. According to some embodiments, pharmaceutical formulations of the described invention inhibit at least 80% of the kinase activity of MK2 kinase. According to some embodiments, pharmaceutical formulations of the described invention inhibit at least 85% of the kinase activity of MK2 kinase. According to some embodiments, pharmaceutical formulations of the described invention inhibit at least 90% of the kinase activity of MK2 kinase. According to some embodiments, pharmaceutical formulations of the described invention inhibit at least 95% of the kinase activity of MK2 kinase.

According to another embodiment, the pharmaceutical formulation is effective to inhibit a kinase activity of Mitogen-Activated Protein Kinase-Activated Protein Kinase 3 (MK3). According to some such embodiments, the pharmaceutical formulation inhibits at least 50% of the kinase activity of MK3 kinase. According to some such embodiments, the pharmaceutical formulation inhibits at least 55% of the kinase activity of MK3 kinase. According to some such embodiments, the pharmaceutical formulation inhibits at least 60% of the kinase activity of MK3 kinase. According to another embodiment, the pharmaceutical formulation inhibits at least 65% of the kinase activity of MK3 kinase. According to another embodiment, the pharmaceutical formulation inhibits at least 70% of the kinase activity of MK3 kinase. According to another embodiment, the pharmaceutical formulation inhibits at least 75% of the kinase activity of MK3 kinase. According to another embodiment, the pharmaceutical formulation inhibits at least 80% of the kinase activity of MK3 kinase. According to another embodiment, the pharmaceutical formulation inhibits at least 85% of the kinase activity of MK3 kinase. According to another embodiment, the pharmaceutical formulation inhibits at least 90% of the kinase activity of MK3 kinase. According to another embodiment, the pharmaceutical formulation inhibits at least 95% of the kinase activity of MK3 kinase.

According to another embodiment, the pharmaceutical formulation is effective to inhibit a kinase activity of calcium/calmodulin-dependent protein kinase I (CaMKI). According to some such embodiments, the pharmaceutical formulation further inhibits at least 50% of the kinase activity of $Ca^{2+}$/calmodulin-dependent protein kinase I (CaMKI). According to some such embodiments, the pharmaceutical formulation further inhibits at least 55% of the kinase activity of $Ca^{2+}$/calmodulin-dependent protein kinase I (CaMKI). According to some such embodiments, the pharmaceutical formulation further inhibits at least 60% of the kinase activity of $Ca^{2+}$/calmodulin-dependent protein kinase I (CaMKI). According to another embodiment, the pharmaceutical formulation further inhibits at least 65% of the kinase activity of $Ca^{2+}$/calmodulin-dependent protein kinase I (CaMKI). According to another embodiment, the pharmaceutical formulation further inhibits at least 70% of the kinase activity of $Ca^{2+}$/calmodulin-dependent protein kinase I (CaMKI). According to another embodiment, the pharmaceutical formulation further inhibits at least 75% of the kinase activity of $Ca^{2+}$/calmodulin-dependent protein kinase I (CaMKI). According to another embodiment, the pharmaceutical formulation further inhibits at least 80% of the kinase activity of $Ca^{2+}$/calmodulin-dependent protein kinase I (CaMKI). According to another embodiment, the pharmaceutical formulation further inhibits at least 85% of the kinase activity of $Ca^{2+}$/calmodulin-dependent protein kinase I (CaMKI). According to another embodiment, the pharmaceutical formulation further inhibits at least 90% of the kinase activity of $Ca^{2+}$/calmodulin-dependent protein kinase I (CaMKI). According to another embodiment, the pharmaceutical formulation further inhibits at least 95% of the kinase activity of $Ca^{2+}$/calmodulin-dependent protein kinase I (CaMKI).

According to another embodiment, the pharmaceutical formulation is capable of inhibiting a kinase activity of BDNF/NT-3 growth factors receptor (TrkB). According to some such embodiments, the pharmaceutical further inhibits at least 50% of the kinase activity of BDNF/NT-3 growth factors receptor (TrkB). According to some such embodiments, the pharmaceutical further inhibits at least 55% of the kinase activity of BDNF/NT-3 growth factors receptor (TrkB). According to some such embodiments, the pharmaceutical further inhibits at least 60% of the kinase activity of BDNF/NT-3 growth factors receptor (TrkB). According to another embodiment, the pharmaceutical further inhibits at least 65% of the kinase activity of BDNF/NT-3 growth factors receptor (TrkB). According to another embodiment, the pharmaceutical further inhibits at least 70% of the kinase activity of BDNF/NT-3 growth factors receptor (TrkB). According to another embodiment, the pharmaceutical further inhibits at least 75% of the kinase activity of BDNF/NT-3 growth factors receptor (TrkB). According to another embodiment, the pharmaceutical formulation inhibits at least 80% of the kinase activity of BDNF/NT-3 growth factors receptor (TrkB). According to another embodiment, the pharmaceutical formulation inhibits at least 85% of the kinase activity of BDNF/NT-3 growth factors receptor (TrkB). According to another embodiment, the pharmaceutical formulation inhibits at least 90% of the kinase activity of BDNF/NT-3 growth factors receptor (TrkB). According to another embodiment, the pharmaceutical formulation inhibits at least 95% of the kinase activity of BDNF/NT-3 growth factors receptor (TrkB).

According to another embodiment, the pharmaceutical formulation is effective to inhibit a kinase activity of Mitogen-Activated Protein Kinase-Activated Protein Kinase 2

(MK2) and a kinase activity of calcium/calmodulin-dependent protein kinase I (CaMKI).

According to another embodiment, the pharmaceutical formulation is effective to inhibit a kinase activity of Mitogen-Activated Protein Kinase-Activated Protein Kinase 2 (MK2) and a kinase activity of BDNF/NT-3 growth factors receptor (TrkB).

According to another embodiment, the pharmaceutical formulation is effective to inhibit a kinase activity of Mitogen-Activated Protein Kinase-Activated Protein Kinase 2 (MK2), a kinase activity of calcium/calmodulin-dependent protein kinase I (CaMKI), and a kinase activity of BDNF/NT-3 growth factors receptor (TrkB).

According to another embodiment, the pharmaceutical formulation inhibits at least 65% of the kinase activity of Mitogen-Activated Protein Kinase-Activated Protein Kinase 2 (MK2) and at least 65% of the kinase activity of calcium/calmodulin-dependent protein kinase I (CaMKI).

According to another embodiment, the pharmaceutical formulation inhibits at least 65% of the kinase activity of Mitogen-Activated Protein Kinase-Activated Protein Kinase 2 (MK2) and at least 65% of the kinase activity of BDNF/NT-3 growth factors receptor (TrkB).

According to another embodiment, the pharmaceutical formulation inhibits at least 65% of the kinase activity of Mitogen-Activated Protein Kinase-Activated Protein Kinase 2 (MK2), at least 65% of the kinase activity of calcium/calmodulin-dependent protein kinase I (CaMKI), and at least 65% of the kinase activity of BDNF/NT-3 growth factors receptor (TrkB).

According to another embodiment, the pharmaceutical formulation inhibits the kinase activity of at least one kinase selected from the group of MK2, MK3, CaMKI, TrkB, without substantially inhibiting the activity of one or more other selected kinases from the remaining group listed in Table 1 herein.

TABLE 1

| | Kinase Profiling Assay | | | | |
|---|---|---|---|---|---|
| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
| Abl(h) | 136 | 107 | 69 | 84 | 16 |
| Abl(H396P)(h) | 130 | 121 | 101 | 105 | 51 |
| Abl(M351T)(h) | 128 | 119 | 90 | 121 | 61 |
| Abl(Q252H)(h) | 105 | 107 | 82 | 98 | 40 |
| Abl(T315I)(h) | 98 | 108 | 97 | 105 | 16 |
| Abl(Y253F)(h) | 104 | 102 | 86 | 78 | 29 |
| ACK1(h) | 106 | 97 | 104 | 95 | 64 |
| ALK(h) | 118 | 95 | 19 | 16 | 12 |
| ALK4(h) | 124 | 152 | 140 | 130 | 81 |
| Arg(h) | 89 | 82 | 72 | 84 | 22 |
| AMPKa1(h) | 107 | 108 | 71 | 87 | 35 |
| AMPKa2(h) | 121 | 88 | 54 | 58 | 9 |
| ARK5(h) | 108 | 93 | 78 | 69 | 20 |
| ASK1(h) | 100 | 101 | 80 | 69 | −4 |
| Aurora-A(h) | 120 | 107 | 92 | 119 | 110 |
| Aurora-B(h) | 94 | 166 | 128 | 150 | 5 |
| Axl(h) | 81 | 99 | 52 | 41 | 12 |
| Bmx(h) | 62 | 76 | N/D | 26 | 45 |
| BRK(h) | 70 | 127 | 35 | 18 | 41 |
| BrSK1(h) | 100 | 93 | 67 | 76 | 72 |
| BrSK2(h) | 129 | 102 | 83 | 86 | 84 |
| BTK(h) | 112 | 100 | 102 | 94 | 18 |
| BTK(R28H)(h) | 91 | 104 | 74 | 24 | 10 |
| CaMKI(h) | 13 | 21 | 1 | 0 | −1 |
| CaMKIIβ(h) | 58 | 53 | 2 | 11 | 3 |

TABLE 1-continued

Kinase Profiling Assay

| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
|---|---|---|---|---|---|
| CaMKIIγ(h) | 106 | 94 | 5 | 3 | 3 |
| CaMKIδ(h) | 59 | 47 | 10 | 17 | 0 |
| CaMKIIδ(h) | 89 | 2 | 1 | 2 | 1 |
| CaMKIV(h) | 87 | 71 | 17 | 18 | -1 |
| CDK1/cyclinB(h) | 96 | 115 | 73 | 74 | 57 |
| CDK2/cyclinA(h) | 97 | 114 | 86 | 92 | 87 |
| CDK2/cyclinE(h) | 106 | 112 | 94 | 83 | 19 |
| CDK3/cyclinE(h) | 106 | 104 | 94 | 92 | 8 |
| CDK5/p25(h) | 114 | 97 | 89 | 92 | 66 |
| CDK5/p35(h) | 94 | 92 | 79 | 76 | 59 |
| CDK6/cyclinD3(h) | 103 | 100 | 86 | 85 | 23 |
| CDK7/cyclinH/MAT1(h) | 89 | 67 | 65 | 47 | 15 |
| CDK9/cyclin T1(h) | 228 | 103 | 91 | 235 | 6 |
| CHK1(h) | 97 | 115 | 91 | 87 | 65 |
| CHK2(h) | 104 | 105 | 66 | 54 | 13 |
| CHK2(I157T)(h) | 97 | 85 | 43 | 41 | 3 |
| CHK2(R145W)(h) | 97 | 81 | 33 | 31 | 3 |
| CK1γ1(h) | 110 | 98 | 111 | 116 | 109 |
| CK1γ2(h) | 119 | 104 | 123 | 114 | 119 |
| CK1γ3(h) | 105 | 96 | 125 | 115 | 114 |
| CK1δ(h) | 115 | 92 | 92 | 93 | 78 |
| CK2(h) | 90 | 83 | 90 | 101 | 93 |
| CK2α2(h) | 104 | 88 | 105 | 96 | 103 |
| CLK2(h) | 88 | 97 | 103 | 116 | 116 |
| CLK3(h) | 108 | 76 | 61 | 84 | 76 |
| cKit(h) | 95 | 110 | 53 | 43 | 45 |
| cKit(D816V)(h) | 117 | 118 | 60 | 35 | 30 |
| cKit(D816H)(h) | 79 | 106 | 126 | 143 | 194 |
| cKit(V560G)(h) | 94 | 115 | 102 | 124 | 198 |
| cKit(V654A)(h) | 69 | 113 | 134 | 150 | 223 |
| CSK(h) | 70 | 33 | 49 | 16 | 2 |
| c-RAF(h) | 97 | 115 | 107 | 102 | 19 |
| cSRC(h) | 70 | 32 | 26 | 14 | 30 |
| DAPK1(h) | 97 | 113 | 46 | 36 | 0 |
| DAPK2(h) | 41 | 92 | 32 | 16 | 3 |
| DCAMKL2(h) | 146 | 131 | 81 | 70 | 56 |
| DDR2(h) | 105 | 104 | 94 | 95 | 79 |

TABLE 1-continued

Kinase Profiling Assay

| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| DMPK(h) | 60 | 66 | 59 | 54 | 12 |
| DRAK1(h) | 47 | 34 | 14 | 14 | 8 |
| DYRK2(h) | 99 | 142 | 155 | 195 | 127 |
| eEF-2K(h) | 113 | 136 | 91 | 43 | 43 |
| EGFR(h) | 95 | 83 | 21 | 16 | -1 |
| EGFR(L858R)(h) | 76 | 120 | N/D | 52 | 26 |
| EGFR(L861Q)(h) | 53 | 74 | 25 | 22 | 15 |
| EGFR(T790M)(h) | 106 | 113 | 100 | 106 | 70 |
| EGFR(T790M,L858R)(h) | 93 | 108 | 85 | 78 | 53 |
| EphA1(h) | 114 | 136 | 73 | 61 | 40 |
| EphA2(h) | 58 | 95 | 31 | 17 | N/D |
| EphA3(h) | 107 | 117 | 6 | 12 | 33 |
| EphA4(h) | 110 | 127 | 88 | 65 | 48 |
| EphA5(h) | 110 | 123 | 18 | 24 | 42 |
| EphA7(h) | 193 | 220 | 159 | 222 | 189 |
| EphA8(h) | 181 | 133 | 93 | 146 | 337 |
| EphB2(h) | 68 | 128 | 18 | 22 | 70 |
| EphB1(h) | 99 | 95 | 44 | 58 | 37 |
| EphB3(h) | 109 | 128 | 62 | 47 | 79 |
| EphB4(h) | 62 | 131 | 44 | 28 | 38 |
| ErbB4(h) | 73 | 82 | 40 | 0 | 2 |
| FAK(h) | 98 | 110 | 111 | 96 | 94 |
| Fer(h) | 117 | 101 | 130 | 108 | 196 |
| Fes(h) | 44 | 74 | 20 | 16 | 23 |
| FGFR1(h) | 120 | 97 | 55 | 59 | 18 |
| FGFR1(V561M)(h) | 108 | 72 | 74 | 74 | 113 |
| FGFR2(h) | 49 | 73 | 14 | 18 | 12 |
| FGFR2(N549H)(h) | 95 | 104 | 116 | 112 | 105 |
| FGFR3(h) | 73 | 208 | 102 | 0 | 10 |
| FGFR4(h) | 67 | 75 | 28 | 19 | 3 |
| Fgr(h) | 54 | 71 | 60 | 47 | 109 |
| Flt1(h) | 109 | 96 | 69 | 48 | 27 |
| Flt3(D835Y)(h) | 120 | 115 | 80 | 71 | 65 |
| Flt3(h) | 104 | 99 | 84 | 18 | 17 |
| Flt4(h) | 135 | 105 | 83 | 89 | 73 |
| Fms(h) | 89 | 92 | 45 | 37 | 14 |
| Fms(Y969C)(h) | 126 | 88 | 72 | 91 | N/D |

TABLE 1-continued

Kinase Profiling Assay

| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
|---|---|---|---|---|---|
| Fyn(h) | 71 | 75 | 74 | 54 | 83 |
| GCK(h) | 98 | 99 | 70 | 66 | 30 |
| GRK5(h) | 117 | 135 | 136 | 131 | 116 |
| GRK6(h) | 131 | 132 | 147 | 141 | 174 |
| GRK7(h) | 111 | 124 | 122 | 100 | 93 |
| GSK3α(h) | 183 | 119 | 157 | 164 | 175 |
| GSK3β(h) | 113 | 132 | 205 | 202 | 238 |
| Haspin(h) | 127 | 71 | 48 | 36 | 25 |
| Hck(h) | 354 | 107 | 72 | 72 | 78 |
| Hck(h) activated | 58 | 100 | 82 | 81 | 67 |
| HIPK1(h) | 94 | 115 | 74 | 91 | 47 |
| HIPK2(h) | 98 | 102 | 73 | 90 | 38 |
| HIPK3(h) | 105 | 105 | 93 | 105 | 85 |
| IGF-1R(h) | 102 | 49 | 119 | 90 | 117 |
| IGF-1R(h), activated | 126 | 94 | 80 | 77 | 45 |
| IKKα(h) | 108 | 104 | 93 | 87 | 50 |
| IKKβ(h) | 105 | 109 | 84 | 84 | 71 |
| IR(h) | 112 | 90 | 96 | 85 | 95 |
| IR(h), activated | 127 | 105 | 79 | 59 | 90 |
| IRR(h) | 85 | 69 | 8 | 8 | 10 |
| IRAK1(h) | 97 | 101 | 95 | 93 | 5 |
| IRAK4(h) | 100 | 110 | 59 | 59 | 3 |
| Itk(h) | 99 | 98 | 77 | 63 | 7 |
| JAK2(h) | 89 | 131 | 133 | 119 | 49 |
| JAK3(h) | 150 | 117 | 121 | 122 | 95 |
| JNK1α1(h) | 91 | 106 | 97 | 98 | 109 |
| JNK2α2(h) | 114 | 109 | 98 | 96 | 81 |
| JNK3(h) | 104 | 90 | 89 | 70 | 171 |
| KDR(h) | 100 | 110 | 101 | 94 | 15 |
| Lck(h) | 346 | 113 | -2 | 228 | 359 |
| Lck(h) activated | 106 | 90 | 243 | 216 | 76 |
| LIMK1(h) | 103 | 109 | 88 | 92 | 87 |
| LKB1(h) | 111 | 99 | 101 | 89 | 51 |
| LOK(h) | 37 | 67 | 37 | 18 | 7 |
| Lyn(h) | 113 | 98 | 69 | 3 | 31 |
| MAPK1(h) | 108 | 97 | 107 | 100 | 102 |
| MAPK2(h) | 98 | 105 | 98 | 93 | 60 |

TABLE 1-continued

| Kinase Profiling Assay | | | | | |
|---|---|---|---|---|---|
| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
| MAPKAP-K2(h) | 19 | 35 | 5 | 5 | 9 |
| MAPKAP-K3(h) | 27 | 39 | 3 | 7 | 9 |
| MEK1(h) | 86 | 116 | 77 | 77 | 21 |
| MARK1(h) | 109 | 102 | 132 | 120 | 110 |
| MELK(h) | 74 | 59 | 16 | 17 | 0 |
| Mer(h) | 47 | 90 | 52 | 50 | 17 |
| Met(h) | 104 | 71 | 65 | 62 | 27 |
| Met(D1246H)(h) | 99 | 139 | 125 | 68 | 150 |
| Met(D1246N)(h) | 114 | 149 | 82 | 31 | 90 |
| Met(M1268T)(h) | 114 | 143 | 255 | 265 | 239 |
| Met(Y1248C)(h) | 77 | 141 | 84 | 36 | 73 |
| Met(Y1248D)(h) | 87 | 118 | 102 | 31 | 218 |
| Met(Y1248H)(h) | 88 | 153 | 117 | 63 | 126 |
| MINK(h) | 96 | 103 | 48 | 52 | 5 |
| MKK6(h) | 74 | 98 | 48 | 44 | 18 |
| MKK7β(h) | 137 | 117 | 100 | 94 | 102 |
| MLCK(h) | 85 | 103 | 2 | 1 | 0 |
| MLK1(h) | 77 | 84 | 40 | 33 | 43 |
| Mnk2(h) | 94 | 106 | 89 | 86 | 6 |
| MRCKα(h) | 98 | 103 | 104 | 97 | 5 |
| MRCKβ(h) | 103 | 102 | 83 | 71 | -10 |
| MSK1(h) | 52 | 50 | 32 | 28 | 8 |
| MSK2(h) | 105 | 88 | 56 | 52 | 14 |
| MSSK1(h) | 82 | 100 | 77 | 75 | 22 |
| MST1(h) | 85 | 72 | 14 | 6 | 3 |
| MST2(h) | 98 | 104 | 19 | 11 | 2 |
| MST3(h) | 104 | 95 | 45 | 36 | 4 |
| mTOR(h) | 102 | 110 | 91 | 93 | 135 |
| mTOR/FKBP12(h) | 117 | 118 | 145 | 125 | 140 |
| MuSK(h) | 85 | 106 | 93 | 93 | 27 |
| NEK2(h) | 102 | 97 | 78 | 61 | 0 |
| NEK3(h) | 100 | 100 | 92 | 85 | 20 |
| NEK6(h) | 109 | 98 | 82 | 85 | 49 |
| NEK7(h) | 97 | 96 | 84 | 87 | 89 |
| NEK11(h) | 102 | 95 | 53 | 33 | 2 |
| NLK(h) | 100 | 106 | 87 | 90 | 19 |
| p70S6K(h) | 89 | 84 | 35 | 33 | 3 |

TABLE 1-continued

Kinase Profiling Assay

| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
|---|---|---|---|---|---|
| PAK2(h) | 71 | 69 | 65 | 59 | 44 |
| PAK4(h) | 92 | 98 | 94 | 89 | 86 |
| PAK3(h) | N/D | 50 | 140 | 121 | 102 |
| PAK5(h) | 97 | 100 | 110 | 117 | 125 |
| PAK6(h) | 121 | 105 | 104 | 100 | 107 |
| PAR-1Bα(h) | 62 | 110 | 113 | 109 | 97 |
| PASK(h) | 81 | 60 | 29 | 28 | 9 |
| PDGFRα(h) | 104 | 108 | 65 | 40 | 40 |
| PDGFRα(D842V)(h) | 103 | 107 | 114 | 118 | 170 |
| PDGFRα(V561D)(h) | 58 | 106 | 82 | 100 | 146 |
| PDGFRβ(h) | 116 | 137 | 81 | 53 | 40 |
| PDK1(h) | 144 | 143 | 135 | 159 | 178 |
| PhKγ2(h) | 62 | 86 | 46 | 38 | 16 |
| Pim-1(h) | 44 | 18 | 8 | 7 | 0 |
| Pim-2(h) | 117 | 74 | 76 | 92 | 46 |
| Pim-3(h) | 98 | 94 | 80 | 80 | 37 |
| PKA(h) | 138 | 110 | 119 | 119 | 118 |
| PKBα(h) | 140 | 110 | 57 | 67 | 30 |
| PKBβ(h) | 284 | 250 | 84 | 98 | 21 |
| PKBγ(h) | 105 | 103 | 20 | 41 | 20 |
| PKCα(h) | 94 | 100 | 89 | 86 | 3 |
| PKCβI(h) | 88 | 98 | 78 | 78 | 1 |
| PKCβII(h) | 102 | 100 | 82 | 75 | 3 |
| PKCγ(h) | 94 | 101 | 89 | 79 | 6 |
| PKCδ(h) | 100 | 101 | 101 | 90 | 61 |
| PKCε(h) | 102 | 98 | 79 | 59 | 23 |
| PKCη(h) | 105 | 101 | 103 | 98 | 45 |
| PKCτ(h) | 110 | 97 | 68 | 46 | 7 |
| PKCμ(h) | 79 | 73 | 22 | 14 | 10 |
| PKCθ(h) | 102 | 101 | 88 | 76 | 62 |
| PKCζ(h) | 82 | 98 | 81 | 75 | 7 |
| PKD2(h) | 84 | 78 | 33 | 25 | 10 |
| PKG1α(h) | 82 | 70 | 64 | 58 | 25 |
| PKG1β(h) | 71 | 57 | 50 | 53 | 24 |
| Plk1(h) | 109 | 128 | 115 | 119 | 104 |
| Plk3(h) | 107 | 107 | 127 | 129 | 122 |
| PRAK(h) | 159 | 115 | 128 | 118 | 95 |

TABLE 1-continued

Kinase Profiling Assay

| | MMI-0100 (SEQ ID NO: 1) (100 µM) | MMI-0200 (SEQ ID NO: 19) (100 µM) | MMI-0300 (SEQ ID NO: 3) (100 µM) | MMI-0400 (SEQ ID NO: 4) (100 µM) | MMI-0500 (SEQ ID NO: 7) (100 µM) |
|---|---|---|---|---|---|
| PRK2(h) | 72 | 74 | 33 | 27 | 7 |
| PrKX(h) | 84 | 112 | 61 | 76 | 57 |
| PTK5(h) | 135 | 108 | 132 | 129 | 96 |
| Pyk2(h) | 113 | 127 | 47 | 34 | 46 |
| Ret(h) | 108 | 96 | 140 | 145 | 174 |
| Ret(V804L)(h) | 113 | 100 | 79 | 73 | 20 |
| Ret(V804M)(h) | 92 | 105 | 95 | 87 | 36 |
| RIPK2(h) | 92 | 98 | 97 | 98 | 30 |
| ROCK-I(h) | 99 | 117 | 79 | 73 | 17 |
| ROCK-II(h) | 102 | 85 | 74 | 77 | 2 |
| Ron(h) | 117 | 120 | 93 | 79 | 46 |
| Ros(h) | 107 | 86 | 95 | 99 | 150 |
| Rse(h) | 109 | 88 | 88 | 89 | 63 |
| Rsk1(h) | 86 | 102 | 46 | 54 | 34 |
| Rsk2(h) | 65 | 101 | 51 | 38 | 14 |
| Rsk3(h) | 76 | 109 | 76 | 71 | 23 |
| Rsk4(h) | 99 | 125 | 90 | 91 | 29 |
| SAPK2a(h) | 110 | 107 | 90 | 85 | 52 |
| SAPK2a(T106M)(h) | 101 | 100 | 97 | 99 | 32 |
| SAPK2b(h) | 99 | 95 | 81 | 82 | 42 |
| SAPK3(h) | 106 | 97 | 84 | 79 | 24 |
| SAPK4(h) | 98 | 106 | 96 | 91 | 48 |
| SGK(h) | 128 | 115 | 48 | 54 | 2 |
| SGK2(h) | 103 | 119 | 56 | 98 | -1 |
| SGK3(h) | 95 | 58 | 10 | 8 | -3 |
| SIK(h) | 113 | 102 | 66 | 68 | 40 |
| Snk(h) | 94 | 109 | 114 | 131 | 122 |
| Src(1-530)(h) | 95 | 75 | 23 | 19 | 21 |
| Src(T341M)(h) | 98 | 56 | 70 | 76 | 59 |
| SRPK1(h) | 69 | 93 | 90 | 96 | 80 |
| SRPK2(h) | 92 | 100 | 106 | 97 | 80 |
| STK33(h) | 99 | 98 | 45 | 52 | 16 |
| Syk(h) | 45 | 36 | 24 | 9 | 5 |
| TAK1(h) | 116 | 124 | 122 | 177 | N/D |
| TAO1(h) | 99 | 105 | 82 | 73 | 24 |
| TAO2(h) | 95 | 93 | 70 | 74 | 15 |
| TAO3(h) | 45 | 102 | 77 | 67 | 12 |

TABLE 1-continued

Kinase Profiling Assay

| | MMI-0100 (SEQ ID NO: 1) (100 μM) | MMI-0200 (SEQ ID NO: 19) (100 μM) | MMI-0300 (SEQ ID NO: 3) (100 μM) | MMI-0400 (SEQ ID NO: 4) (100 μM) | MMI-0500 (SEQ ID NO: 7) (100 μM) |
|---|---|---|---|---|---|
| TBK1(h) | 106 | 98 | 37 | 39 | 16 |
| Tec(h)activated | 100 | 77 | 56 | 29 | 33 |
| Tie2(h) | 28 | 53 | 26 | 21 | 22 |
| Tie2(R849W)(h) | 102 | 89 | 117 | 108 | 106 |
| Tie2(Y897S)(h) | 99 | 85 | 83 | 87 | 80 |
| TLK2(h) | 113 | 129 | 114 | 151 | 133 |
| TrkA(h) | 74 | N/D | 25 | 17 | 24 |
| TrkB(h) | 4 | 7 | 5 | 8 | 12 |
| TSSK1(h) | 99 | 98 | 79 | 79 | 46 |
| TSSK2(h) | 107 | 91 | 98 | 94 | 92 |
| Txk(h) | 87 | 98 | 48 | 37 | 10 |
| ULK2(h) | 123 | 132 | 122 | 131 | 124 |
| ULK3(h) | 142 | 164 | 167 | 147 | 177 |
| WNK2(h) | 95 | 94 | 64 | 54 | 8 |
| WNK3(h) | 100 | 97 | 77 | 74 | 9 |
| VRK2(h) | 112 | 109 | 161 | 185 | 169 |
| Yes(h) | 49 | 93 | 67 | 14 | N/D |
| ZAP-70(h) | 79 | 58 | 75 | 33 | 1 |
| ZIPK(h) | 80 | 67 | 28 | 13 | 1 |

N/D: % activity could not be determined as the duplicates.
MMI-0100: YARAAARQARAKALARQLGVAA (SEQ ID NO: 1)
MMI-0200: YARAAARQARAKALNRQLGVA (SEQ ID NO: 19)
MMI-0300: FAKLAARLYRKALARQLGVAA (SEQ ID NO: 3)
MMI-0400: KAFAKLAARLYRKALARQLGVAA (SEQ ID NO: 4)
MMI-0500: HRRIKAWLKKIKALARQLGVAA (SEQ ID NO: 7)

According to some embodiments, inhibitory profiles of MMI-0100 (SEQ ID NO: 1) and its functional equivalents in vivo depend on dosages, routes of administration, and cell types responding to the inhibitors.

According to some embodiments, the pharmaceutical formulation inhibits less than 65% of the kinase activity of the other selected kinase(s). According to some embodiments, the pharmaceutical formulation inhibits less than 60% of the kinase activity of the other selected kinase(s). According to some embodiments, the pharmaceutical formulation inhibits less than 55% of the kinase activity of the other selected kinase(s). According to another embodiment, the pharmaceutical formulation inhibits less than 50% of the kinase activity of the other selected kinase(s). According to some embodiments, the pharmaceutical formulation inhibits less than 45% of the kinase activity of the other selected kinase(s). According to another embodiment, the pharmaceutical formulation inhibits less than 40% of the kinase activity of the other selected kinase(s). According to some embodiments, the pharmaceutical formulation inhibits less than 35% of the kinase activity of the other selected kinase(s). According to some embodiments, the pharmaceutical formulation inhibits less than 30% of the kinase activity of the other selected kinase(s). According to some embodiments, the pharmaceutical formulation inhibits less than 25% of the kinase activity of the other selected kinase(s). According to another embodiment, the pharmaceutical formulation inhibits less than 20% of the kinase activity of the other selected kinase(s). According to another embodiment, the pharmaceutical formulation inhibits less than 15% of the kinase activity of the other selected kinase(s). According to another embodiment, the pharmaceutical formulation inhibits less than 10% of the kinase activity of the other selected kinase(s). According to another embodiment, the pharmaceutical formulation inhibits less than 5% of the kinase activity of the other selected kinase(s). According to another embodiment, the pharmaceutical formulation increases the kinase activity of the other selected kinases.

According to the embodiments of the immediately preceding paragraph, the one or more other selected kinase that is not substantially inhibited is selected from the group of Ca2+/calmodulin-dependent protein kinase II (CaMKII, including its subunit CaMKIIδ), Proto-oncogene serine/threonine-protein kinase (PIM-1), cellular-Sarcoma (c-SRC), Spleen Tyrosine Kinase (SYK), c-Src Tyrosine Kinase (CSK), and Insulin-like Growth Factor 1 Receptor (IGF-1R).

According to some embodiments, kinases that are substantially inhibited (i.e., kinases whose kinase activity is inhibited by at least 65%) by at least one MMI inhibitor (i.e., at least one of MMI-0100 (SEQ ID NO: 1), MMI-0200 (SEQ ID NO: 19), MMI-0300 (SEQ ID NO: 3), MMI-0400 (SEQ ID NO: 4), and MMI-0500 (SEQ ID NO: 7)) of the present invention is selected from the group consisting of: Abelson murine leukemia viral oncogene homolog 1 (Abl), Abelson murine leukemia viral oncogene homolog 1 (T3151) (Abl (T3151)), Abelson murine leukemia viral oncogene homolog 1 (Y253F) (Abl (Y253F)), Anaplastic lymphoma kinase (ALK), Abelson-related gene (Arg), 5′-AMP-activated protein kinase catalytic subunit alpha-1 (AMPKα1), 5′-AMP-activated protein kinase catalytic subunit alpha-2 (AMPKα2), AMPK-related protein kinase 5 (ARK5), Apoptosis signal regulating kinase 1 (ASK1), Aurora kinase B (Aurora-B), AXL receptor tyrosine kinase (Axl), Bone marrow tyrosine kinase gene in chromosome X protein (Bmx), Breast tumor kinase (BRK), Bruton's tyrosine kinase (BTK), Bruton's tyrosine kinase (R28H) (BTK (R28H)), $Ca^{2+}$/calmodulin-dependent protein kinase I (CaMKI), $Ca^{2+}$/calmodulin-dependent protein kinase IIβ (CaMIIβ), $Ca^{2+}$/calmodulin-dependent protein kinase IIγ (CaMKIIγ), $Ca^{2+}$/calmodulin-dependent protein kinase δ (CaMKIδ), $Ca^{2+}$/calmodulin-dependent protein kinase IIδ (CaMKIIδ), $Ca^{2+}$/calmodulin-dependent protein kinase IV (CaMKIV), Cell devision kinase 2 (CDK2/cyclinE), Cell devision kinase 3 (CDK3/cyclinE), Cell devision kinase 6 (CDK6/cyclinD3), Cell devision kinase 7 (CDK7/cyclinH/MAT1), Cell devision kinase 9 (CDK9/cyclin T1), Checkpoint kinase 2 (CHK2), Checkpoint kinase 2 (1157T) (CHK2 (1157T)), Checkpoint kinase 2 (R145W) (CHK2 (R145W)), Proto-oncogene tyrosine-protein kinase cKit (D816V) (cKit (D816V)), C-src tyrosine kinase (CSK), Raf proto-oncogene serine/threonine protein kinase (c-RAF), Proto-oncogene tyrosine-protein kinase (cSRC), Death-associated protein kinase 1 (DAPK1), Death-associated protein kinase 2 (DAPK2), Dystrophia myotonica-protein kinase (DMPK), DAP kinase-related apoptosis-inducing protein kinase 1 (DRAK1), Epidermal growth factor receptor (EGFR), Epidermal growth factor receptor (EGFR L858R), Epidermal growth factor receptor L861Q (EGFR (L861Q)), Eph receptor A2 (EphA2) (EphA2), Eph receptor A3 (EphA3), Eph receptor A5 (EphAS), Eph receptor B2 (EphB2), Eph receptor B4 (EphB4), Erythroblastic leukemia viral oncogene homolog 4 (ErbB4), c-Fes protein tyrosine kinase (Fes), Fibroblast growth factor receptor 2 (FGFR2), Fibroblast growth factor receptor 3 (FGFR3), Fibroblast growth factor receptor 4 (FGFR4), Fms-like tyrosine kinase receptor-3 (Flt3), FMS proto-oncogene (Fms), Haploid germ cell-specific nuclear protein kinase (Haspin), Insulin receptor-related receptor (IRR), Interleukin-1 receptor-associated kinase 1 (IRAK1), Interleukin-1 receptor-associated kinase 4 (IRAK4), IL2-inducible T-cell kinase (Itk), Kinase insert domain receptor (KDR), Lymphocyte cell-specific protein-tyrosine kinase (Lck), Lymphocyte-oriented kinase (LOK), Lyn tyrosine protein kinase (Lyn), MAP kinase-activated protein kinase 2 (MK2), MAP kinase-activated protein kinase 3 (MK3), MEK1, Maternal embryonic leucine zipper kinase (MELK), c-Mer proto-oncogene tyrosine kinase (Mer), c-Met proto-oncogene tyrosine kinase (Met), c-Met proto-oncogene tyrosine kinase D1246N (Met (D1246N)), c-Met proto-oncogene tyrosine kinase Y1248D (Met Y1248D), Misshapen/NIK-related kinase (MINK), MAP kinase 6 (MKK6), Myosin light-chain kinase (MLCK), Mixed lineage kinase 1 (MLK1), MAP kinase signal-integrating kinase 2 (MnK2), Myotonic dystrophy kinase-related CDC42-binding kinase alpha (MRCKα), Myotonic dystrophy kinase-related CDC42-binding kinase beta (MRCKβ), Mitogen- and stress-activated protein kinase 1 (MSK1), Mitogen- and stress-activated protein kinase 2 (MSK2), Muscle-specific serine kinase 1 (MSSK1), Mammalian STE20-like protein kinase 1 (MST1), Mammalian STE20-like protein kinase 2 (MST2), Mammalian STE20-like protein kinase 3 (MST3), Muscle, skeletal receptor tyrosine-protein kinase (MuSK), Never in mitosis A-related kinase 2 (NEK2), Never in mitosis A-related kinase 3 (NEK3), Never in mitosis A-related kinase 11 (NEK11), 70 kDa ribosomal protein S6 kinase 1 (p70S6K), PAS domain containing serine/threonine kinase (PASK), Phosphorylase kinase subunit gamma-2 (PhKγ2), Pim-1 kinase (Pim-1), Protein kinase B alpha (PKBα), Protein kinase B beta (PKBβ), Protein kinase B gamma (PKBγ), Protein kinase C, alpha (PKCα), Protein kinase C, beta1 (PKCβ1), Protein kinase C, beta II (PKCβII), Protein kinase C, gamma (PKCγ), Protein kinase C, epsilon (PKCε), Protein kinase C, iota (PCKι), Protein kinase C, mu (PKCμ), Protein kinase C, zeta (PKCζ), protein kinase D2 (PKD2), cGMP-dependent protein kinase 1 alpha (PKG1α), cGMP-dependent protein kinase 1 beta (PKG1β, Protein-kinase C-related kinase 2 (PRK2), Proline-rich tyrosine kinase 2 (Pyk2), Proto-oncogene tyrosine-protein kinase receptor Ret V804L (Ret (V804L)), Receptor-interacting serine-threonine kinase 2 (RIPK2), Rho-associated protein kinase I (ROCK-I), Rho-associated protein kinase II (ROCK-II), Ribosomal protein S6 kinase 1 (Rsk1), Ribosomal protein S6 kinase 2 (Rsk2), Ribosomal protein S6 kinase 3 (Rsk3), Ribosomal protein S6 kinase 4 (Rsk4), Stress-activated protein kinase 2A T106M (SAPK2a, T106M), Stress-activated protein kinase 3 (SAPK3), Serum/glucocorticoid regulated kinase (SGK), Serum/glucocorticoid regulated kinase 2 (SGK2), Serum/glucocorticoid-regulated kinase 3 (SGK3), Proto-oncogene tyrosine-protein kinase Src 1-530 (Src, 1-530), Serine/threonine-protein kinase 33 (STK33), Spleen tyrosine kinase (Syk), Thousand and one amino acid protein 1 (TAO1), Thousand and one amino acid protein 2 (TAO2), Thousand and one amino acid protein 3 (TAO3), TANK-binding kinase 1 (TBK1), Tec protein tyrosine kinase (Tec), Tunica interna endothelial cell kinase 2 (Tie2), Tyrosine kinase receptor A (TrkA), BDNF/NT-3 growth factors receptor (TrkB), TXK tyrosine kinase (Txk), WNK lysine deficient protein kinase 2 (WNK2), WNK lysine deficient protein kinase 3 (WNK3), Yamaguchi sarcoma viral oncogene homolog 1 (Yes), Zeta-chain (TCR) Associated Protein kinase 70 kDa (ZAP-70), and ZIP kinase (ZIPK).

According to some other embodiments, kinases that are substantially inhibited (i.e., kinases whose kinase activity is inhibited by at least 65%) by at least two MMI inhibitors (i.e., at least two of MMI-0100 (SEQ ID NO: 1), MMI-0200 (SEQ ID NO: 19), MMI-0300 (SEQ ID NO: 3), MMI-0400 (SEQ ID NO: 4), and MMI-0500 (SEQ ID NO: 7)) of the present invention is selected from the group consisting of: Anaplastic lymphoma kinase (ALK), Breast tumor kinase (BRK), Bruton's tyrosine kinase (BTK), $Ca^{2+}$/calmodulin-dependent protein kinase I (including CaMKIδ), $Ca^{2+}$/calmodulin-dependent protein kinase II (CaMKII, including CaMKIIβ, CaMKIIδ and CaMKIIγ), $Ca^{2+}$/calmodulin-dependent protein kinase IV (CaMKIV), Checkpoint kinase 2 (CHK2 (R145W)), Proto-oncogene tyrosine-protein kinase cKit (D816V) (cKit (D816V)), C-src tyrosine kinase (CSK), Proto-oncogene tyrosine-protein kinase (cSRC), Death-associated protein kinase 1 (DAPK1), Death-associated protein kinase 2 (DAPK2), DAP kinase-related apoptosis-inducing protein kinase 1 (DRAK1), Epidermal growth factor receptor (EGFR), Epidermal growth factor receptor L861Q (EGFR (L861Q)), Eph receptor A2 (EphA2), Eph receptor A3 (EphA3), Eph receptor A5 (EphAS), Eph receptor B2 (EphB2), Erythroblastic leukemia viral oncogene homolog 4 (ErbB4), c-Fes protein tyrosine kinase (Fes), Fibroblast growth factor receptor 2 (FGFR2), Fibroblast growth factor receptor 3 (FGFR3), and Fibroblast growth factor receptor 4 (FGFR4), Fms-like tyrosine kinase receptor-3 (Flt3), Insulin receptor-related receptor (IRR), Lymphocyte-oriented kinase (LOK), Lyn tyrosine protein kinase (Lyn), MAP kinase-activated protein kinase 2 (MK2), MAP kinase-activated protein kinase 3 (MK3), Maternal embryonic leucine zipper kinase (MELK), Myosin light-chain kinase (MLCK), Mitogen- and stress-activated protein kinase (MSK1), Mammalian STE20-like protein kinase 1 (MST1), Mammalian STE20-like protein kinase 2 (MST2), Never in mitosis A-related kinase 11(NEK11), 70 kDa ribosomal protein S6 kinase 1 (p70S6K), PAS domain containing serine/threonine kinase (PASK), Pim-1 kinase (Pim-1), Protein kinase B, gamma (PKBγ), Protein kinase C, mu (PKCμ), protein kinase D2 (PKD2), Protein-kinase C-related kinase 2 (PRK2), Serum/glucocorticoid-regulated kinase 3 (SGK3), Proto-oncogene tyrosine-protein kinase Src (Src), Spleen tyrosine kinase (Syk), Tec protein tyrosine kinase (Tec), Tunica interna endothelial cell kinase 2 (Tie2), Tyrosine kinase receptor A (TrkA), BDNF/NT-3 growth factors receptor (TrkB), Zeta-chain (TCR) Associated Protein kinase 70 kDa (ZAP-70), and ZIP kinase (ZIPK).

According to some embodiments, the pharmaceutical formulation comprises a small-molecule inhibitor of MK2, including, but not limited to:

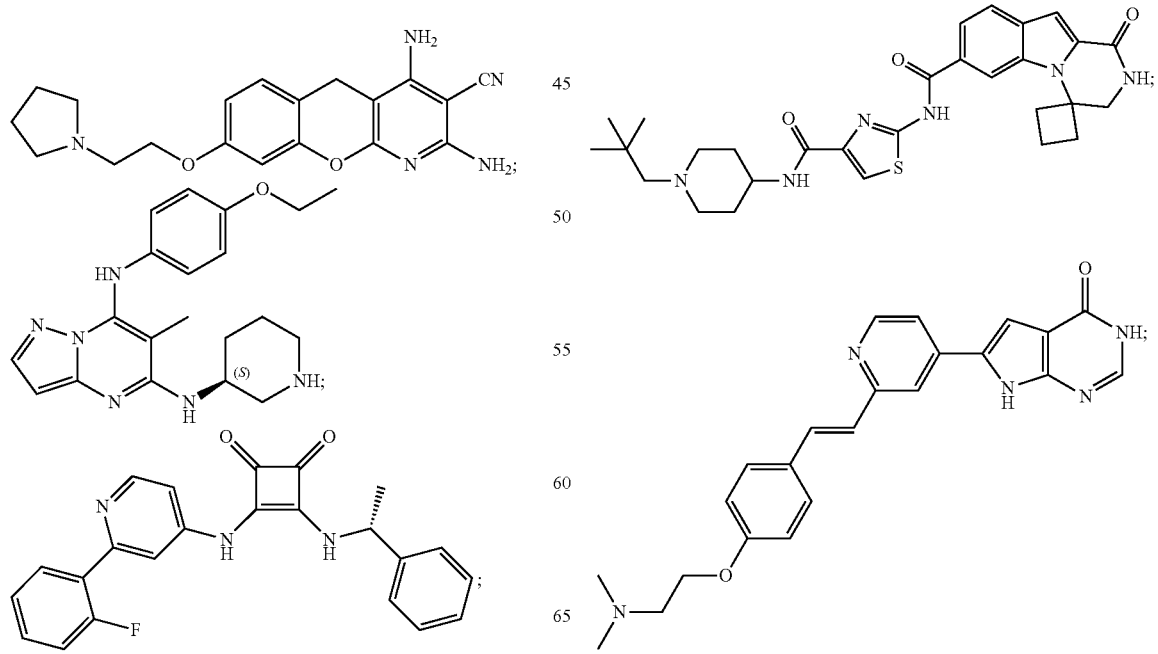

71
-continued
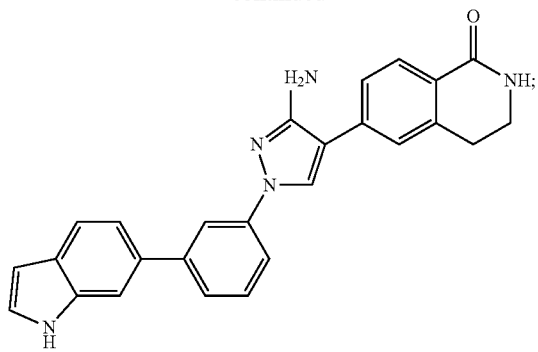
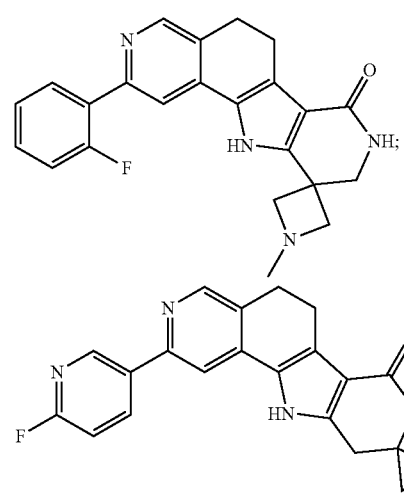
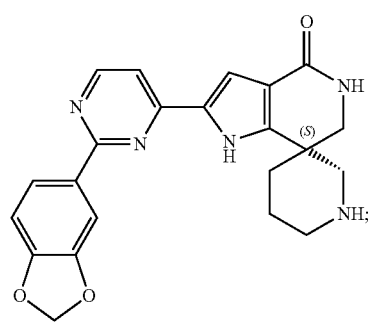
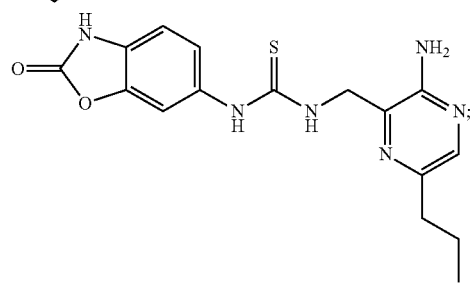
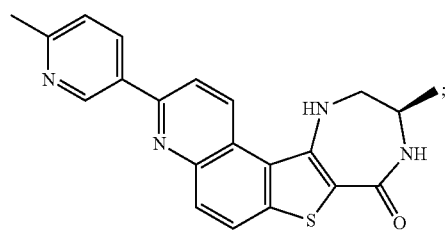
72
-continued
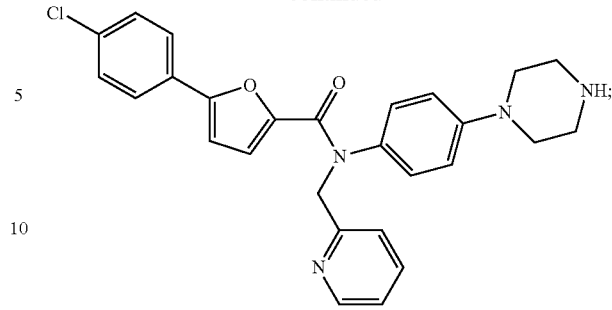
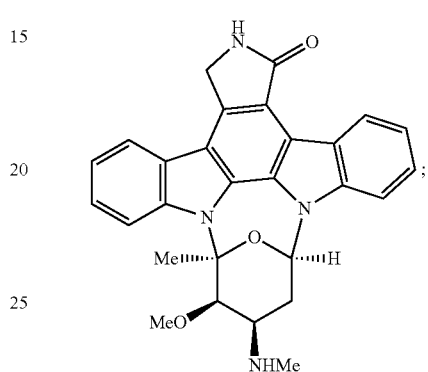
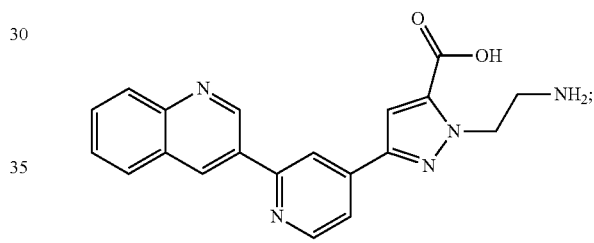
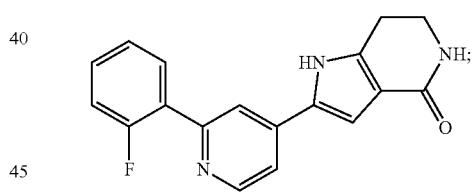
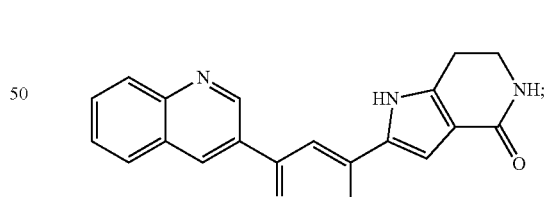
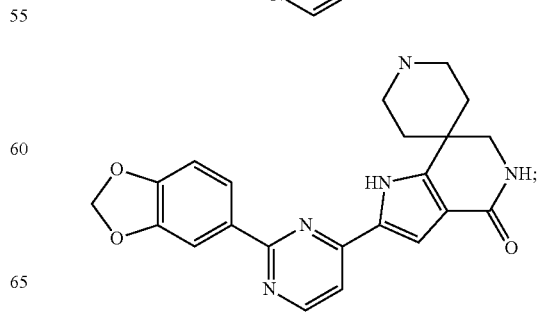

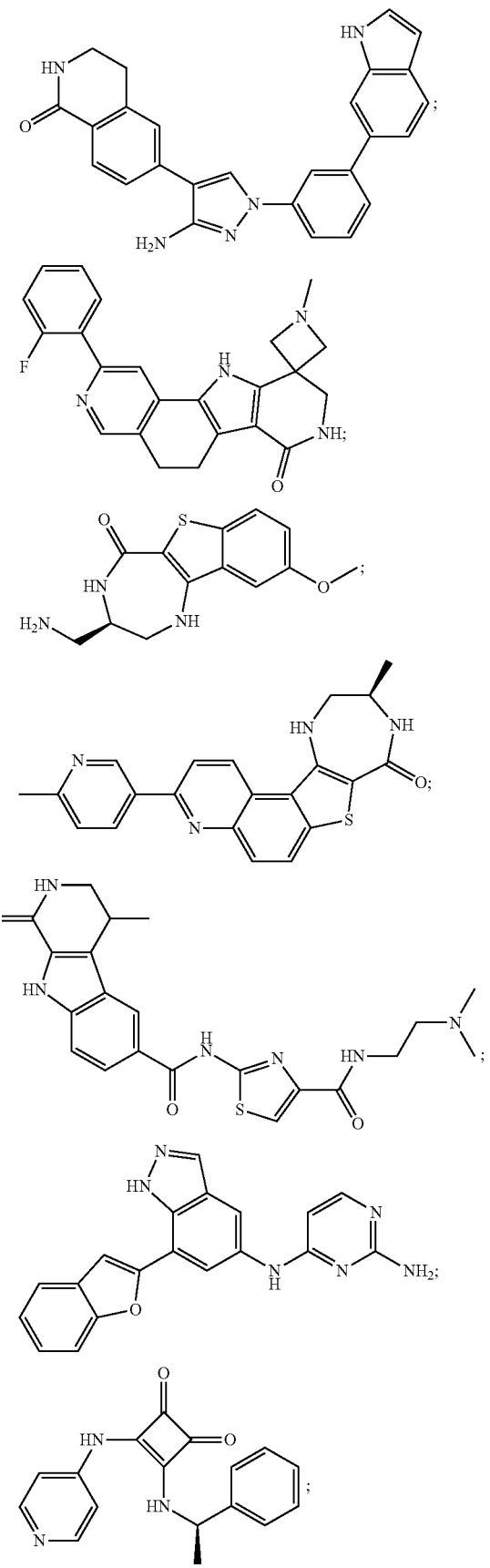

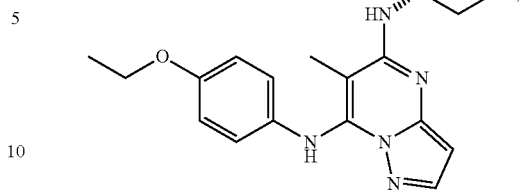

or a combination thereof.

According to some embodiments, the polypeptide of amino acid sequence YARAAARQARAKALARQLGVAA (SEQ ID NO: 1) and its functional equivalents are effective to reduce a level of TGF-β expression, infiltration of immunomodulatory cells, or both.

According to another embodiment, pharmaceutical formulations of the described invention are effective to reduce infiltration of one or more types of inflammatory or stem cells, including, without limitation, monocytes, fibrocytes, macrophages, lymphocytes, and mast or dendritic cells, into the wound.

According to another embodiment, the cell type is characterized by expression of cell surface marker(s) including, without limitation, CD4 and/or CD8.

According to some embodiments, the therapeutic amount of the therapeutic inhibitor peptide of the pharmaceutical formulation is of an amount from about 0.000001 mg/kg body weight to about 100 mg/kg body weight. According to another embodiment, the therapeutic amount of the therapeutic inhibitory peptide of the pharmaceutical formulation is of an amount from about 0.00001 mg/kg body weight to about 100 mg/kg body weight. According to another embodiment, the therapeutic amount of the therapeutic inhibitory peptide of the pharmaceutical formulation is of an amount from about 0.0001 mg/kg body weight to about 100 mg/kg body weight. According to another embodiment, the therapeutic amount of the therapeutic inhibitory peptide of the pharmaceutical formulation is of an amount from about 0.001 mg/kg body weight to about 10 mg/kg body weight. According to another embodiment, the therapeutic amount of the therapeutic inhibitory peptide of the pharmaceutical formulation is of an amount from about 0.01 mg/kg body weight to about 10 mg/kg body weight. According to another embodiment, the therapeutic amount of the therapeutic inhibitory peptide of the pharmaceutical formulation is of an amount from about 0.1 mg/kg (or 100 mg/kg) body weight to about 10 mg/kg body weight. According to another embodiment, the therapeutic amount of the therapeutic inhibitory peptide of the pharmaceutical formulation is of an amount from about 1 mg/kg body weight to about 10 mg/kg body weight. According to another embodiment, the therapeutic amount of the therapeutic inhibitory peptide of the pharmaceutical formulation is of an amount from about 10 mg/kg body weight to about 100 mg/kg body weight. According to another embodiment, the therapeutic amount of the therapeutic inhibitory peptide of the pharmaceutical formulation is of an amount from about 2 mg/kg body weight to about 10 mg/kg body weight. According to another embodiment, the therapeutic amount of the therapeutic inhibitory peptide of the pharmaceutical formulation is of an amount from about 3 mg/kg body weight to about 10 mg/kg body weight. According to another embodiment, the therapeutic amount of the therapeutic inhibitory peptide of the pharmaceutical formulation is of an amount from about 4 mg/kg body weight to about 10 mg/kg body weight. According to another embodiment, the therapeutic amount of the therapeutic inhibitory peptide of the pharmaceutical formulation is of an amount from about 5 mg/kg body weight to about 10 mg/kg body weight. According to another embodiment, the therapeutic amount of the therapeutic inhibitory peptide of the pharmaceutical formulation is of an amount from about 60 mg/kg body weight to about 100 mg/kg body weight. According to another embodiment, the therapeutic amount of the therapeutic inhibitory peptide of the pharmaceutical formulation is of an amount from about 70 mg/kg body weight to about 100 mg/kg body weight. According to another embodiment, the therapeutic amount of the therapeutic inhibitory peptide of the pharmaceutical formulation is of an amount from about 80 mg/kg body weight to about 100 mg/kg body weight. According to another embodiment, the therapeutic amount of the therapeutic inhibitory peptide of the pharmaceutical formulation is of an amount from about 90 mg/kg body weight to about 100 mg/kg body weight. According to another embodiment, the therapeutic amount of the therapeutic inhibitor peptide of the pharmaceutical formulation is of an amount from about 0.000001 mg/kg body weight to about 90 mg/kg body weight. According to another embodiment, the therapeutic amount of the therapeutic inhibitor peptide of the pharmaceutical formulation is of an amount from about 0.000001 mg/kg body weight to about 80 mg/kg body weight. According to another embodiment, the therapeutic amount of the therapeutic inhibitor peptide of the pharmaceutical formulation is of an amount from about 0.000001 mg/kg body weight to about 70 mg/kg body weight. According to another embodiment, the therapeutic amount of the therapeutic inhibitor peptide of the pharmaceutical formulation is of an amount from about 0.000001 mg/kg body weight to about 60 mg/kg body weight. According to another embodiment, the therapeutic amount of the therapeutic inhibitor peptide of the pharmaceutical formulation is of an amount from about 0.000001 mg/kg body weight to about 50 mg/kg body weight. According to another embodiment, the therapeutic amount of the therapeutic inhibitor peptide of the pharmaceutical formulation is of an amount from about 0.000001 mg/kg body weight to about 40 mg/kg body weight. According to another embodiment, the therapeutic amount of the therapeutic inhibitor peptide is of an amount from about 0.000001 mg/kg body weight to about 30 mg/kg body weight. According to another embodiment, the therapeutic amount of the therapeutic inhibitor peptide of the pharmaceutical formulation is of an amount from about 0.000001 mg/kg body weight to about 20 mg/kg body weight. According to another embodiment, the therapeutic amount of the therapeutic inhibitor peptide of the pharmaceutical formulation is of an amount from about 0.000001 mg/kg body weight to about 10 mg/kg body weight. According to another embodiment, the therapeutic amount of the therapeutic inhibitor peptide of the pharmaceutical formulation is of an amount from about 0.000001 mg/kg body weight to about 1 mg/kg body weight. According to another embodiment, the therapeutic amount of the therapeutic inhibitor peptide of the pharmaceutical formulation is of an amount from about 0.000001 mg/kg body weight to about 0.1 mg/kg body weight. According to another embodiment, the therapeutic amount of the therapeutic inhibitor peptide of the pharmaceutical formulation is of an amount from about 0.000001 mg/kg body weight to about 0.1 mg/kg body weight. According to another embodiment, the therapeutic amount of the therapeutic inhibitor peptide of the pharmaceutical formulation is of an amount from about 0.000001 mg/kg body weight to about 0.01 mg/kg body weight. According to another embodiment, the therapeutic amount of the therapeutic inhibitor peptide of the pharmaceutical formulation is of an amount from about 0.000001 mg/kg body weight to about 0.001 mg/kg body weight. According to another embodiment, the therapeutic amount of the therapeutic inhibitor peptide of the pharmaceutical formulation is of an amount from about 0.000001 mg/kg body weight to about 0.0001 mg/kg body weight. According to another embodiment, the therapeutic amount of the therapeutic inhibitor peptide of the pharmaceutical formulation is of an amount from about 0.000001 mg/kg body weight to about 0.00001 mg/kg body weight.

According to some other embodiments, the therapeutic dose of the therapeutic inhibitor peptide of the pharmaceutical formulation ranges from 1 µg/kg/day to 25 µg/kg/day. According to some other embodiments, the therapeutic dose of the therapeutic inhibitor peptide of the pharmaceutical formulation ranges from 1 µg/kg/day to 2 µg/kg/day. According to some other embodiments, the therapeutic dose of the therapeutic inhibitor peptide of the pharmaceutical formulation ranges from 2 µg/kg/day to 3 µg/kg/day. According to some other embodiments, the therapeutic dose of the therapeutic inhibitor peptide of the pharmaceutical formulation ranges from 3 µg/kg/day to 4 µg/kg/day. According to some other embodiments, the therapeutic dose of the therapeutic inhibitor peptide of the pharmaceutical ranges from 4 µg/kg/day to 5 µg/kg/day. According to some other embodiments, the therapeutic dose of the therapeutic inhibitor peptide of the pharmaceutical formulation ranges from 5 µg/kg/day to 6 µg/kg/day. According to some other embodiments, the therapeutic dose of the therapeutic inhibitor peptide of the pharmaceutical formulation ranges from 6 µg/kg/day to 7 µg/kg/day. According to some other embodiments, the therapeutic dose of the therapeutic inhibitor peptide of the pharmaceutical formulation ranges from 7 µg/kg/day to 8 µg/kg/day. According to some other embodiments, the therapeutic dose of the therapeutic inhibitor peptide of the pharmaceutical formulation ranges from 8 µg/kg/day to 9 µg/kg/day. According to some other embodiments, the therapeutic dose of the therapeutic inhibitor peptide of the pharmaceutical formulation ranges from 9 µg/kg/day to 10 µg/kg/day. According to some other embodiments, the therapeutic dose of the therapeutic inhibitor peptide of the pharmaceutical formulation ranges from 1 µg/kg/day to 5 µg/kg/day. According to some other embodiments, the therapeutic dose of the therapeutic inhibitor peptide of the pharmaceutical formulation ranges from 5 µg/kg/day to 10 µg/kg/day. According to some other embodiments, the therapeutic dose of the therapeutic inhibitor peptide of the pharmaceutical formulation ranges from 10 µg/kg/day to 15 µg/kg/day. According to some other embodiments, the therapeutic dose of the therapeutic inhibitor peptide of the pharmaceutical formulation ranges from 15 µg/kg/day to 20 µg/kg/day. According to some other embodiments, the therapeutic dose of the therapeutic inhibitor peptide of the pharmaceutical formulation ranges from 25 µg/kg/day to 30 µg/kg/day. According to some other embodiments, the therapeutic dose of the therapeutic inhibitor peptide of the pharmaceutical formulation ranges from 30 µg/kg/day to 35 µg/kg/day. According to some other embodiments, the therapeutic dose of the therapeutic inhibitor peptide of the pharmaceutical formulation ranges from 35 µg/kg/day to 40 µg/kg/day. According to some other embodiments, the therapeutic dose of the therapeutic inhibitor peptide of the pharmaceutical formulation ranges from 40 µg/kg/day to 45 µg/kg/day. According to some other embodiments, the therapeutic dose of the therapeutic inhibitor peptide of the pharmaceutical formulation ranges from 45 µg/kg/day to 50 µg/kg/day. According to some other embodiments, the therapeutic dose of the therapeutic inhibitor peptide of the pharmaceutical formulation ranges from 50 µg/kg/day to 55 µg/kg/day. According to some other embodiments, the therapeutic dose of the therapeutic inhibitor peptide of the pharmaceutical formulation ranges from 55 µg/kg/day to 60 µg/kg/day. According to some other embodiments, the therapeutic dose of the therapeutic inhibitor peptide of the pharmaceutical formulation ranges from 60 µg/kg/day to 65 µg/kg/day. According to some other embodiments, the therapeutic dose of the therapeutic inhibitor peptide of the pharmaceutical formulation ranges from 65 µg/kg/day to 70 µg/kg/day. According to some other embodiments, the therapeutic dose of the therapeutic inhibitor peptide of the pharmaceutical formulation ranges from 70 µg/kg/day to 75 µg/kg/day. According to some other embodiments, the therapeutic dose of the therapeutic inhibitor peptide of the pharmaceutical formulation ranges from 80 µg/kg/day to 85 µg/kg/day. According to some other embodiments, the therapeutic dose of the therapeutic inhibitor peptide of the pharmaceutical formulation ranges from 85 µg/kg/day to 90 µg/kg/day. According to some other embodiments, the therapeutic dose of the therapeutic inhibitor peptide of the pharmaceutical formulation ranges from 90 µg/kg/day to 95 µg/kg/day. According to some other embodiments, the therapeutic dose of the therapeutic inhibitor peptide of the pharmaceutical formulation ranges from 95 µg/kg/day to 100 µg/kg/day.

According to another embodiment, the therapeutic dose of the therapeutic inhibitor peptide of the pharmaceutical formulation is 1 µg/kg/day.

According to another embodiment, the therapeutic dose of the therapeutic inhibitor peptide of the pharmaceutical formulation is 2 µg/kg/day.

According to another embodiment, the therapeutic dose of the therapeutic inhibitor peptide of the pharmaceutical formulation is 3 µg/kg/day.

According to another embodiment, the therapeutic dose of the therapeutic inhibitor peptide of the pharmaceutical formulation is 4 µg/kg/day.

According to another embodiment, the therapeutic dose of the therapeutic inhibitor peptide of the pharmaceutical formulation is 5 µg/kg/day.

According to another embodiment, the therapeutic dose of the therapeutic inhibitor peptide of the pharmaceutical formulation is 6 µg/kg/day.

According to another embodiment, the therapeutic dose of the therapeutic inhibitor peptide of the pharmaceutical formulation is 7 µg/kg/day.

According to another embodiment, the therapeutic dose of the therapeutic inhibitor peptide of the pharmaceutical formulation is 8 µg/kg/day.

According to another embodiment, the therapeutic dose of the therapeutic inhibitor peptide of the pharmaceutical formulation is 9 µg/kg/day.

According to another embodiment, the therapeutic dose of the therapeutic inhibitor peptide of the pharmaceutical formulation is 10 µg/kg/day.

The polypeptide of amino acid sequence YARAAAR-QARAKALARQLGVAA (SEQ ID NO: 1) or a functional equivalent thereof may be administered in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. Pharmaceutically acceptable salts are well-known. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the described invention or may be prepared by separately reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The formulations may be presented conveniently in unit dosage form and may be prepared by methods known in the art of pharmacy. Such methods include the step of bringing into association a therapeutic agent(s), or a pharmaceutically acceptable salt or solvate thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

According to some embodiments, the carrier is a controlled release carrier. The term "controlled release" is intended to refer to any drug-containing formulation in which the manner and profile of drug release from the formulation are controlled. This includes immediate as well as non-immediate release formulations, with non-immediate release formulations including, but not limited to, sustained release and delayed release formulations. According to some embodiments, the controlled release of the pharmaceutical formulation is mediated by changes in temperature. According to some other embodiments, the controlled release of the pharmaceutical formulation is mediated by changes in pH.

Injectable depot forms may be made by forming microencapsulated matrices of a therapeutic agent/drug in biodegradable polymers such as, but not limited to, polyesters (polyglycolide, polylactic acid and combinations thereof), polyester polyethylene glycol copolymers, polyamino-derived biopolymers, polyanhydrides, polyorthoesters, polyphosphazenes, sucrose acetate isobutyrate (SAIB), photopolymerizable biopolymers, naturally-occurring biopolymers, protein polymers, collagen, and polysaccharides. Depending upon the ratio of drug to polymer and the nature of the particular polymer employed, the rate of drug release may be controlled. Such long acting formulations may be formulated with suitable polymeric or hydrophobic materials (for example as an emulsion in acceptable oil) or ion exchange resins, or as sparingly soluble derivatives, for example, as a sparingly soluble salt. Depot injectable formulations also are prepared by entrapping the drug in liposomes or microemulsions which are compatible with body tissues.

According to some embodiments, the carrier is a delayed release carrier. According to another embodiment, the delayed release carrier comprises a biodegradable polymer. According to another embodiment, the biodegradable polymer is a synthetic polymer. According to another embodiment, the biodegradable polymer is a naturally occurring polymer.

According to some embodiments, the carrier is a sustained release carrier. According to another embodiment, the sustained-release carrier comprises a biodegradable polymer. According to another embodiment, the biodegradable polymer is a synthetic polymer. According to another embodiment, the biodegradable polymer is a naturally occurring polymer.

According to some embodiments, the carrier is a short-term release carrier. The term "short-term" release, as used herein, means that an implant is constructed and arranged to deliver therapeutic levels of the active ingredient for about 1, 2, 3, 4, 5, 6, 7, 8, 9, 10, 11, 12, 13, 14, 15, 16, 17, 18, 19, 20, 21, 22, or 23 hours. According to some other embodiments, the short term release carrier delivers therapeutic levels of the active ingredient for about 1, 2, 3, or 4 days.

According to some embodiments, the carrier is a long-term release carrier. The term "long-term" release, as used herein, means that an implant is constructed and arranged to deliver therapeutic levels of the active ingredient for at least about 5, 6, 7, 8, 9, 10, 11, 12, 13, 14, 15, 16, 17, 18, 19, 20, 21, 22, 23, 24, 25, 26, 27, 29, 29, 30, 31, 32, 33, 34, 35, 36, 37, 38, 39, 40, 41, 42, 43, 44, 45, 46, 47, 48, 48, 50, 51, 52, 53, 54, 55, 56, 57, 58, 59, or 60 days. According to another embodiment, the long-term-release carrier comprises a biodegradable polymer. According to another embodiment, the biodegradable polymer is a synthetic polymer.

According to some embodiments, the carrier comprises particles. According to some embodiments, formulations as described herein are contained in the particle. According to some embodiments, formulations as described herein are contained on the particle. According to some embodiments, formulations as described herein are contained both in and on the particle.

The formulations also may contain appropriate adjuvants, including, without limitation, preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

According to some embodiments, the polypeptides of the present invention can be covalently attached to polyethylene glycol (PEG) polymer chains. According to some other embodiments, the polypeptides of the present invention are stapled with hydrocarbons to generate hydrocarbon-stapled peptides that are capable of forming stable alpha-helical structure (Schafmeister, C. et al., J. Am. Chem. Soc., 2000, 122, 5891-5892, incorporated herein by reference in its entirety).

According to some other embodiments, the polypeptides of the present invention are encapsulated or entrapped into microspheres, nanocapsules, liposomes, or microemulsions, or comprises d-amino acids in order to increase stability, to lengthen delivery, or to alter activity of the peptides. These techniques can lengthen the stability and release simultaneously by hours to days, or delay the uptake of the drug by nearby cells.

The formulations of therapeutic agent(s) may be administered in pharmaceutically acceptable solutions, which may routinely contain pharmaceutically acceptable concentrations of salt, buffering agents, preservatives, compatible carriers, adjuvants, and optionally other therapeutic ingredients.

According to some embodiments, the pharmaceutical formulation further comprises at least one additional therapeutic agent.

According to some such embodiments, the additional therapeutic agent comprises EXC001 (an anti-sense RNA against connective tissue growth factor (CTGF)), AZX100 (a phosphopeptide analog of Heat Shock Protein 20 (HSP20)), PRM-151 (recombinant human serum amyloid P/Pentaxin 2), PXL01 (a synthetic peptide derived from human lactoferrin), DSC127 (an angiotensin analog), RXI-109 (a self-delivering RNAi compound that targets connective tissue growth factor (CTGF)), TCA (trichloroacetic acid), Botulium toxin type A, or a combination thereof.

According to another embodiment, the additional therapeutic agent is an anti-inflammatory agent.

According to some embodiments, the anti-inflammatory agent is a steroidal anti-inflammatory agent. The term "steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflucortolone valerate, fluadrenolone, fluclorolone acetonide, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

According to another embodiment, the anti-inflammatory agent is a nonsteroidal anti-inflammatory agent. The term "non-steroidal anti-inflammatory agent" as used herein refers to a large group of agents that are aspirin-like in their action, including, but not limited to, ibuprofen (Advil®), naproxen sodium (Aleve®), and acetaminophen (Tylenol®). Additional examples of non-steroidal anti-inflammatory agents that are usable in the context of the described invention include, without limitation, oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents also may be employed, as well as the dermatologically acceptable salts and esters of these agents. For example, etofenamate, a flufenamic acid derivative, is particularly useful for topical application.

According to another embodiment, the anti-inflammatory agent includes, without limitation, Transforming Growth Factor-beta3 (TGF-β3), an anti-Tumor Necrosis Factor-alpha (TNF-α) agent, or a combination thereof.

According to some embodiments, the additional agent is an analgesic agent. According to some embodiments, the analgesic agent relieves pain by elevating the pain threshold without disturbing consciousness or altering other sensory modalities. According to some such embodiments, the analgesic agent is a non-opioid analgesic. "Non-opioid analgesics" are natural or synthetic substances that reduce pain but are not opioid analgesics. Examples of non-opioid analgesics include, but are not limited to, etodolac, indomethacin, sulindac, tolmetin, nabumetone, piroxicam, acetaminophen, fenoprofen, flurbiprofen, ibuprofen, ketoprofen, naproxen, naproxen sodium, oxaprozin, aspirin, choline magnesium trisalicylate, diflunisal, meclofenamic acid, mefenamic acid, and phenylbutazone. According to some other embodiments, the analgesic is an opioid analgesic. "Opioid analgesics", "opioid", or "narcotic analgesics" are natural or synthetic substances that bind to opioid receptors in the central nervous system, producing an agonist action. Examples of opioid analgesics include, but are not limited to, codeine, fentanyl, hydromorphone, levorphanol, meperidine, methadone, morphine, oxycodone, oxymorphone, propoxyphene, buprenorphine, butorphanol, dezocine, nalbuphine, and pentazocine.

According to another embodiment, the additional agent is an anti-infective agent. According to another embodiment, the anti-infective agent is an antibiotic agent. The term "antibiotic agent" as used herein means any of a group of chemical substances having the capacity to inhibit the growth of, or to destroy bacteria, and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefmetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

Other examples of at least one additional therapeutic agent include, but are not limited to, rose hip oil, vitamin E, 5-fluorouracil, bleomycin, onion extract, pentoxifylline, prolyl-4-hydroxylase, verapamil, tacrolimus, tamoxifen, tretinoin, colchicine, a calcium antagonist, tranilst, zinc, an antibiotic, and a combination thereof.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the described invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range.

Where the stated range includes one or both of the limits, ranges excluding either both of those included limits are also included in the invention.

It must be noted that as used herein and in the appended claims, the singular forms "a", "and", and "the" include plural references unless the context clearly dictates otherwise. All technical and scientific terms used herein have the same meaning.

The publications discussed herein, the contents of which are incorporated herein by reference, are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

The described invention may be embodied in other specific forms without departing from the spirit or essential attributes thereof and, accordingly, reference should be made to the appended claims, rather than to the foregoing specification, as indicating the scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

A. Dry Powder Formulations of MMI-0100 (YARAAAR-QARAKALARQLGVAA; SEQ ID NO: 1)

MMI-0100 Formulations:

MMI-0100 (YARAAARQARAKALARQLGVAA; SEQ ID NO: 1), Lyophilized (American Peptide, Inc., Sunnyvale Calif.) Lot number 100429, Date of Manufacture 29 Jun. 2010, 500 mg.

Neat Spray Dried MMI-0100 (YARAAARQARAKA-LARQLGVAA; SEQ ID NO: 1), 5% w/w solids (Bend Research, Bend Oreg.) Lot Number BREC 00708-003A, Date of Manufacture 27 Jul. 2012, 1 g.

Neat Spray Dried MMI-0100 (YARAAARQARAKA-LARQLGVAA; SEQ ID NO: 1), 1% w/w solids (Bend Research, Bend Oreg.) Lot Number BREC 00708-003B, Date of Manufacture 27 Jul. 2012, 1 g.

Spray Dried 80/20 MMI-0100 (YARAAARQARAKA-LARQLGVAA; SEQ ID NO: 1)/Trehalose (Santa Cruz Biotechnology, Inc. Dallas Tex.), 1% w/w solids (Bend Research, Bend Oreg.) Lot Number BREC 00708-011C, Date of Manufacture w/c 10 Sep. 2012, 500 mg.

Spray Dried 92.5/7.5 MMI-0100 (YARAAARQARAKA-LARQLGVAA; SEQ ID NO: 1)/Trehalose (Santa Cruz Biotechnology, Inc. Dallas Tex.), 1% w/w solids (Bend Research, Bend Oreg.) Lot Number BREC 00708-011F, Date of Manufacture w/c 10 Sep. 2012, 500 mg.

Rapid HPLC and NGI Sample Extraction Method
Materials and Equipment
Water, Millipore or equivalent
Acetonitrile, HPLC grade
Methanol, HPLC grade
Trifluoroacetic Acid
Tween 20
MMI-0100 Neat lyophilized drug substance
Microbalance (Mettler-Toledo, Columbus Ohio)
Next Generation Impactor (NGI) (MSP Corp, Shoreview Minn.)
Dose Unit Sampling Apparatus (Copley, Nottingham UK)
TPK Controller (Copley, Nottingham UK)
HPLC System
HPLC instrument (Waters Alliance 2695, Milford Mass.) with thermostatted column compartment or column oven and sample compartments
Column: Supelco, Ascentis Express® Peptide ES-C18, 50×4.6 mm (Sigma-Aldrich, St Louis Mo.)
Flow rate: 1.5 mL/min
Injection volume: 40 ILL
Column Temperature: 40° C.
Sample Temperature: 5° C.
Detector Wavelength: 215 nm
Mobile Phase A: 0.1% IT A in Water (72%)
Mobile Phase B: 0.1% TFA in 1:1 Methanol: Acetonitrile (28%)
Run time: 3 minutes. Retention time of MMI-0100 is about 2.35 minutes.
Solution Preparation
Mobile Phase A: 0.1% TFA in Water
Pipet 2.0 mL of TFA into 1000 mL of water in a 2 L volumetric flask and dilute to volume with water. Mix and degas. Alternate volumes may be prepared provided that proportions are kept equal.
Mobile Phase B: 0.1% TFA in 1:1 Methanol: Acetonitrile
Pipet 1.0 mL of TFA into 500 mL of methanol in a 1 L volumetric flask and dilute to volume with methanol. Mix and degas. Alternate volumes may be prepared provided that proportions are kept equal. Pipet 1.0 mL of TFA into 500 mL of acetonitrile in a 1 L volumetric flask and dilute to volume with acetonitrile. Mix and degas. Alternate volumes may be prepared provided that proportions are kept equal. Mix the above prepared solutions for 2,000 mL of mobile phase.
Sample Solvent: 0.02% Tween 20 in Water
Using a graduated wide-mouth TC pipette transfer 0.8 mL of Tween 20 into a 4,000 mL volumetric flask containing approximately 3,000 mL of water. Tween 20 is viscous. Be sure to rinse the pipette with the water into the flask several times to flush the Tween 20 out of the pipette. Dilute to volume with water. Mix well.
Coating Solution: 5% Tween 20 in methanol
Using a graduated wide-mouth TC pipette transfer 5 mL of Tween 20 into a 100.0 mL volumetric flask containing approximately 75 mL of methanol. Tween 20 is viscous. Be sure to rinse the pipette with methanol into the flask several times to flush the Tween 20 out of the pipette. Dilute to volume with methanol. Mix well.
NOTE: MMI-0100 is hygroscopic. All handling of the neat drug substance should be performed in a glove box maintained at 5% relative humidity.
NOTE: Lyophilized MMI-0100 is stored between −10° C. and −20° C. Prior to use, the lyophilized MMI-0100 should be thawed in a desiccator or a glove box maintained at 5% relative humidity for at least 2 hours.
Standard stock solution—1.1 mg/mL
Weigh an amount of MMI-0100 equivalent to 11 mg of pure MMI-0100, into an appropriate weighing vessel. The actual weight needed can be calculated by dividing 11 mg by the purity factor reported on the Certificate of Analysis. The amount of MMI-0100 actually weighed out should be within ±0.250 mg of this calculated weight. Record the weight of MMI-0100 (as is) plus the weighing vessel as $W_i$. Transfer the MMI-0100 to a 10.0 mL volumetric flask. Place the empty weighing vessel onto the balance and record the weight ($W_f$). The standard amount is equal to $W_t$-$W_f$. Add approximately 6 mL of sample solvent. Swirl the volumetric flask to dissolve and dilute to volume with sample solvent. Mix well and immediately transfer the solution to a polypropylene centirfuge tube. Prepare a second solution for check standard stock solution.

Working standard solution—110 µg/mL.

Pipette 5.0 mL of standard stock solution into a 50-mL volumetric flask. Dilute to volume with sample solvent and immediately transfer the solution to a polypropylene centrifuge tube. Final concentration: 110 µg/mL.

Working standard solution—11 µg/mL.

Pipette 5.0 mL of standard stock solution into a 50-mL volumetric flask. Dilute to volume with sample solvent. Final concentration: 11 µg/mL.

Limit of Quantification (LOQ) solution

Pipette 1.0 mL of 110 µg/mL working standard solution into a 50-mL volumetric flask. Dilute to volume with sample solvent. Final concentration: 2.2 µg/mL.

Procedure

Equilibrate the HPLC with mobile phase until a stable signal is achieved.

Perform system suitability and sample injections using one of the following sequences as appropriate.

NOTE: The HPLC autosampler temperature is maintained at 5° C. MMI-0100 sample solutions should be transferred to the HPLC immediately after preparation and allowed to thermally equilibrate for at least 10-15 minutes prior to injecting.

NOTE: Glass will absorb the MMI-0100 peptide from solution. Only polypropylene HPLC vials should be used for analysis.

NGI Samples

Sample solvent (1×)

LOQ solution (6×)

11 µg/mL Working Standard (5×)

11 µg/mL Check Standard (1×)

NGI Samples—1 replicate, Blister through MOC (1×each)

11 µg/mL Working Standard (1×)

Additional replicates of NGI samples

11 µg/mL Working Standard (1× after each NGI replicate)

System suitability is achieved if the following target requirements are met.

Sample solvent peaks: none detected at retention time of MMI-0100

LOQ solution: % RSD (relative standard deviation) for n=6 injections should be ≤10%

First n=5 injections of Working standard:

% RSD should be ≤1.5%

Tailing factor should be ≤2.0 k' should be >2.0. Use the first peak in the solvent front as the to void time.

Theoretical plates should be recorded for information only.

Check standard: 98.0-102.0%

Working Standard injections through run: % RSD of all working standard injections should be ≤2.0%

NGI Sample Preparation

Blisters for NGI analysis should be dosed according to the normal use instructions for the inhaler used in the study.

Blisters, Flow Channel, Throat, and NGI Impaction Cups should be extracted with sample solvent using normal lab practices for the stages with extraction volumes listed in Table 2.

TABLE 2

Summary of Test Solutions

| Test Solution | Volume (mL) |
|---|---|
| Blister | 20.0 |
| Flow Channel | 5.0 |
| Throat | 20.0 |
| Preseparator Insert | 10.0 |
| Preseparator Base | 10.0 |
| Impaction Cups 1 through 3 | 10.0 |
| Impaction Cups 4 through 6 | 20.0 |
| Impaction Cup 7 | 10.0 |
| Microorifice Collector (MOC) | 5.0 |

NGI Impaction Cups do not need to be covered when mixing. Mixing time should be 3 minutes.

Preseparator extraction

The Preseparator is not extracted into volumetric glassware.

Preseparator Top: The Preseparator Top is not extracted.

Preseparator Insert: The Preseparator Insert will have 10.0 mL of sample solvent added to the central cup during dosing. This solution will be mixed briefly by pipette in the central cup prior to transfer to HPLC vial with no additional dilution.

Preseparator Base: Close the Preseparator Base tightly with a stopper. Add 10.0 mL sample solvent to the flat portion of the base. Rinse the entire surface area of the flat portion several times by pipette. Using this same sample solution, rinse the inner wall of the stem of the base. Mix the sample solution by pipette.

Calculations

Calculate check standard accuracy using the following equation:

$$(A_{check\ standard})(C_{standard})(100\%)/(A_{standard})(C_{check\ standard})$$

Where:

$A_{check\ standard}$=Peak area of the MMI-0100 peak in the check standard solution $C_{standard}$=Concentration of MMI-0100 in the working standard solution $A_{standard}$=Mean peak area of the MMI-0100 peak in the first five (5) injections of the working standard solution $C_{check\ standard}$=Concentration of MMI-0100 in the check standard solution Calculate the amount of MMI-0100 in individual test solutions in µg using the following equation:

$$(A_{sample})(C_{standard})(V_{sample})(P)/(A_{standard})$$

Where:

$A_{sample}$=Peak area of the MMI-0100 peak in the test solution $C_{standard}$=Concentration of MMI-0100 in the working standard solution P=Potency factor of the reference substance (if applicable)

$A_{standard}$=Mean peak area of the MMI-0100 peak in the first five (5) injections of the working standard solution The blister and device parameters listed in Table 3 were used as a starting point for optimization of aerosol performance.

TABLE 3

Blister, device and test conditions (Final Conditions)

| Blister Information | |
|---|---|
| Blister design | 4.5 mm flat-top blisters (manufactured at MDTx (Monmouth Junction NJ) with Rohrer 750 equipment |
| Filling information | Blister filling inside a glove box at ambient room temperature and <5% relative humidity |
| Fill weight | Target fill weight ±5% (95%-105% target) |
| Foils: Blister, Lidding | Blister Lidding Material and Blister Forming Material: Alcan (Shelbyville KY) (FIG. 1 and FIG. 2) |
| Sealing Parameters | ST3 Sealer Sealing Temperature: 136° C. Sealing Time: 0.5 sec Pressure set at 100 psi Vacuum Cooling Time: 5 sec |
| Sealing Information | ST3 Sealer was contained in a glove box with microbalance; blisters were sealed immediately following filling |
| Blister Stamping | Blisters stamped to 15 mm flange using Arbor Press |
| Blister Height Measurement | Ames Pneumatic AG-698 (Ames IA) Air Guage Range: 4.48-4.63 mm |
| Device Information | |
| Platform #(s) | EPIC S0361F-24 |
| Flow channel | S0619 |
| Electronics | Function generators |
| Drive Scheme | F1 = 39.8 kHz, F2 = 54.0 kHz, 100 Hz Modulation, 90/10 Duty Cycle |
| Drive Voltage | 240 V |
| Transducer on-time | 2 × 2 sec |
| Piercing Tool # | A0101A-5 (4 × 0.011" OD pins in square pattern |
| Flow rate | 25 L/min |

B. Nebulizer Formulations of MMI-0100 (YARAAAR-QARAKALARQLGVAA; SEQ ID NO: 1)

MMI-0100 Formulations:

Formulation A: 7 mg/mL; 1.8 g of lyophilized peptide weighed into a volumetric flask containing 200 mL of 0.9% saline.

Formulation B: 0.7 mg/mL; 0.18 g of lyophilized peptide weighed into a volumetric flask containing 200 mL of 0.9% saline.

Instruments:

Malvern MasterSizer X V2.15: Malvern Instruments GmbH, München II

HPLC Alliance 2695 with column oven, 2487 dual absorbance detector and chromatographic data system (Empower 3); Waters Mass flow controller 0-30 l/min, e.g. PR4000; MKS Measuring system for relative humidity and temperature, e.g. testo 645

Digital manometer, e.g. testo 525

Precision balance, e.g. Excellence X56035 DR, Mettler Toledo

Conditioning system

Bubble Flow Meter, e.g. Gilibrator2, Gillian

Breath simulator Z

Filter pads (Polypropylene)

Filter casings

Laboratory shaker e.g. 3015, IKA Werke

Temperature-/Humidity sensor, e.g. Testo 645, Testo

Gas meter, G4, Elster Instromet

Pipette Research 1000, Eppendorf

Multipette stream, Eppendorf

Waterbath, e.g. F12; Julabo

Magnet stirrer, e.g. IKA RCT basic

Rheometer, e.g. Rheostressl, Haake

Tensiometer, e.g. science line t60, Sita Messtechnik

Osmomat, e.g. Gonotec auto

C. Nano-Polyplex Formulations of MMI-0100 (YARAAARQARAKALARQLGVAA; SEQ ID NO: 1)

Synthesis of Cell Penetrant MK2 Inhibitory Peptide

MK2 inhibitory peptide (MK2i) MMI-0100 (YARAAAR-QARAKALARQLGVAA; SEQ ID NO: 1) was synthesized on a PS3 peptide synthesizer (Protein Technologies, Inc. Tucson, Ariz.) utilizing standard Fmoc Chemistry. N-methylpyrrolidone (NMP, Fischer Scientific) was utilized as a solvent in all peptide syntheses. HCTU (1H-Benzotriazolium 1-[bis(dimethylamino)methylene]-5chloro-,hexafluorophosphate (1-),3-oxide) was used as an activator (Chempep, Wellington, Fla.) in the presence of N-methylmorpholine. All amino acids were double coupled in order to maximize yield and purity. Peptides were cleaved/deprotected in trifluoroacetic acid (TFA)/Phenol/$H_2O$/triisopropylsilane (88/5/5/2). The peptide was then further purified by reverse phase HPLC on a Waters 1525 binary HPLC pump outfitted with an extended flow kit, a Waters 2489 UV/Visible detector, and a phenomenex Luna C18(2) AXIA packed column (100A, 250×21.2 mm, 5 micron). A) HPLC grade water with 0.05% formic acid and B) HPLC grade acetonitrile were used as the mobile phase, and the peptide was purified utilizing a 90% A to 90% B gradient over 25 mins (16 mL/min). Acetonitrile was removed from purified fractions with a rotary evaporator, and the purified fractions were then lyophilized. Peptide purity was verified through electrospray ionization mass spectrometry (ESI-MS) on a Waters Synapt ESI-MS.

Monomer and Polymer Synthesis

All reagents were purchased from Sigma and were of analytical grade unless otherwise stated. 2-propylacrylic acid was synthesized according to the procedure outlined by Ferrito et al. (Macromolecular Syntheses 11,59-62 (1992)) utilizing diethyl propylmalonate (Alfa Aesar) as a precursor. The 4-cyano-4-(ethylsulfanylthiocarbonyl) sulfanylvpentanoic acid (ECT) chain transfer agent (CTA) was synthesized as describe by Convertine et al. (J. Control Release 133,221-229 (2009)). Reversible addition-fragmentation chain transfer (RAFT) polymerization of the poly(propylacrylic acid) (PPAA) homopolymer was carried out in bulk under a nitrogen atmosphere at 70° C. for 48 hours using 2,2'-azo-bis-isobutyrylnitrile (AIBN) as the free radical initiator. The reaction mix was put through three freeze-vacuum-thaw cycles and purged with nitrogen for thirty minutes prior to polymerization. The molar ratio of chain transfer agent (CTA) to AIBN was 1 to 1, and the monomer to CTA ratio was set so that a degree of polymerization (DP) of 190 would be achieved at 100% conversion. Following polymerization, the resultant polymer was dissolved in dimethylformamide (DMF) and precipitated into ether 5 times before drying overnight in vacuo. RAFT polymerization of the poly(acrylic acid) (PAA) homopolymer was carried out in distilled dioxane under a nitrogen atmosphere at 70° C. for 18 hours using AIBN as the free radical initiator. The reaction mix was purged with nitrogen for thirty minutes prior to polymerization. The molar ratio of CTA to AIBN was 5 to 1 and the monomer to CTA ratio was set so that a degree of polymerization of 150 would be achieved at 100% conversion. Following polymerization, the resulting polymer was dissolved in dioxane and precipitated into ether 5 times before drying overnight in vacuo. Gel permeation chromatography (GPC, Agilent) was used to determine molecular weight and polydispersity ($M_w/M_n$, PDI) of the PPAA and PAA homopolymers using HPLC-grade DMF containing 0.1% LiBr at 60° C. as the mobile phase. Molecular weight calculations were performed with ASTRA V software (Wyatt Technology) and were based on experimentally-determined dn/dc values determined through offline injections of the polymer through a refractive index detector (calculated PPAA dn/dc=0.087 mL/g, DP=193 (GPC), PDI=1.47 (GPC); calculated PAA dn/dc=0.09 mL/g, DP=150 (GPC), PDI=1.27 (GPC)). Polymer purity and molecular weight were verified through NMR spectroscopy utilizing $D_6MSO$ as a solvent (PPAA DP=190 ($H^1$ NMR); PAA DP=106 ($H^1$ NMR)).

MMI-0100 Nano-Polyplex (MK2i-NP) and Phosphor-HSP20 Nano-Plex (HSP20-NP) Synthesis and Characterization PPAA was dissolved in 1 M NaOH and diluted into a phosphate buffer (pH 8) to obtain a stock solution. Purified MMI-0100 peptide was dissolved in phosphate buffer (pH 8). The MMI-0100 peptide and PPAA polymer were mixed at a range of charge ratios (CRs) from $[NH_3^+]:[COO^-]$=10:1 to 1:10 to form MK2i-NPs. The resulting polyplexes were syringe filtered through 0.45 μm polytetrafluoroethylene (PTFE) filter, and the hydrodynamic diameter and ζ-potential were characterized on a Malvern Zetasizer Nano-ZS with a reusable dip cell kit (Malvern Instruments Ltd., Worcestershire, U.K.).

A CR of 1:3 was then chosen as the optimal MK2i-NP formulation, whereas a charge ratio of 3:1 was chosen as the lead p-HSP20-NP formulation. These formulations were used in subsequent in vitro, ex vivo, and in vivo studies. Nano-polyplexes formulated at the same CR with the non-endosomolytic polymer PAA (i.e., NE-MK2i-NPs) were analyzed by dynamic light scattering (DLS) and used as a vehicle control in all subsequent studies. In order to verify the sizes indicated by DLS analysis, MK2i-NPs and HSP20-NPs were visualized through transmission electron microscopy (TEM) imaging. TEM samples were prepared by inverting carbon film-backed copper grids (Ted Pella) onto a 20 μL droplet of aqueous polyplex suspensions (1 mg/mL) and blotted dry. All samples were then inverted onto a 20 μL droplet of 3% Uranyl Acetate and stained for 2 min. After blotting the sample dry, samples were desiccated in vacuo for 2 hr prior to imaging on a Philips CM20 system operating at 200 kV. Images were collected using a charge-coupled device (CCD) camera with AMT Image capture Engine software (Advanced Microscopy Techniques, Danvers, Mass.). The pH-dependent size changes of polypexes at a CR of 1:3 were then quantified by DLS analysis at various pH values in PBS −/− (i.e. pH 7.4, 6.8, 6.2, and 5.6).

pH-Dependent Membrane Disruption Hemolysis Assay

To assess the endosomal disruptive potential of MK2i-NPs, a red blood cell hemolysis assay was utilized as previously described by Henry et al. (Biomacromolecules 7,2407-2414 (2006)) to measure MK2i-NP pH-dependent disruption of lipid bilayers. Whole human blood was drawn from an anonymous donor, and plasma was removed through centrifugation and saline washes. The remaining erythrocytes were washed three times with 150 mM NaCl and resuspended into phosphate buffers corresponding to physiologic (pH 7.4), early endosome (pH 6.8), early/late endosome (pH 6.2), and late endosome/lysosomal (pH 5.8) environments. MK2i-NPs, NE-MK2i-NPs, MMI-0100 (MK2i) peptide alone (1-40 μg/mL), PBS (negative control), or 1% Triton X-100 (positive control) were added to the erythrocyte suspensions and incubated at 37° C. for 1 hour. Intact erythrocytes were pelleted via centrifugation, and supernatant was transferred to a new 96-well plate. The hemoglobin content within the supernatant was then measured via absorbance at 541 nm. Percent hemolysis was determined relative to Triton X-100 and PBS controls.

Cell Culture

Primary human coronary artery vascular smooth muscle cells (HCAVSMCs) were obtained from Lonza. HCAVSMCs were cultured in complete growth medium [vascular cell basal medium (ATCC) supplemented with 5% FBS, human basic fibroblast growth factor (bFGF, 5 ng/mL), human insulin (5 μg/mL), ascorbic acid (50 μg/mL), L-glutamine (10 mM), human epidermal growth factor (EGF, 5 ng/mL), and 1% penicillin-streptomycin].

All cultures were maintained in 75 $cm^2$ polystyrene tissue culture flasks in a 37° C. and 5% $CO_2$ environment with cell culture media refreshed every other day. Cells were grown to 80-90% confluence prior to being harvested and passaged. All cells were seeded at a density of 20,000-30,000 cells/$cm^2$, as required for each specific experiment. Only cells from early passages (numbers 3-8) were used in experiments.

Inflammatory Cytokine Analysis

200 μL of cell suspension (at 10,000 cells/well) was seeded onto 96-well plates to yield an approximate 70% confluence per well. Cells were allowed to adhere to the plate overnight.

Tumor Necrosis Factor-α ELISA

HCAVSMCs were treated in low serum media (DMEM, 1% FBS, and 1% P/S, to achieve cellular quiescence) with 10 μM ANG-II for 4 hours followed by treatment with MK2i-NPs, MK2i, or NE-MK2i-NPs for 2 hours. Following treatment, each well was aspirated and supplemented with fresh medium. After 24 hours, 100 μL of supernatant was collected and frozen at −80° C. until cytokine analysis was performed. A Human TNF-α (cat#900-K25) ELISA development kit (Peprotech; Rocky Hill, N.J.) was used to measure cytokine levels in supernatant collected from treated cells according to the manufacturer's protocol. Briefly, microtiter plates (Nunc MaxiSorp, cat. #439454) were prepared by diluting polyclonal capture antibody with phosphate-buffered saline (PBS; Gibco BRL, cat. #14200-075) (1×, pH 7.20) to a concentration of 1 μg/mL and adding 100 μL of the diluted capture antibody to each well of the microtiter plate. The plate was sealed and incubated overnight at room temperature. After incubation, the wells were aspirated and washed 4 times with 300 μL of wash buffer (0.05% Tween-20 (Sigma, cat. # P7949) in PBS) per well. Next, 300 μL of blocking buffer (1% bovine serum albumin (BSA; Sigma, cat. # A-7030) in PBS) was added to each well and the microtiter plate was incubated for 1 hour at room temperature. After incubation, the wells were aspirated and washed 4 times with 300 μL of wash buffer per well. Next, TNF-α standard was serially diluted from 0.01 μg/mL to 0 μg/mL in diluent (0.05% Tween-20, 0.1% BSA in PBS). Diluted standard and samples were added (100 μL/well) to the microtiter plate in triplicate and the plate was incubated for 2 hours at room temperature. Wells were aspirated and the plate was washed 4 times with wash buffer. After washing, 100 μL of biotinylated detection antibody (at a concentration of 0.5 μg/mL; 500 ng/mL in diluent) was added to each well and the microtiter plate was incubated for 2 hours at room temperature. Following incubation, wells were aspirated and washed 4 times with wash buffer. Avidin-HRP conjugate (Sigma, cat. # A-7419) was diluted 1:2000 in diluent and added to each well of the plate (100 μL/well). The plate was incubated for 30 minutes at room temperature. After incubation, the wells were aspirated and the plate was washed 4 times with wash buffer. Next, 100 μL of ABTS liquid substrate solution (Sigma, cat. # A3219) was added to each well and the plate was incubated at room temperature for color development. Plates were read with a plate reader (Molecular Devices) at 405 nm (650 nm wavelength correction). All data were then normalized to cell viability determined by a CytoTox-ONE™ Homogenous Membrane Integrity assay (Promega) according to the manufacturer's protocol. Briefly, 200 μL of a HCAVSMC cell suspension was seeded (at 10,000 cells/well) onto a 96-well plate to yield an approximate 70% confluence per well. Cells were allowed to adhere to the plate overnight. Next, the plate was equilibrated to 22° C. for approximately 30 minutes. Following equilibration, 200 μL of YtoTox-ONE™ reagent was added to each well, the plate was shaken for 30 seconds and then incubated for 10 minutes at 22° C. After incubation, 100 μL of Stop Solution was added to each well, the plate was shaken for 10 seconds and fluorescence was recorded at an excitation wavelength of 560 nm and an emission wavelength of 590 nm using a plate reader (Molecular Devices).

Interleukin-6 ELISA

HCAVSMCs were treated in low serum media with 20 ng/mL TNF-α for 4 hours followed by treatment with MK2i-NPs, MMI-0100 (MK2i), or NE-MK2i-NPs for 2 hours. Following treatment, each well was aspirated and supplemented with fresh medium. After 24 hours, 100 μL of supernatant was collected and frozen at −80° C. until cytokine analysis could be performed. A human IL-6 (cat#900-K16) ELISA development kit (Peprotech; Rocky Hill, N.J.) was used to measure cytokine levels in supernatant collected from treated cells according to the manufacturer's protocol. Briefly, microtiter plates (Nunc MaxiSorp, cat. #439454) were prepared by diluting polyclonal capture antibody with phosphate-buffered saline (PBS; Gibco BRL, cat. #14200-075) (1×, pH 7.20) to a concentration of 1 μg/mL and adding 100 μL of the diluted capture antibody to each well of the microtiter plate. The plate was sealed and incubated overnight at room temperature. After incubation, the wells were aspirated and washed 4 times with 300 μL of wash buffer (0.05% Tween-20 (Sigma, cat. # P7949) in PBS) per well. Next, 300 μL of blocking buffer (1% bovine serum albumin (BSA; Sigma, cat. # A-7030) in PBS) was added to each well and the microtiter plate was incubated for 1 hour at room temperature. After incubation, the wells were aspirated and washed 4 times with 300 μL of wash buffer per well. Next, IL-6 standard was serially diluted from 0.01 μg/mL to 0 μg/mL in diluent (0.05% Tween-20, 0.1% BSA in PBS). Diluted standard and samples were added (100 μL/well) to the microtiter plate in triplicate and the plate was incubated for 2 hours at room temperature. Wells were aspirated and the plate was washed 4 times with wash buffer. After washing, 100 μL of biotinylated detection antibody (at a concentration of 0.5 μg/mL; 500 ng/mL in diluent) was added to each well and the microtiter plate was incubated for 2 hours at room temperature. Following incubation, wells were aspirated and washed 4 times with wash buffer. Avidin-HRP conjugate (Sigma, cat. # A-7419) was diluted 1:2000 in diluent and added to each well of the plate (100 μL/well). The plate was incubated for 30 minutes at room temperature. After incubation, the wells were aspirated and the plate was washed 4 times with wash buffer. Next, 100 μL of ABTS liquid substrate solution (Sigma, cat. # A3219) was added to each well and the plate was incubated at room temperature for color development. Plates were read with a plate reader (Molecular Devices) at 405 nm (650 nm wavelength correction). All data were then normalized to cell viability determined by a CytoTox-ONE Homogenous Membrane Integrity assay (Promega) according to the manufacturer's protocol.

Monocyte Chemoattractant Protein-1(MCP-1) ELISA

HCAVSMCs were treated in low serum media with MK2i-NPs, MK2i, or NE-MK2i-NPs for 2 hours. Following treatment, each well was aspirated and supplemented with fresh medium. After 3 or 5 days, cells were stimulated with TNF-α (20 ng/ml) for 24 hours. Following stimulation, 100 μl of supernatant was collected and frozen at −80° C. until cytokine analysis could be performed. A human monocyte chemoattractant protein-1 (cat#EH2MCP1) ELISA development kit (ThermoFisher Scientific/Pierce Biotechnology; Rockford, Ill.) was used to measure cytokine levels in supernatant collected from treated cells according to the manufacturer's protocol. Briefly, 50 μL of standard diluent was added to each well of the anti-human MCP-1 precoated 96-well strip plate. Next, 50 μL of standards or samples were added to the strip plate in duplicate, the strip plate was covered with an adhesive plate sealer and incubated at room temperature for 1 hour. Following incubation, the strip plate was washed three times with Wash Buffer. After washing, 100 μL of Biotinylated Antibody Reagent was added to each well of the strip plate, the plate was covered with an adhesive plate sealer and incubated at room temperature for 1 hour. Following incubation, the strip plate was washed three times with Wash Buffer. Next, 100 μL of Streptavidin-HRP Solution was added to each well of the strip plate, the strip plate was covered with an adhesive plate sealer and incubated at room temperature for 30 minutes. Following incubation, the strip plate was washed three times with Wash Buffer. After washing, 100 μL of TMB Substrate Solution was added to each well of the strip plate and the strip plate was developed at room temperature for 20 minutes. Next, 100 μL of Stop Solution was added to each well of the strip plate. Absorbance was measured on a plate reader (Molecular Devices) at 450 nm (550 nm wavelength correction) and results were calculated using curve-fitting statistical software.

Migration Assays

Scratch Wound Chemokinesis Assay

HCAVSMCs were seeded in Lab-TEK II 8-well chambered coverglass at a density of 20,000 cells/well in 250 μl low serum growth media and allowed to adhere overnight to achieve a nearly confluent (90-95%) monolayer. Cells were treated with MK2i-NPs, NE-MK2i-NPs, MMI-0100 (MK2i) peptide or PBS −/− for 30 minutes. Following treatment, scratch wounds were made with a 10 uL pipette tip through the middle of each cell monolayer. The media was then replaced with low serum growth media containing a Cell-Tracker™ Green BODIPY® dye (Invitrogen) according to the manufacturer's protocol for thirty minutes to enable visualization of migrating cells. Following treatment with the dye, media was replaced with low serum growth media containing 50 ng/ml platelet-derived growth factor-BB (PDGF-BB) (or with PBS −/− for the negative control). Scratch wound areas were then imaged at 0,3,6,12, and 24 hours using a Nikon Eclipse Ti inverted fluorescence microscope (Nikon Instruments Inc, Melville, N.Y.) with NIS Elements imaging software. Wound closure was calculated with imageJ software by quantifying the scratch wound area around the periphery of migrating cells normalized to the original scratch wound area. Scratch wound assays for each treatment group were performed in 3 independent experiments.

Boyden Chamber Chemotaxis Assay

HCAVSMCs were seeded in a 24 well plate at a density of 30,000 cells/well in low serum media (DMEM, 1% FBS, and 1% P/S) and allowed to adhere overnight. Cells were treated for 30 mins with MK2i-NPs, NE-MK2i-NPs, MMI-0100 (MK2i) peptide, or PBS. Following treatment, each well was washed 2× with PBS −/−, trypsinized, resuspended in 100 µl low serum growth media, and plated onto 6.5 mm, 8 µm pore polycarbonate inserts (Corning) in a 24 well plate with 600 µl low serum growth media containing 50 ng/ml PDGF-BB (or PBS −/− for the negative control) in the lower chamber. Cells were allowed to migrate for 8 hours, and then cells on the upper side of each insert were gently removed with a cotton swab. Cells on the lower side of each insert were then fixed and stained using a Modified Giemsa Differential Quik Stain Kit (Polysciences). Inserts were fixed in solution A for at least 10 seconds, dipped 5 times in solution B, and then dipped 5 times in solution C. After staining, 4 images were taken from the four quadrants of each insert, and the number of cells/high power field were quantified in ImageJ by thresholding each image and manually counting the cells. Each treatment was performed in triplicate, and average cell #/field was calculated.

Cell Proliferation Assay

HCAVSMCs were seeded in a 96 well plate at 10,000 cells/well in low serum media (DMEM, 1% FBS, and 1% P/S) and allowed to adhere overnight. Cells were treated for 30 minutes with MK2i-NPs, NE-MK2i-NPs, MMI-0100 (MK2i) peptide or PBS −/− (for positive and negative controls). Each treatment was then aspirated and replaced with 100 µl low serum growth media ±50 ng/mL PDGF-BB. After 24 hours of incubation, a CellTiter 96® Aqueous Non-Radioactive Cell Proliferation Assay (Promega) was performed according to the manufacturer's protocol. Briefly, 100 µl phenazine methosulfate (PMS) solution was added to 2.0 ml MTS solution and mixed. 20 µl of PMS/MTS solution was then added to each well of the 96 well plate containing 100 µl medium, and the plate was incubated for 4 hours at 37° C. in a humidified, 5% $CO_2$ atmosphere. Following incubation, the absorbance of each well was recorded at 490 nm with a TECAN Infinite M1000 Pro plate reader to determine the relative proliferation rate of all treatment groups.

Microscopic Analysis of Cellular Uptake and Intracellular Trafficking

An amine-reactive Alexa-488 succinimidyl ester was dissolved in DMSO and mixed at a 1 to 3 molar ratio with the MMI-0100 (MK2i) peptide in 100 mM sodium bicarbonate buffer (pH=8.3). Unreacted fluorophore and organic solvent were removed using a PD-10 miditrap G-10 desalting column, and the fluorescently labeled peptide was lyophilized. PPAA and PAA polymers were mixed with fluorescently labeled MMI-0100 (MK2i) peptide at a CR of $[NH_3^+]/[COO^-]=1:3$ and syringe filtered through a 0.45 µm PTFE filter to form fluorescent MK2i-NPs and control NE-MK2i-NPs, respectively. Fluorescent MK2i-NP and NE-MK2i-NP hydrodynamic diameter and surface charge were measured by DLS and Zeta potential analysis, respectively. Fluorescent MK2i-NPs, NE-MK2i-NPs, or MMI-0100 (MK2i) peptide alone were applied to HCAVSMCs grown on Lab-Tek II 8-well chambered coverglass (Thermo Scientific Nunc) at a concentration of 10 µM MMI-0100 (MK2i) peptide in DMEM media supplemented with 1% FBS and 1% P/S. Cells were treated for 2 hours, washed 2× with PBS −/−, and media was replaced. Cells were then incubated for an additional 0, 2, 4, 10, or 22 hours in fresh media. For the final two hours of incubation, 50 nM Lysotracker Red DND-99 (Invitrogen) was added to each well in order to visualize acidic endo/lysosomal vesicles within cells. After incubation, cells were washed with 0.1% trypan blue for 1 minute to quench extracellular fluorescence followed by 2 additional washes with PBS −/−. Cells were then imaged using a LSM 710 META fluorescence microscope with ZEN imaging software (Carl Zeiss Thornwood, N.Y.). Gain settings were kept constant for all images acquired.

All images were processed using ImageJ and colocalization was analyzed using Just Another Colocalization Plugin (JACoP)(62). Mander's overlap coefficients (the fraction of pixels with positive pixel values in both fluorescent channels) were then calculated for n≥3 separate images for each treatment group to quantify colocalization. To determine treatment effects on the size of the compartments where the peptide was found, the free hand selection tool in ImageJ was used to outline n≥50 individual intracellular compartments for each treatment group, and the area of each was quantified and averaged.

Flow Cytometric Quantification of Intracellular Uptake and Retention

HCAVSMCs were grown to 80-90% confluence, harvested, and seeded at 20,000 cells/well in a 24 well plate and allowed to adhere overnight in low serum media (DMEM, 1% FBS, and 1% P/S). Fluorescent MMI-0100 (MK2i) peptide, MK2i-NPs, and NE-MK2i-NPs were synthesized as noted above for microscopy analysis, and HCAVSMCs were treated at a concentration of 10 µM MMI-0100 (MK2i) for 2 hours. Following treatment, cells were washed with PBS −/−, washed with CellScrub buffer (Genlantis) for 10 minutes at room temperature to remove extracellular polyplexes and/or peptide, washed 2× in PBS −/−, and given fresh complete growth media. Cells were then incubated for an additional 0, 12, 24, 72, or 120 hours. Cells were then washed with PBS −/−, trypsinized, and resuspended in 0.1% Trypan blue in PBS (−/−) for analysis on a FACSCalibur flow cytometer (Becton Dickinson) with BD CellQuest™ Pro software (V 5.2). Data was exported and analyzed with FlowJo software (V 7.6.4). All samples were run in triplicate.

For MK2i-NP and HSP20-NP studies, An amine-reactive Alexa-488 succinimidyl ester (Life Technologies) was dissolved in DMSO and mixed at a 1 to 3 molar ratio with the MK2i or p-HSP20 peptide in 100 mM sodium bicarbonate buffer (pH=8.3) and allowed to react for 3 hours. Unreacted fluorophore and organic solvent were removed using a PD-10 miditrap G-10 desalting column, and the fluorescently labeled MK2i and p-HSP20 peptides were lyophilized. PPAA polymer was mixed with fluorescently labeled MK2i peptide at a CR of $[NH_3^+]/[COO^-]=1:3$ and syringe filtered through a 0.45 µm PTFE filter to form fluorescent MK2i-NPs. Similarly, PPAA was mixed with fluorescently labeled p-HSP20 at a CR of $[NH_3^+]/[COO^-]=1:3$ and syringe filtered through a 0.45 µm PTFE filter to form fluorescent HSP20-NPs. HCAVSMCs were grown to 80-90% confluence, harvested, and seeded at 20,000 cells/well in a 24 well plate and allowed to adhere overnight. HCAVSMCs were treated with fluorescent MK2i peptide, MK2i-NPs, p-HSP20 peptide, p-HSP20-NPs, or PBS as a control at a concentration of 10 µM peptide in Opti-MEM medium supplemented with 1% penicillin-streptomycin for 30 minutes. Following treatment, cells were washed 2× in PBS, and either immediately harvested or incubated in complete growth media for an additional 72 hours. Cells were harvested with 0.05% trypsin-EDTA, centrifuged, and suspended in 0.1% Trypan blue in PBS (−/−) for analysis on a FACSCalibur flow cytometer (Becton Dickinson) with BD CellQuest™ Pro software (V 5.2). Data was exported and analyzed with FlowJo software (V 7.6.4). All samples were run in triplicate.

The intracellular MK2i half-life ($t_{1/2}$) was calculated by exponential decay nonlinear regression analysis of intracellular peptide fluorescence at 0 and 5 days following treatment removal using the exponential decay function [where N=intracellular fluorescence and λ=the decay rate]:

$$N(t)=N_o e^{-\lambda s} \quad (eq.S1)$$

And calculating the $t_{1/2}$ from the decay constant of each exponential decay function as follows:

$$t_{1/2}=\ln(2)/\lambda \quad (eq.S2)$$

Human Saphenous Vein (HSV)

De-identified, discarded segments of HSV were collected from consented patients undergoing coronary or peripheral vascular bypass surgeries. Following surgical resection, HSV segments were stored in saline solution until the end of the surgical procedure, at which time they were placed in cold transplant harvest buffer (100 mM potassium lactobionate, 25 mM $KH_2PO_4$, 5 mM $MgSO_4$, 30 mM raffinose, 5 mM adenosine, 3 mM glutathione, 1 mM allopurinol, 50 g/L hydroxyethyl starch, pH 7.4). All HSV segments were used within 24 hours of harvest. Utilizing sterile technique in a sterile culture hood, HSV segments were transferred to a 60 mm Petri dish. The end of each segment (0.5 mm) was removed with a blade, and excess adventitial and adipose tissue was removed with minimal manipulation. HSV segments were cut into consecutive rings with an approximate width of 1.0 mm to be utilized in organ culture experiments. Two rings from each segment were immediately fixed in 10% formalin at 37° C. for 30 min to obtain pre-culture intimal thickness measurements.

Prior to experiments, HSV viability was confirmed. HSV rings were weighed and their lengths recorded. HSV rings were then suspended in a muscle bath containing a bicarbonate buffer (120 mM NaCl, 4.7 mM KCl, 1.0 mM MgSO4, 1.0 mM NaH2PO4, 10 mM glucose, 1.5 mM CaCl2, and 25 mM Na2HCO3, pH 7.4) equilibrated with 95% O2 and 5% CO2 at 37° C. The rings were stretched and the length progressively adjusted until maximal tension was obtained 49. Normalized reactivity was obtained by determining the passive length-tension relationship for each vessel segment. Rings were maintained at a resting tension of 1 g, which produces maximal responses to contractile agonists, as previously determined, and equilibrated for 2 h in buffer. Force measurements were obtained using a Radnoti Glass Technology (Monrovia, Calif.) force transducer (159901A) interfaced with a Powerlab data acquisition system and LabChart software (AD Instruments, Colorado Springs, Colo.).

HSV rings were initially isometrically contracted with 110 mM KCl (with equimolar replacement of NaCl in bicarbonate buffer), and the generated force was measured. 110 mM KCl causes membrane depolarization, leading to contraction of vessels containing functionally viable smooth muscle. After vessel viability was verified with multiple KCl challenges, additional rings were cut to be utilized in smooth muscle physiology experiments and for F-actin staining.

HSV Smooth Muscle Physiology Studies

Inhibition of HSV Contraction

Viable HSV rings were washed, allowed to equilibrate in bicarbonate solution for 30 min, and then contracted with phenylephrine (PE, 1 μM). All rings were washed and equilibrated in fresh buffer and allowed to relax until baseline contraction was achieved. Rings were then incubated with either MK2i peptide, MK2i-NPs, p-HSP20 peptide, p-HSP20-NPs, or buffer alone for 2 h. Treated HSV rings were then contracted with the same doses of PE, and the forces generated were again recorded. Measured force was normalized for ring weight and length and percent inhibition of contraction was calculated by dividing the post-treatment contractile force with the pre-treatment contractile force; pre-treatment force generated with 1 μM PE was set as 100% contraction. Data was obtained in HSV from n ≥3 separate patients.

Enhanced HSV Vasorelaxation

Viable HSV rings were washed and allowed to equilibrate in bicarbonate solution for 30 min, and then contracted with phenylephrine (PE, 1 μM). Rings were relaxed with a cumulative log dose of sodium nitroprusside (SNP, 0.1-10 μM), a nitric oxide donor, and the resulting decrease in contractile force was recorded over time. All rings were again washed and equilibrated in buffer for 15 min. Rings were then incubated with either MK2i peptide, MK2i-NPs, p-HSP20, p-HSP20-NPs, or buffer alone for 2 h, followed by treatment with the same doses of PE and SNP. The forces generated were again recorded, and measured force was normalized for ring weight and length and percent relaxation was calculated; force generated with 100 μM PE was set as 0% relaxation. Data was obtained in HSV from n≥3 separate patients.

Actin Staining of Angiotensin II Stimulated HSV

Viable HSV rings were placed in a 24 well plate in RPMI medium supplemented with 10% FBS and 1% penicillin-streptomycin and allowed to equilibrate in an incubator at 37° C. and 5% $CO_2$ for several hours. HSV rings were then treated with 100 μM MK2i peptide, 100 μM MK2i-NPs, 500 μM p-HSP20, or 500 μM p-HSP20-NPs or PBS −/− as a negative control for 30 minutes in Opti-MEM medium supplemented with 1% penicillin-streptomycin and then washed 2× in PBS −/−. Subsequently, treated HSV rings were stimulated with 10 μM angiotensin II for 2 hours and then washed 2× in PBS −/−. HSV rings were then immediately fixed in 4% paraformaldehyde for 4 hours at 37° C. HSV rings were then incubated overnight in 30% sucrose in 1×PBS −/−. HSV rings were washed 2× in PBS −/−, embedded in OCT and frozen. 10 micron cryosections were cut from the midportion of each HSV rings and placed onto SuperFrost Plus microscope slides (Fisher Scientific). The slides were then stained and imaged according to the procedure stated in the F-actin stress fiber assay section above. Full HSV sections were compiled through the image stitching capability in the NIS Elements software.

HSV Organ Culture and Assay for Ex Vivo Intimal Hyperplasia (IH)

Prior to organ culture experiments, HSV viability was confirmed. HSV rings were weighed and their lengths recorded. HSV rings were then suspended in a muscle bath containing a bicarbonate buffer (120 mM NaCl, 4.7 mM KCl, 1.0 mM $MgSO_4$, 1.0 mM $NaH_2PO_4$, 10 mM glucose, 1.5 mM $CaCl_2$, and 25 mM $Na_2HCO_3$, pH 7.4) equilibrated with 95% $O_2$ and 5% $CO_2$ at 37° C. The rings were stretched and the length progressively adjusted until maximal tension was obtained. Normalized reactivity was obtained by determining the passive length-tension relationship for each vessel segment. Rings were maintained at a resting tension of 1 g, which produces maximal responses to contractile agonists, as previously determined, and equilibrated for 2 hr in buffer. Force measurements were obtained using a Radnoti Glass Technology (Monrovia, Calif.) force transducer (159901A) interfaced with a Powerlab data acquisition system and Chart software (AD Instruments, Colorado Springs, Colo.).

HSV rings were initially contracted with 110 mM KCl (with equimolar replacement of NaCl in bicarbonate buffer) and the force generated was measured. 110 mM KCl causes membrane depolarization, leading to contraction of vessels containing functionally viable smooth muscle. After vessel viability was verified with multiple KCl challenges, additional rings were cut and placed in a 24 well plate and maintained in RPMI 1640 medium supplemented with 30% FBS, 1% L-glutamine and 1% penicillin/streptomycin for 14 days at 37° C. in an atmosphere of 5% CO2 in air. The rings were untreated, treated with MK2i-NPs, NE-MK2i-NPs, MMI-0100 (MK2i) peptide, or buffer alone for 2 hours, washed, and given fresh media. The culture medium without treatments was replaced every 2 days for 14 days.

HSV Viability

To ensure that the treatments did not impact tissue viability, an MTT assay (Life Technologies) for assessing cell viability was performed on HSV rings at 1 and 14 days after treatment. HSV rings were prepared and treated as noted above, and following 1 or 14 days of organ culture, HSV rings were weighed and then placed in 250 μL of 0.01% methyl tetrazolium dissolved in DPBS. The rings were placed in a 37° C. incubator for 1 hour. The reaction was stopped by placing the rings into distilled water. The rings were then placed into 1 mL of CelloSolve and incubated at 37° C. overnight. Following incubation, rings were mixed in solution, and the CelloSolve was extracted and placed into a cuvette where the optical density at 570 nm was determined. Relative viability calculations were based on the optical density normalized to the wet weight of the ring.

Vessel Morphometry

After 14 days of organ culture, vein segments were fixed in 0.5 ml of 10% formalin at 37° C. for 30 min and embedded in paraffin for sectioning. Beginning at the mid-portion of each ring, 5 transverse sections, spaced 5 μm apart, were cut from each specimen. Sections were then stained with Verhoeff-van Gieson stain. Histology sections were imaged using a Nikon Eclipse Ti inverted fluorescence microscope (Nikon Instruments Inc, Melville, N.Y.), and 6 radially parallel measurements of intimal and medial thickness were randomly taken from each section using NIS Elements imaging software (total of 6-12 measurements per ring, n≥3 rings per treatment group from separate donors). Intima was defined as tissue on the luminal side of the internal elastic lamina or the chaotic organization of the cells contained within it, whereas the medial layer was contained between the intimal layer and the external elastic lamina. Intimal and medial thickening was measured for each section at 10× magnification with the microscope's computerized image analysis software.

Microscopic Analsyis of MK2i Delivery to HSV

After verifying viability, HSV rings were treated with Alexa-568 labeled MMI-0100 (MK2i) peptide, MK2i-NPs, or NE-MK2i-NPs for 30 minutes, washed 2× in PBS −/−, and immediately embedded in optimal cutting temperature (OCT) compound (Fisher Scientific) and frozen over dry ice. 5 μm cryosections were cut from the middle of each treated vessel and mounted on microscope slides for analysis of peptide delivery into the vessel wall. Immunofluorescence staining was then carried out with CD31 and α-SMA primary antibodies and a FAM labeled secondary antibody. Microscopy images were obtained using a Nikon Eclipse Ti inverted fluorescence microscope or a LSM 710 META fluorescence microscope with ZEN imaging software (Carl Zeiss Thornwood, N.Y.). Gain settings were kept constant for all images acquired for every treatment group, and images were stitched together in Adobe Photoshop to provide a macroscopic image of the entire section of the HSV ring.

Western Blot Analysis

Following 2 hours of treatment with MMI-0100 (MK2i) peptide, a portion of the treated HSV rings was snap-frozen with liquid nitrogen, pulverized, and homogenized using urea-DTT-CHAPS buffer. For analysis of heterogeneous nuclear ribonucleoprotein A0 (hnRNP A0) phosphorylation, treated HSV rings were maintained in organ culture in fresh media for 24 hours prior to homogenization. For analysis of CREB and HSP27 phosphorylation, HSV rings were frozen after the 2 hour treatment. Lysates were centrifuged (6000 g, 20 minutes), and the supernatant was collected for evaluation of hnRNP A0, cAMP response element-binding (CREB) protein, and heat shock protein 27 (HSP27) phosphorylation. Equal amounts of protein (20 μg per lane) were loaded on 15, 10, or 4-20% SDS-PAGE gels; proteins were electrophoretically separated, and then transferred to Immobilon membranes (Millipore, Billerica, Mass.). For hnRNP A0 phosphorylation, membranes were probed overnight at 4° C. with primary antibodies for phospho-hnRNP A0 (Millipore) and unphosphorylated hnRNP A0 (Santa Cruz). For CREB phosphorylation, membranes were probed overnight at 4° C. with primary antibodies for phospho-CREB (abcam) and unphosphorylated CREB (abcam). For HSP27 phsophorylation membranes were probed overnight at 4° C. with primary antibodies for phospho-HSP27 (Epitomics) and unphosphorylated HSP27 (Santa Cruz). After washing, the membranes were incubated with appropriate secondary antibodies (Li-Cor) for 1 hour at room temperature. The secondary antibody was imaged using the Odyssey direct infrared fluorescence imaging system (Li-Cor) and densitometrically quantified with LiCor Odyssey software v2.1 at 800 and 680 nm wavelengths. For each biological replicate, all treated samples were normalized to untreated control tissue.

For MK2i-NP and HSP20-NP studies, western blot analysis of the cytosolic and organelle fractions from the digitonin semi-permeabilization procedure was performed. Briefly, cytosolic and organelle fractions were concentrated on a centrifuge using Vivacon 500 DNA concentrators (2000 MWCO). Equal amounts of protein (20 μg per lane) were loaded on 4-20% SDS-PAGE gels; proteins were electrophoretically separated and then transferred to Immobilon membranes. The membranes were then probed overnight at 4° C. with primary antibodies for the cytosolic proteins mitogen-activated protein kinase 1/2 (MEK1/2) and glyceraldehyde 3-phosphate dehydrogenase (GAPDH) and the endo-lysosomal markers early endosomal antigen 1 (EEA1) and lysosomal-associated protein 1 (LAMP1). All antibodies were obtained from Cell Signaling Technologies. After washing, the membranes were incubated with appropriate secondary antibodies (Li-Cor) for 1 hour at room temperature. The secondary antibody was imaged using the Odyssey direct infrared fluorescence imaging system and densitometrically quantified with LiCor Odyssey software v2.1 at 800 and 680 nm wavelengths.

Rabbit Bilateral Jugular Vein Graft Interposition Model

Male New Zealand White rabbits (3.0-3.5 kg; n=24) were anesthetized b an intramuscular injection with ketamine hydrochloride (1.4 mg/kg) and xylazine (0.2 mg/kg). Anesthesia was maintained with endotracheal intubation and inhaled isoflurane (2.0-5.0%). A high-dose IV heparin bolus (250 U/kg) was administered immediately prior to carotid cross clamp. The operative procedure was performed with aseptic technique under optical magnification (magnification ×2.5).

Vein bypass grafts were constructed with an anastomotic cuff technique as described by Jiang et al. (Am. J. Physiol. Heart Circ. Phyisol. 286,H240-245 (21004). Briefly, polymer cuffs consisting of a 2.0-mm body loop were fashioned from a 4-Fr introducer sheath (Terumo Medical, Elkton, Md.). Following ligation of smaller tributary vessels, the external jugular veins were harvested (3.0-4.0 cm in length) for creation of an interposition graft into the common carotid artery. Jugular vein ends were passed through a cuff, everted, and fixed with 6-0 silk. Vein grafts were subsequently treated for 30 minutes in 2 mL of Heparin Plasma-Lyte solution containing either 30 µM MK2i-NP, 30 µM MMI-0100 (MK2i) peptide, or PBS (no treatment). Following treatment, the carotid artery lumen was exposed with a 2.0-cm arteriotomy, and the cuffed, reversed vein ends were inserted. A 3-0 silk was used to secure the artery around the cuff. Finally, 1.0 cm of carotid artery back wall was cut away between the cuffs to permit vein graft extension.

Rabbits were euthanized at 28 days post-operatively, and vein grafts were perfusion fixed in situ with 10% neutral buffered formalin under ~50 mm Hg pressure with a roller pump. Vein grafts were subsequently excised and sectioned into four segments avoiding the tissue overlying the cuff in order to allow for evaluation of morphological variation along the length of the graft. Histological sections were prepared, and intimal and medial thicknesses were quantified by taking 3 measurements from each quadrant of each vessel section (12 measurements/segment=48 measurements/graft). Separate sections were stained with the rabbit macrophage antibody RAM-11 (Dako) to evaluate treatment effect on the infiltration of immune cells into the intima of each graft. Macrophage positive staining in the intima was quantified by manually counting the number of positively stained cells in the intima of stained graft sections. 16 histological images from 4 different graft sections were analyzed for each treatment group.

Cytotoxicity Assay

200 µL of cell suspension (at 10,000 cells/well) were seeded onto 96-well plates to yield an approximate 70% confluence per well. Cells were allowed to adhere to the plate overnight. Cells were then treated with 10, 50, 100, and 500 µM doses of MK2i-NPs, p-HSP20-NPs, MK2i peptide, p-HSP20 peptide, or PBS as a control treatment for 2 hours in Opti-MEM medium supplemented with 1% penicillin-streptomycin. Treatments were subsequently removed and the cells were cultured in fresh complete growth medium for 24 hours. Cells were then washed 2× with PBS +/+ and cell viability was then determined by a CytoTox-ONE Homogenous Membrane Integrity assay (Promega) according to the manufacturer's protocol. Briefly, 100 µL of Ambion KDalert Lysis Buffer was added to each well, and then 100 µL of freshly prepared CytoTox-ONE reagent was added to each well. After 10 minutes of incubation, 50 µL of stop solution was added, and the fluorescence of each well (k$\lambda_{ex}$=560 nm, $\lambda_{em}$, =590 nm) was determined with a TECAN Infinite M1000 Pro plate reader.

F-Actin Stress Fiber Assay

HCAVSMCs were seeded in Lab-Tek II 8-well chambered coverglass (Thermo Scientific Nunc) at 15,000 cells/well and allowed to adhere overnight. Cells were then treated in low serum media (Optimem, 1% FBS, and 1% P/S) with MK2i-NPs, p-HSP20-NPs, MK2i peptide, p-HSP20 peptide, or at concentrations of 10, 25, and 50 µM (PBS -/- as a control) for 1 hour. Following treatment, cells were washed 2× with PBS -/- and subsequently treated with 1 µM Angiotensin II (Sigma Aldrich) or PBS -/- (negative control) for 2 hours. After ANG-II stimulation cells were washed 2× with PBS, fixed in 4% paraformaldehyde for 5 minutes, permeabilized with 0.4% Triton-X 100 for 10 minutes, and blocked with 1% BSA in PBS -/- for 15 minutes. Cells were then stained with Hoechst solution (1/5000 dilution in PBS -/-) for 10 minutes followed by staining with Alexa-488-Phallodin (Life Technologies) for 30 minutes according to the manufacturer's instructions. Stained coverslips were then inverted onto glass cover slides with ProLong Gold Antifade mounting medium (Invitrogen). Slides were allowed to dry for 24 hours prior to sealing and imaging. Treated cells were imaged using a Nikon Eclipse Ti inverted fluorescence microscope (Nikon Instruments Inc, Melville, N.Y.) with NIS Elements imaging software. Gain settings and exposure times were kept constant for all images taken. The number of stress fibers per cell was quantified as previously described[48]. Briefly, in the NIS elements software, 3 separate intensity profiles were generated across the axis of stained cells perpendicular to the cell's polarity. Prior to image analysis, the background noise from each image was removed using a rolling ball background subtraction filter with a radius of 70 pixels. A fluorescence level of 2000 RFU was set as the threshold for positive F-actin fiber staining as the background fluorescence outside of the stained cells was never greater than this value. The stress fibers per cell were then quantified from the average of 3 intensity profiles from n≥6 cells from 2 separate experiments for each treatment group (total n≥36 ROIs for each treatment group). Relative quantification of cellular F-actin content was further quantified using imageJ software to free hand select individual cells and to calculate the relative fluorescence intensity of n≥12 cells from 2 separate experiments for each treatment group.

Figure 3:
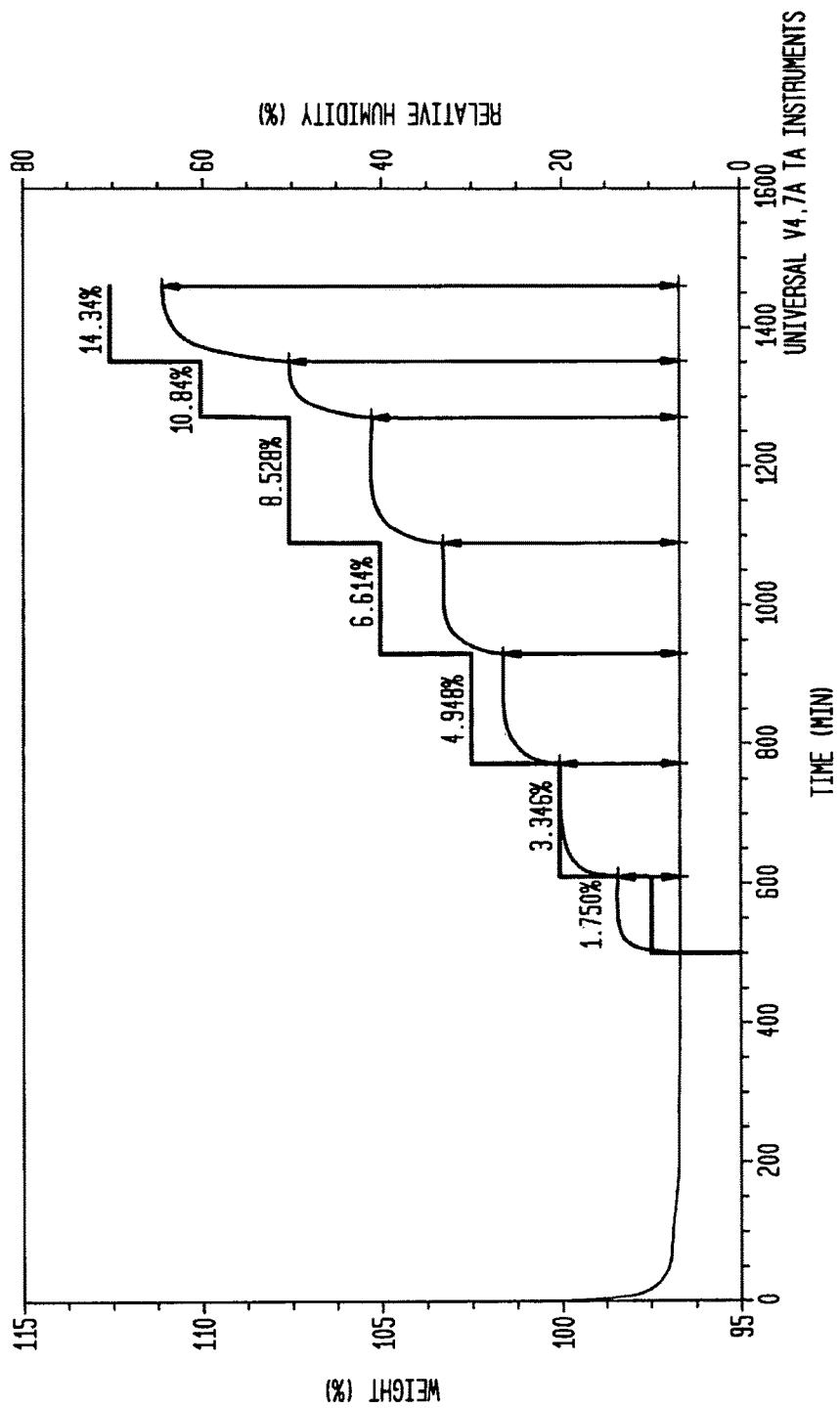
FIG. 3 shows a dynamic vapor sorption isotherm for a MMI-0100 5% solids formulation.

Quantification of Cytosolic Vs. Organell Bound Peptide Through Semi-Permeabilization In order to quantify the cytosolic bioavailability of the MK2i and HSP20 peptides a method to separate cytosolic and organelle bound (i.e. endosomal, lysosomal, golgi, etc.) peptide was adapted from the methods developed by Liu et a140. The procedure was optimized for this experiment based upon LDH release from HCAVSMCs treated with varying concentrations of digitonin (Calbiochem) in buffer (150 mM NaCl, 0.2 mM EDTA, 20 mM HEPES-NaOH (pH 7.4), 2 mM DTT and 2 mM MgCL2) on ice for 10 mins on a rotary shaker operating at 100 RPM (supplementary FIG. 3). A concentration of 25 µg/mL was then chosen as the optimal digitonin concentration for selective semi-permeabilization of the HCAVSMC membrane and subsequently used for the analysis of intracellular peptide distribution.

To quantify intracellular distribution of the MK2i and p-HSP20 peptides, HCAVSMCs were seeded into a 96 well plate at a density of 20,000 cells/cm2 and allowed to adhere overnight in complete growth medium. A portion of the cells were pretreated with 500 nM Bafilomycin A1 (Sigma) for 30 minutes, and the Bafilomycin was included in subsequent peptide/NP treatment and in the post-treatment incubation phase to inhibit endosomal acidification. Cells were then treated with Alexa-488 labeled MK2i peptide, MK2i-NPs, p-HSP20 peptide, p-HSP20-NPs at a concentration of 10 µM peptide (or PBS -/- as a control) in Opti-MEM medium supplemented with 1% penicillin-streptomycin with or without 500 nM Bafilomycin A1 for 30 minutes. Treatments were removed and cells were incubated in fresh medium with or without 500 nM Bafilomycin A1 for 6 hours. Each well was then washed 1× with ice cold PBS +/+ and then subsequently incubated with 20 uL of 25 µg/mL digitonin solution at 0° C. (on ice) on a rotary shaker operating at 100 RPM for 10 minutes. The supernatant from each well was then transferred to a new 96 well plate, and each well was washed with 80 µL ice cold PBS +/+ which was then transferred to the 96 well plate containing the digitonin (cytosolic) fractions. 100 uL of 1% triton X-100 in PBS −/− was then added to each well to obtain a 96 well plate containing all non-cytosolic (i.e. organelle bound) cellular components, and the fluorescence of each well (λex=495 nm, λem=519 nm) was determined with a TECAN Infinite M1000 Pro plate reader. Readings were normalized to cell number and cytosolic content as determined by a CytoTox-ONE Homogenous Membrane Integrity assay (Promega) according to the manufacturer's protocol (section 4.5).

Statistics

Statistical analysis was performed with one-way ANOVA followed by Tukey's post-hoc test to compare experimental groups. Analyses were done with OriginPro 8 software (Originlab, Northampton, Mass.) or Minitab 16 software (State College, Pa.). Statistical significance was accepted within a 95% confidence limit. Results are presented as arithmetic mean±SEM graphically and p-values are included within figures or in the figure legends.

Example 1. Dry Powder Formulations of MMI-0100 (YARAAARQARAKALARQLGVAA; SEQ ID NO: 1)

Gravimetric clearance testing of blisters filled with 1 and 2 mg of neat spray dried MMI-0100 (YARAAARQARAKALARQLGVAA; SEQ ID NO: 1) 5% solids formulation was used to optimize and determine aerosol performance. Blisters were filled inside a glove box at 4-5% relative humidity. Sealing of blisters occurred inside the glove box using a bench-top heat sealer. An EPIC style inhaler was coupled with function generators to perform all aerosol tests. Table 3 contains information on final (optimal) blister, device and test conditions.

Uptake of water by the spray dried formulation was investigated. Dynamic Vapor Sorption (DVS) Isotherm confirmed the rapid uptake of water in the spray dried formulation as the % relative humidity (RH) was increased over time (FIG. 3). In order to maintain less than 3% water in the formulation, the DVS indicated that the material should be handled at less than 20% RH (FIG. 3). In addition, a controlled charge dissipating unit was installed inside a glove box to neutralize the positively charged filling station (i.e., due to the glove box's polycarbonate construction) Negative ions were released by a pulsed DC controller around the vicinity of filling to neutralize positive charges.

A rapid HPLC method was developed to determine, for example, formulation impurities and the concentration of MMI-0100 contained in the formulations. Briefly, a Supelco Ascentis Express® Peptide ES-C18 column was used. The flow rate, column temperature, and mobile phase were adjusted to give a run time of 3 minutes. Evaluation of the linearity of the rapid HPLC method indicated acceptable linearity between 6.5 to 32 mg/mL based on % response factor of the mean response factor for the 10.8 μg/mL working standard (97.0 to 101.4% of the mean response factor). A decrease in linearity was observed at 2.2 μg/mL, however, this decrease was at an acceptable level for limit of quantitation (LOQ) to quantitate low deposition next generation impactor (NGI) stages (such as microorifice collector (MOC)). An example chromatogram of the working standard is shown in FIG. 4. A summary of the final HPLC method parameters are listed below:

Column: Supelco Ascentis Express® Peptide ES-C18, 50×4.6 mm, 2.7 Jim
Flow rate: 1.5 mL/min
Injection volume: 40 μL
Column Temperature: 40° C.
Sample Temperature: 5° C.
Detector Wavelength: 215 nm
Mobile Phase A: 0.1% TFA in Water (72%)
Mobile Phase B: 0.1% TFA in 1:1 Methanol: Acetonitrile (28%).

A next generation impactor (NGI) method was developed. NGI cups were coated with 5% Tween 20 in methanol. Blisters filled with formulation neat spray dried MMI-0100 5% w/w solids were dosed at 15 L/min using an EPIC device as outlined in Table 3. Although the use of a preseparator is not typically required for non-lactose based formulations, it was included to collect possible large aggregates. All NGI components were initially extracted with 10 mL of 0.02% Tween 20 in water as the sample solvent. Adjustments to the extraction volumes varied throughout the project based on the fill weight and amount of MMI-0100 dosed into the impactor. Recovery was assessed and method alterations were developed to maintain recoveries of greater than 85%.

Aerosol performance was evaluated and optimized using an EPIC inhaler similar to the device shown in FIG. 5. A function generator set-up was used affording greater flexibility in drive scheme development. Blisters filled with 1 and 2 mg of the 5% solids and 2 mg of the 1% solids formulation were evaluated for gravimetric clearance to assess powder clearance from the blister and device. A drive scheme consisting of a single pulse of 2.0 second duration was used with the EPIC inhaler with a standard EPIC flow channel. Since the baseline clearance results were acceptable (>80% mass cleared from the blister), NGI tests were performed to evaluate the aerodynamic particle size distribution (PSD). Table 4 contains the aerosol results summary. FIG. 6 shows the particle size distribution plots.

TABLE 4

Initial Aerosol Performance Results

| 5% Solids - Spray Dried MMI-0100 5% w/w solids | |
|---|---|
| 1.0 mg Fill Weight<br>Gravimetric Clearance = 88.3%<br>Loaded Dose = 775 μg<br>Delivered Dose = 500 μg<br>Fine Particle Dose (FPD) ≤5.0 μm = 379 μg<br>FPD ≤3.0 μm = 206 μg<br>Mass Median Aerodynamic Diameter (MMAD) = 3.2 μm | 2.0 mg Fill Weight<br>Gravimetric Clearance = 83.0%<br>Loaded Dose = 1563 μg<br>Delivered Dose = 1105 μg<br>FPD ≤5.0 μm = 650 μg<br>FPD ≤3.0 μm = 305 μg<br>MMAD = 3.8 μm |
| 1% Solids - Spray Dried MMI-0100 1% w/w Solids | |
| 1.0 mg Fill Weight<br>Not tested (higher fill weights were preferred to maximize the FPD) | 2.0 mg Fill Weight<br>Gravimetric Clearance = 88.3%<br>Loaded Dose = 1580 μg<br>Delivered Dose = 1183 μg<br>FPD ≤5.0 μm = 508 μg<br>FPD ≤3.0 μm = 352 μg<br>MMAD = 3.6 μm |

The results of initial aerosol performance testing indicated that the 5% and 1% solids formulations can be disbursed from the inhaler with good efficiency and offerred a good starting point for optimization to reduce the MMAD values closer to the target of 2 μm. The results at 1.0 mg fill weight were closest to the target MMAD at 3.2 μm. At the 2 mg dose level, the 1% solids formulation provided a finer distribution as shown by the higher Fine Particle Dose (FPD)<3.0 μm and particle size distribution centered around stage 5 of the NGI (FIG. 6). With additional optimization, the 1% solids formulation was more likely to meet the aerosol performance targets as defined at the onset of the project and therefore was selected as the lead formulation moving forward.

Figure 7:
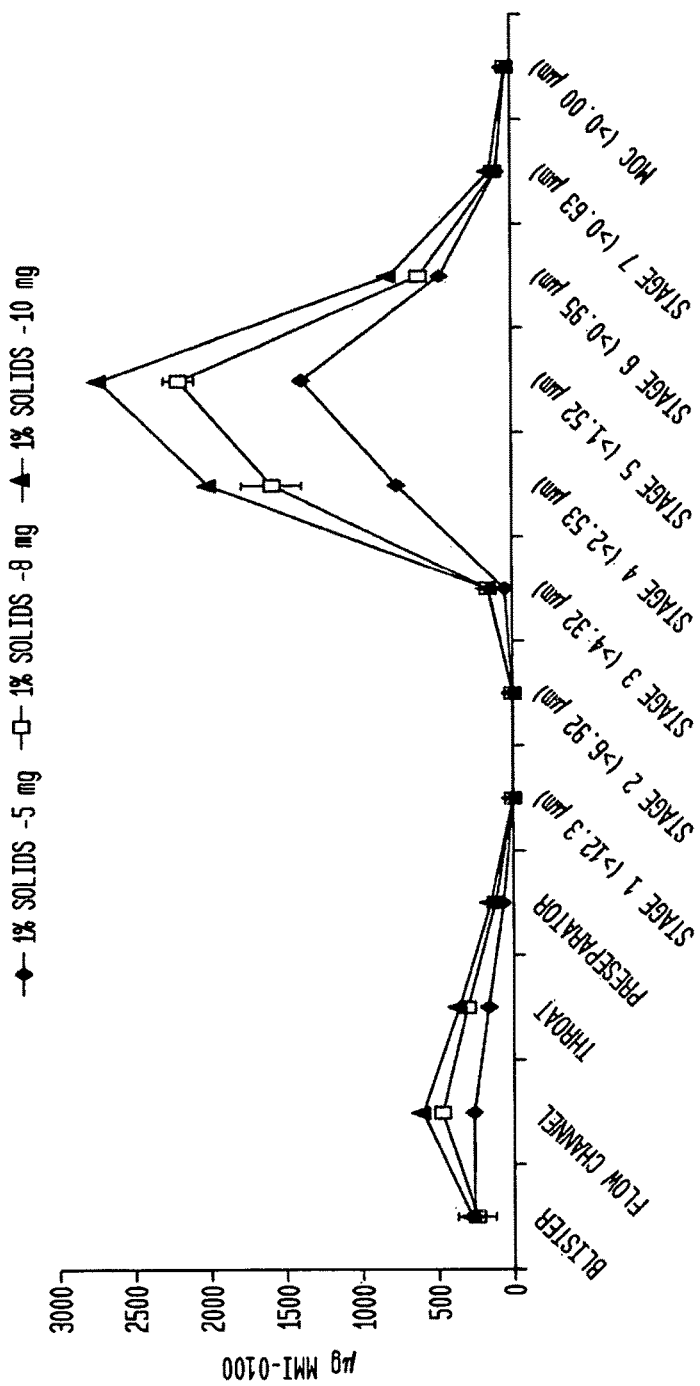
FIG. 7 shows a particle size distribution plot of fill weights up to 10 mg for MMI-0100 1% solids formulation (after optimization).

In an effort to increase the fill weight above 2 mg, modifications were made to the existing flow channel of the inhaler to increase the air velocity over the pierced holes of the blister. Without being bound by theory, an increase in the air velocity is thought to increase the rate of clearance of particles from the blister. The gravimetric clearance of blisters filled with up to 10 mg of the 1% solids formulation was found to be acceptable (>90%) at a flow rate of 25 L/min. Three NGI tests were performed at fill weights of 5 and 8 mg, and a single NGI was performed to assess the feasibility of dosing 10 mg. These results are summarized in Table 5 and FIG. 7. Error bars are included for the 5 and 8 mg fill weights. The 5 mg aerosol performance tests were highly reproducible.

TABLE 5

Aerosol Performance Results at Fill Weights up to 10 mg After Optimization

| Fill Weight (mg) | % Clearance | Delivered Dose (μg) | FPD ≤5.0 μm (μg) | FPF ≤5.0 μm (% of Delivered) | FPD ≤3.0 μm (μg) | FPF ≤3.0 μm (% of Delivered) | MMAD (μm) |
|---|---|---|---|---|---|---|---|
| 5 | 92.1 | 3135 | 2791 | 89.0 | 2362 | 75.3 | 2.1 |
| 8 | 94.9 | 5249 | 4615 | 87.9 | 3675 | 70.0 | 2.2 |
| 10 | 95.3 | 6575 | 5839 | 88.8 | 4658 | 70.8 | 2.2 |

*FPF = Fine Particle Fraction

Figure 8:
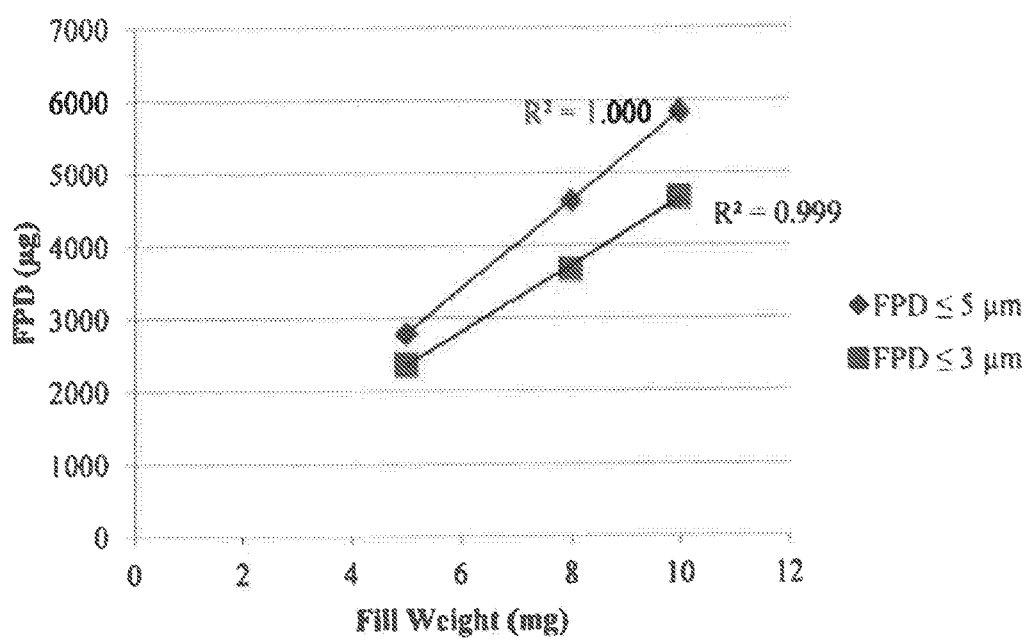
FIG. 8 shows a linearity plot of fine particle dose (FPD) from 5 to 10 mg of MMI-0100 1% solids formulation.

Device optimization permitted efficient formulation dispersion as noted by increased Fine Particle Dose (FPD), decreased MMAD, and decreased throat and pre-separator retention. The resulting MMADs of 2.1 to 2.2 μm met the project target and the successful delivery of 10 mg of formulation results in a Fine Particle Dose <3.0 μm of 4.7 mg. The results from 5 to 10 mg also indicate dose linearity which will allow for adjustment of both the fill weight and number of blisters to achieve the required clinical doses (See FIG. 8 for linearity plot).

Figure 9:
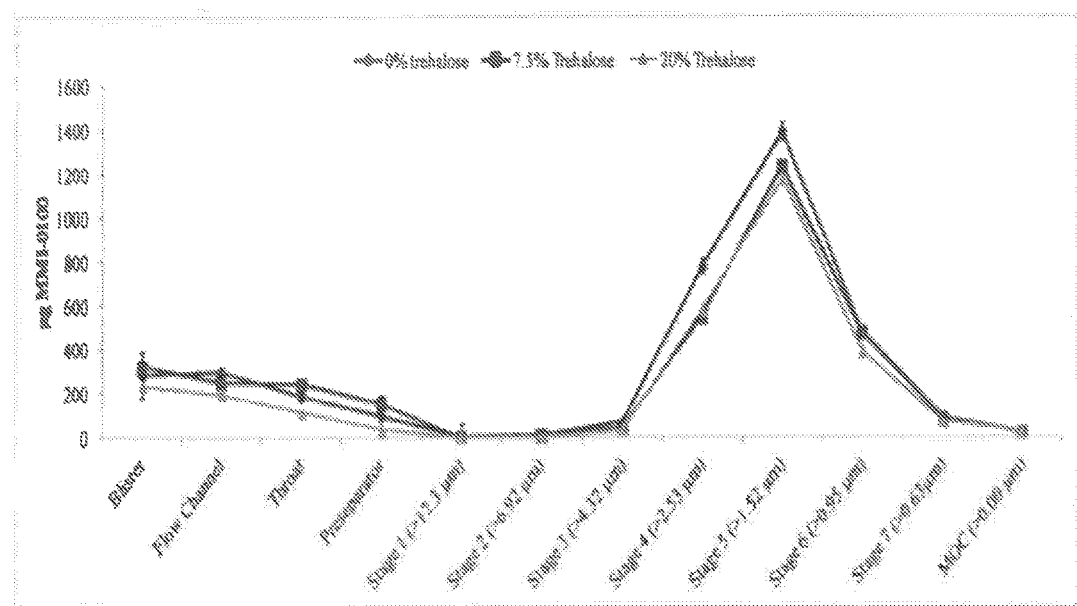
FIG. 9 shows a particle size distribution plot of MMI-0100/Trehalose variant formulations.

Using identical device conditions, the formulations co-spray dried with 7.5 and 20% Trehalose (Santa Cruz Biotechnology, Inc. Dallas Tex.) were screened for aerosol performance by performing a single NGI for each at a fill weight of 5 mg. The results are summarized and compared to the neat formulation at 5 mg in Table 6 and FIG. 9.

TABLE 6

Aerosol Performance Results with Trehalose Variants at a Fill Weight of 5 mg

| % Trehalose | % Clearance | Delivered Dose (μg) | FPD ≤5.0 μm (μg) | FPF ≤5.0 μm (% of Delivered) | FPD ≤3.0 μm (μg) | FPF ≤3.0 μm (% of Delivered) | MMAD (μm) |
|---|---|---|---|---|---|---|---|
| 0 (Neat) | 92.1 | 3135 | 2791 | 89.0 | 2362 | 75.3 | 2.1 |
| 7.5 | 90.4 | 2812 | 2370 | 84.3 | 2087 | 74.2 | 2.0 |
| 20 | 91.6 | 2423 | 2248 | 92.8 | 1967 | 81.2 | 2.0 |

The trehalose variants at percentages of 7.5 and 20% showed very similar aerosol distribution compared to the neat formulation at the same fill weight. This demonstrated that MMI-0100 can be successfully co-spray dried with trehalose and efficiently dispersed from the inhaler with little or no change in performance over the neat formulation.

Two stability studies were conducted to assess the effect of various conditions on the aerosol performance and impurities of the MMI-0100 (YARAAARQARAKALARQL-GVAA; SEQ ID NO: 1) formulations. Blisters were filled with 5 mg of each of the four formulations (Neat Spray MMI-0100 5% w/w solids; Neat Spray MMI-0100 1% w/w solids; Spray Dried 80/20 MMI-0100/Tehalose 1% w/w solids; Spray Dried 92/5/7.5 MMI-0100/Trehalose 1% w/w solids). Blisters were placed in a 1×5 blister holder and sealed into an aluminum pouch. The pouch blisters were stored, pulled and tested for aerosol performance (n=3 NGI tests per pull condition) according to Table 7.

TABLE 7

Blister Stability Storage and Pull Schedule

| Storage Condition | 0 (Initial) | 2 weeks | 4 weeks |
|---|---|---|---|
| Ambient | X | N/A | N/A |
| 40° C. 75% Relative humidity | N/A | X | X |

TABLE 7-continued

Blister Stability Storage and Pull Schedule

| Storage Condition | 0 (Initial) | 2 weeks | 4 weeks |
|---|---|---|---|
| 25° C./60% Relative humidity | N/A | X | X |
| 2-8° C. | N/A | N/A | X |

Chemical stability in blisters was tested using 5% solids neat MMI-0100 formulation. Blisters were filled with 10 mg, placed in a 1×5 blister holder and sealed into an aluminum pouch. The pouched blisters were stored at 40° C./75% relative humidity, pulled at 2 and 4 weeks, and tested for assay and impurities.

Bulk stability was tested using approximately 50 mg of 1% and 5% solid MMI-0100 formulations. Formulations were transferred to amber glass vials, caps were wrapped with parafilm and the entire vial was placed into an aluminum overwrap pouch and sealed. For trehalose variants, the original glass bottle was treated in a similar manner. Each vial was placed into a stability chamber at 40° C./75% relative humidity and pulled after 4 weeks for assay and impurities testing.

The stability results with respect to aerosol performance (n=3 NGI) for all four formulations stored in single dose blisters with overwrap pouch at 5 mg fill weight are presented in Table 8, Table 9, and Table 10.

TABLE 8

Stability Results for Formulations after 4 Weeks Storage in Blisters at 2-8° C.

| | MMI-0100 1% w/w solids | MMI-0100 5% w/w solids | 92.5/7.5 MMI-0100/Trehalose 1% w/w solids | 80/20 MMI-0100/Trehalose 1% w/w solids |
|---|---|---|---|---|
| % solids in water on spray drying | 1 | 5 | 1 | 1 |
| % Trehalose | 0 | 0 | 7.5 | 20 |
| Mean Theoretical Drug Load (μg) | 3948 | 3913 | 3647 | 3162 |
| % Gravimetric Clearance | 95.8 | 95.8 | 95.4 | 94.8 |
| Derived Delivered Dose (DDD) (μg) | 3260 | 3292 | 2976 | 2599 |
| % DDD of Initial | 96.8 | 93.6 | 99.5 | 99.6 |
| FPD ≤5.0 μm (μg) | 2886 | 2613 | 2634 | 2344 |
| FPD ≤5.0 μm (μg) (% of Initial) | 97.5 | 93.4 | 101.0 | 99.7 |
| FPD ≤3.0 μm (μg) | 2437 | 1769 | 2230 | 2032 |
| FPD ≤3.0 μm (μg) (% of Initial) | 98.4 | 95.2 | 100.8 | 100.7 |
| MMAD (μm) | 2.1 | 2.7 | 2.1 | 2.0 |
| Geometric Standard Deviation (GSD) | 1.6 | 1.6 | 1.6 | 1.5 |

TABLE 9

Stability Results for Formulations after 4 Weeks Storage in Blisters at 25° C./60% RH

| | MMI-0100 1% w/w solids | MMI-0100 5% w/w solids | 92.5/7.5 MMI-0100/Trehalose 1% w/w solids | 80/20 MMI-0100/Trehalose 1% w/w solids |
|---|---|---|---|---|
| % solids in water on spray drying | 1 | 5 | 1 | 1 |
| % Trehalose | 0 | 0 | 7.5 | 20 |
| Mean Theoretical Drug Load (μg) | 3982 | 3925 | 3578 | 3077 |
| % Gravimetric Clearance | 95.2 | 95.4 | 95.8 | 95.7 |
| Derived Delivered Dose (DDD) (μg) | 3256 | 3402 | 2941 | 2525 |
| % DDD of Initial | 96.7 | 96.8 | 98.4 | 96.7 |
| FPD ≤5.0 μm (μg) | 2840 | 2720 | 2522 | 2291 |
| FPD ≤5.0 μm (μg) (% of Initial) | 95.9 | 97.2 | 96.7 | 97.4 |
| FPD ≤3.0 μm (μg) | 2375 | 1783 | 2134 | 1978 |
| FPD ≤3.0 μm (μg) (% of Initial) | 95.9 | 95.9 | 96.4 | 98.0 |
| MMAD (μm) | 2.1 | 2.7 | 2.1 | 2.0 |
| Geometric Standard Deviation (GSD) | 1.6 | 1.5 | 1.7 | 1.5 |

TABLE 10

Stability Results for Formulations after 4 Weeks Storage in Blisters at 40° C./75% RH

| | MMI-0100 1% w/w solids | MMI-0100 5% w/w solids | 92.5/7.5 MMI-0100/Trehalose 1% w/w solids | 80/20 MMI-0100/Trehalose 1% w/w solids |
|---|---|---|---|---|
| % solids in water on spray drying | 1 | 5 | 1 | 1 |
| % Trehalose | 0 | 0 | 7.5 | 20 |
| Mean Theoretical Drug Load (μg) | 3925 | 3914 | 3606 | 3145 |
| % Gravimetric Clearance | 95.2 | 94.4 | 94.2 | 94.3 |
| Derived Delivered Dose (DDD) (μg) | 3223 | 3333 | 2939 | 2532 |
| % DDD of Initial | 95.7 | 94.8 | 98.3 | 97.0 |
| FPD ≤5.0 μm (μg) | 2742 | 2499 | 2472 | 2222 |
| FPD ≤5.0 μm (μg) (% of Initial) | 92.6 | 89.3 | 94.8 | 94.5 |
| FPD ≤3.0 μm (μg) | 2309 | 1695 | 2096 | 1890 |
| FPD ≤3.0 μm (μg) (% of Initial) | 93.3 | 91.1 | 94.7 | 93.6 |
| MMAD (μm) | 2.1 | 2.7 | 2.1 | 2.1 |
| Geometric Standard Deviation (GSD) | 1.7 | 1.7 | 1.8 | 1.6 |

Figure 10:
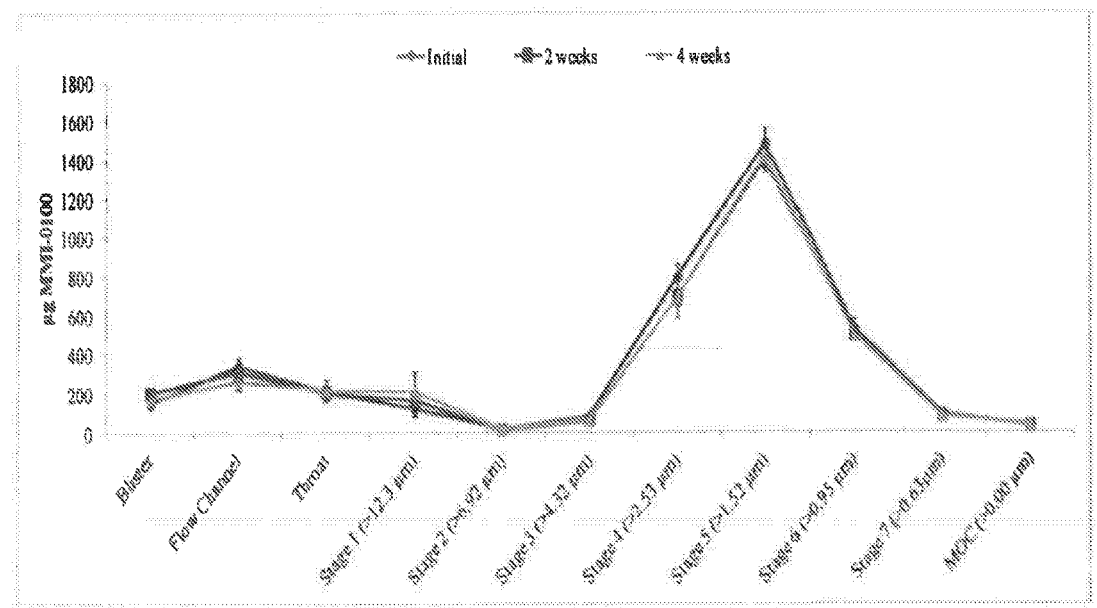
FIG. 10 shows a particle size distribution plot of MMI-0100 1% solids formulation after 4 weeks storage in blisters at 40° C./75% RH.
Figure 11:
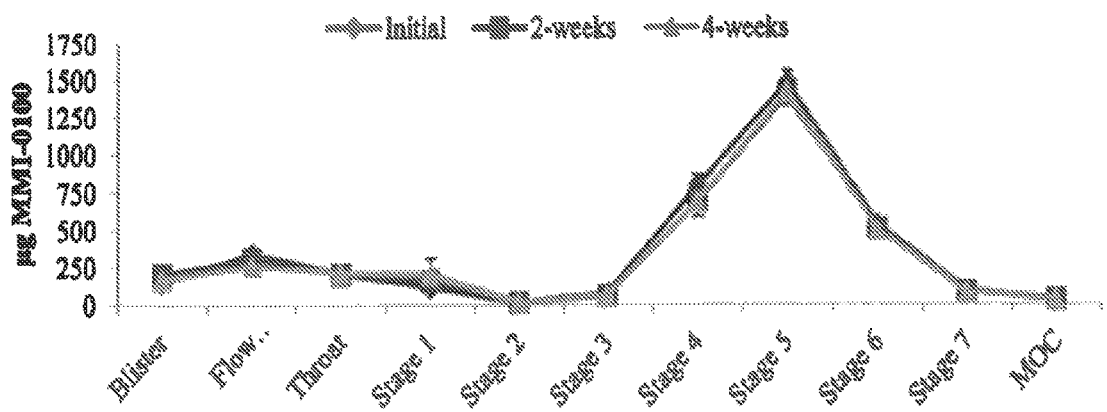
FIG. 11 shows a particle size distribution plot of recovered drug at 40° C./75% relative humidity (RH) for the MMI-0100 1% solids formulation.
Figure 12:
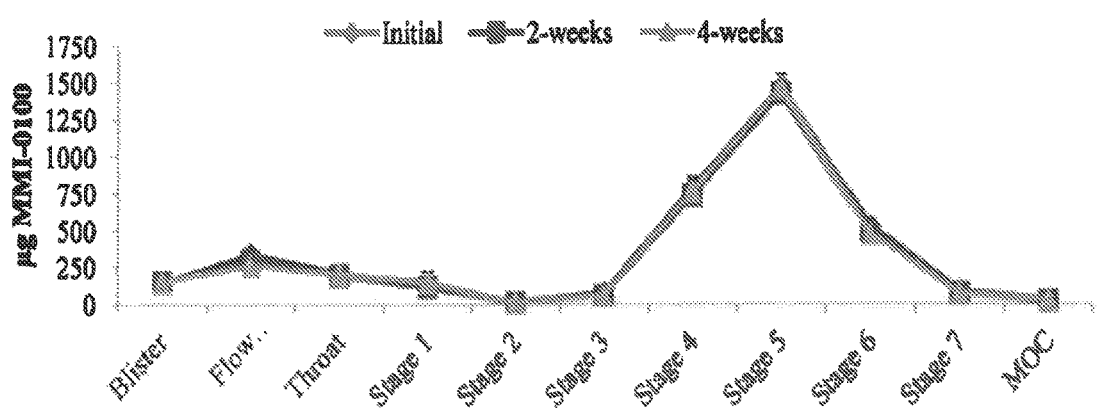
FIG. 12 shows a particle size distribution plot of recovered drug at 25° C./60% RH for the MMI-0100 1% solids formulation.
Figure 13:
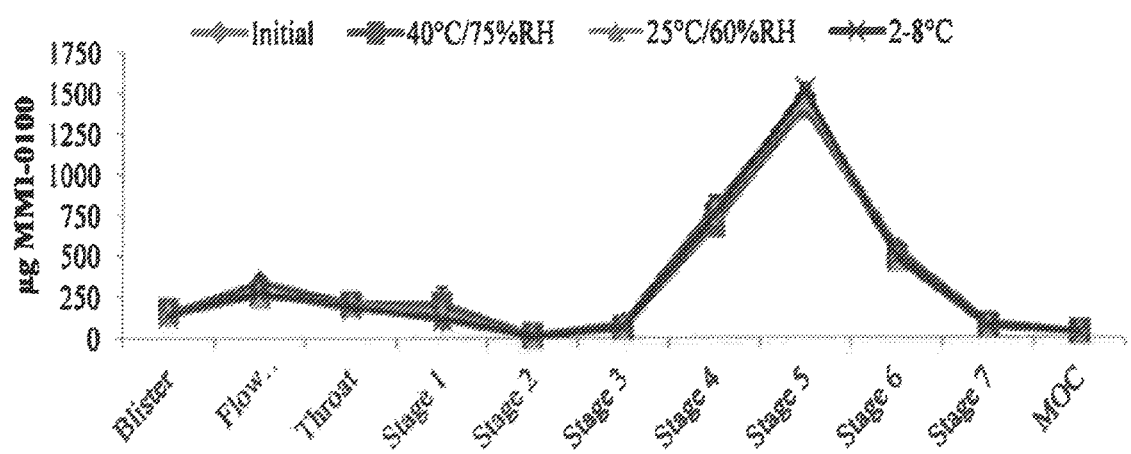
FIG. 13 shows a particle size distribution plot of recovered drug at 4 weeks for the MMI-0100 1% solids formulation.
Figure 14:
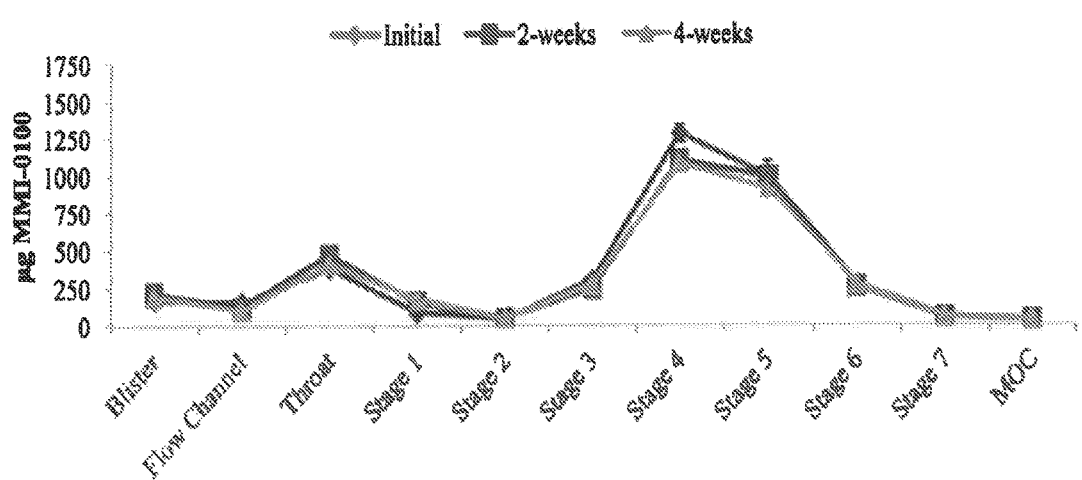
FIG. 14 shows a particle size distribution plot of recovered drug at 40° C./75% relative humidity (RH) for the MMI-0100 5% solids formulation.
Figure 15:
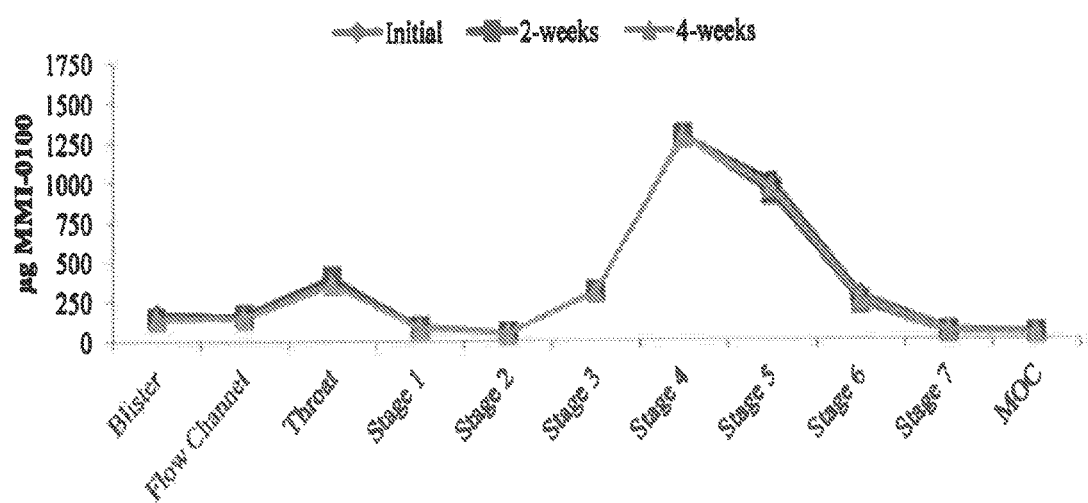
FIG. 15 shows a particle size distribution plot of recovered drug at 25° C./60% RH for the MMI-0100 5% solids formulation.
Figure 16:
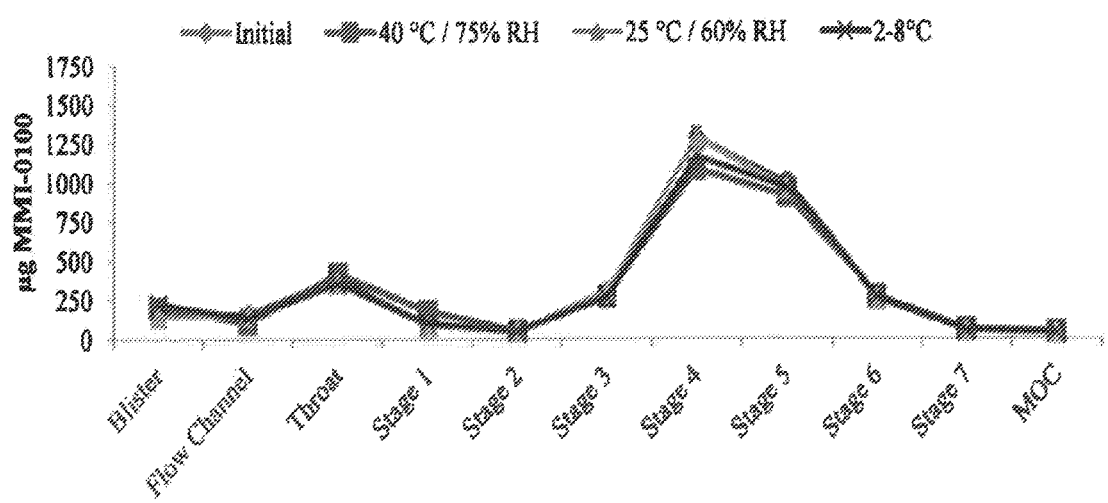
FIG. 16 shows a particle size distribution plot of recovered drug at 4 weeks for the MMI-0100 5% solids formulation.
Figure 17:
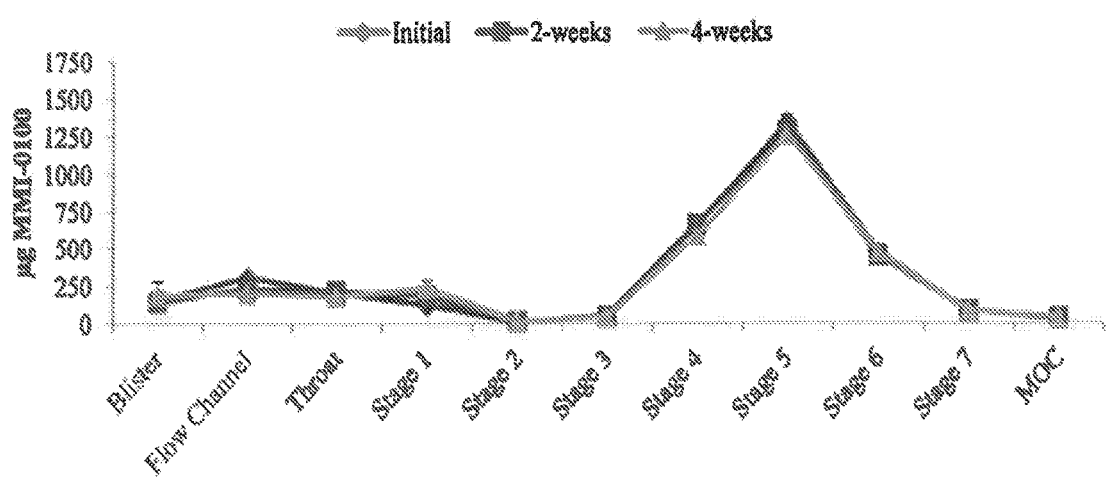
FIG. 17 shows a particle size distribution plot of recovered drug at 40° C./75% relative humidity (RH) for the MMI-0100 1% solids, 7.5% Trehalose formulation.
Figure 18:
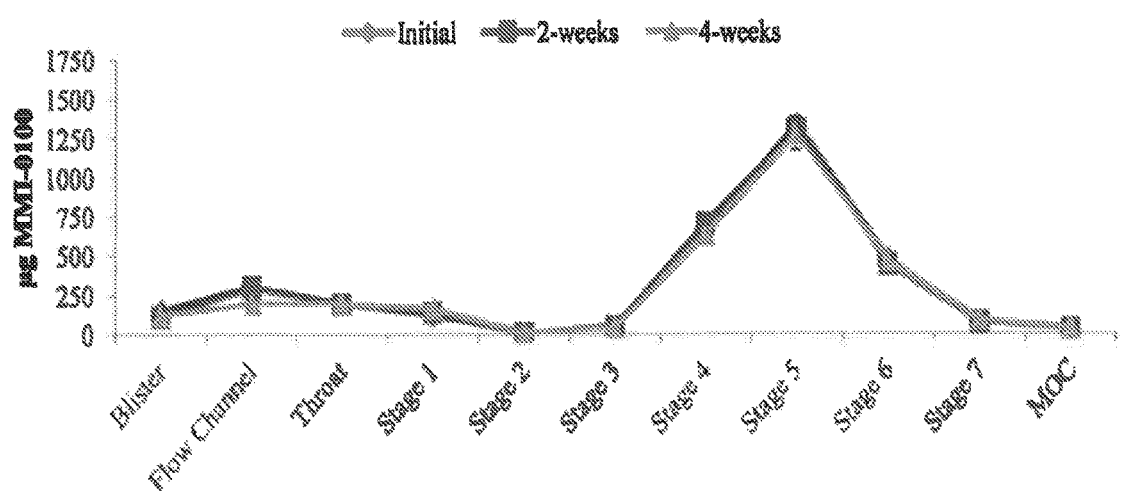
FIG. 18 shows a particle size distribution plot of recovered drug at 25° C./60% RH for the MMI-0100 1% solids, 7.5% Trehalose formulation.
Figure 19:
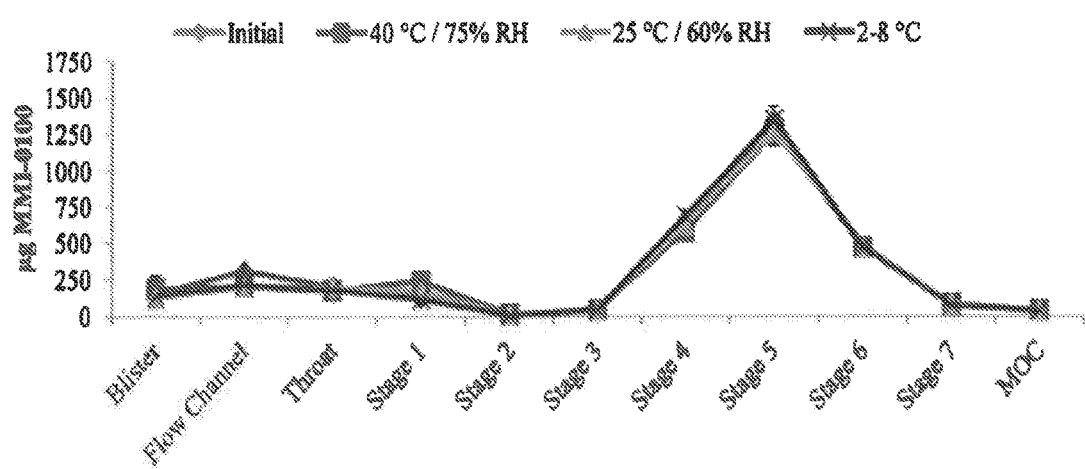
FIG. 19 shows a particle size distribution plot of recovered drug at 4 weeks for the MMI-0100 1% solids, 7.5% Trehalose formulation.
Figure 20:
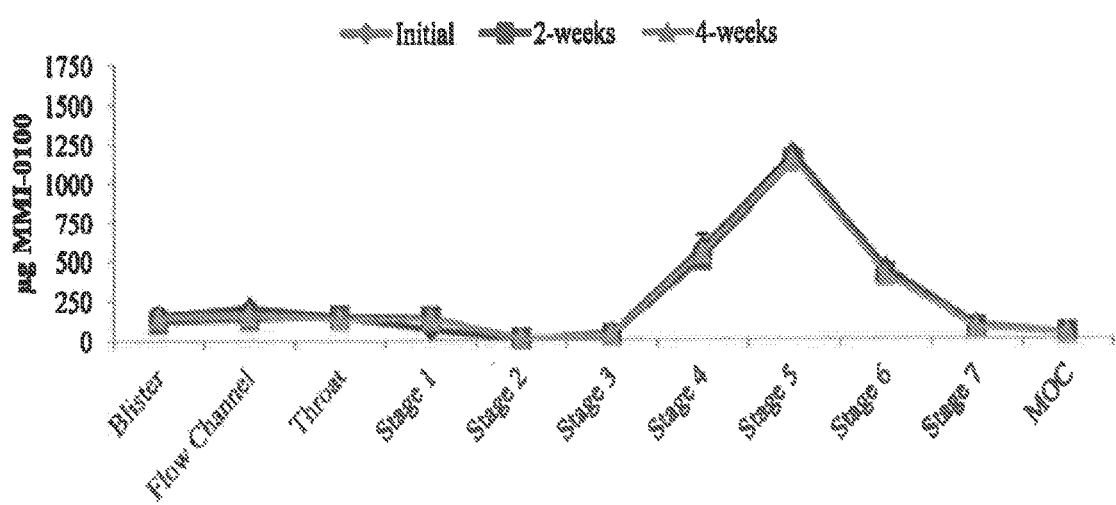
FIG. 20 shows a particle size distribution plot of recovered drug at 40° C./75% relative humidity (RH) for the MMI-0100 1% solids, 20% Trehalose formulation.
Figure 21:
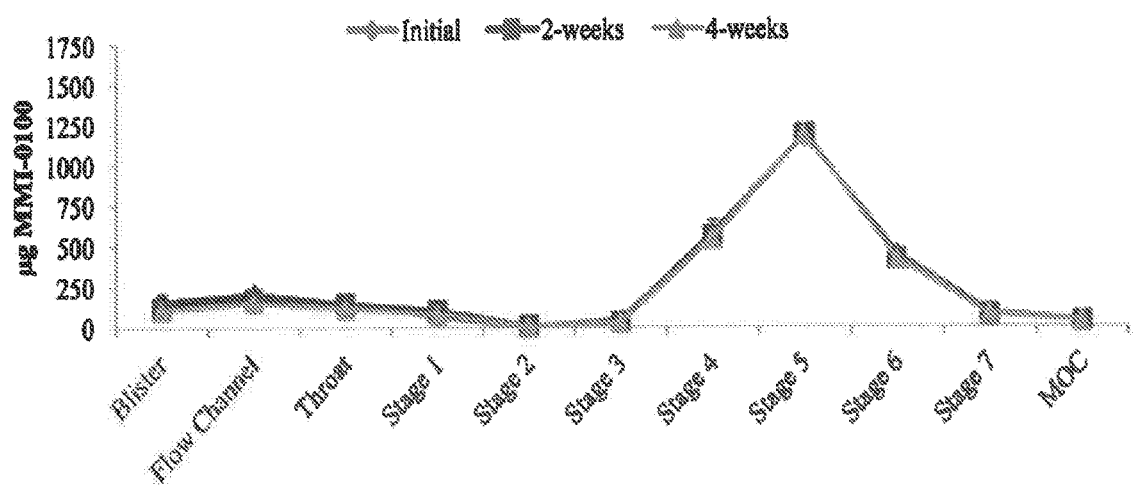
FIG. 21 shows a particle size distribution plot of recovered drug at 25° C./60% RH for the MMI-0100 1% solids, 20% Trehalose formulation.
Figure 22:
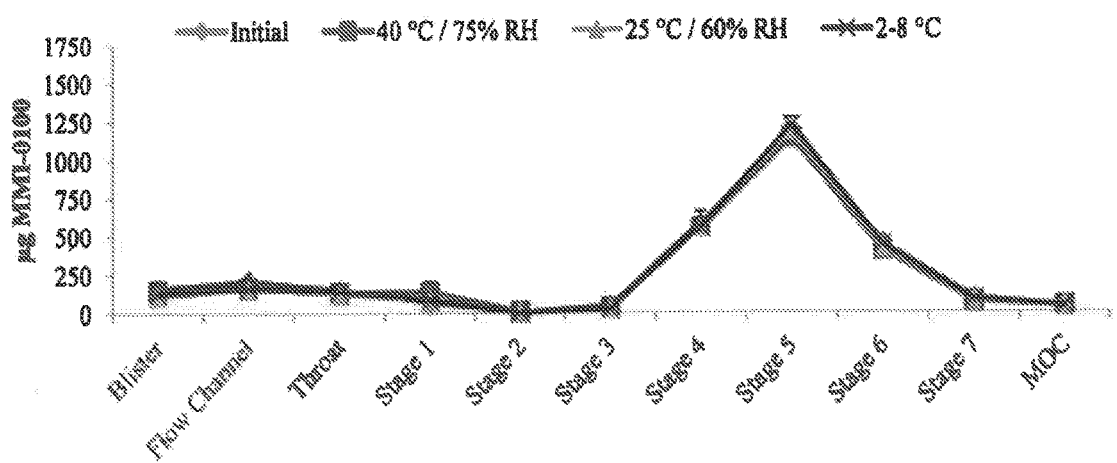
FIG. 22 shows a particle size distribution plot of recovered drug at 4 weeks for the MMI-0100 1% solids, 20% Trehalose formulation.
Figure 23:
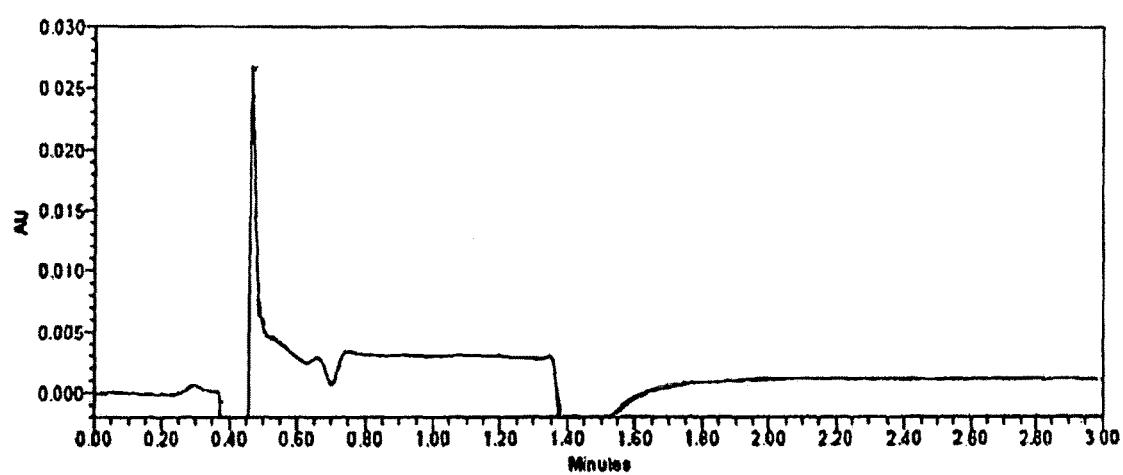
FIG. 23 shows a chromatogram of the sample solvent.
Figure 24:
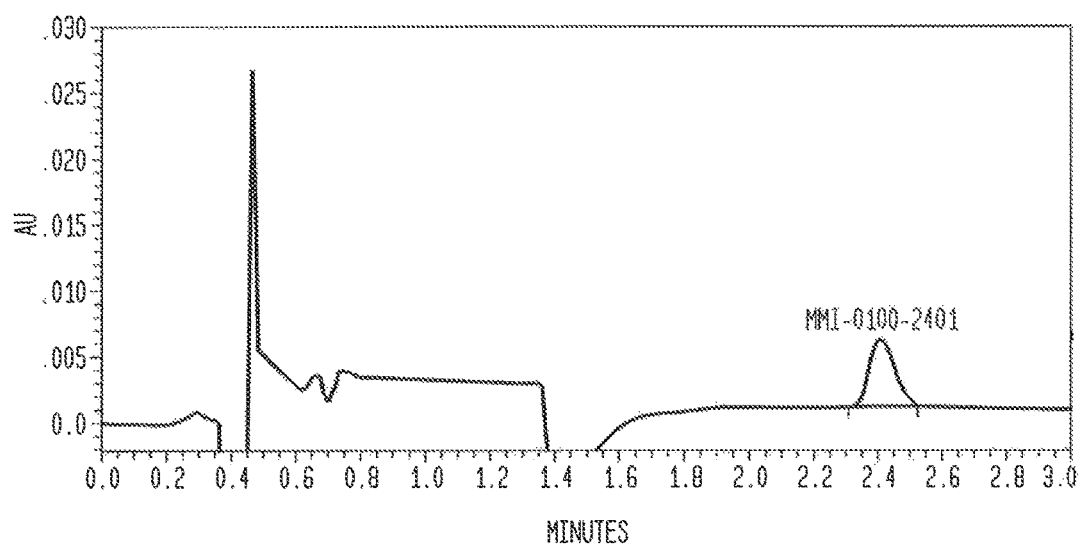
FIG. 24 shows a chromatogram of the limit of quantitation (LOQ).
Figure 25:
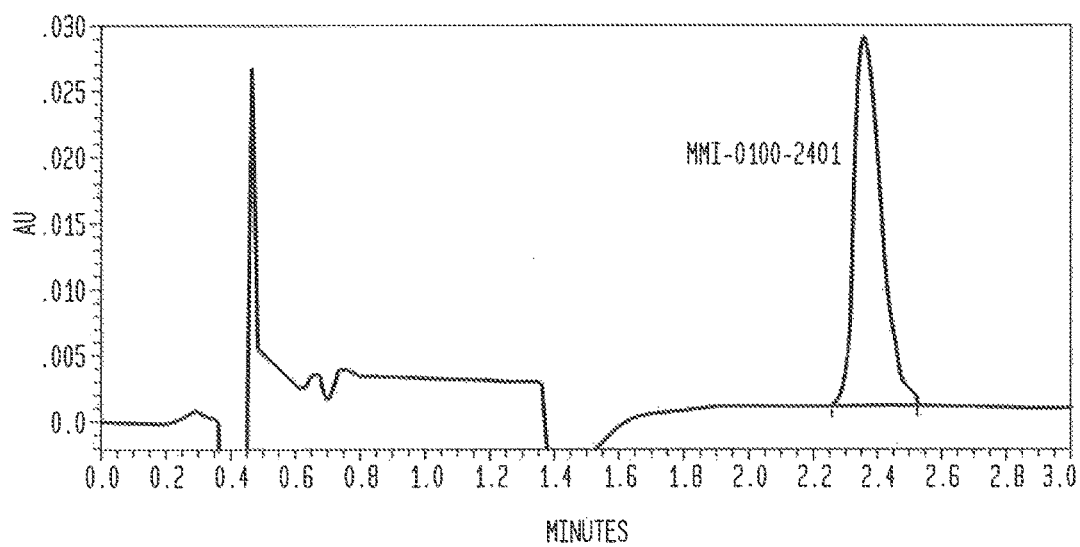
FIG. 25 shows a chromatogram of the 11 µg/mL working standard (full scale).
Figure 26:
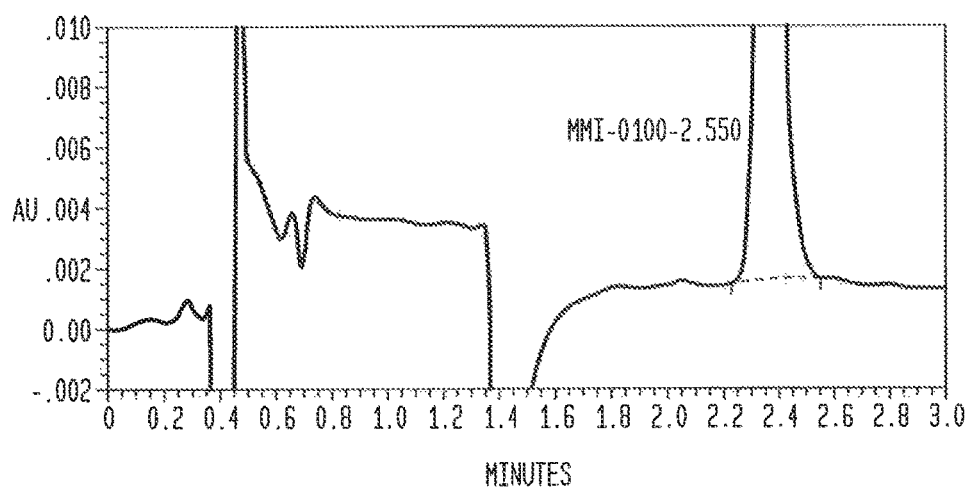
FIG. 26 shows a chromatogram of the 11 µg/mL working standard (expanded scale).

The results indicate a less than 10% change in aerosol performance from the initial time point for all formulation variants except for the 5% solids formulation (10.7% change). The three MMI-0100 formulations containing 1% solids are stable for up to 4 weeks at 40° C./75% RH giving them an effective shelf life of 3-4 months at ambient conditions when placed in an overwrap pouch. There was essentially no difference in performance from the addition of trehalose to the formulation with either the 7.5% or the 20% variants, in terms of aerosol performance. A representative particle size distribution plot from the 1% solids/0% trehalose formulation after 4 weeks storage at 40° C./75% RH is shown in FIG. 10. The particle size distribution for each of the formulations at each stability condition at 0, 2, and 4 weeks as well as a complete listing of the aerosol results can be found in FIGS. 11-22. The impurities and MMI-0100 content for the 5% solids formulation were also assessed after storage in single dose blisters within a foil overwrap pouch after 2 and 4 weeks at 40° C./75% RH. The 5% formulation was used for this study based upon available remaining supply of material. The results are summarized in Table 11.

TABLE 11

Impurities and Content Summary for Single Dose Blisters - 5% Solids Formulation

| Sample | Impurities | | Assay |
|---|---|---|---|
| | Total Peaks | Total Impurity Content (% Area) | % Content |
| Initial | | | |
| Initial | 6 | 0.9 | 100.6 |
| 2 Weeks | | | |
| 40° C./75% RH | 6 | 0.9 | 100.0 |
| 25° C./60% RH | 6 | 0.9 | 100.9 |
| 2-8° C. | N/A | N/A | N/A |
| 4 Weeks | | | |
| 40° C./75% RH | 7 | 1.2 | 99.4 |
| 25° C./60% RH | 7 | 0.9 | 100.2 |
| 2-8° C. | 6 | 0.8 | 100.4 |

There was a slight decrease in assay content at 40° C./75% RH after 4 weeks (from 100.6 to 99.4%) with one extra unidentified peak detected in the impurity profile. The impurity profile and % content were stable at all other time-points and conditions. This data also supports an effective shelf life of 3-4 months at ambient conditions for the 5% solids formulation.

The assay and impurity profile of the formulations stored in bulk in glass jars after 4 weeks storage at 40° C./75% RH is summarized in Table 12. There was not enough available formulation to determine aerosol performance of samples stored in bulk (by filling and dosing blisters after the time point). Again, due to limited stock of formulation, the trehalose containing formulations were not assessed at the initial time point. Initial results for neat formulations were determined during method transfer of the assay/impurity method. Samples were handled/prepared in the same manner.

TABLE 12

Impurities and Content Summary for Formulations Stored in Glass for 4 Weeks at 40° C./75% RH

| Sample | Impurities | | Assay % Content |
|---|---|---|---|
| | Total Peaks | Total Impurity Content (% Area) | |
| Initial | | | |
| 92.5/7.5 MMI-0100/Trehalose 1% w/w solids | N/A | N/A | N/A |
| 80/20 MMI-0100/Trehalose 1% w/w solids | N/A | N/A | N/A |
| MMI-0100 1% w/w solids | 6 | 0.9 | 100.5 |
| MMI-0100 5% w/w solids | 6 | 0.9 | 100.6 |
| 4 Weeks | | | |
| 92.5/7.5 MMI-0100/Trehalose 1% w/w solids | 6 | 1.0 | 96.2 |
| 80/20 MMI-0100/Trehalose 1% w/w solids | 6 | 1.0 | 97.2 |
| MMI-0100 1% w/w solids | 6 | 1.1 | 100.4 |
| MMI-0100 5% w/w solids | 7 | 1.4 | 98.7 |

The stability results for the 1% solids formulation stored in glass bottles exhibited little change from the initial results. The 5% solids formulation showed some increase in impurity content from 0.9 to 1.4% with a corresponding decrease in assay content from 100.6 to 98.7%, and an increase in the number of peaks observed (from 6 to 7). The trehalose containing formulations were not tested at initial, but the results after 4 weeks are in the range of the results obtained for the 1% neat formulation, in terms of total impurities and number of peaks. Without being bound by theory, based on the improved stability of the 1% neat formulations when stored in bulk in glass, it is possible that the 1% formulations would also be stable in blisters, in terms of chemical stability (based on the data for the 5% neat formulation in blisters).

Example 2. Nebulizer Formulations of MMI-0100 (YARAAARQARAKALARQLGVAA; SEQ ID NO: 1)

In this study, aerosolization of MMI-0100 inhalation formulations at two concentrations was characterized using an electronic nebulizer containing a vibrating mesh with pore sizes of 3 μm and 4 μm (Type 1 and Type 2, respectively). Laser defraction measurements were used to determine droplet size distribution. Breath simulation experiments were performed to determine delivered dose and nebulization time. In addition, physicochemical parameters (e.g., viscosity, surface tension, osmolality and density) were determined. The study design is outlined in Table 13.

TABLE 13

Nebulizer Formulation Study Design

| Task | Description of Task |
|---|---|
| 1 | Lyophilized MMI-0100 peptide<br>Two concentrations of MMI-0100 solutions were prepared by dissolving the lyophilized MMI-0100 peptide in 0.9% NaCl (saline): Formulation A: 7 mg/mL; Formulation B: 0.7 mg/mL in order to cover the range of theoretical delivered dose of 5-200 μg/kg |

TABLE 13-continued

Nebulizer Formulation Study Design

| Task | Description of Task |
|---|---|
| 2 | Physicochemical characterization was performed on both formulations with respect to:<br>Viscosity<br>Surface tension<br>Osmolality<br>Density |
| 3 | Laser diffraction measurements of MMI-0100 formulations upon nebulization with Nebulizer Type 1 and Nebulizer Type 2. For each nebulizer type, three were analyzed in duplicate (=12 measurements per concentration for 24 measurements)<br>Target fill volume was 2 mL of Formulation A and B each<br>Information obtained from these experiments included:<br>Mass Median Diameter (MMD (μg))<br>Respirable fraction (RF (droplets <5 μm (%)))<br>Geometric Standard Deviation (GSD)<br>Total output rate (TOR (mg/min)) |
| 4 | Breath simulation upon nebulization of two (2) fill volumes (1 mL and 4 mL) of MMI-0100 of each formulation (Formulation A and Formulation B) using Nebulizer Type 1 and Nebulizer Type 2. For each nebulizer type, three were analyzed in duplicate (=48 measurements).<br>Adult breathing pattern was applied: Tidal volume = 500 mL; Frequency = 15 breath/min; Inhalation/Exhalation ratio = 1<br>Results obtained were:<br>Nebulization time (min)<br>Respirable Dose (RD (μg in droplets <5 μm) = dose which is expected to reach lungs) calculated from laser diffraction measurement and breath simulation<br>Samples from breath simulation experiments were analyzed using HPLC<br>Prior to breath simulation experiments, filter recovery tests for method qualification were conducted (n = 3) |

Figure 27:
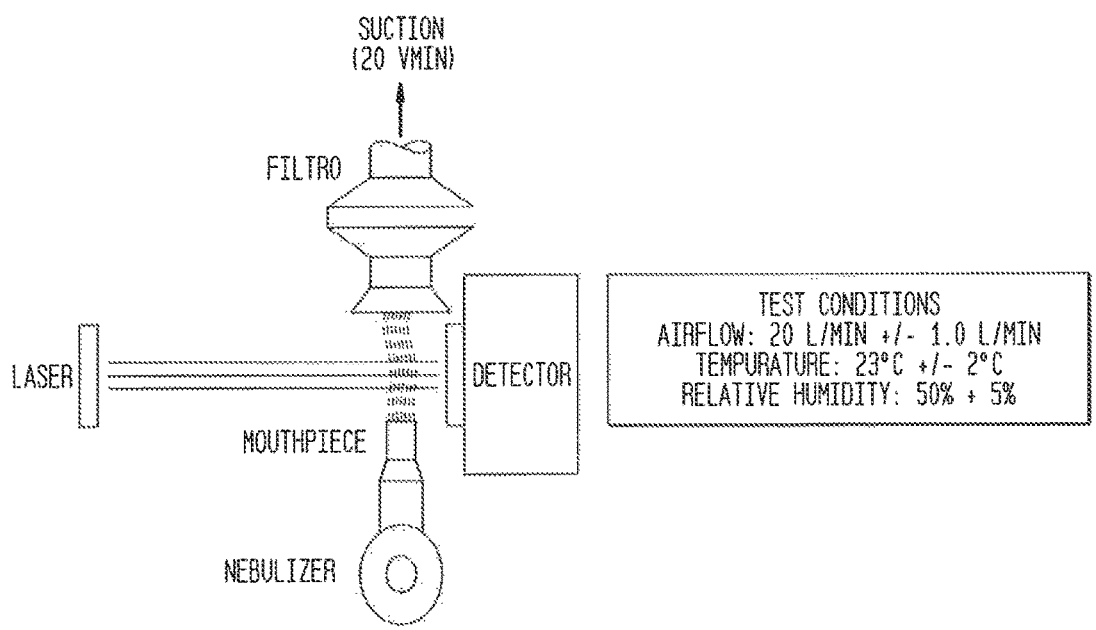
FIG. 27 shows a schematic of a laser diffraction device.

Assessment of geometric droplet size distribution was performed by laser diffraction (Malvern MasterSizerX). FIG. 27 shows a schematic of the laser diffraction test set-up. Fill volume was 2 mL for each test solution. Before testing of the formulations, the nebulizer was tested with 0.9% NaCl (saline) solution. Results of the laser diffraction measurements are displayed in Table 14.

TABLE 14

Comparison of Values of Laser Diffraction Measurements for the Tested MMI-0100 Formulations and 0.9% Saline Solution

| Formulation | | MMD (μm) | GSD | RF <5 μm (%) | RF <3.3 μm (%) | TOR (mg/mL) |
|---|---|---|---|---|---|---|
| | | | Nebulizer Type 1 | | | |
| B (0.7 mg/mL) | Mean | 3.30 | 1.51 | 83.79 | 50.09 | 353.17 |
| | SD | 0.07 | 0.00 | 1.28 | 1.91 | 17.79 |
| | RSD | 2.15 | 0.19 | 1.53 | 3.82 | 5.04 |
| | | | Nebulizer Type 2 | | | |
| | Mean | 4.39 | 1.63 | 61.90 | 28.34 | 900.50 |
| | SD | 0.23 | 0.10 | 6.17 | 1.26 | 193.39 |
| | RSD | 5.27 | 6.18 | 9.96 | 4.46 | 21.48 |
| | | | Nebulizer Type 1 | | | |
| A (7.0 mg/mL) | Mean | 3.03 | 1.53 | 86.40 | 57.12 | 352.33 |
| | SD | 0.07 | 0.01 | 1.26 | 2.00 | 44.16 |
| | RSD | 2.37 | 0.68 | 1.46 | 3.50 | 12.53 |
| | | | Nebulizer Type 2 | | | |
| | Mean | 4.03 | 1.65 | 67.58 | 35.15 | 797.17 |
| | SD | 0.10 | 0.02 | 1.61 | 1.57 | 35.92 |
| | RSD | 2.55 | 0.93 | 2.38 | 4.46 | 4.51 |
| 0.9% Saline | Mean | 3.26 | 1.56 | 82.33 | 50.99 | 370 |
| | SD | 0.04 | 0.01 | 0.78 | 0.95 | 54 |
| | RSD | 1.2 | 0.5 | 0.9 | 1.9 | 14.7 |
| | | | Nebulizer Type 2 | | | |
| | Mean | 4.44 | 1.68 | 59.70 | 28.95 | 922 |
| | SD | 0.21 | 0.06 | 4.12 | 1.72 | 79 |
| | RSD | 4.7 | 3.8 | 6.9 | 6.0 | 8.5 |

Figure 28:
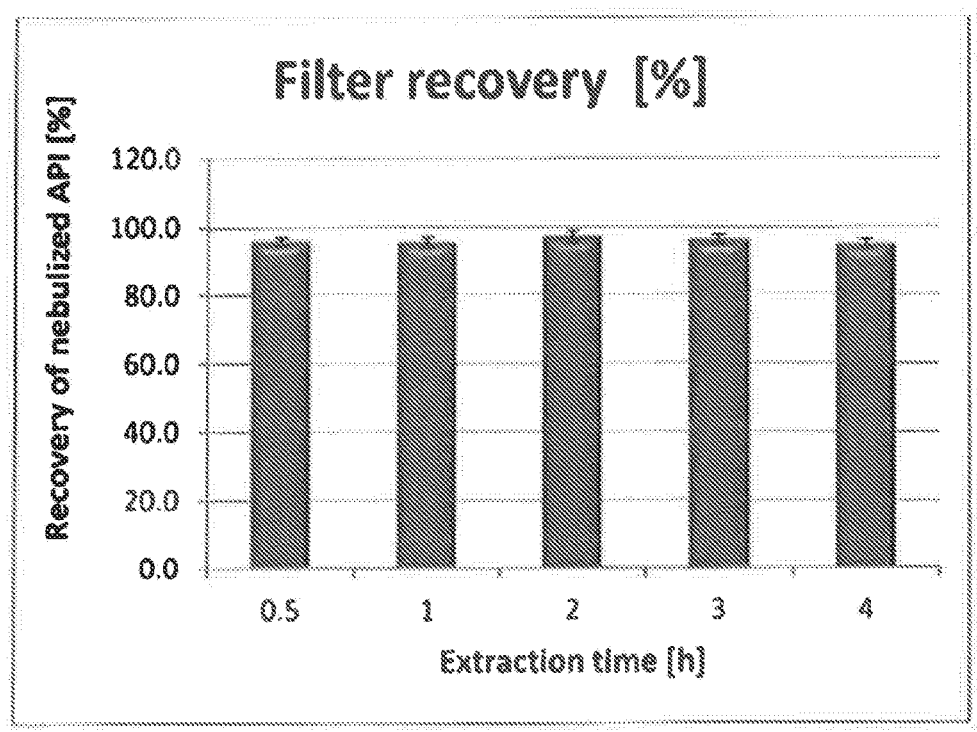
FIG. 28 shows a bar graph representing percent recovery of MMI-0100 after extraction times of 0.5, 1, 2, 3 and 4 hours.

TOR = total output rate (mg/mL); mass of aerosol delivered per minute;
SD = standard deviation;
RSD = relative standard deviation Filter recovery was determined using 0.9% saline for sample extraction from inhalation filters. Briefly, approximately 1,000 mg of formulation A (7.0 mg/mL) was nebulized on an inhalation filter (n=3) while a constant airflow was applied to the filter by a pump. After the application of Formulation A, the filter pads were placed in a 50 mL conical tube containing 30 mL of 0.9% saline and shaken at 250 rpm for up to 4 hours. Samples (approximately 800 μL) were collected after 0.5, 1, 2, 3 and 4 hours. Results of the filter recovery experiment are displayed in Table 15 and graphically represented in FIG. 28.

TABLE 15

MMI-0100 Recovery (%) from Filter Extraction After Increasing Extraction Times with 0.9% Saline

| Filter No. | Recovery (%) of MMI-0100 after different extraction times | | | | |
|---|---|---|---|---|---|
| | 0.5 hr | 1 hr | 2 hr | 3 hr | 4 hr |
| #1 | 97.1 | 97.0 | 99.2 | 97.2 | 96.0 |
| #2 | 94.3 | 93.6 | 95.1 | 94.9 | 92.9 |
| #3 | 96.5 | 96.2 | 97.5 | 97.0 | 96.0 |
| Mean | 96.0 | 95.6 | 97.2 | 96.4 | 95.0 |
| SD | 1.2 | 1.5 | 1.7 | 1.1 | 1.5 |

SD = standard deviation

A maximum of roughly 96% recovery was reached after 0.5 hr extraction time. Longer extraction times (1, 2, 3 and 4 hr) did not improve recovery.

Breath simulations were conducted using an adult breathing pattern (Tidal Volume: 500 mL, Breath per minute: 15; Inhalation/Exhalation ratio: 50:50). Table 16 contains fill volumes chosen to meet desired respirable doses of 5-200 µg/kg (assuming an average weight of 70 kg).

TABLE 16

Fill Volumes for Formulation A and Formulation B

| | Formuation | | | |
|---|---|---|---|---|
| | A | | B | |
| Concentration | 7 mg/mL | | 0.7 mg/mL | |
| Fill Volume | 1 mL | 4 mL | 1 mL | 4 mL |

Fill volumes were loaded into a medication cup of a nebulizer connected to a sinus pump. Inspiratory filters were installed between the nebulizer, including the mouth piece and the pump, and fixed with rubber connectors. The nebulizer filled with the formulation was driven until the automatic shut off stopped the device. The MMI-0100-containing aerosol was collected on inhalation polypropylene inhalation filters. After nebulization, the inhalation filters were removed from the filter casings with forceps and were put in glass vials with plastic screw caps. The filter casings were rinsed with 0.9% saline and the saline was collected in 50 mL conical tubes. Corresponding filters were transferred to the conical tubes containing 0.9% saline and shaken at 250 rpm for 0.5 hr. After 0.5 hr., HPLC analysis was used to determine extracted MMI-0100 from the filters. The nebulizer was rinsed several times with 0.9% saline and the saline was collected in a glass beaker.

Peptide content of the saline samples was determined by gradient HPLC with linear standard calibration. The HPLC instrument and settings were as follows:

HPLC with column oven, UV detector and chromatographic data system;
Zorbax 300SB, 3.5 µm, 150×3.0 mm (L×ID) column (or equivalent);
Column temperature: 25° C.;
Sample temperature: 4° C.;
Flow: 0.5 mL/min;
Mobile Phase A: 0.1% trifluoroacetic acid (TFA) in water;
Mobile Phase B: 0.1% TFA in acetonitrile/methanol (50: 50);
Injection volume: 20 µL
Run time: 15 minutes; and
Detector wavelength: 215 nm.

The HPLC gradient used is shown in Table 17.

TABLE 17

| Gradient Table | | | | |
|---|---|---|---|---|
| Time (min) | Flow (mL/min) | % Phase A | % Phase B | Curve |
| 0.00 | 0.50 | 68.0 | 32.0 | 6 |
| 5.00 | 0.50 | 63.0 | 37.0 | 6 |
| 6.00 | 0.50 | 10.0 | 90.0 | 6 |
| 9.00 | 0.50 | 10.0 | 90.0 | 6 |
| 10.00 | 0.50 | 68.0 | 32.0 | 6 |
| 15.00 | 0.50 | 68.0 | 32.0 | 6 |

Accuracy by recovery and method precision experiments were performed. MMI-0100 was weighed and dissolved in 0.9% saline and determined by the HPLC method described. Samples 2 and 4 from the accuracy by recovery experiment were divided into six (6) vials each and used in the method precision experiment. The results of these experiments are shown in Tables 18 and 19. This HPLC method was able to determine an MMI-0100 peptide content in the range of 12-600 µg/mL.

TABLE 18

| Accuracy by Recovery | | | |
|---|---|---|---|
| Sample | Concentration (target) (µg/mL) | Concentration (actual) (µg/mL) | Recovery (%) |
| 1 | 600.43 | 589.53 | 98.18 |
| 2 | 300.22 | 286.53 | 95.44 |
| 3 | 120.09 | 123.78 | 103.08 |
| 4 | 48.03 | 49.60 | 103.25 |
| 5 | 24.02 | 24.69 | 102.80 |
| Mean | | | 100.55 |
| SD | | | 3.55 |
| RSD (%) | | | 3.5 |

SD = standard deviation
RSD = relative standard deviation

TABLE 19

| Method Precision | | |
|---|---|---|
| Vial No. | Sample 2 Concentration (µg/mL) | Sample 4 Concentration (µg/mL) |
| Vial 1 | 284.62 | 49.62 |
| Vial 2 | 285.72 | 49.76 |
| Vial 3 | 285.86 | 49.6 |
| Vial 4 | 287.09 | 49.63 |
| Vial 5 | 288.24 | 49.77 |
| Vial 6 | 287.67 | 49.19 |
| Mean | 286.53 | 49.60 |
| SD | 1.36 | 0.21 |
| RSD | 0.48 | 0.43 |

Results of the breath simulation experiments are summarized in Tables 20 and 21 and FIGS. 29-33.

TABLE 20

Breath Simulation Data Summarized for Nebulizer Type 1

| | | Formulation | | | |
|---|---|---|---|---|---|
| | | B: MMI-0100 (0.7 mg/mL) | | A: MMI-0100 (7.0 mg/mL) | |
| Label claim | | 700 µg/mL | | 7000 µg/mL | |
| Fill volume | mL | 1 mL | 4 mL | 1 mL | 4 mL |
| Number of replicates | | n = 6 | n = 6 | n = 6 | n = 6 |
| Filled drug amount (based on determined values of the formulations) | mg | 0.72 | 2.84 | 6.93 | 27.68 |
| Deposition of Nebulized Formulation | | | | | |
| DD | mg | 0.43 | 1.81 | 5.13 | 20.07 |
| SD | | 0.03 | 0.05 | 0.24 | 0.57 |
| DD | % | 59.8 | 63.6 | 74.0 | 72.5 |
| SD | | 3.5 | 1.6 | 3.4 | 2.0 |
| Residue | % | 0.0 | 6.3 | 5.0 | 7.3 |
| SD | | 0.0 | 0.8 | 0.7 | 0.8 |
| Nebulized Time | | | | | |
| Time | min | 3.34 | 11.39 | 3.40 | 15.81 |
| SD | | 0.33 | 1.28 | 0.57 | 1.96 |
| Caluculated Values | | | | | |
| RD <5 µm | mg | 0.36 | 1.51 | 4.43 | 17.34 |
| SD | | 0.02 | 0.06 | 0.24 | 0.69 |
| RD <5 µm | % | 50.07 | 53.28 | 63.96 | 62.66 |
| SD | | 2.94 | 2.19 | 3.55 | 2.49 |
| RD <3.3 µm | mg | 0.22 | 0.91 | 2.93 | 11.47 |
| SD | | 0.02 | 0.07 | 0.19 | 0.63 |
| RD <3.3 µm | % | 29.92 | 31.87 | 42.29 | 41.43 |
| SD | | 2.19 | 2.32 | 2.80 | 2.28 |

DD = delivered dose
SD = standard deviation
RD = respirable dose

TABLE 21

Breath Simulation Data Summarized for Nebulizer Type 2

| | | Formulation | | | |
|---|---|---|---|---|---|
| | | B: MMI-0100 (0.7 mg/mL) | | A: MMI-0100 (7.0 mg/mL) | |
| Label claim | | 700 µg/mL | | 7000 µg/mL | |
| Fill volume | mL | 1 mL | 4 mL | 1 mL | 4 mL |
| Number of replicates | | n = 6 | n = 6 | n = 6 | n = 6 |
| Filled drug amount (based on determined values of the formulations) | mg | 0.71 | 2.84 | 6.97 | 27.59 |
| Deposition of Nebulized Formulation | | | | | |
| DD | mg | 0.34 | 1.50 | 4.71 | 17.62 |
| SD | | 0.01 | 0.07 | 0.38 | 0.57 |
| DD | % | 48.1 | 52.7 | 67.6 | 63.9 |
| SD | | 1.6 | 2.3 | 5.6 | 2.3 |
| Residue | % | 2.6 | 17.4 | 15.1 | 17.1 |
| SD | | 6.4 | 2.8 | 5.1 | 3.0 |
| Nebulized Time | | | | | |
| Time | min | 1.16 | 3.99 | 1.28 | 4.37 |
| SD | | 0.09 | 0.23 | 0.14 | 0.36 |
| Caluculated Values | | | | | |
| RD <5 µm | mg | 0.21 | 0.93 | 3.19 | 11.91 |
| SD | | 0.03 | 0.11 | 0.40 | 1.16 |
| RD <5 µm | % | 29.81 | 32.69 | 45.74 | 43.19 |
| SD | | 3.61 | 3.93 | 5.79 | 4.42 |
| RD <3.3 µm | mg | 0.10 | 0.42 | 1.66 | 6.20 |
| SD | | 0.01 | 0.03 | 0.21 | 0.60 |
| RD <3.3 µm | % | 13.63 | 14.95 | 23.82 | 22.47 |
| SD | | 0.94 | 1.07 | 3.12 | 2.28 |

DD = delivered dose
SD = standard deviation
RD = respirable dose

The Delivered Dose (DD [mg] or [%]) represents the amount of MMI-0100 delivered to the patient assuming a specified breathing pattern. The respirable doses<x pm (RD<x µm [mg] or [%]) gives the amount of MMI-0100 contained in the part of the droplets<x pm. The droplet size defines where the particles in the aerosol cloud are likely to deposit. Without being bound by theory, it is assumed that, to be therapeutically effective, particles should be in the range of 1-5 µm in order to deposit in the lungs. In contrast, particles with >5 µm will generally impact in the oropharynx and be swallowed, whereas particles below <1 µm will remain entrained in the air stream and be exhaled. Respirable dose is calculated by multiplying the DD [mg] with the percentage of the Respirable Fraction (RF [%]]) determined by laser diffraction measurement.

Figure 29:
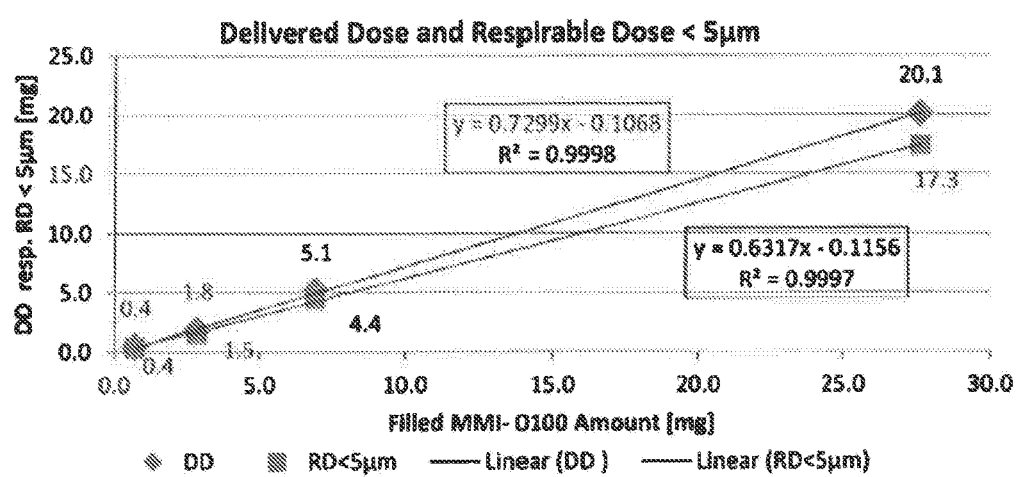
FIG. 29 shows the linear correlation between the filled drug amount and the delivered dose (DD) (respirable dose <5 µm) nebulized using Nebulizer Type 1.
Figure 30:
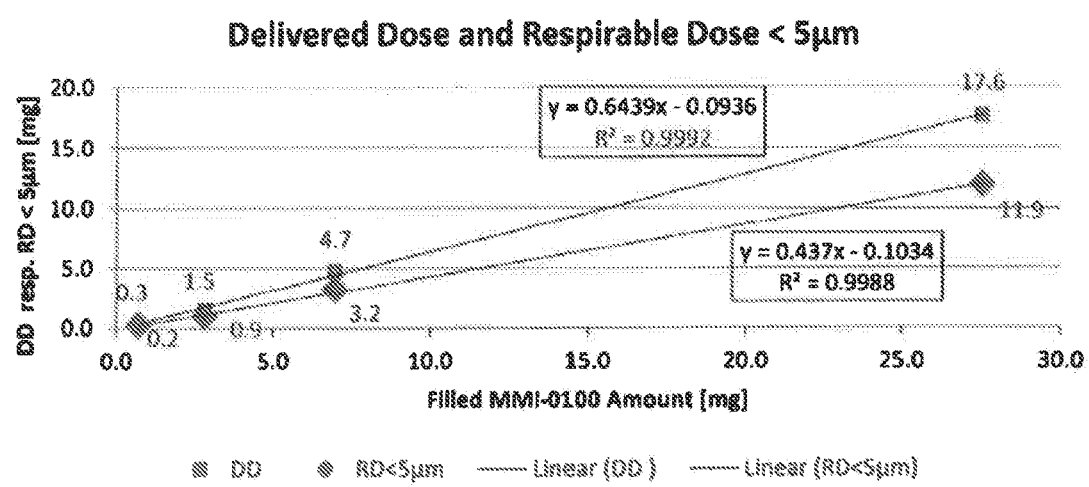
FIG. 30 shows the linear correlation between the filled drug amount and the delivered dose (DD) (respirable dose <5 µm) nebulized using Nebulizer Type 2.
Figure 31:
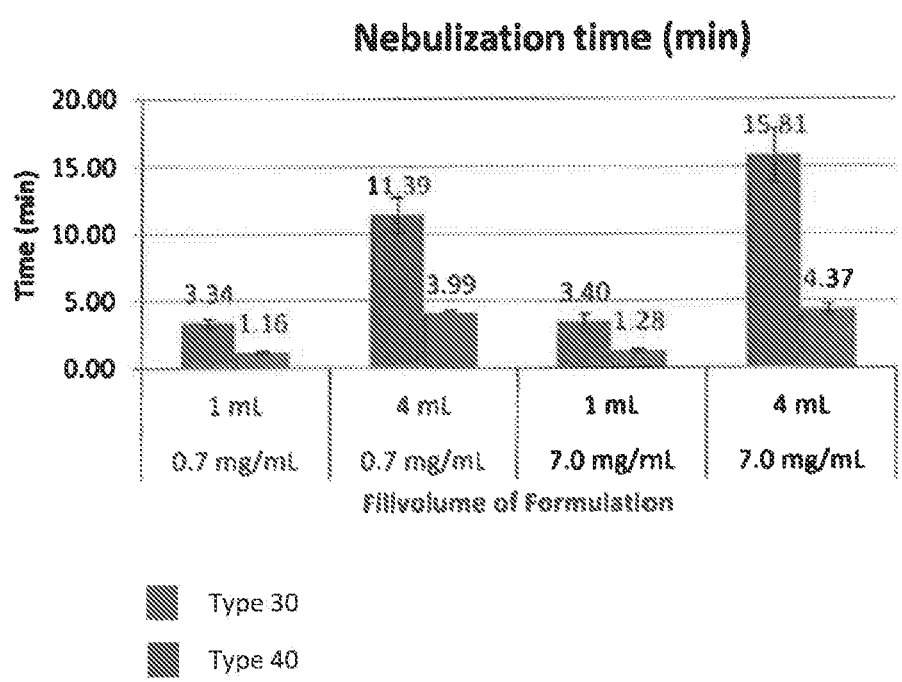
FIG. 31 shows a bar graph representing nebulization time of different fill volumes and concentrations nebulized using Nebulizer Type 1 and Nebulizer Type 2.
Figure 32:
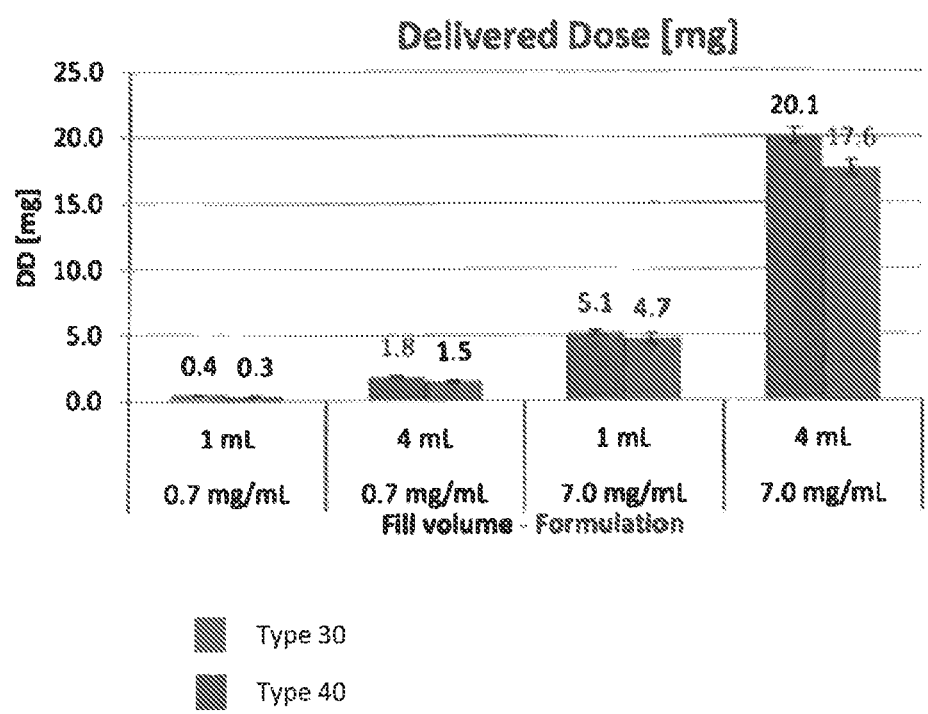
FIG. 32 shows a bar graph representing delivered dose of different fill volumes and concentrations nebulized using Nebulizer Type 1 and Nebulizer Type 2.
Figure 33:
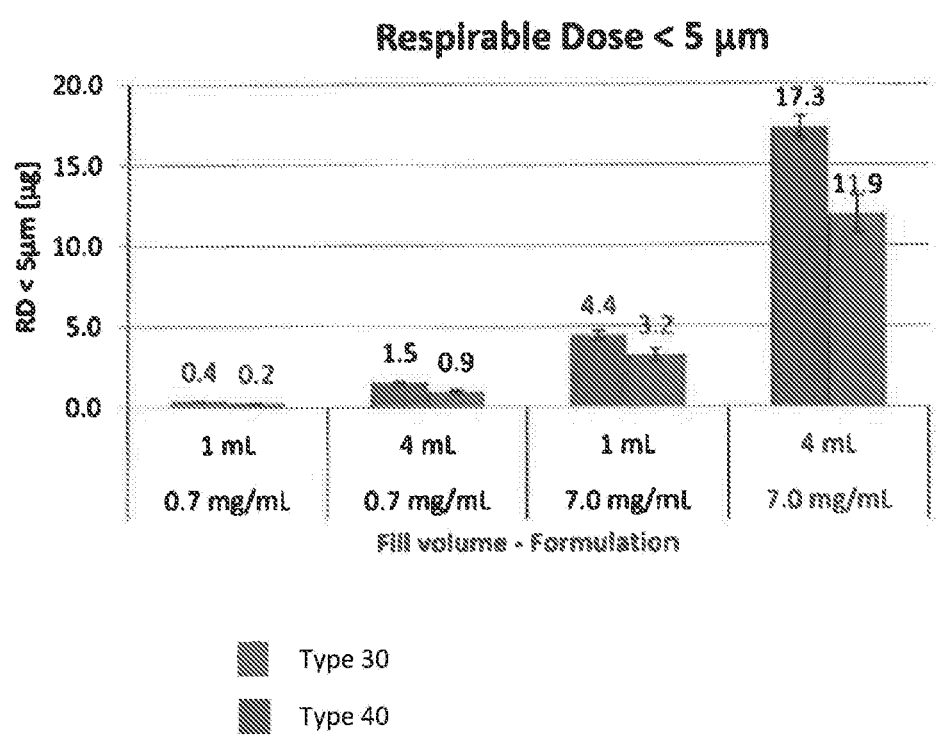
FIG. 33 shows a bar graph representing respirable dose<5 µm of different fill volumes and concentrations nebulized using Nebulizer Type 1 and Nebulizer Type 2.
Figure 34:
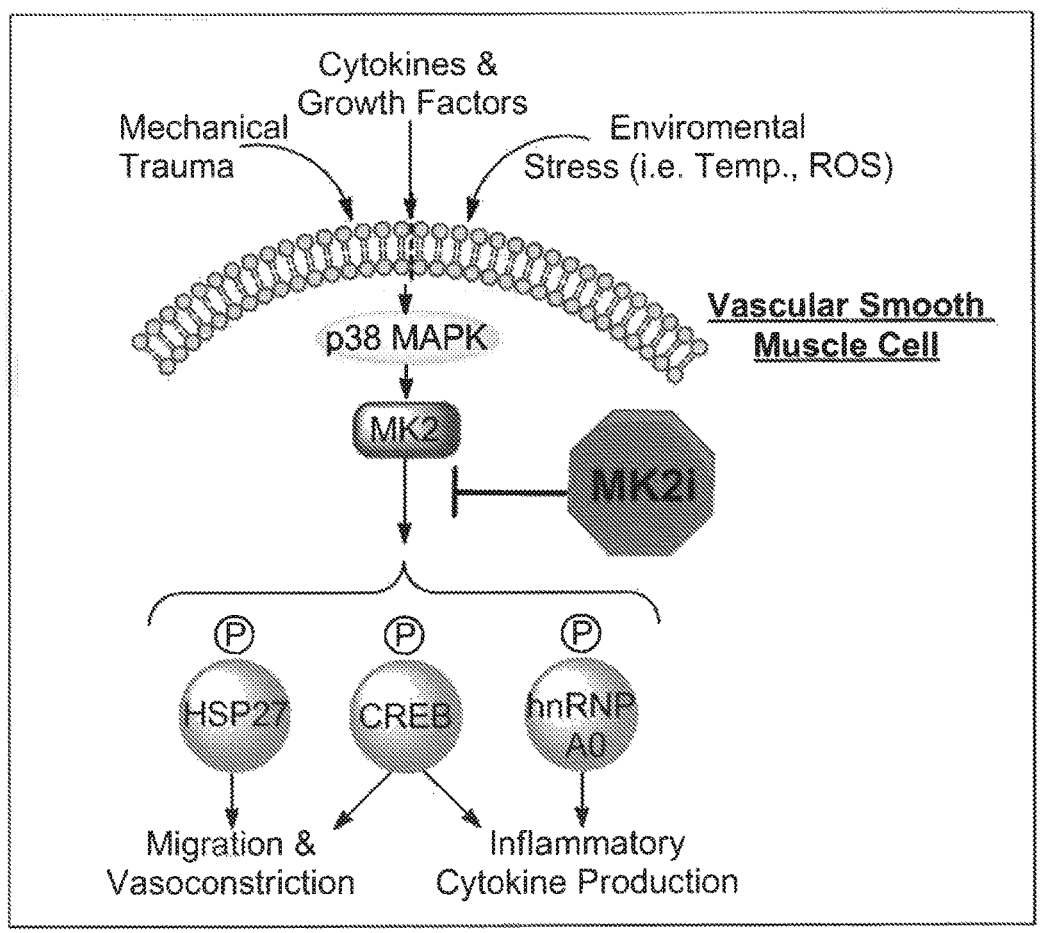
FIG. 34 shows a schematic of the p38-MK2 pathway.

FIGS. 29 and 30 show that there is a linear correlation between the filled drug amount and the amount of drug delivered (DD [mg]) as well as the amount respired into the lungs given as the respirable dose<5 µm (RD<5 µm). The linearity is given for both nebulizer devices (Nebulizer Type 1 and Nebulizer Type 2). Based on the results, nebulization performance appears to be independent of formulation concentration.

Physicochemical characterization was performed on both MMI-0100 formulations with respect to osmolality, viscosity, surface tension and density. The results of each experiment are shown in Table 22.

TABLE 22

Physicochemical Characterization of Formulation A and Formulation B

| | | Formulation | |
|---|---|---|---|
| | | A | B |
| Concentration | mg/mL | 7.0 | 0.7 |
| Osmolality | Osmol/kg | 0.297 (SD 0.001) | 0.286 (SD 0.001) |
| Dynamic Viscosity (20° C.) | mPa · s | 1.04 (SD 0.01) | 0.99 (SD 0.01) |
| Surface Tension | mN/m | 65.0 (SD 0.2) | 67.5 (SD 0.1) |
| Density (23.8° C.) | g/cm$^3$ | 1.0047 | 1.0031 |

SD = standard deviation

The results of these experiments indicate that the mass median diameter (MMD) for Formulation A (Nebulizer Type 1=3.0 µm; Nebulizer Type 2=4.0 µm) was slightly less than that of Formulation B (Nebulizer Type 1=3.3 µm; Nebulizer Type 2=4.4 µm). These values were comparable to the data determined for pure 0.9% saline. Likewise, geometrical standard deviation (GSD), respirable fraction (RF) and total output rate (TOR) values were also slightly less for Formulation A as compared to Formulation B. A linear correlation was found to exist between the delivered dose (respirable dose<5 μm) and the filled MMI-0100 amount. Without being bound by theory, this correlation can be used to calculate the amount of MMI-0100 administered to a patient via a nebulizer device.

Figure 36:
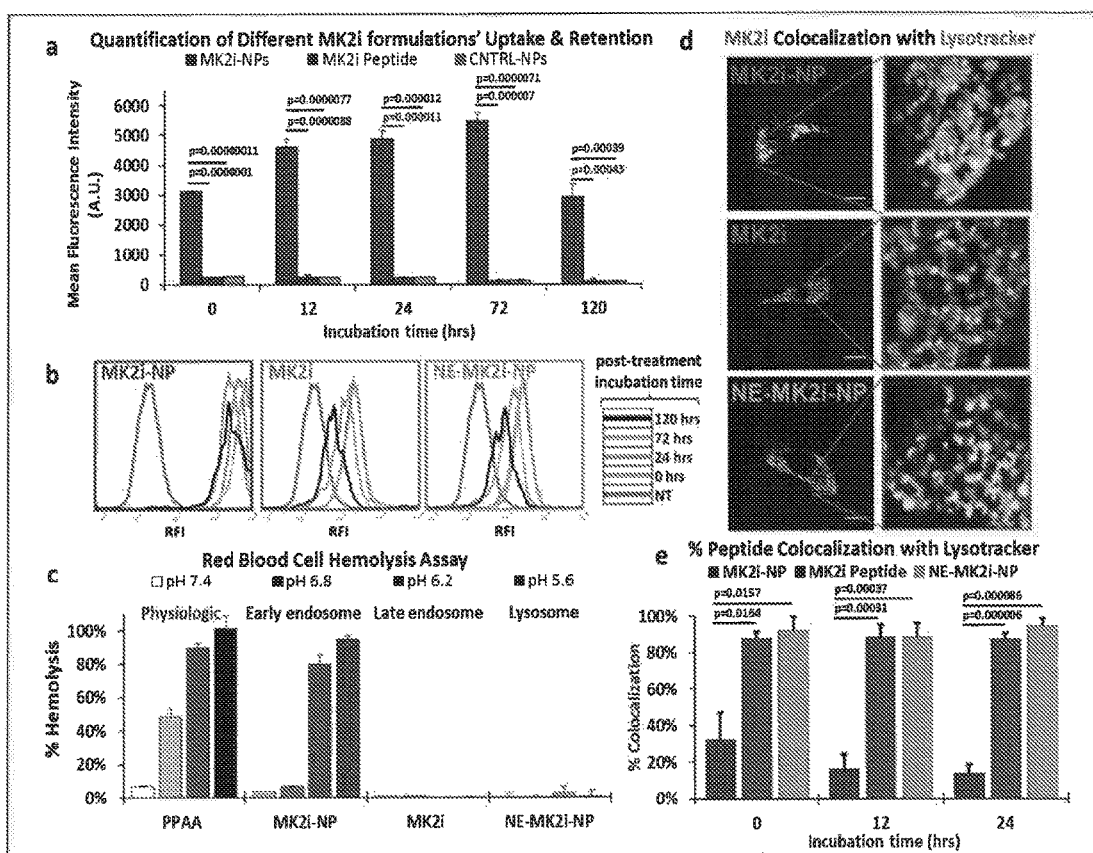
FIG. 36 shows MMI-0100 (MK2i)-NP formulations increase cellular uptake, extend intracellular retention, and reduce endo-lysosomal colocalization of MK2i. a) Flow cytometric quantification of cellular uptake and retention of fluorescently labeled MMI-0100 (MK2i), MK2i-NPs, and NE-MK2i-NPs. n=3. b) Representative flow histograms demonstrate increased cellular uptake and longer intracellular retention of fluorescently labeled MK2i peptide delivered via MK2i-NPs. c) Red blood cell hemolysis assay shows that MK2i-NPs have similar pH-dependent membrane disruptive activity to the PPAA polymer while membrane disruption of NE-MK2i-NPs and the MK2i peptide is negligible in the range tested. d) Representative confocal microscopy images of Alexa-488 labeled MK2i colocalization with Lysotracker red 24 hours after 2 hours of treatment demonstrate that MK2i-NPs have reduced endo-lysosomal colocalization. Scale bars=20 µm. e) Quantification of MK2i peptide colocalization with the endolysosomal dye Lysotracker red 0, 12, and 24 hours after treatment, n≥3 independent images.
Figure 54:
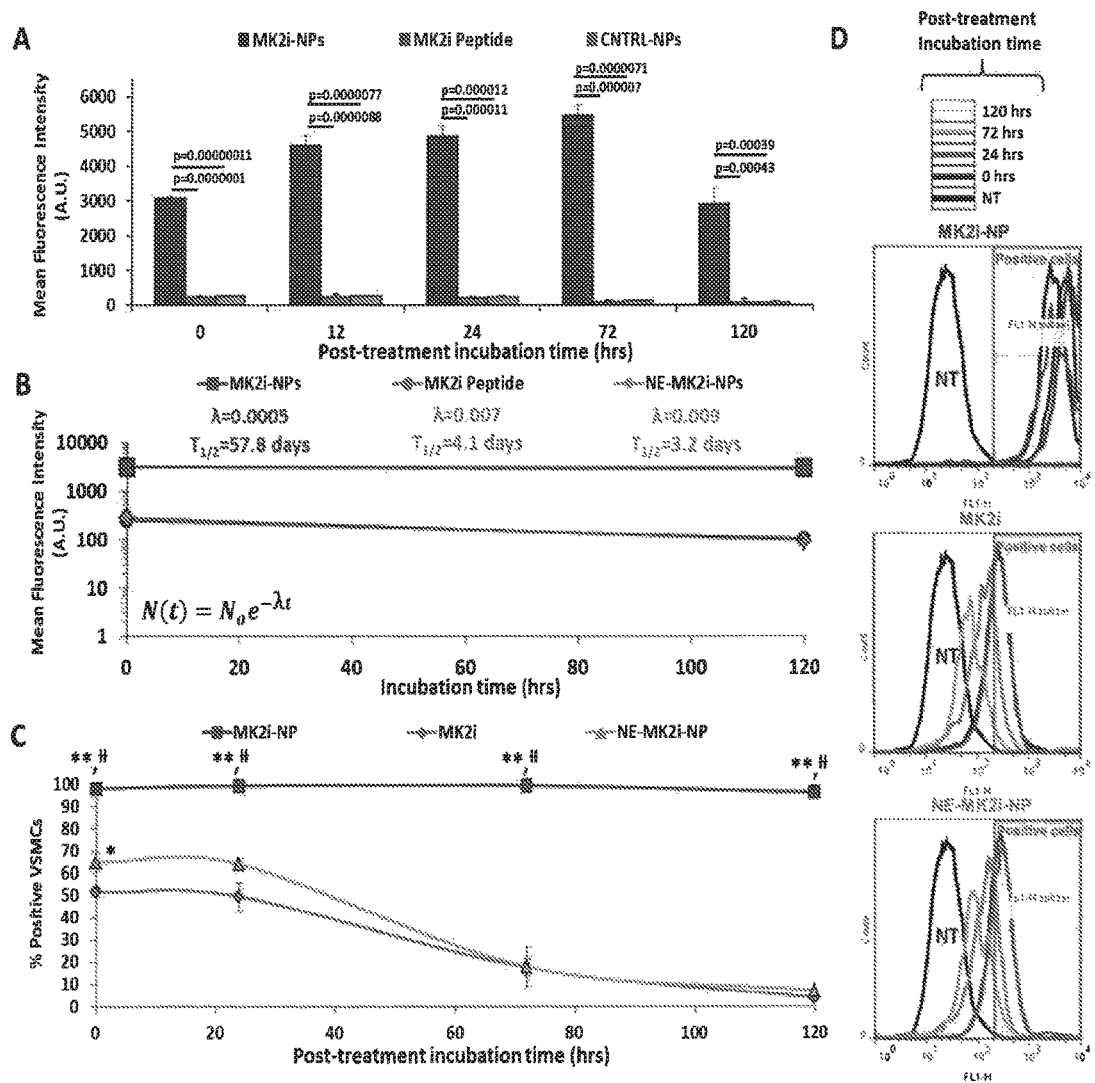
FIG. 54 shows (A) Flow cytometric quantification of HCAVSMC uptake and retention of fluorescently labeled MK2i, MK2i-NPs, and NE-MK2i-NPs. Data are means±SEM (n=3). P values determined by single factor ANOVA. (B) Quantification of intracellular MK2i half-life (t1/2) by exponential decay nonlinear regression analysis of intracellular peptide fluorescence 0 and 5 days following treatment removal. (C and D) Longitudinal quantification (C) and representative flow histograms and subsets (D) used to calculate the percentage of HCAVSMCs positive for MK2i internalization following removal of treatment with free MK2i, MK2i-NPs, or NE-MK2i-NPs. Data are means±SEM (n=3). *P<0.01, **P<0.001 vs. MK2i; ɪP<0.01, ɫɫP<0.001 vs. NE-MK2i-NPs; single factor ANOVA.
Figure 55:
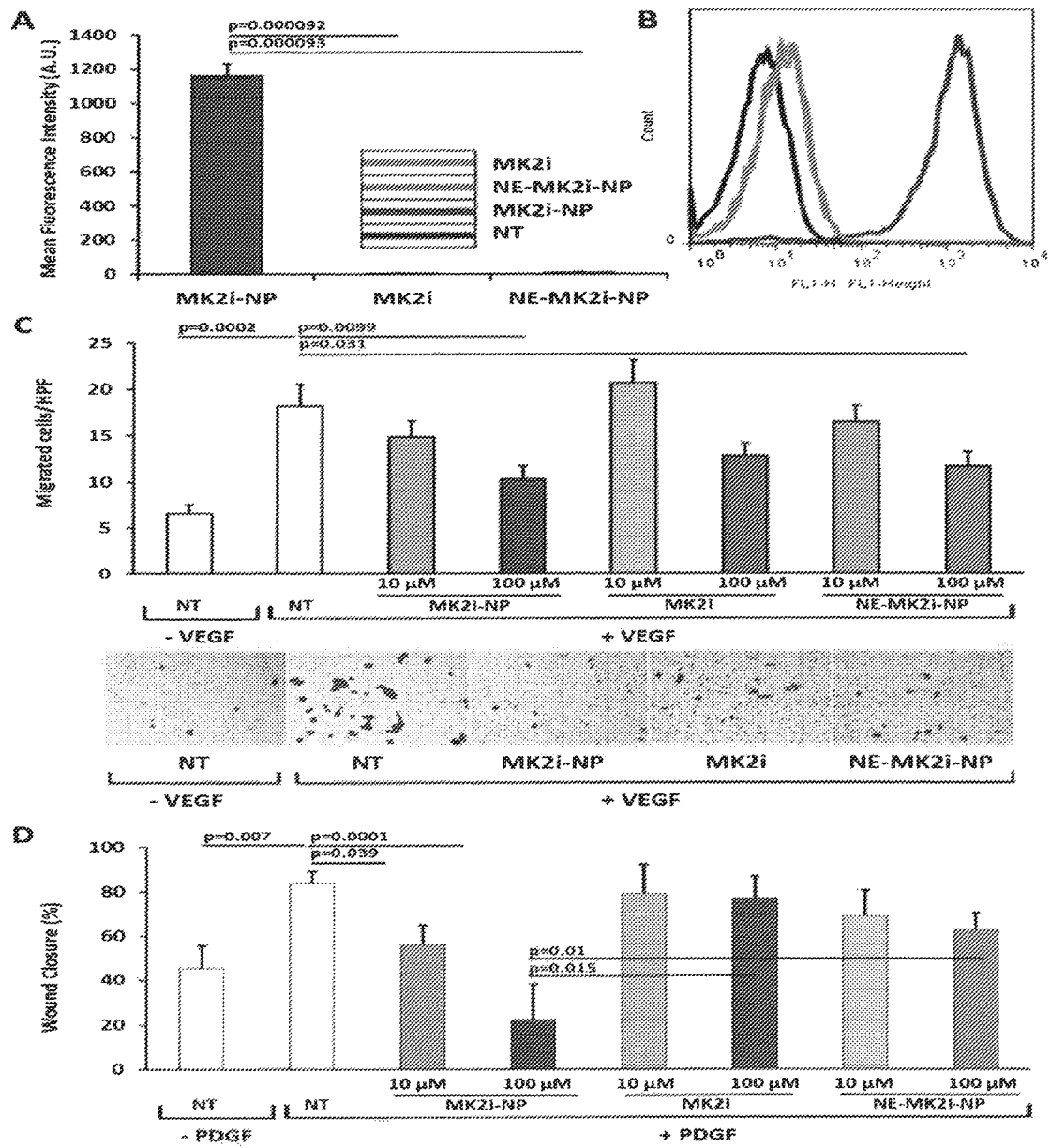
FIG. 55 shows (A and B) Flow cytometric quantification (A) and representative flow histograms (B) of endothelial cell uptake of fluorescently labeled MK2i, MK2i-NPs, and NE-MK2i-NPs. Data are means±SEM (n=3). P values determined by single factor ANOVA. (C) Quantification and representative images of endothelial cell migration immediately after treatment removal determined by Boyden transwell migration assay. (D) Quantification of MK2i-treated VSMC migration in the presence of the chemoattractant PDGF-BB. Migration was determined by calculating percent wound closure 24 hours after scratch wound application in vitro. (C and D) Data are means±SEM (n=3). P values determined by single factor ANOVA.
Figure 56:
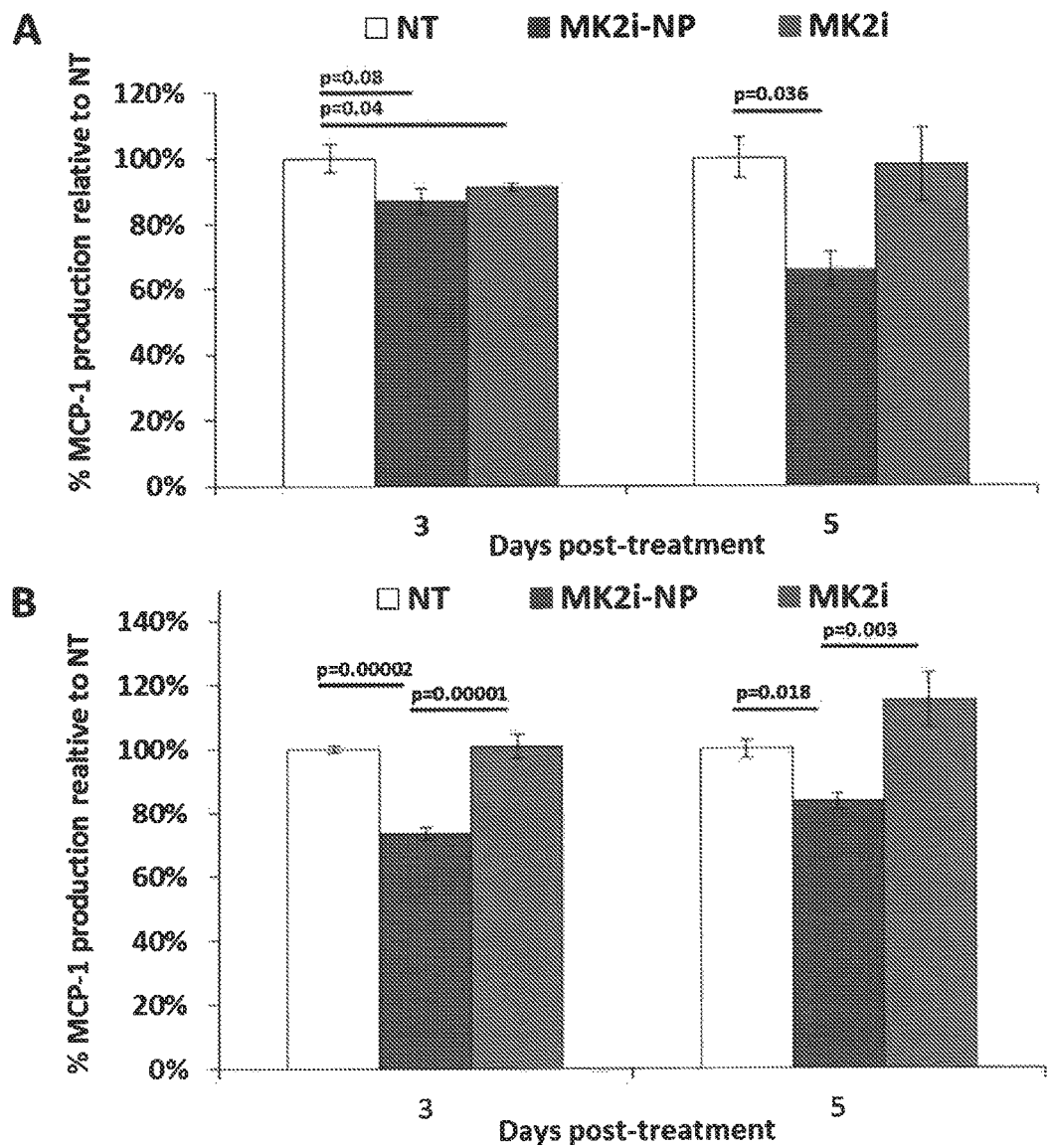
FIG. 56 shows bar graphs representing MK2i-NP and MK2i treatment effects on vascular smooth muscle and endothelial monocyte chemoattractant protein-1 (MCP-1) production over time. Quantification of MCP-1 production over time relative to untreated controls in both (A) vascular smooth muscle cells (VSMCs) and (B) endothelial cells (ECs). Cells were treated for 2 hours and then cultured in fresh medium after MK2i treatment removal. After 3 or 5 days cells were stimulated with 20 ng/ml TNFα for 24 hours and supernatants were collected for cytokine analysis. All treatments used a 10 µM dose of MK2i. Data are means±SEM (n=4). P values determined by single factor ANOVA.
Figure 57:
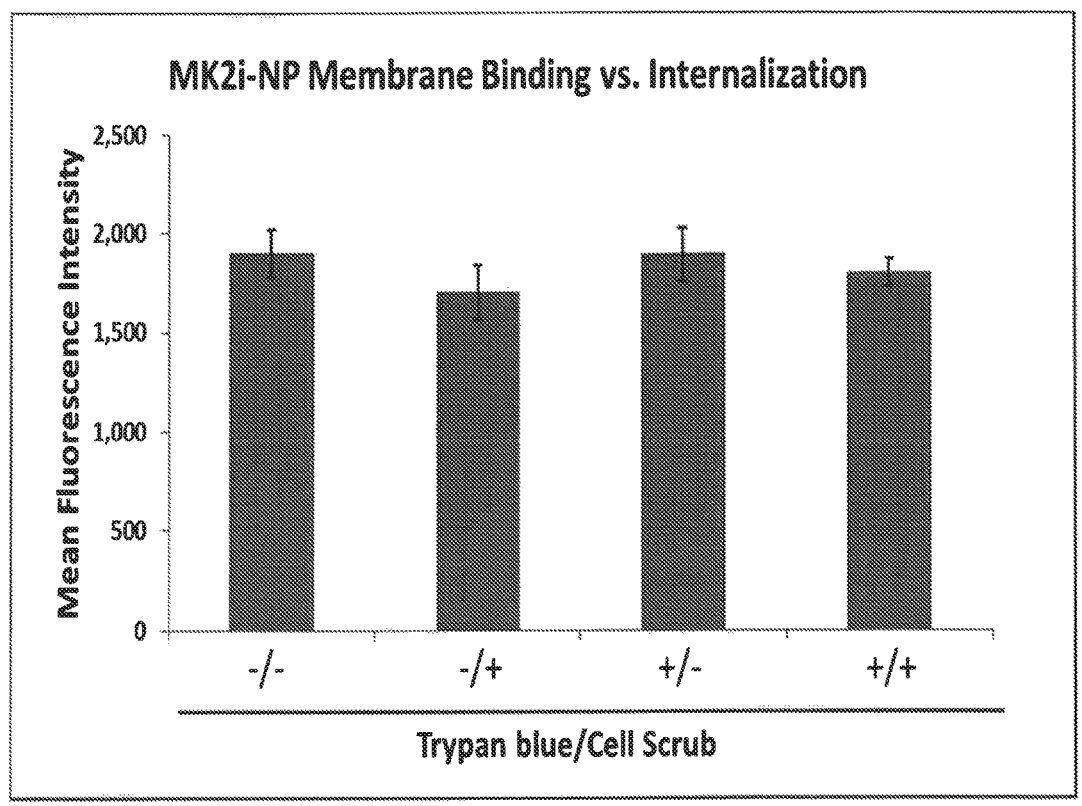
FIG. 57 shows a bar graph representing MK2i-NP internalization. MK2i-NP internalization is not affected by membrane bound NPs as shown by minimal differences in MK2i-NP uptake in vascular smooth muscle cells (VSMCs) that either had extracellular fluorescence quenched by trypan blue and/or were extensively washed with cell scrub buffer to remove any extracellular NPs following treatment removal.

Example 3. Nano-Polyplex (NP) Formulations of MMI-0100 (YARAAARQARAKALARQLGVAA; SEQ ID NO: 1)

Synthesis and Physicochemical Characterization of MMI-0100 (MK2i)-NPs

Formulation of the positively charged, CPP-based MMI-0100 (MK2i) peptide with the anionic, endosomolytic polymer poly(propylacrylic acid) (PPAA) was conceptualized as a method to enhance peptide endolysosomal escape and therapeutic potency. This approach was inspired by the convention for nonviral delivery of nucleic acids, which is based on electrostatic formation of polyplexes between anionic nucleic acids and positively charged CPP sequences, lipids, or polymeric transfection agents to enhance uptake and endosome escape (K. A. Mislick et al., Proc Natl Acad Sci USA 93, 12349-12354 (1996); J. P. Richard et al., J Biol Chem 280, 15300-15306 (2005); C. E. Nelson et al., ACS Nano 7, 8870-8880 (2013)).

MMI-0100 (MK2i) peptide (YARAAARQARAKALARQLGVAA; SEQ ID NO: 1) was synthesized via solid phase synthesis and purity was verified through electrospray-ionization mass spectrometry (FIG. 40). Reversible addition fragmentation chain transfer (RAFT) polymerization was utilized to synthesize poly(acrylic acid) (PAA) [DP=150 (GPC), DP=106 ($H^1$ NMR), PDI=1.27 (GPC) FIGS. 41A and 42A] and poly(propylacrylic acid) (PPAA) [DP=193 (GPC), DP=190 ($H^1$ NMR), PDI=1.47 (GPC) FIGS. 41B and 42B]. NPs were formed by simple mixing of the PAA or PPAA homopolymers with the MMI-0100 (MK2i) peptide in PBS at pH 8.0, which is between the pKa values of the primary amines present on the MMI-0100 (MK2i) peptide and the carboxylic acid moieties in the PPAA polymer; this ensures optimal solubility and net charge on both molecules (FIG. 35A). PPAA was utilized because of its well-defined pH-dependent membrane disruptive activity (R. A. Jones et al., Biochem J 372, 65-75 (2003); C. A. Lackey et al., Bioconjugate Chemistry 13, 996-1001 (2002); N. Murthy et al., J Control Release 61, 137-143 (1999); S. Foster et al., Bioconjug Chem 21, 22015-2212 (2010)) and previous safe use in animal model (S. Foster et al., Bioconjug Chem 21, 2205-2212 (2010); E. Crownover et al., *J Control Release* 155, 167-174 (2011) (FIG. 35B). PAA was utilized as a vector control as it is an anionic polymer with structural similarity to PPAA but lacks pH-response in a physiologically relevant range due to its lower pKa (pKa~4.3) (FIG. 35C).

To determine optimal nanoparticle formulation conditions, a library of MK2i-NPs was prepared at a range of charge ratios [i.e. CR=([$NH_3^+$]$_{MK2i}$:[$COO^-$]$_{PPAA}$)], and the size distribution and particle surface charge were characterized through dynamic light scattering (DLS) and ζ-potential analysis, respectively. Table 23 contains a size summary of MMI-0100 (MK2i)-NPs prepared at different charge ratios as determined by DLS analysis. As expected, MK2i-NP ζ-potential was directly proportional to the CR, with an apparent isoelectric point at CR~2:1 (FIG. 35D). The CR also significantly affected MMI-0100 (MK2i)-NP size, with only a narrow range of CRs yielding a unimodal size distribution (i.e. CR=1:2 and 1:3, supplementary table 1). A CR of 1:3 was chosen as the optimal formulation as this ratio consistently yielded a unimodal size distribution with minimal particle size and polydispersity ($d_h$=119±28 nm, ζ=−11.9±3.2 mV). Non-endosomolytic MK2i nano-polyplexes (NE-MK2i-NPs) were formulated with PAA as a vehicle control for biological studies. NE-MK2i-NPs prepared at CR=1:3 with PAA had size and ζ-potential statistically equivalent to the endosomolytic MK2i-NPs ($d_h$=114±38 nm, ζ=−16.4±5.1 mV). Fluorescent MMI-0100 (MK2i)-NPs and NE-MK2i-NPs were prepared with an Alexa-488 conjugated MMI-0100 (MK2i) peptide at a CR of 1:3 in order to enable intracellular tracking and yielded similar size and charge to the unlabeled NPs. NPs prepared at a CR=1:3 were also characterized through TEM imaging (FIG. 43), which was in agreement with DLS results. The PPAA-MK2i formulations yielded net negatively charged NPs.

TABLE 23

Size Summary of MMI-0100 (MK2i)-NPs Prepared at Different Charge Ratios

| NH2:COOH | Z-ave Diameter (nm) |
|---|---|
| 10:1 | 10.32 ± 2.63* |
| 2:1 | 52.1 ± 46.86* |
| 1:1 | 970.6 ± 662.4 |
| 1:1.5 | 465.1 ± 138.4* |
| 1:2 | 474.2 ± 32.59 |
| 1:3 | 118.8 ± 26.76 |
| 1:4 | 607.4 ± 285.2* |
| 1:5 | 213.0 ± 67.95* |
| 1:10 | 21.57 ± 9.89* |
| 1:3 (Alexa) | 168.5 ± 24.63 |
| 1:3 (NE) | 113.7 ± 14.47 |
| 1:3 (NE Alexa) | 197.4 ± 12.85 |

*indicate multimodal size distributions (multiple peaks).

1:3 (Alexa) polyplexes were formulated with an Alexa488-conjugated MMI-0100 (MK2i) peptide to use in cellular uptake studies. 1:3 (NE) polyplexes were formulated with a non-endosomolytic (NE) poly(acrylic acid) polymer that does not exhibit pH-dependent membrane disruptive activity in the endosomal pH range as a vehicle control.

MMI-0100 (MK2i)-NP unpackaging under endolysosomal conditions was assessed using DLS at a range of pHs and revealed that the MK2i-NPs dissociated as the pH was lowered from extracellular pH toward the pKa of the carboxylic acids (pH~6.7) on PPAA, which also correlates to early endosomal conditions (A. Sorkin et al., Nat Rev Mol Cell Biol 3, 600-614 (2002)) (FIG. 35E). Without being bound by theory, it is hypothesized that at the lower pH, the PPAA polymer becomes protonated/deionized, and the net positive charge on the peptide causes electrostatic repulsion and disassembly of the MK2i-NPs. NP disassembly under early endosome-like conditions reduces the possibility that peptide bioactivity and/or PPAA endosomal membrane disruptive function is sterically hindered by polymer-peptide interactions.

MMI-0100 (MK2i)-NP Cell Internalization, Endosome Escape, and Intracellular Retention Quantity of MMI-0100 (MK2i)-NP uptake and intracellular retention over time were assessed through flow cytometric analysis of human coronary artery vascular smooth muscle cells (HCAVSMCs) treated for 2 hours, washed, and maintained in fresh medium for 5 days. More than an order of magnitude increase in peptide uptake was measured in MK2i-NP treated cells compared to NE-MK2i-NPs and MMI-0100 (MK2i) (FIG. 36A and FIG. 54A). Because NE-MK2i-NP uptake was equivalent to the free peptide, these data indicate that differences in cell internalization are due to NP formulation and independent of particle morphology and charge. Enhanced peptide delivery via the MK2i-NP formulation was also detected in analogous studies on endothelial cells suggesting that this is not a cell type-specific observation (FIG. 56). Half-life calculations (FIG. 54B) showed that MK2i-NPs increased the intracellular half-life of the MK2i peptide by over an order of magnitude from 4 days to 58 days. Additionally, HCAVSMCs treated with MMI-0100 (MK2i)-NPs demonstrated longer peptide intracellular retention compared to NE-MK2i-NP and MK2i treated cells, likely due to a higher rate of peptide degradation in the endolysosomal pathway and/or exocytotic recycling out of the cell (I. R. Ruttekolk et al., Mol Pharmaceut 9, 1077-1086 (2012)) (FIG. 36B). Interestingly, MK2i-NPs showed an increase in fluorescence over the first 72 hours of incubation following treatment/washing. It was verified that this effect was not due to delayed internalization of MK2i-NPs bound to the outer membrane of the cells but that this increase in fluorescence is due to an Alexa-488 self-quenching mechanism (W. H. t. Humphries et al., Anal Biochem 424, 178-183 (2012)); increased fluorescence over time may be due to diminished quenching as the MMI-0100 (MK2i) is unpackaged from the NPs intracellularly (FIG. 57).

Figure 44:
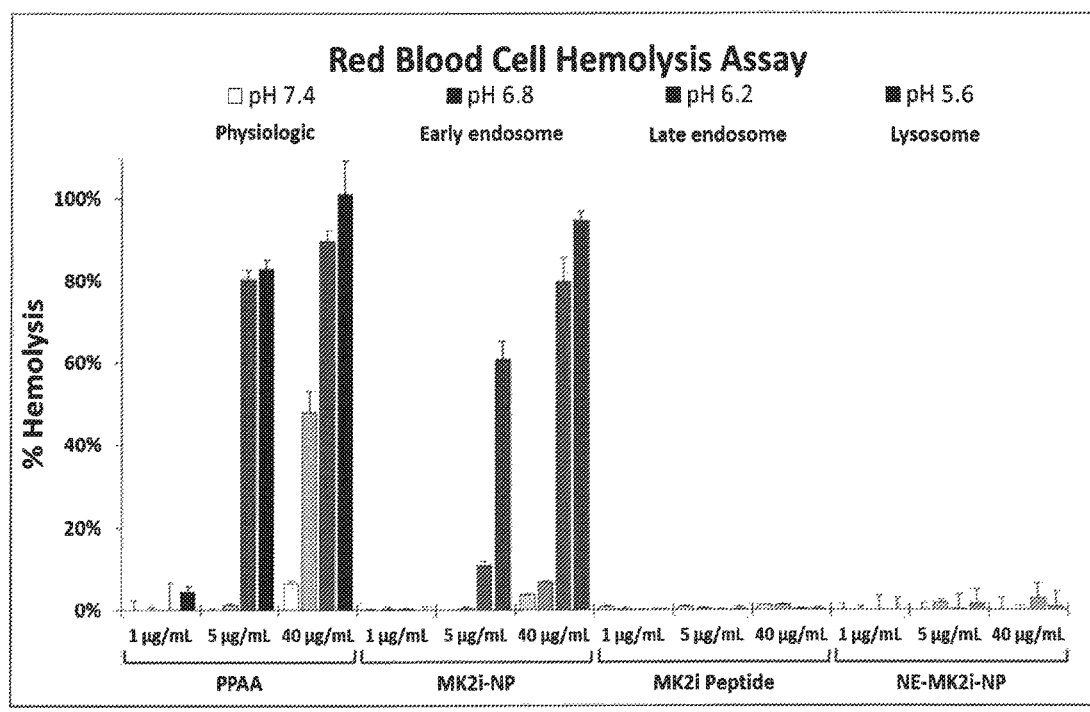
FIG. 44 shows a bar graph representing a full data set for pH-dependent red blood cell membrane disruption. Red blood cell hemolysis assay shows that MMI-0100 (MK2i)-NPs have similar pH-dependent and dose-dependent membrane disruptive activity to the PPAA polymer but NE-MK2i-NPs and the MK2i peptide alone do not.

To gain clarity into the mechanism of improved intracellular retention of peptide delivered via MMI-0100 (MK2i)-NPs, a red blood cell hemolysis assay (B. C. Evans et al., J Vis Exp, e50166 (2013)) and microscopy/colocalization studies were used to assess pH-dependent membrane disruptive activity and endosomal escape of MK2i-NPs. PPAA disrupts erythrocyte membranes at pHs at or below its pKa (~6.7) (FIG. 36C). At extracellular (7.4) and early endosomal (6.8) pH, MK2i-NPs showed little membrane disruptive activity. However, at pH representative of late endosomes (6.2) and lysosomes (5.6), a significant increase in hemolysis was observed. The hemolytic behavior of the MK2i-NPs at late endosome/lysosomal pH was directly proportional to polymer concentration (FIG. 44), with >90% erythrocyte lysis occurring at 40 µg/mL MK2i-NPs at pH 5.6. MK2i-NPs retain the inherent membrane disruptive activity of the PPAA polymer, although formulation into NPs partially masked the membrane disruptive activity relative to free PPAA at pH 6.8. As expected, neither the MK2i peptide alone nor the non-endosomolytic NE-MK2i-NP formulation displayed any membrane disruptive activity in the endolysosomal pH range.

Figure 45:
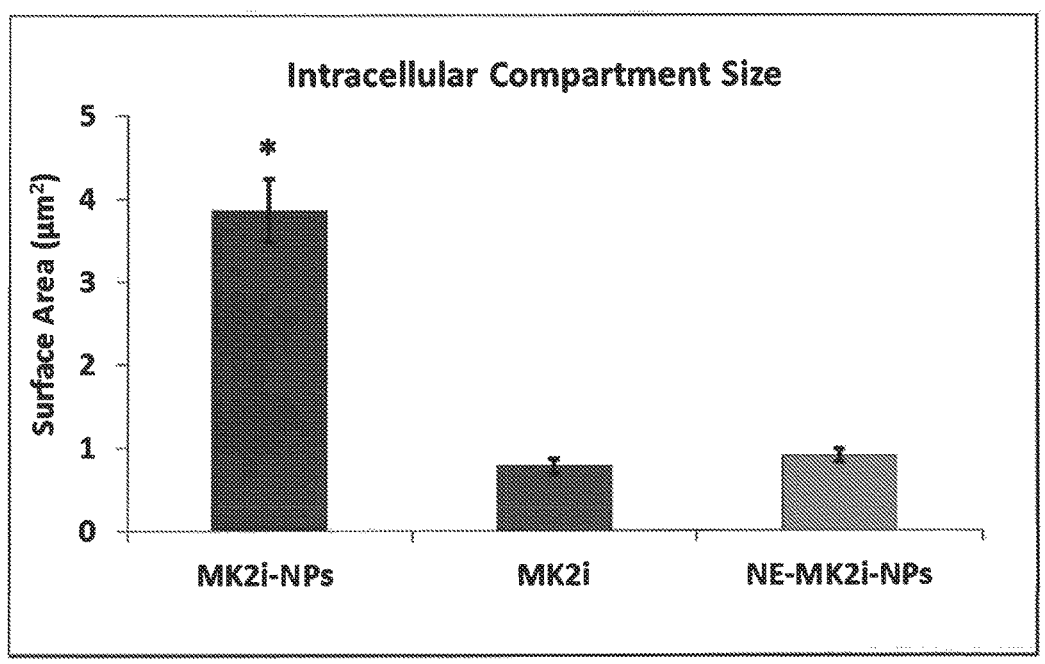
FIG. 45 shows a bar graph representing average size of intracellular compartments containing MMI-0100 (MK2i) 24 hours after treatment with different peptide formulations. Compartment area was quantified with ImageJ software. *p<0.001 vs. MK2 and NE-MK2i-NPs, n=50 vesicles from at least 3 different images.
Figure 58:
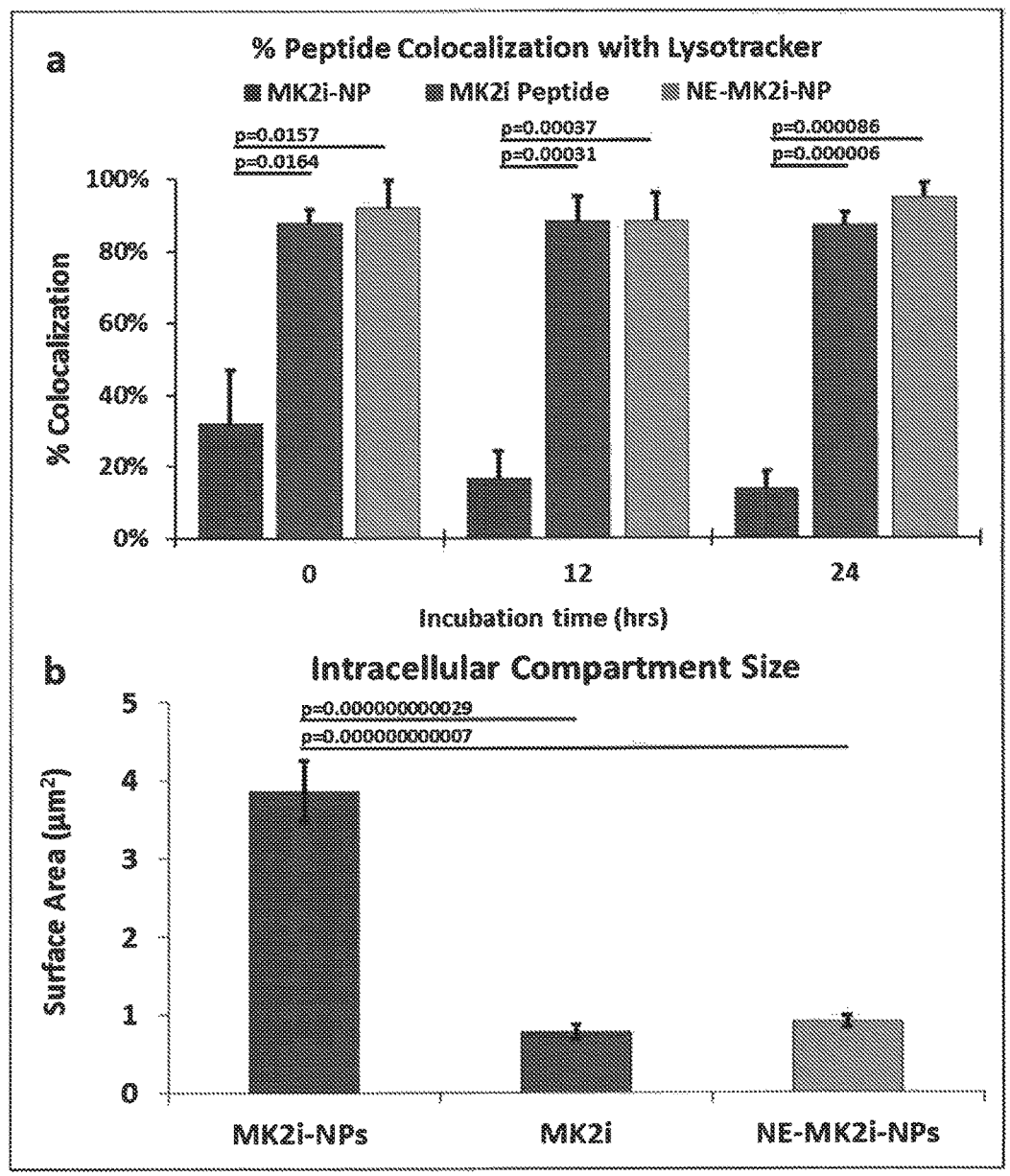
FIG. 58 shows (A) Quantification of MK2i peptide colocalization with the endolysosomal dye Lysotracker red 0, 12, and 24 hours after treatment, n≥3 independent images; (B) average size of intracellular compartments containing MK2i 24 hours after treatment with different peptide formulations. Compartment area was quantified with ImageJ software. n=50 vesicles from at least 3 different images.

MK2i-NP endosomal escape was imaged and quantified in vitro in HCAVSMCs (FIG. 36D). Approximately 90% of the MK2i delivered as free peptide or via NE-MK2i-NPs colocalized with the Lysotracker dye, while MK2i-NP formulation significantly reduced MK2i endolysosomal colocalization. Longitudinal quantification of MK2i/Lysotracker colocalization following a 2-hr treatment and wash revealed significantly reduced MK2i/Lysotracker colocalization for the MK2i-NP formulations at all time points (FIG. 36E). Interestingly, quantification of compartment size revealed that NE-MK2i-NP or MK2i treated cells showed MK2i localization within smaller vesicles representative of endosomes, whereas MK2i delivered via MK2i-NPs was found within larger compartments, potentially representative of the cytosol or disrupted vesicles (FIGS. 45 and 58B).

Figure 35:
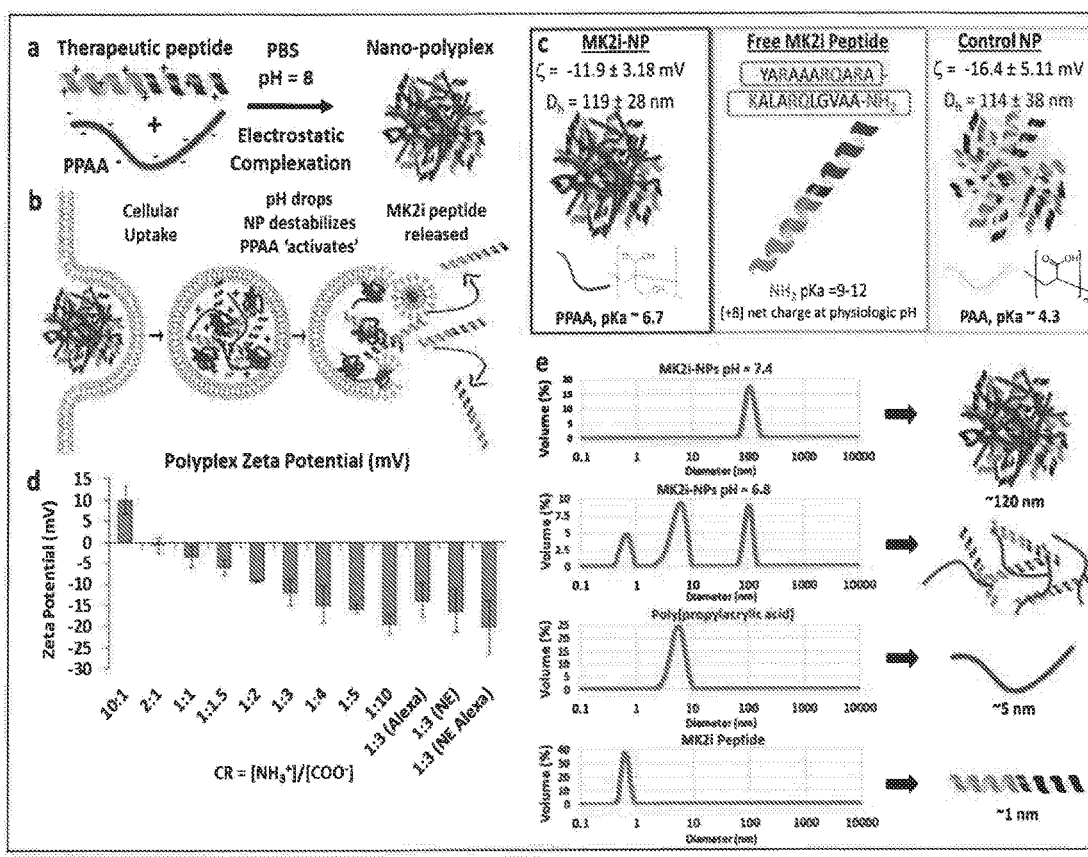
FIG. 35 shows MMI-0100 (MK2i)-NP synthesis and characterization. a) MK2i-NP synthesis scheme. b) MK2i-NPs were designed and optimized to mediate endosome escape and release peptide therapeutics intracellularly. c) Treatment comparison summary: MK2i-NPs were formulated with an endosomolytic PPAA polymer whereas the NE-MK2i-NPs were formulated with a PAA polymer that is structurally similar to PPAA but is not endosomolytic due to its lower pKa. Both the MK2i-NPs and NE-MK2i-NPs are made with the MK2i peptide with the sequence shown (red=modified TAT mimetic cell penetrating peptide sequence, green=MK2 inhibitory sequence). d) Zeta potential of polyplexes prepared at different charge ratios ([NH3+]/[COO—]). For imaging and uptake studies, Alexa NPs were formulated from MK2i peptide labeled with an Alexa-488 fluorophore. NE-NPs are formulated with a non-endosomolytic (NE) PAA polymer. Values shown are an average of at least 3 independent measurements. e) MK2i-NPs undergo pH-triggered disassembly in the endosomal pH range as demonstrated by DLS analysis.

The NP formulation significantly increased peptide uptake by vascular smooth muscle cells (VSMCs) relative to the free, CPP-based MMI-0100 (MK2i) peptide (FIG. 36A). Without being bound by theory, the in vitro comparisons of MMI-0100 (MK2i)-NPs and NE-MK2i-NPs shown in FIG. 35 suggest that the high levels of MK2i-NP cell internalization was dependent on the specific formulation of PPAA, rather than purely dictated by NP morphology and surface charge. The α-alkyl substitution of the propyl moiety makes PPAA more lipophilic/hydrophobic relative to acrylic acid, suggesting that the observed differences in uptake may be the result of increased hydrophobic interactions of MMI-0100 (MK2i)-NPs with the cell membrane. Hydrophobic interactions may nonspecifically trigger MK2i-NP cell internalization, or MK2i-NP internalization may be mediated by VSMC scavenger receptors that are upregulated in settings of vascular stress and that internalize negatively charged/hydrophobic particles (e.g., LDL).

In addition to efficient cell internalization, avoiding endolysosomal degradation and extracellular recycling is vital to optimizing therapeutic potency and longevity of action of cytosolically-active peptides (C. L. Duvall et al., Mol Pharm 7, 468-476 (2010)). This sustained therapeutic effect is of particular importance for a peptide-based vein graft therapeutic where a single, intraoperative treatment should achieve prolonged bioactivity throughout the post-transplant inflammatory and healing phases. To this end, the MK2i-NP formulation significantly improved intracellular retention of the MMI-0100 (MK2i) peptide (FIGS. 36A and B). This enhanced retention is achieved through the pH-dependent membrane disruptive activity of PPAA, which is ideally tuned for directing endolysosomal escape (FIG. 36C-E). Cell imaging studies supported the endosomolytic function of PPAA and showed that peptide delivered via MK2i-NPs had significantly decreased colocalization with an endolysosomal dye (FIG. 36D,E). Avoiding endosomal entrapment was associated with increased longevity of intracellular peptide retention. Estimation of the intracellular half-life ($T_{1/2}$) of MMI-0100 (MK2i) based upon exponential decay nonlinear regression analysis of intracellular peptide fluorescence at 0 and 5 days following treatment removal revealed that intracellular $T_{1/2}$ was increased 14-fold by incorporation into MK2i-NPs (MK2i-NP $T_{1/2}$=57.8 days vs. MK2i $T_{1/2}$=4.1 days) (data not shown).

Figure 38:
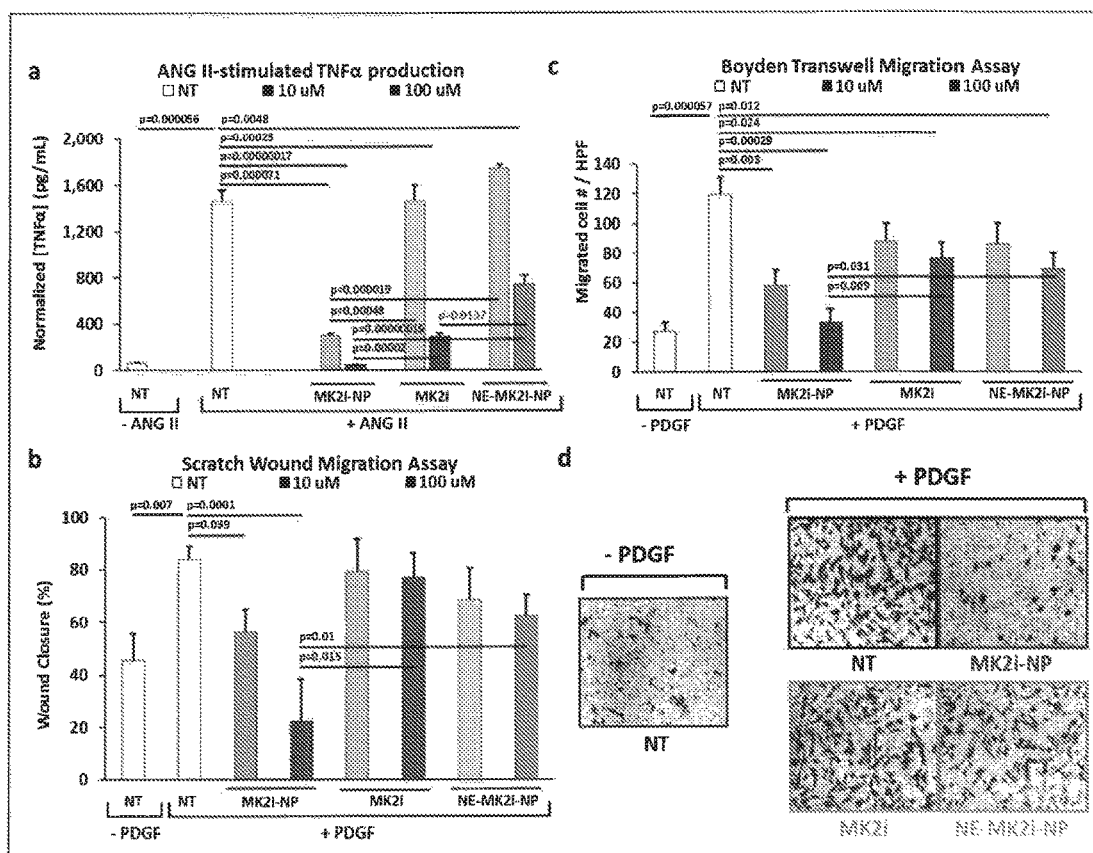
FIG. 38 shows MMI-0100 (MK2i)-NP formulation enhances MMI-0100 (MK2i) bioactivity in HCAVSMCs. a) MK2i-NP treatment blocked TNFα production in HCAVSMCs stimulated with ANG II. All data is normalized to cell number (data shown in supplementary FIG. 11). NT=no treatment, n=4. b) MK2i-NP treatment blocked migration in human coronary artery vascular smooth muscle cells (HCAVSMCs) stimulated with the chemoattractant PDGF-BB (50 ng/mL) 24 hours after formation of a scratch wound, n=3. c) MK2i-NPs inhibited cell migration towards the chemoattractant PDGF-BB in a Boyden Chamber assay 8 hours after seeding onto the membrane, n=7. d) Representative microscopy images of stained transwell insert membranes for each treatment group.

MMI-0100 (MK2i)-NPs improved peptide potency based on shifting the dose response curve (i.e., increased potency ~10-fold in most assays, FIG. 38). However, the longer intracellular half-life of MK2i peptide via the NP formulation may also enable superior longevity of action and improve, for example, long-term graft patency. Without being bound by theory, the intracellular half-life of MMI-0100 (MKi) delivered via NPs is expected to be therapeutically relevant, as TGF-β-mediated transdifferentiation and cell migration mediated by the p38 MAPK pathway has been found to contribute to pathological vein graft remodeling out to 35 days post-transplant (A. V. Bakin et al., J Cell Sci 115, 3193-3206 (2002)). Other studies on the kinetics of intimal hyperplasia (IH) pathogenesis in rabbit and canine models detected an initial burst in cellular proliferation during the first week, followed by continued graft adaptation that reaches steady state by week 12 (M. Kalra et al., J Vasc Res 37, 576-584 (2000); R. M. Zwolak et al., J Vasc Surg 5, 126-136 (1987)). The extended half-life achieved with MK2i-NPs is expected to yield significantly improved long-term performance following a single treatment prior to, for example, implantation, by inhibiting underlying signaling pathways and accelerating resolution of inflammation and the time required to reach steady-state conditions.

Figure 59:
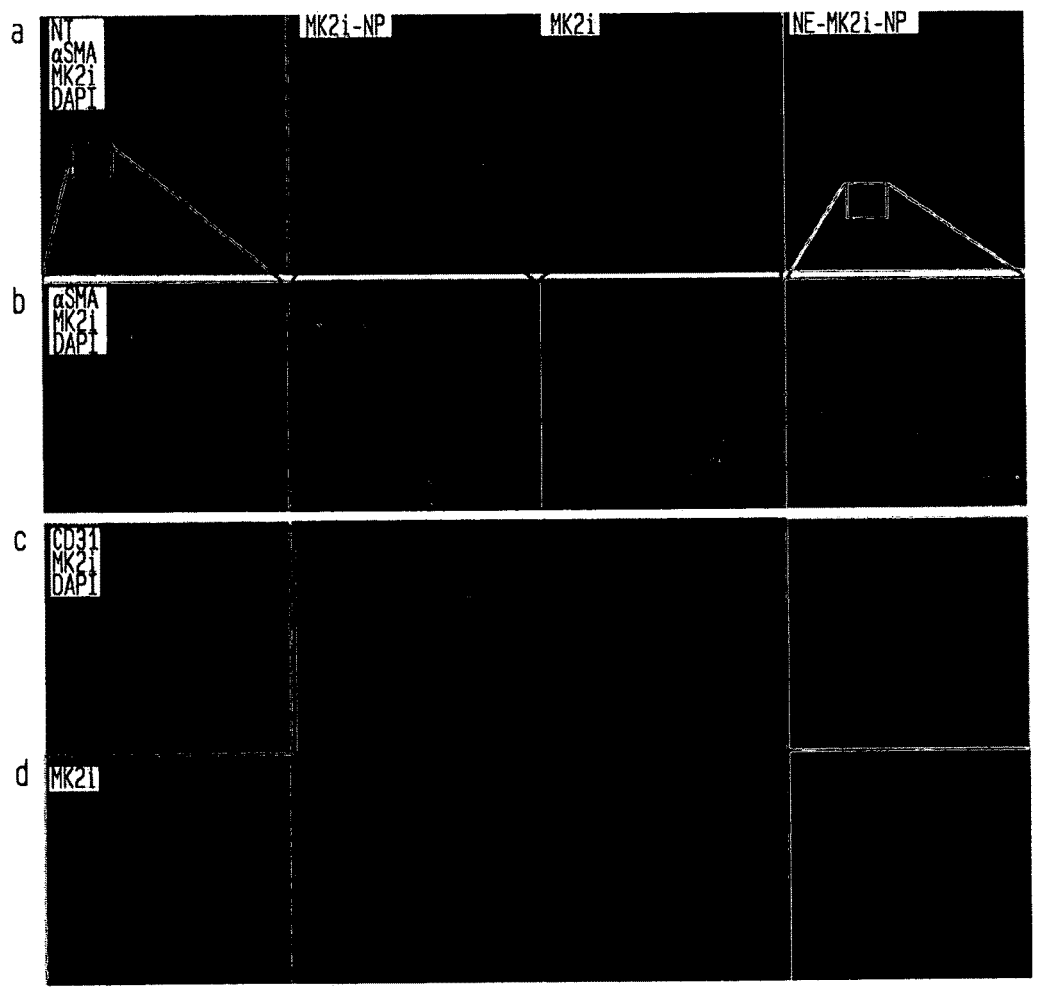
FIG. 59 shows (a) immunofluorescence microscopy images of human saphenous vein cross sections treated with Alexa-568 labeled MK2i, MK2i-NPs, or NE-MK2i-NPs (red) and stained for the vascular smooth muscle marker α-smooth muscle actin (green) showing MK2i-NP colocalization with α-smooth muscle actin; (b) zoomed insets from images in (a); (c) zoomed immunofluorescence microscopy images of human saphenous vein treated with Alexa-568 labeled MK2i, MK2i-NPs, or NE-MK2i-NPs (red) and stained for the endothelial marker CD31(green) demonstrating MK2i colocalization with endothelial cells; (d) zoomed insets showing MK2i penetration into the vessel wall for all treatment groups; (e) pixel intensity distribution of the images shown in (a) demonstrating increased MK2i uptake (red channel) in vessels treated with MK2i-NPs.
Figure 59:
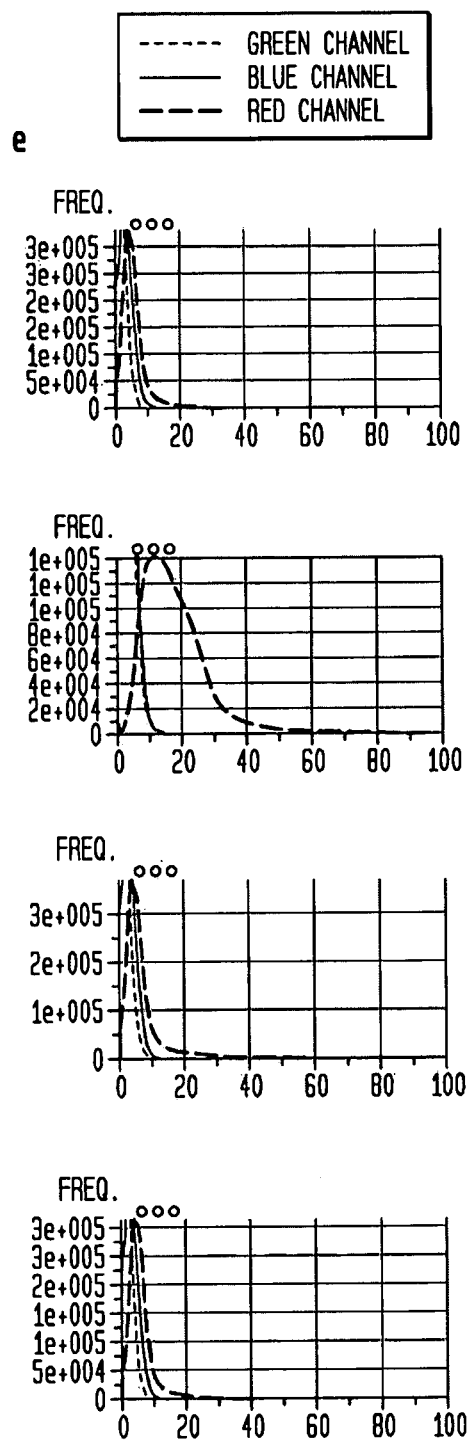
Figure 60:
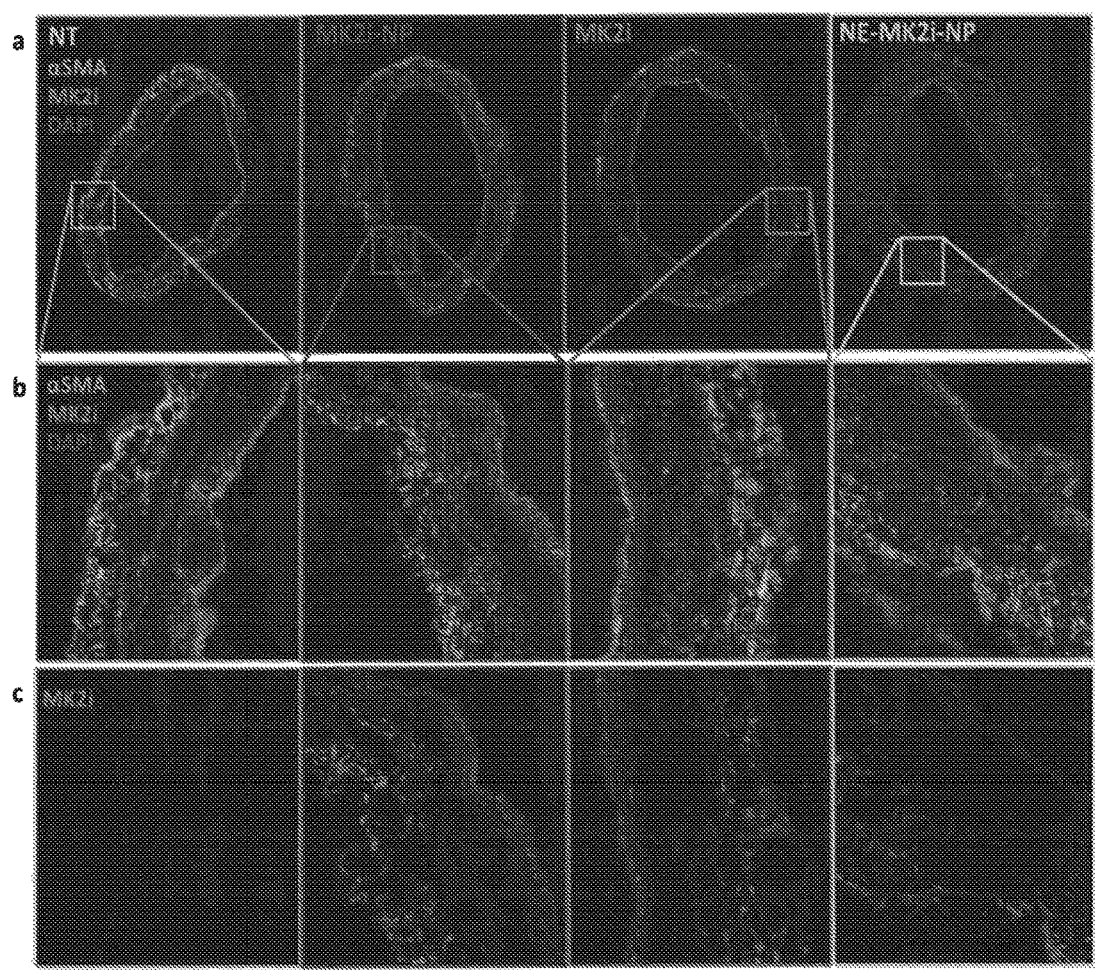
FIG. 60 shows (a-b) immunofluorescence microscopy images of human saphenous vein treated with Alexa-568 labeled MK2i, MK2i-NPs, or NE-MK2i-NPs (red) and stained for the vascular smooth muscle cell marker α-smooth muscle actin (green) showing MK2i-NP colocalization with α-smooth muscle actin; (c) immunofluorescence microscopy of demonstrating increased uptake and penetration of MK2i-NPs into the vessel wall relative to the MK2i and NE-MK2i-NP treated vessels.

MK2i-NP delivery of peptide into intact human saphenous vein (HSV) was also assessed. The results of this experiment suggested that uptake occurs in both endothelial and smooth muscle cells. As expected, MK2i-NPs and controls showed more concentrated uptake at the luminal and adventitial surfaces that act as diffusion barriers (FIG. 59). MK2i penetration into the intimal and medial layers was verified by colocalization with the smooth muscle marker α-SMA (FIG. 60a-b). Furthermore, in accordance with in vitro results, MK2i-NPs increased the overall peptide uptake within the vessel wall (FIG. 60c; FIG. 59e).

Inhibition of Intimal Hyperplasia (IH in Human Saphenous Vein (HSV)

Figure 37:
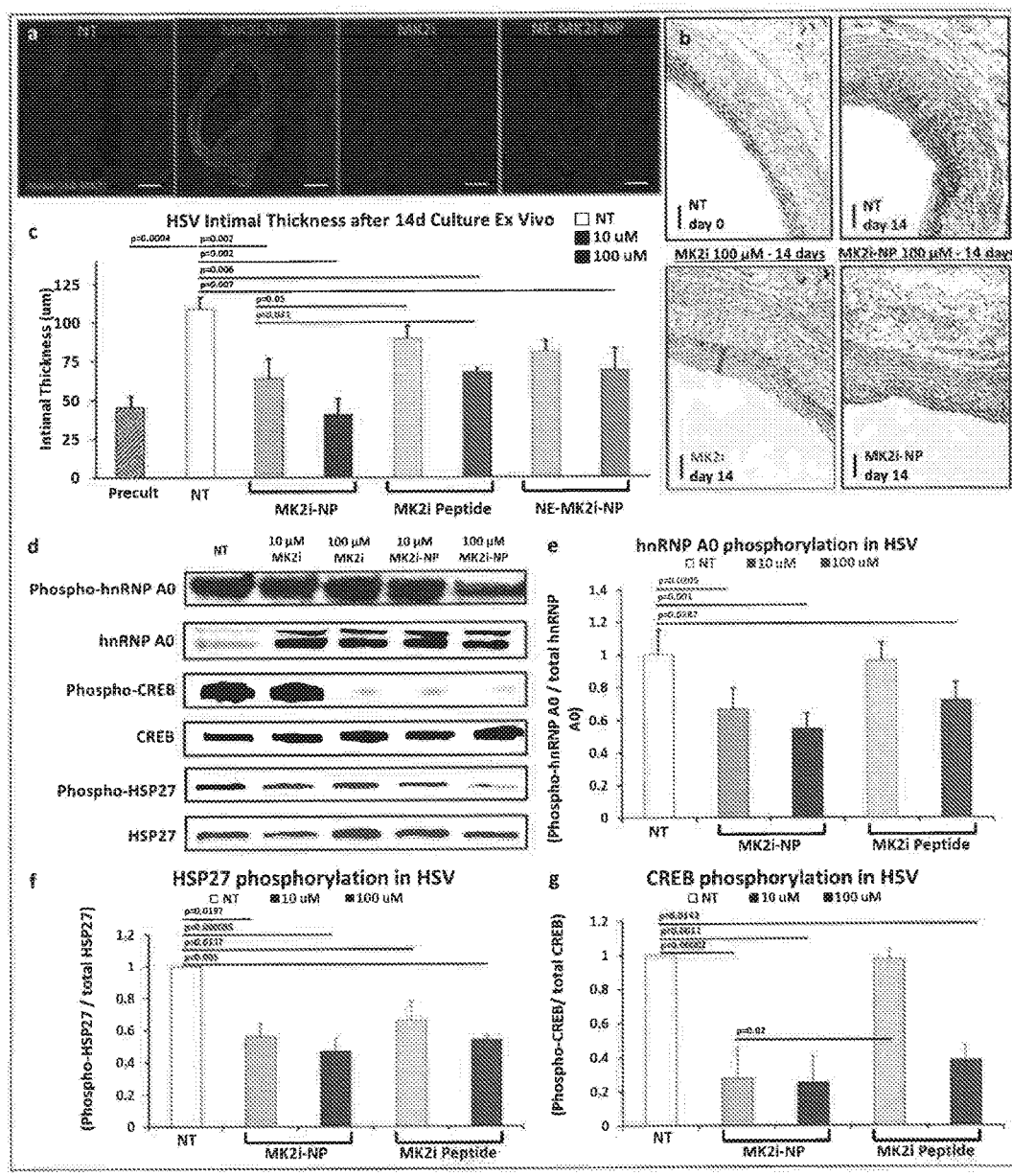
FIG. 37 shows ex vivo treatment with MK2-NPs reduces neointima formation and alters phosphorylation of molecules downstream of MK2 in human saphenous vein. a) MK2i-NP formulation increased delivery of Alexa 568-MK2i to HSV tissue ex vivo, scale bars=200 µm. b) Representative microscopy images of Verhoeff Van-Gieson (VVG) stained human saphenous vein sections that were treated for 2 hours and maintained in organ culture for 14 days. MK2i-NPs potently blocked neointima formation. Red bars demarcate intimal thickness. Scale bars=100 µm. c) Quantification of intimal thickness from VVG stained histological sections; measurements are average of 6-12 radially parallel measurements from at least 3 vein rings from separate donors. d) Representative western blots showing the phosphorylation of MK2 substrates hnRNP A0, CREB, and HSP27. e-g) Quantification of western blot analysis from n≥3 separate donors demonstrating that MK2i-NPs enhanced MK2i mediated inhibition of several factors activated downstream of MK2 that are implicated in migration and inflammation.
Figure 46:
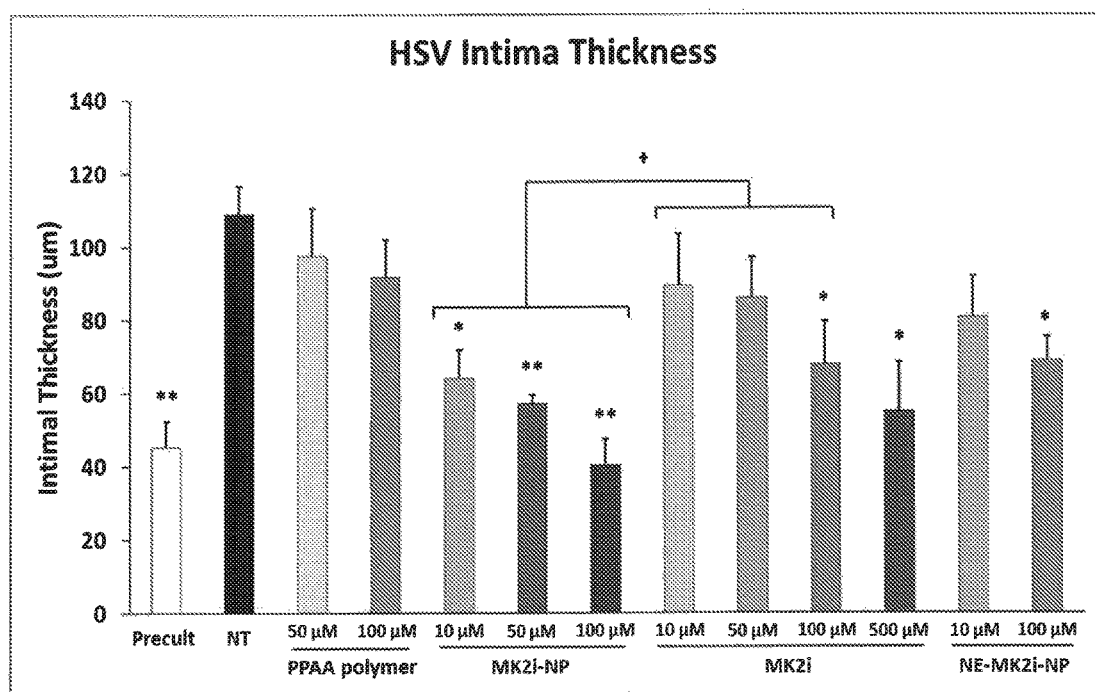
FIG. 46 shows a bar graph representing a full dose response data set of intimal thickness measurements of human saphenous vein (HSV) explants treated for 2 hours and then maintained in organ culture for 14 days, n≥3 from at least 3 different donors. *p≤0.01 compared to no treatment control (NT), **p≤0.001 compared to NT, $^‡$p ≤0.05.
Figure 47:
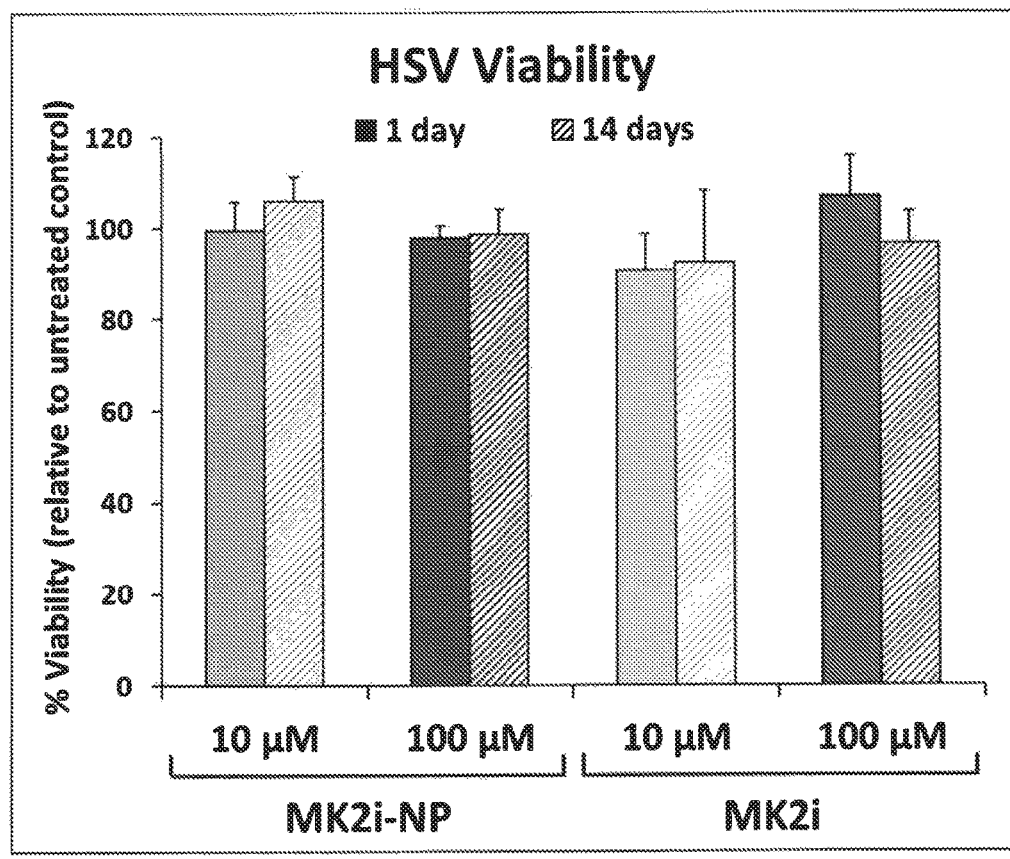
FIG. 47 shows a bar graph representing tissue viability in HSV rings treated for 2 hours and maintained in organ culture for 1 or 14 days as assessed through an MTT assay. n≥3 vein rings from at least 3 separate donors.

To confirm efficient delivery and MMI-0100 (MK2i)-NP bioactivity in three dimensional human vascular graft tissue, an ex vivo organ culture model of vein IH was completed using human saphenous vein (HSV). HSV rings were cut from HSV samples that were confirmed to be viable based on contractile response to KCl challenges in a muscle bath. Rings were treated for 2 hours, washed, and maintained in high serum conditions that accelerate neointima formation. An Alexa-568 conjugated MK2i peptide was used to visualize peptide delivery to the vessel wall immediately following treatment, and, similar to the in vitro results, MMI-0100 (MK2i)-NPs consistently increased peptide delivery relative to free MMI-0100 (MK2i) (FIG. 37A). After 14 days in culture, Verhoeff-Van Gieson (VVG) staining of the elastic laminae was performed on tissue sections (FIG. 37B). Quantification of intimal thickness of samples from multiple human donors revealed that MK2i-NPs significantly inhibited IH in a dose-dependent fashion and at an order of magnitude lower peptide dose than free MMI-0100 (MK2i) (FIG. 37C and FIG. 46). Furthermore, MK2i-NP therapy at 100 μM MK2i was the only treatment that fully abrogated IH, yielding intimal thickness statistically equivalent to control tissues prepared for histology immediately after harvest (p=0.49). MTT assays were performed 1 and 14 days post-treatment and verified that organ culture results were not affected by treatment effects on tissue viability (FIG. 47). Treatment of human saphenous vein with 100 μM MK2i-NPs completely abrogated neointimal growth over 2 weeks in the ex-vivo organ culture model of IH.

Mechanistic Elucidation of MMI-0100 (MK2i)-NP Bioactivity

Figure 48:
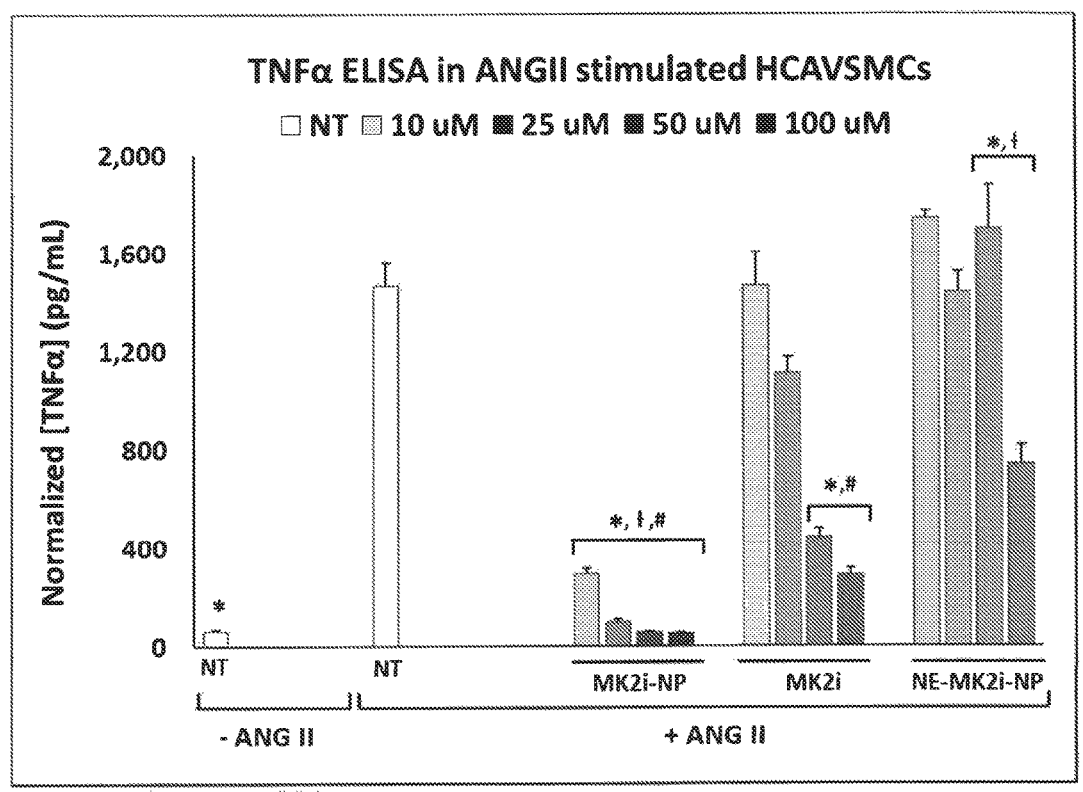
FIG. 48 shows a bar graph representing TNFα production in HCAVSMCs stimulated with ANG II for 6 hours, treated for two hours with MMI-0100 (MK2i)-NPs, NE-MK2i-NPs, or the MMI-0100 (MK2i) peptide alone and cultured for 24 hours in fresh media. All data is normalized to cell number. NT=no treatment. *p<0.05 compared to NT+TNFα group, $^‡$p <0.05 compared to MK2i at the same concentration, #p<0.05 compared to NE-MK2i-NPs at the same concentration, n=4.
Figure 49:
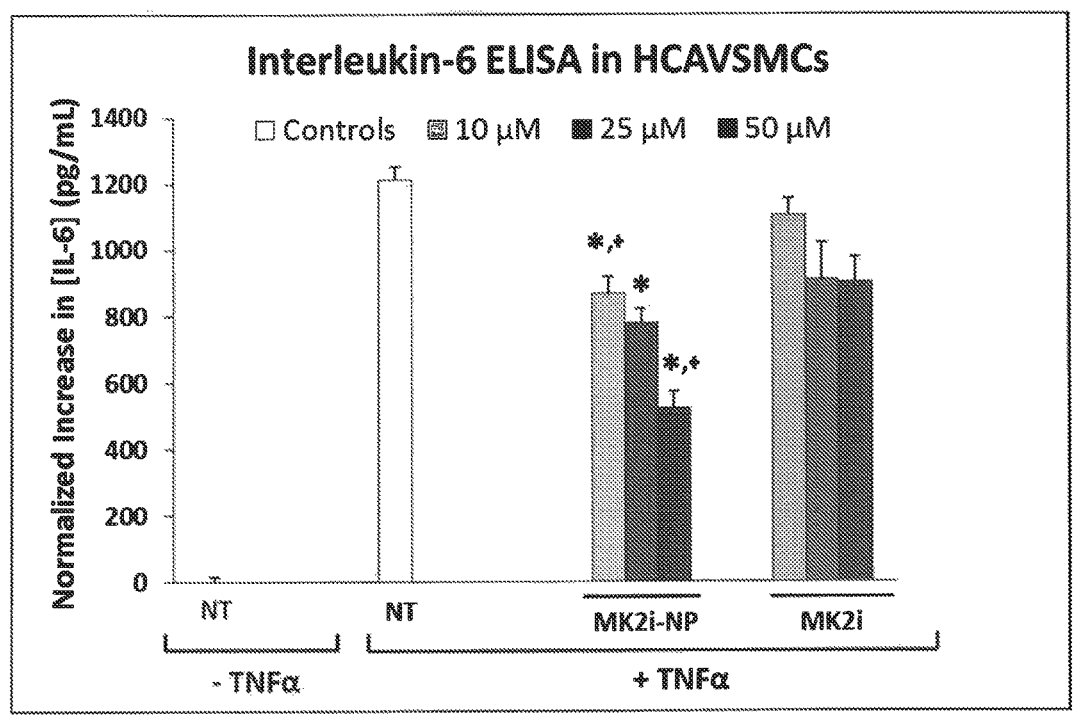
FIG. 49 shows a bar graph representing MMI-0100 (MK2i)-NPs partially block TNFα-induced increase in IL-6 production in HCAVSMCs. Cells were stimulated with TNFα for 6 hours, treated for two hours with MK2i-NPs or MMI-0100 (MK2i) peptide alone, and cultured for 24 hours in fresh media. All data is normalized to cell number. NT=no treatment. *p<0.05 compared to NT+TNFα group, $^‡$p <0.05 compared to MK2i at the same concentration, n=4.
Figure 50:
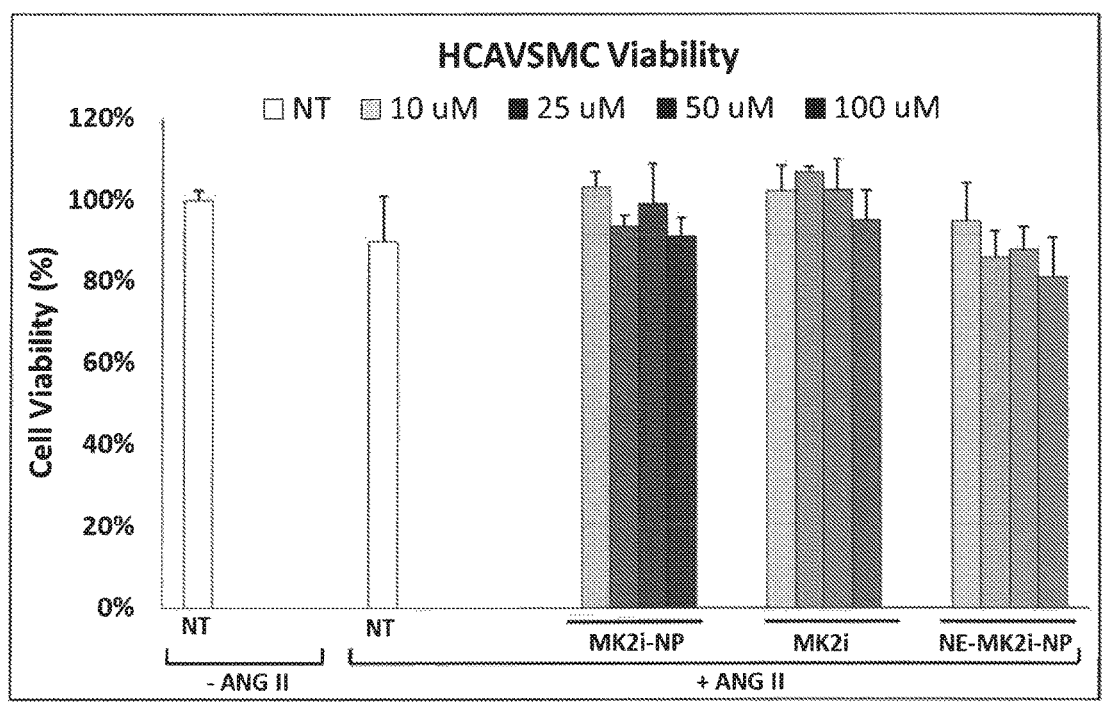
FIG. 50 shows a bar graph representing cell viability in HCAVSMCs stimulated with 10 μM ANG II for 6 hours, treated for two hours with MMI-0100 (MK2i)-NPs, NE-MK2i-NPs, or the MMI-0100 (MK2i) peptide alone and cultured for 24 hours in fresh media. NT=no treatment, n=4.
Figure 51:
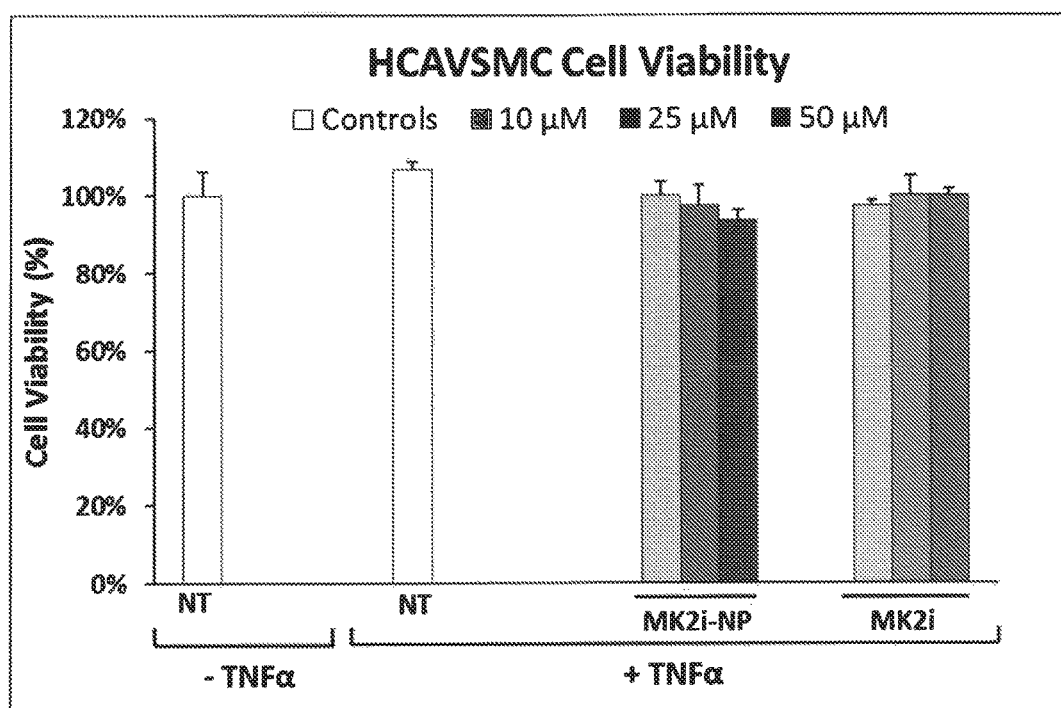
FIG. 51 shows a bar graph representing cell viability in HCAVSMCs stimulated with TNFα for 6 hours, treated for two hours with MMI-0100 (MK2i)-NPs or MMI-0100 (MK2i) peptide alone and cultured for 24 hours in fresh media. n=4.

To elucidate the mechanism by which MK2i-NPs reduced IH in human vein, phosphorylation of hnRNP A0 and CREB was first assessed using Western blot analysis. Downstream of MK2, hnRNP A0 stabilizes the mRNA and increases translation of inflammatory cytokines (S. Rousseau et al., EMBO J 21, 6505-6514 (2002); N. Ronkina et al., Biochem Pharmacol 80, 1915-1920 (2010); E. Hitti et al., Mol Cell Biol 26, 2399-2407 (2006)), and CREB binds to cAMP-responsive elements to promote expression of genes that induce smooth muscle cell migration (S. Jalvy et al., Circulation Research 100, 1292-1299 (2007); H. Ono et al., Arterioscl Throm Vas 24, 1634-1639 (2004)), proliferation (P. Molnar et al., J Cell Commun Signal 8, 29-37 (2014); K. Nakanishi et al., Journal of Vascular Surgery 57, 182-U254 (2013)), and production of the inflammatory cytokines such as IL-6 (G. L. Lee et al., Arterioscl Throm Vas 32, 2751-+ (2012)). MMI-0100 (MK2i)-NPs significantly reduced both hnRNP A0 and CREB phosphorylation in HSV (FIG. 37D, E). In further support of this mechanism, MK2i-NPs also significantly inhibited secretion of the primary hnRNP A0 target TNFα (S. Rousseau et al., EMBO J 21, 6505-6514 (2002)) in vitro in angiotensin-II stimulated HCAVSMCs (FIG. 38A, FIG. 48). In this study, MK2i-NPs achieved TNFα inhibition equivalent to NE-MK2i-NP and MK2i at an order of magnitude lower dose (i.e. 10 μM MMI-0100 (MK2i) produced an effect equivalent to 100 μM MMI-0100 (MK2i)), and 100 μM MK2i-NPs fully abrogated Angiotensin II-stimulated TNFα production. It was also confirmed that MK2i-NPs significantly reduced production of IL-6, a CREB target gene (G. L. Lee et al., Arterioscl Throm Vas 32, 2751-+(2012)), in TNFα-stimulated HCAVSMCs. This study also showed that MK2i-NPs were significantly more bioactive than free MK2i (FIG. 49). None of the in vitro treatments resulted in significant toxicity as assessed by tissue viability at 1 and 14 days post-treatment compared to untreated controls (FIGS. 50 and 51).

It was also confirmed that MK2i-NPs significantly decreased phosphorylation of HSP-27 (FIG. 37D,F), which along with CREB, is believed to promote pathological vascular smooth muscle cell migration characteristic of IH (T. Zarubin et al., Cell Res 15, 11-18 (2005); H. F. Chen et al., Mol Cell Biochem 327, 1-6 (2009); L. B. Lopes et al., J Vasc Surg 52, 1596-1607 (2010)).

Figure 52:
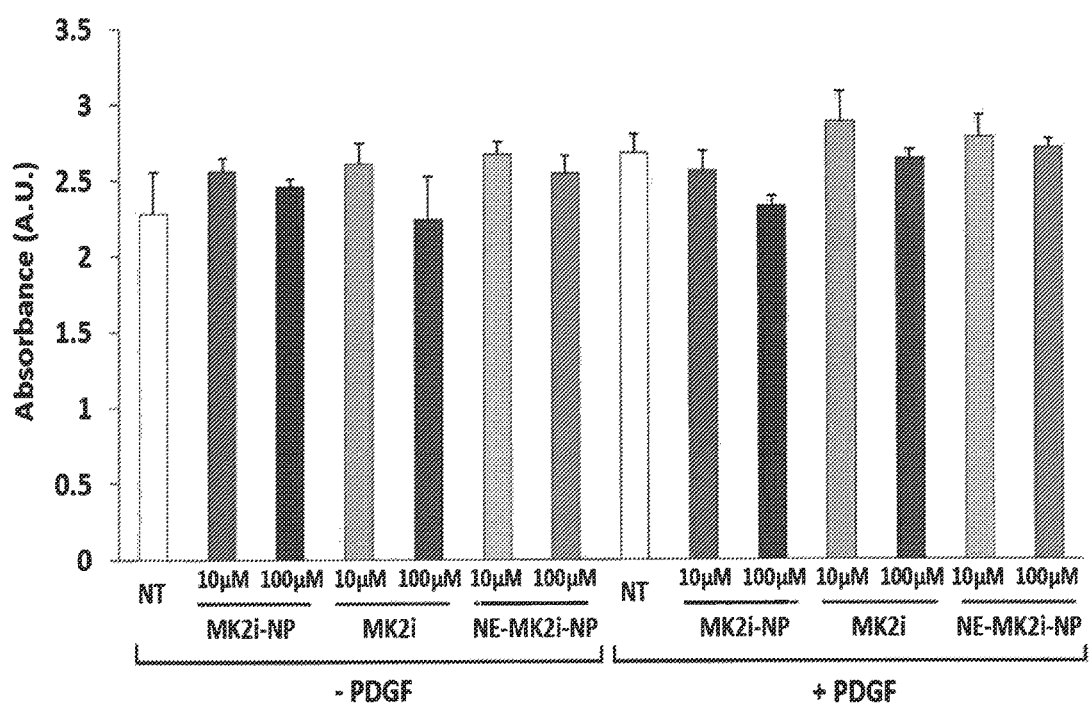
FIG. 52 shows a bar graph representing cell proliferation in HCAVSMCs stimulated treated for 30 minutes with MMI-0100 (MK2i) peptide alone, MK2i-NPs, or NE-MK2i-NPs and cultured for 24 hours in fresh media with (+) or without (−) 50 ng/mL PDGF-BB. NT=no treatment, n=4.
Figure 61:
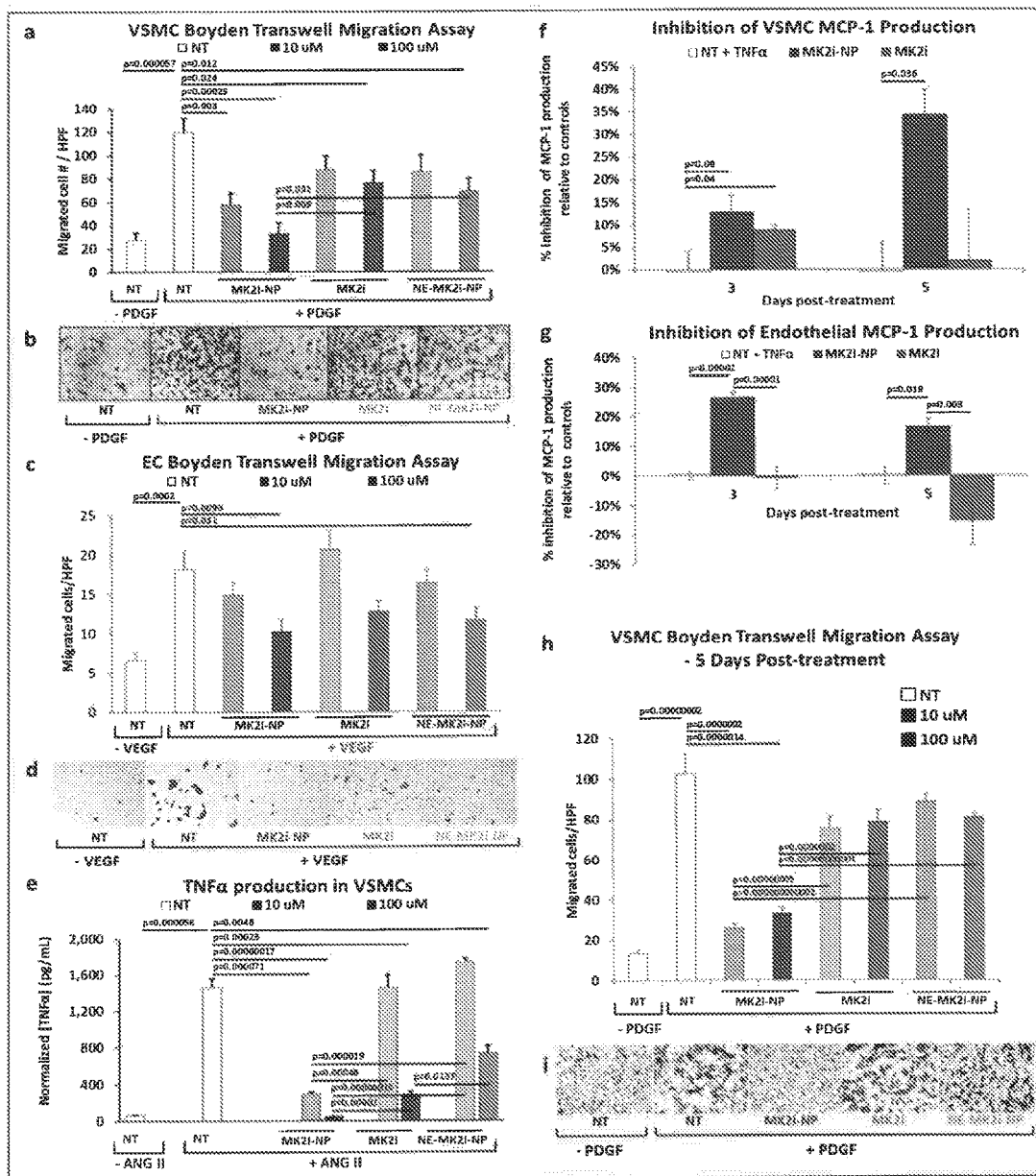
FIG. 61 shows (a) MK2i-NPs inhibited vascular smooth muscle cell migration towards the chemoattractant PDGF-BB in a Boyden Chamber assay 8 hours after seeding onto the membrane. NT=no treatment; (b) MK2i-NPs inhibited endothelial cell migration towards the chemoattractant VEGF in a Boyden Chamber assay 8 hours after seeding onto the membrane; (c) MK2i-NP treatment blocked TNFα production in HCAVSMCs stimulated with ANG II (all data is normalized to cell number); (d) MK2i-NP treatment showed sustained inhibition of TNFα stimulated production of MCP-1 in both vascular smooth muscle and endothelial cells whereas treatment with free MK2i or NE-MK2i-NPs did not; (e) MK2i-NPs showed sustained inhibition of vascular smooth muscle cell migration towards the chemoattractant PDGF-BB 5 days after treatment removal.

The effects of MK2i-NPs on HCAVSMC migration in the presence of the chemokine PDGF-BB were also investigated in vitro using both scratch wound chemokinetic and Boyden chamber chemotactic migration assays (FIG. 38B,-D). MK2i-NPs significantly inhibited cell migration and did so at an order of magnitude lower dose than free MMI-0100 (MK2i) peptide. MK2i-NPs did not significantly affect HCAVSMC proliferation, confirming that these results were not attributable to treatment effects on cell growth (FIG. 52). Additionally, MK2i-NPs potently inhibited both vascular smooth muscle (VSMC) and endothelial cell (EC) migration (FIG. 61a-d), and MK2i-NPs were significantly more potent at inhibiting VSMC migration compared to the free MK2i peptide (FIG. 61a). These results correlated with the MK2i-NP inhibition of CREB and HSP27 phosphorylation detected in human vascular tissue.

An ex vivo organ culture model of IH in HSV also revealed that MK2i-NPs significantly inhibited neointima formation in a dose-dependent fashion and at an order of magnitude lower peptide dose than free MK2i (FIGS. 37b and c; FIGS. 48-51).

These studies also validated the broad anti-inflammatory and anti-migratory mechanism of action of MMI-0100 (MK2i)-NPs (FIG. 38) and confirmed the utility of targeting the p38-MK2 pathway to inhibit multiple factors underlying IH pathogenesis. MK2i-NPs were shown to modulate pro-inflammatory mediators activated downstream of MK2 such as hnRNP A0 and CREB. MMI-0100 (MK2i)-NP decreased hnRNP A0 phosphorylation in human tissue, which correlated to a decrease in angiotensin-II stimulated production of the pro-inflammatory cytokines TNF-α and IL-6 in vitro. MK2i-NPs were also shown to modulate migration-related pathways in human tissue, as demonstrated by reduced phosphorylation of HSP27, which triggers VSMC transition to a migratory and fibrotic myofibroblast phenotype and causes vein graft vasoconstriction. The effects of HSP27 are mediated through regulation of cytoskeleton dynamics, which impacts migration towards pathologically relevant stimuli such as angiotensin II and PDGF. Additionally, MK2i-NPs decreased phosphorylation of the CREB transcription factor, which is also known to contribute to VSMC migration and lead to the pathological VSMC phenotype characteristic of IH (See, e.g., H. F. Chen et al., Mole Cell Biochem 327, I-6 (2009); K. Nakanishi et al., Journal of Vascular Surgery 57, 182-U254 (2013); G. L. Lee et al., Arterioscl Throm Vas 32, 2751-+(2012); L. C. Fuchs et al., Am J Physiol-Reg I 279, R492-R498 (2000)). Inhibition of activation of HSP27 and CREB correlated to reduced VSMC migration towards PDGF in vitro.

Because the intracellular half-life of MK2i was significantly higher when delivered via MK2i-NPs, in vitro bioactivity assays were also carried out at 3 and 5 days post-treatment to assess the impact of the NP formulation on longevity of peptide therapeutic action. In accord with our intracellular half-life calculations, the ability of the free MK2i peptide to inhibit the production of monocyte chemoattractant protein-1 (MCP-1, which is upregulated both through hnRNP A0 and by TNFα(Rousseau S, Morrice N, Peggie M, Campbell D G, Gaestel M, Cohen P. Inhibition of sapk2a/p38 prevents hnrnp a0 phosphorylation by mapkap-k2 and its interaction with cytokine mrnas. EMBO J. 2002; 21:6505-6514; Mueller L, von Seggern L, Schumacher J, Goumas F, Wilms C, Braun F, Broering DC. Tnf-alpha similarly induces il-6 and mcp-1 in fibroblasts from colorectal liver metastases and normal liver fibroblasts. Biochem Biophys Res Commun. 2010; 397:586-591) and implicated in vein graft intinmal hyperplasia (IH) (Stark V K, Hoch J R, Warner T F, Hullett D A. Monocyte chemotactic protein-1 expression is associated with the development of vein graft intimal hyperplasia. Arterioscl Throm Vas. 1997; 17:1614-1621), was significantly decreased at 3 and 5 days post-treatment in both vascular smooth muscle cells (VSMC) and endothelial cells (EC) (FIG. 61*f-g*). In contrast, MK2i-NPs demonstrated sustained inhibitory bioactivity at 5 days post-treatment in both cell types. Moreover, MK2i-NPs demonstrated significant inhibition of VSMC migration 5 days post-treatment whereas free MK2i or NE-MK2i-NPs showed minimal effect (FIG. 61*h-i*). The decrease in anti-inflammatory and anti-migratory activity between days 3 and 5 corresponded with the calculated intracellular half-life of the free MK2i peptide.

These results establish the relationship between MK2 and the downstream pro-inflammatory and pro-migratory factors hnRNP A0, CREB, and HSP27 in intact, human vascular tissue. The collective anti-inflammatory and anti-migratory actions of MK2i-NPs emphasize the utility of this therapy against a multifactorial process, for example, like IH, which involves a complex interplay of cell proliferation, migration, inflammation, and matrix synthesis. Because this translationally-relevant MK2i-NP formulation (formed by simple mixing; no complex syntheses, conjugations, or purifications required) comprehensively targets multiple factors involved in IH, it has potential to overcome the shortfalls of prior therapeutic candidates with more narrow mechanisms of action.

In Vivo Bioactivity in a Rabbit Vein Graft Interposition Model

Figure 62:
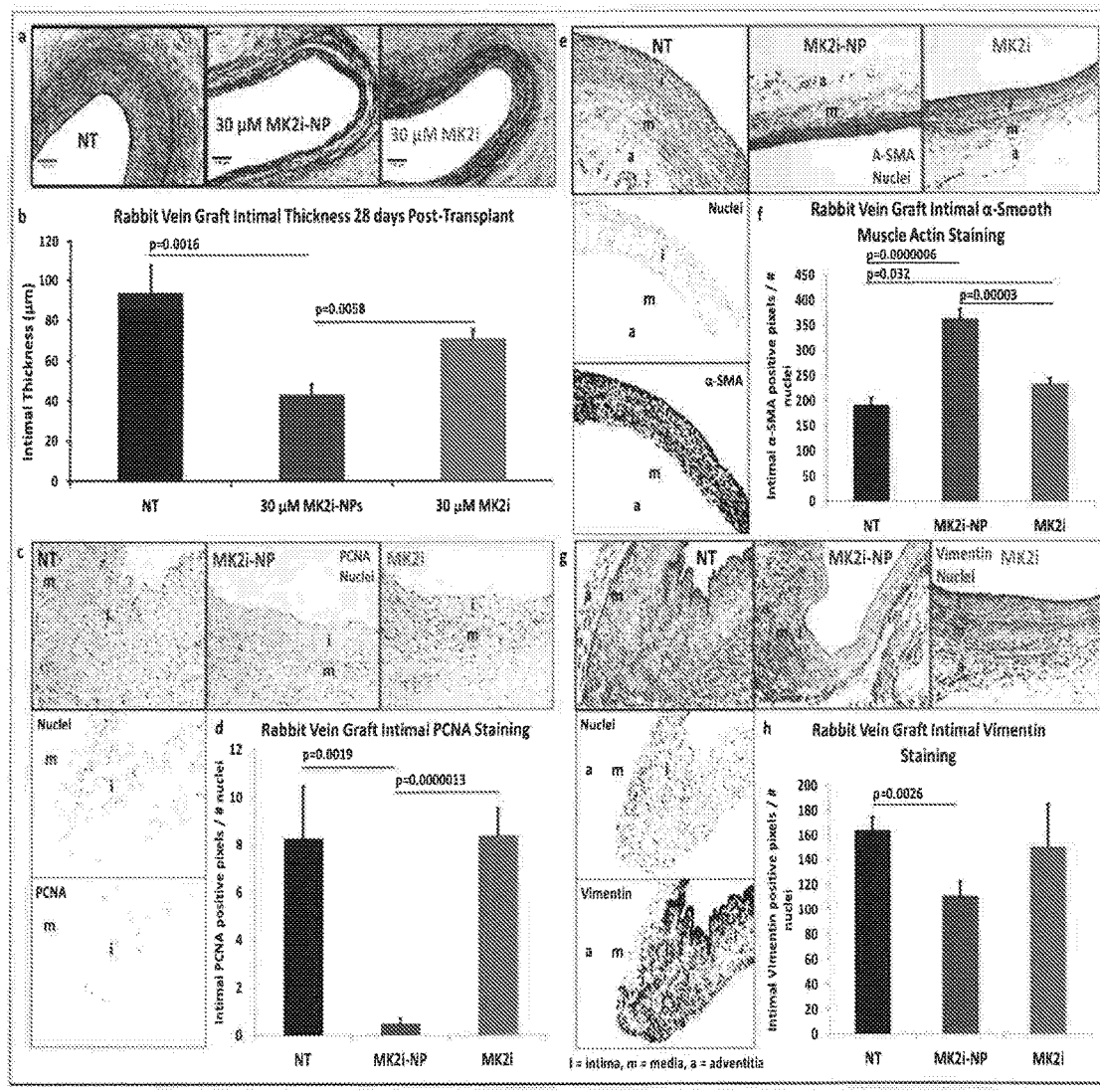
FIG. 62 shows (a) MK2i-NP treatment reduced neointima formation as shown in representative images of Verhoeff Van Gieson stained histological sections of vein grafts; (b) quantification of intimal thickness in perfusion fixed jugular vein interposition grafts 28 days post-op. n≥7 grafts per treatment group; (c) MK2i-NP treatment reduced proliferation of intimal cells as shown using ki67 immunohistochemistry on vein grafts; (d) quantification of ki67 positive nuclear staining in jugular vein graft sections normalized to intimal nuclei number; (e) MK2i-NP treatment maintained higher intimal expression of the contractile marker α-smooth muscle actin; (f) quantification of intimal α-smooth muscle actin positive staining in jugular vein graft sections normalized to intimal nuclei number; (g) MK2i-NP treatment reduced intimal expression of the synthetic vascular smooth muscle phenotypic marker vimentin; (h) quantification of intimal vimentin positive staining in jugular vein graft sections normalized to intimal nuclei number.

The therapeutic benefit of MMI-0100 (MK2i)-NPs in vivo was assessed in a rabbit bilateral jugular vein graft interpositional transplant model that employs a polymeric cuff method to induce turbulent blood flow and accelerate graft IH. In this model, jugular vein grafts were treated or given vehicle control for 30 minutes ex vivo, which is representative of the amount of time that grafts are explanted during human revascularization procedures. Grafts were harvested 28 days post-operatively, and VVG stained histological sections were used for intimal thickness quantification (FIG. 39A and FIG. 62*a*). Treatment with 30 µM MMI-0100 (MK2i)-NPs significantly inhibited neointima formation compared to both untreated controls and the free MMI-0100 (MK2i) peptide, which did not produce any significant change in neointima formation relative to vehicle controls at the 30 µM dose tested (FIG. 39B and FIG. 62*b*).

To assess in vivo cell-based mechanisms underlying MK2i-NP mediated inhibition of neointimal thickening, proliferating cell nuclear antigen (PCNA), α-smooth muscle actin (α-SMA), and vimentin stained histological sections were used to analyze cellular proliferation and vascular smooth muscle cell phenotype. Intimal PCNA staining was significantly decreased by ~17-fold in grafts treated with MK2i-NPs, whereas treatment with the free MK2i were similar to untreated grafts (FIG. 62*c-d*). MK2i-NP treated grafts also demonstrated increased staining intensity for α-SMA, which is a marker for contractile SMC phenotype (Rensen SSM, Doevendans PAFM, van Eys GJJM. Regulation and characteristics of vascular smooth muscle cell phenotypic diversity. Neth Heart J. 2007; 15:100-108), relative to untreated grafts or grafts treated with free MK2i (FIG. 62*f*). Images of α-SMA immunostained sections revealed that untreated and free MK2i treatment groups showed sparse intimal staining (FIG. 62*e*), indicating loss of the contractile VSMC phenotype and/or excess production of extracellular matrix proteins, both of which are implicated in vein graft IH. In agreement with increased contractile marker expression, intimal expression of the synthetic VSMC marker vimentin was also decreased in MK2i-NP treated grafts but not in grafts treated with free MK2i peptide (FIG. 62*g-h*).

Figure 39:
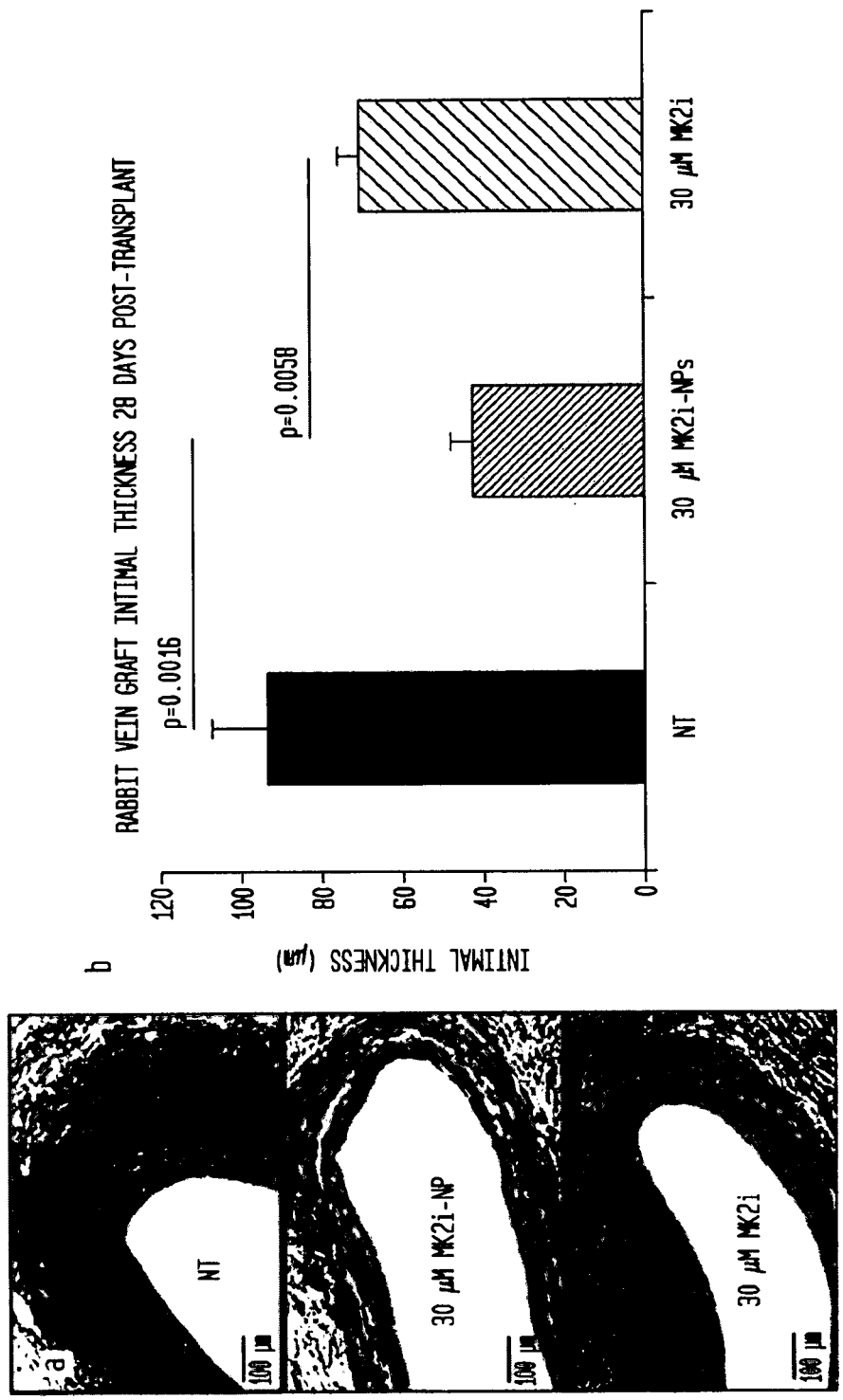
FIG. 39 shows intraoperative treatment with MMI-0100 (MK2i)-NPs reduces neointima formation and macrophage persistence in vivo in transplanted vein grafts. a) MK2i-NP treatment reduced neointima formation as shown in representative images of Verhoeff Van Gieson stained histological sections of vein grafts. b) Quantification of intimal thickness in perfusion fixed jugular vein interposition grafts 28 days post-op. n≥7 grafts per treatment group. c) MK2i-NP treatment also reduced persistence of macrophages in the neointima as shown using RAM-11 immunohistochemsitry on vein grafts. Arrows demarcate positively stained cells. Left column scale bar=100 μm, right column zoomed view scale bar=50 μm. d) Quantification of RAM-11 positive macrophage staining in jugular vein graft sections, n=16 histological images from 4 vein segments per treatment group.
Figure 39:
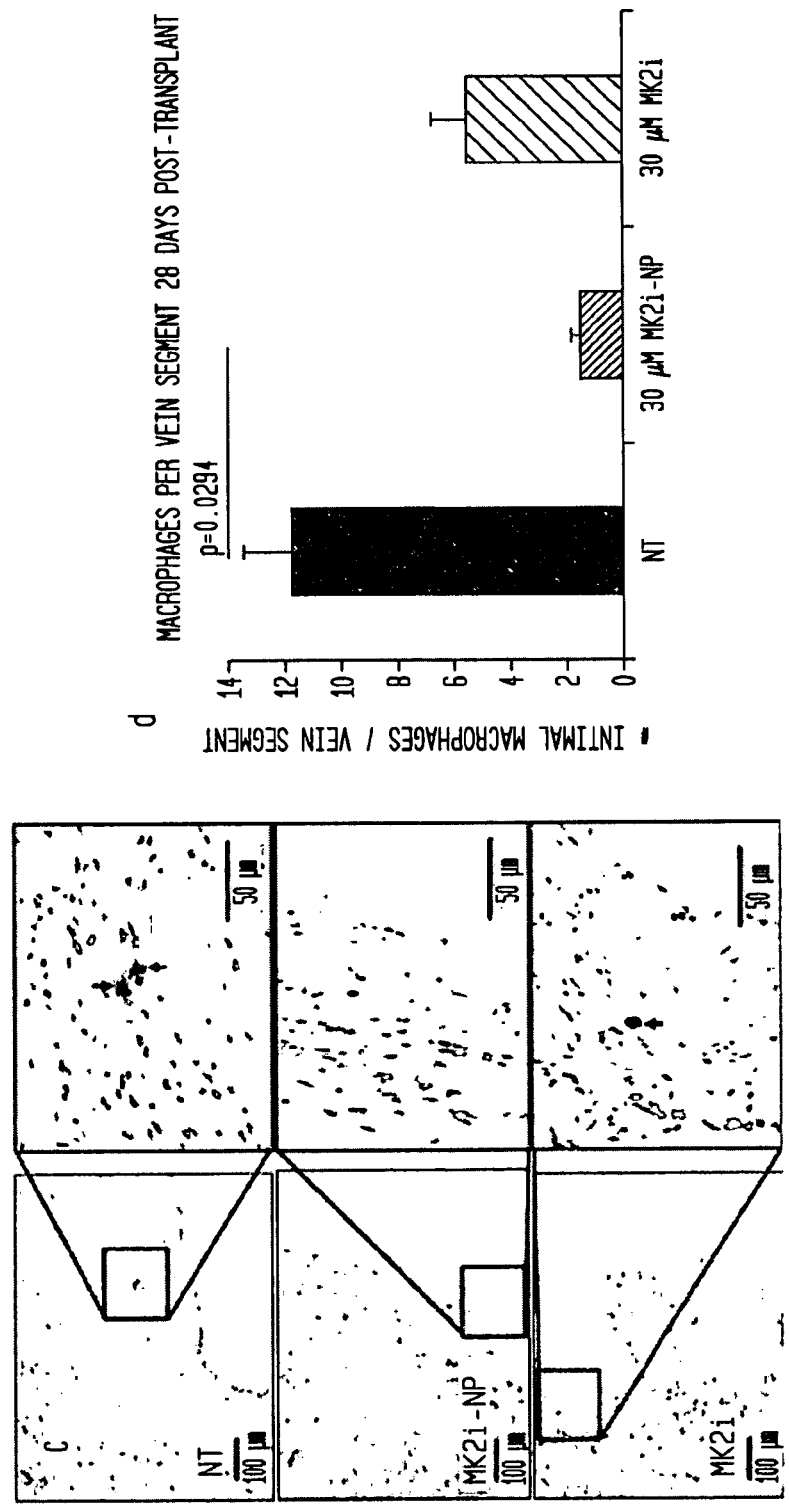
Figure 40:
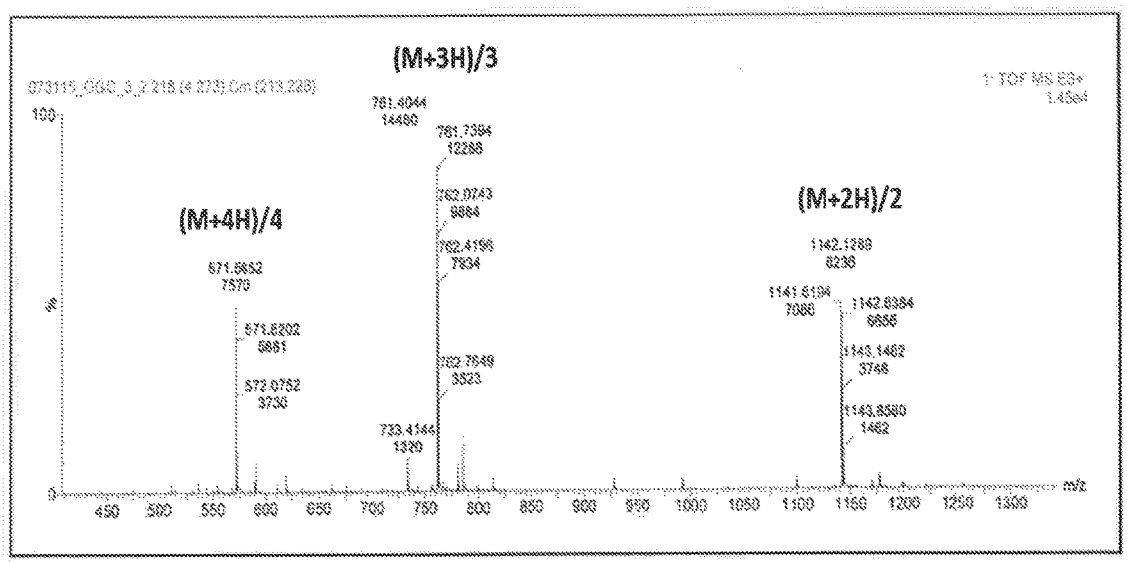
FIG. 40 shows electrospray-ionization mass spectrometry (ESI-MS) mass spectrum for the HPLC-purified CPP-MMI-0100 (MK2i) fusion peptide (YARAAARQARAKALAR-QLGVAA (SEQ ID NO: 1), MW=2283.67 g/mol). The mass spectrum shows three major peaks each corresponding to the fragmentation of the full peptide sequence.
Figure 41:
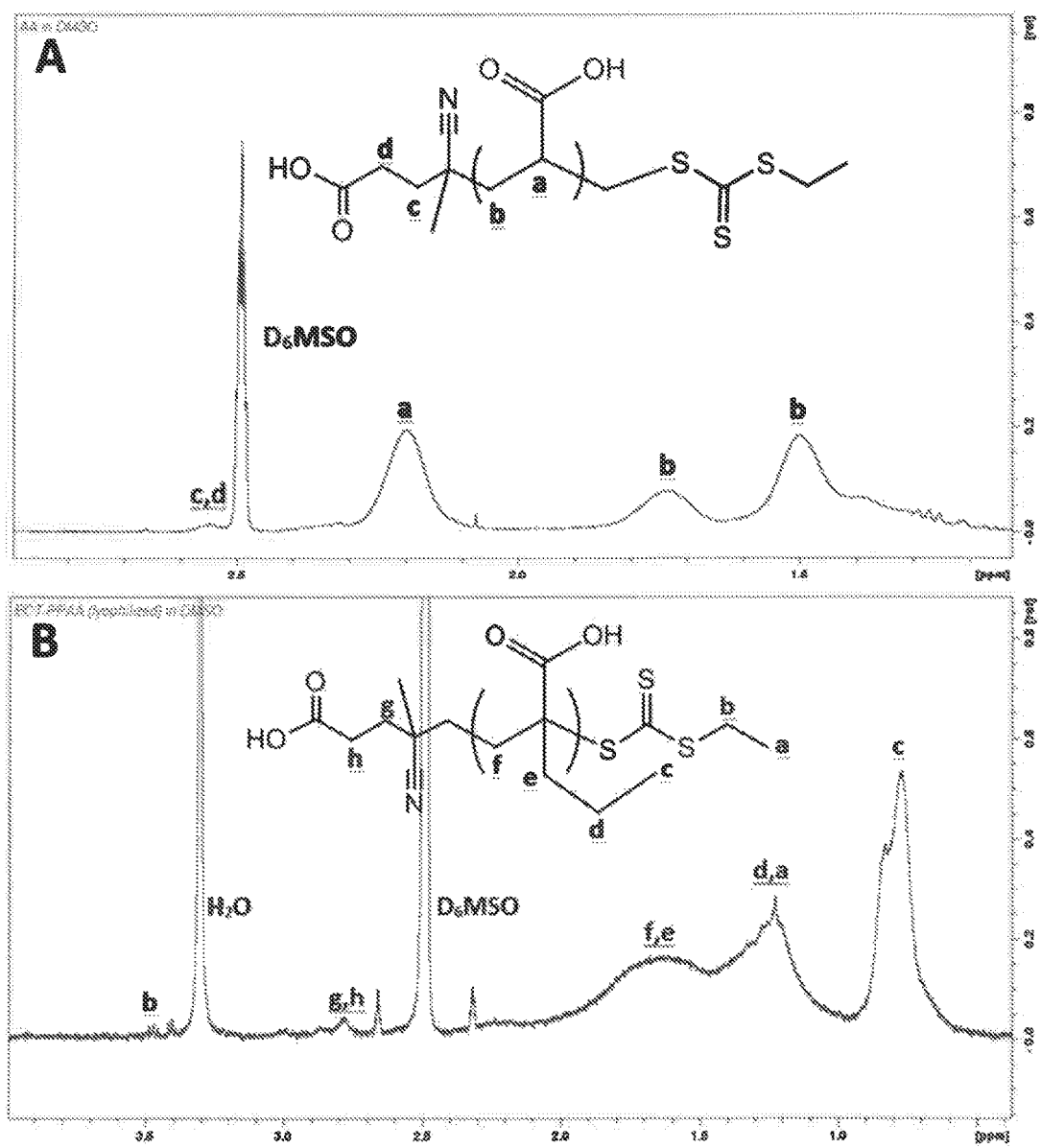
FIG. 41 shows $^1$H NMR spectrum of A) poly(acrylic acid) (PAA) and B) poly(propylacrylic acid) (PPAA) homopolymer in D$_6$MSO. Molecular weight was determined by comparing the area of peaks associated with the chain transfer agent (i.e. peaks c,d for PAA and peak b for PPAA) to peaks associated acrylic acid/propylacrylic acid (i.e. peak a for PAA and peak c for PPAA): PAA degree of polymerization=106, PPAA degree of polymerization=190.
Figure 42:
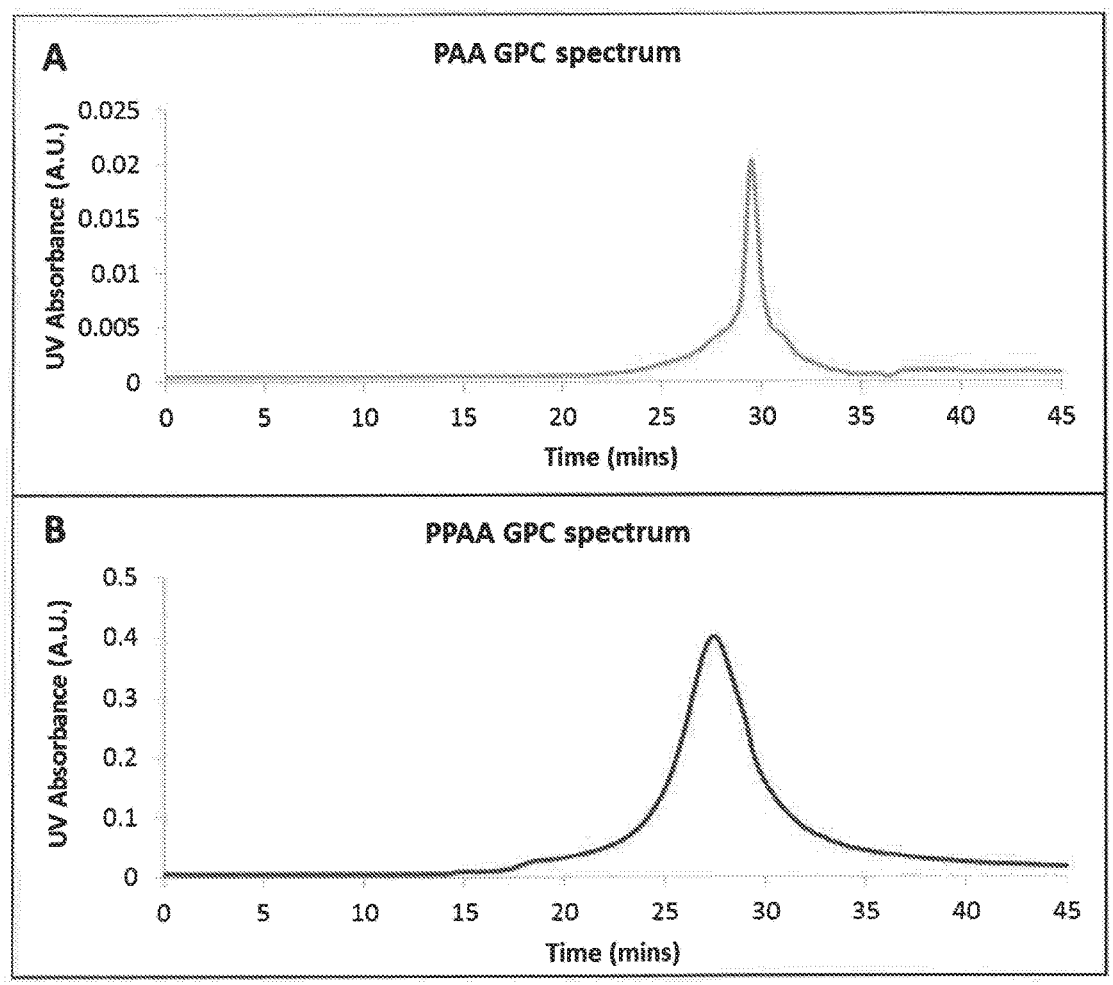
FIG. 42 shows gel permeation chromatography (GPC) chromatograms of A) poly(acrylic acid) (PAA): degree of polymerization=150, PDI=1.27, dη/dC=0.09 (mL/g) and B) poly(propylacrylic acid) (PPAA): degree of polymerization=193, PDI=1.471, dη/dC=0.087 (mL/g) polymers in DMF. The trace shows UV absorbance at the characteristic absorption peak of the trithiocarbonate moiety (310 nm) present in the 4-cyano-4-(ethylsulfanylthiocarbonyl) sulfanylvpentanoic acid (ECT) chain transfer agent utilized in the polymerization.
Figure 43:
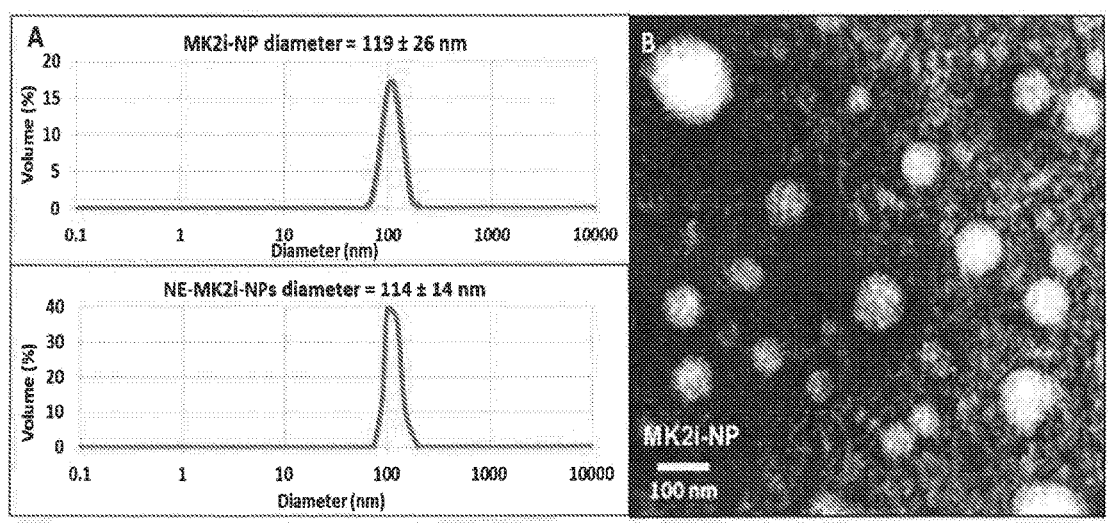
FIG. 43 shows A) Dynamic light scattering analysis and B) representative TEM images of uranyl acetate counterstained MMI-0100 (MK2i)-NPs. Scale bar=100 nm.
Figure 53:
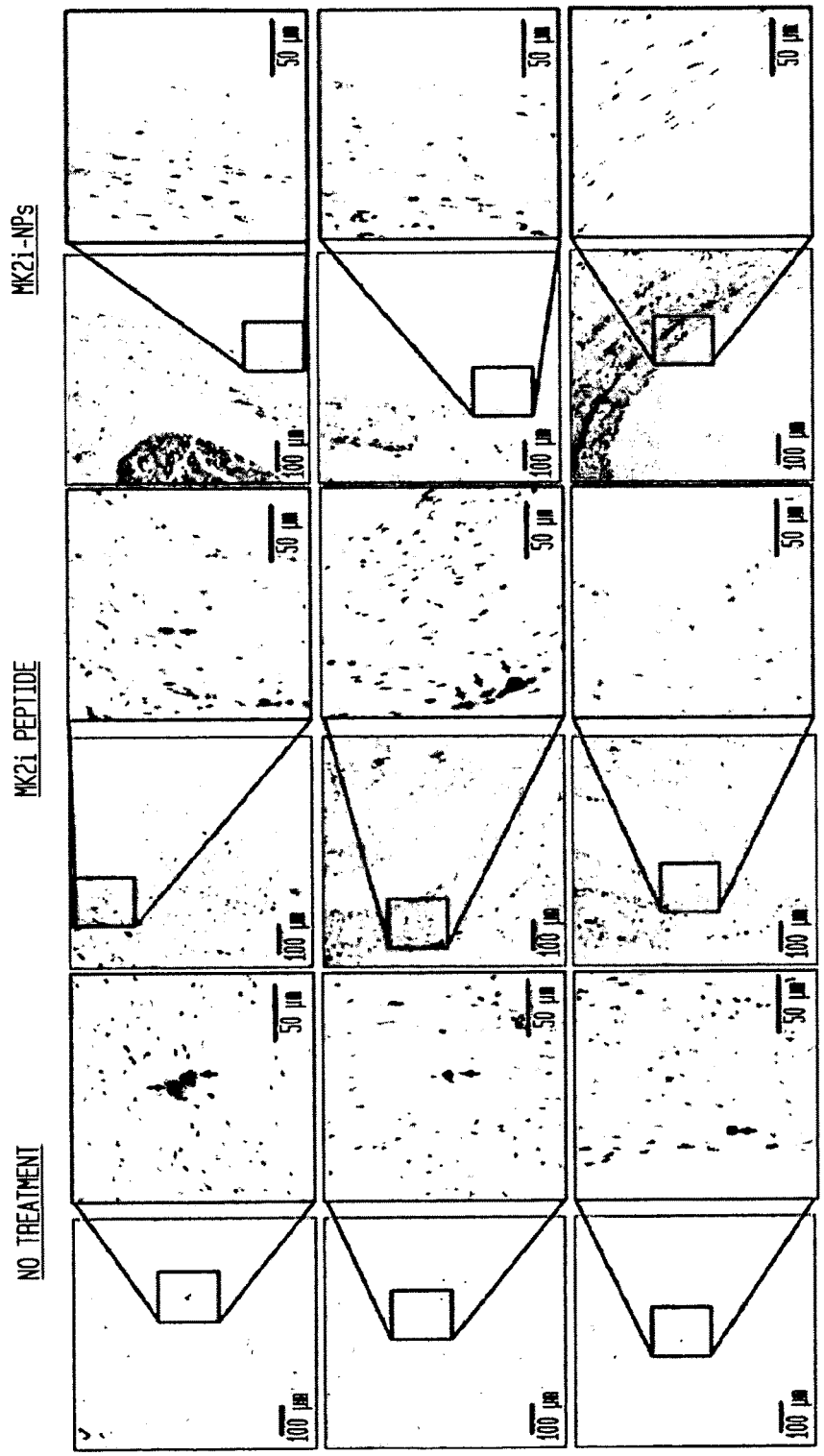
FIG. 53 shows representative RAM-11 staining images of rabbit jugular vein graft explants for each treatment group. Arrows demarcate positively stained cells. Left column scale bar=100 μm, right column zoomed view scale bar=50 μm.
Figure 63:
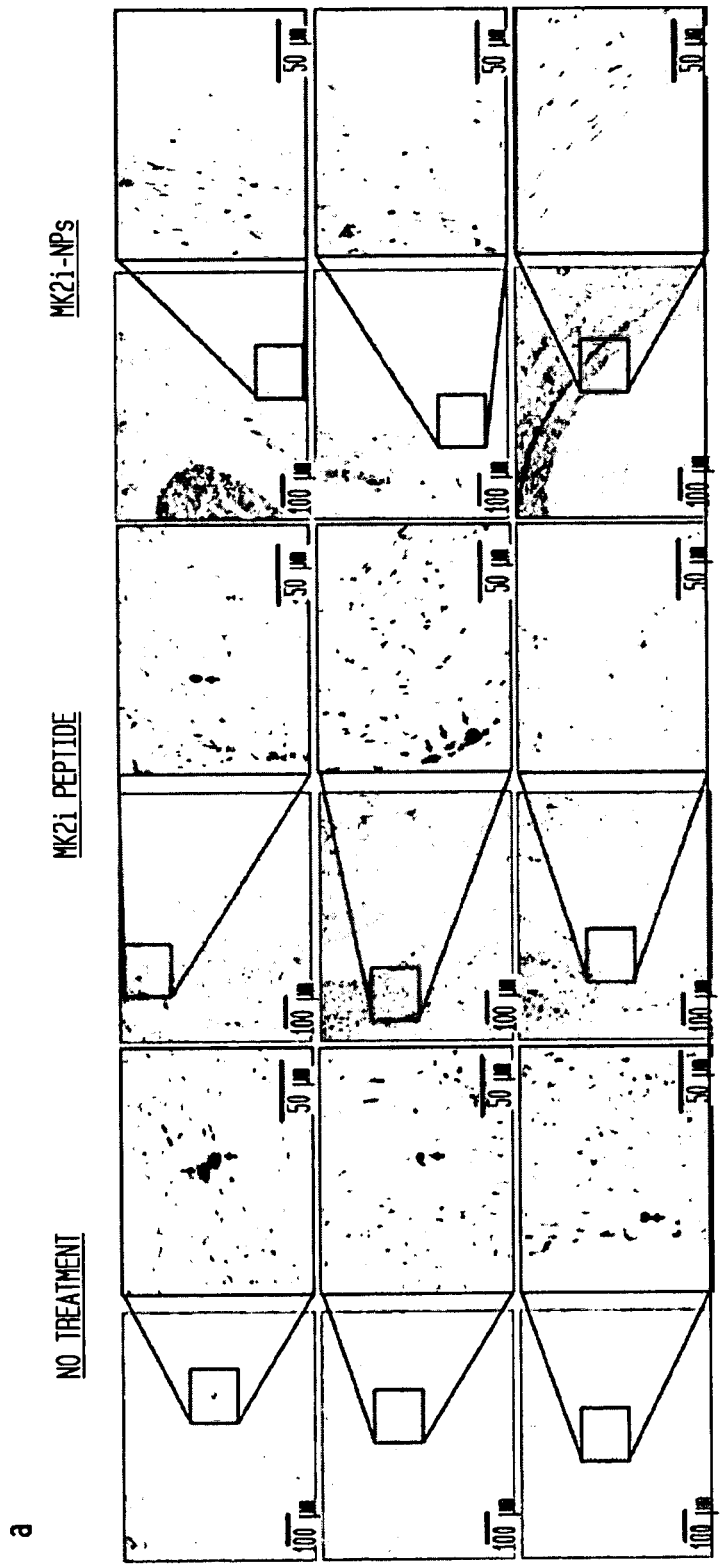
FIG. 63 shows (a) representative RAM-11 staining images of rabbit jugular vein graft explants for each treatment group. Arrows demarcate positively stained cells. Left column scale bar=100 µm, right column zoomed view scale bar=50 µm; (b) example images from the color deconvolution method utilized to quantify positive RAM-11 staining in the intima of rabbit jugular vein explants; (c) quantification of intimal RAM-11 positive macrophage staining in jugular vein graft sections, n=16 histological images from 4 vein segments per treatment group.
Figure 63:
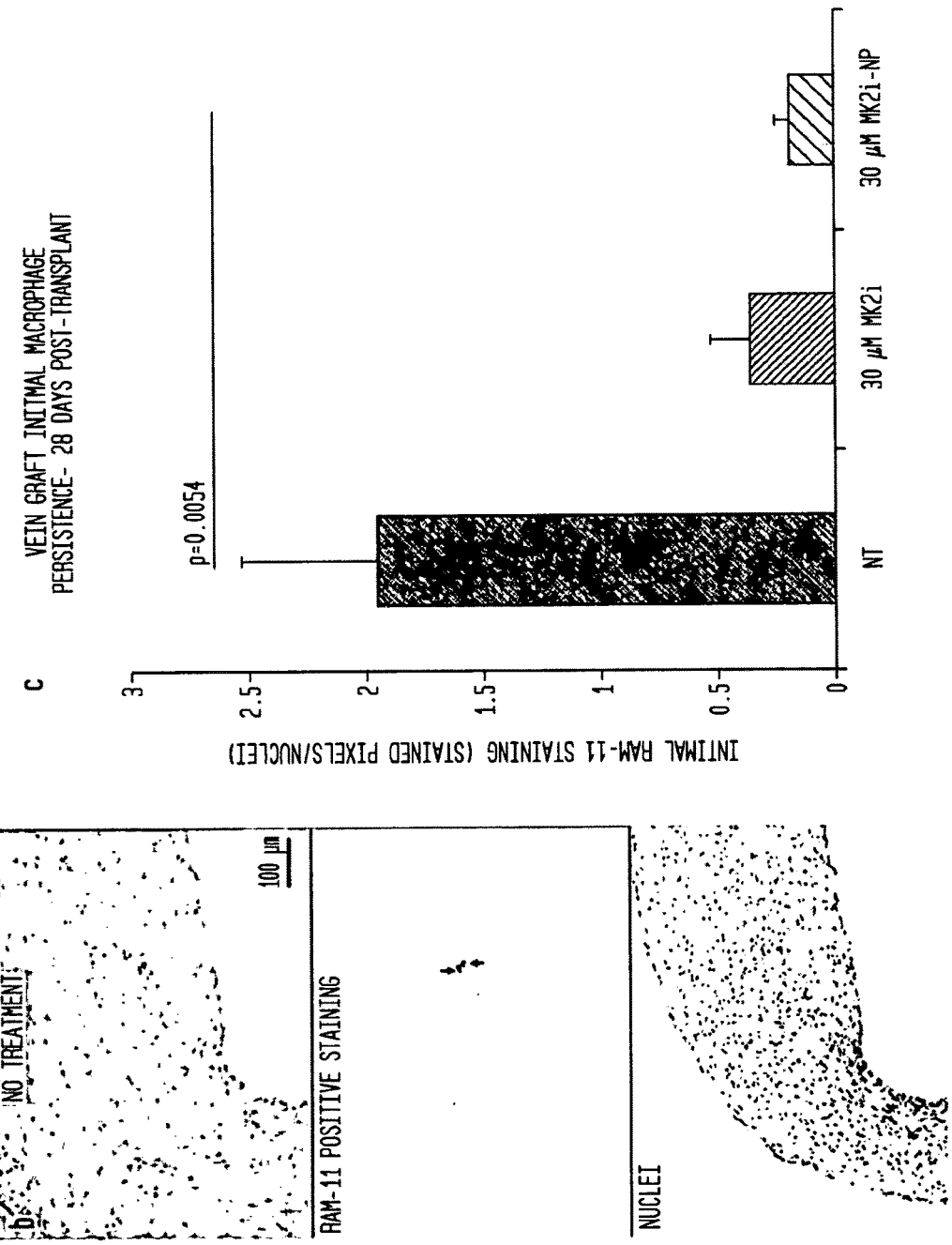

The number of residual inflammatory cells present in the intima of the vein grafts 28-day post-transplant was assessed in tissue sections using a rabbit macrophage specific antibody, RAM-11 (FIG. 39C, FIG. 53 and FIG. 63). Significantly less intimal macrophages were detected in MK2i-NP treated grafts, suggesting that MK2i-NPs blunted local macrophage recruitment and/or persistence (FIG. 39D). This mechanism is potentially mediated through decreased secretion of macrophage inflammatory protein 2 (MIP-2, also known as CXCL2) and/or monocyte chemoattractant protein-1 (MCP-1) (A. Muto et al., Vascul Pharmacol 56, 47-55 (2012)), both of which attract inflammatory cells and are upregulated either directly or indirectly through hnRNP A0 (S. Rousseau et al., EMBO J 21, 6505-6514 (2002); L. Mueller et al., Biochem Biophys Res Commun 397, 586-591 (2010); R. N. Mitchell et al., Circ Res 100, 967-978 (2007)). Our in vitro study results showing that MK2i-NPs inhibited MCP-1 production in both smooth muscle and endothelial cells support this mechanism. Though the inflammatory response was predominately resolved in all samples at 28-days, macrophage persistence in untreated samples agrees with previous observations that MCP-1 can be elevated even at 8 weeks after vein grafting, resulting in local recruitment of monocytes and pathogenesis of IH (V. K. Stark et al., Arterioscl Throm Vas 17, 1614-1621 (1997)). Treatment with 100 µM MK2i-NPs completely abrogated neointimal growth over 2 weeks in the rabbit transplant model. Intraoperative treatment with 30 µM MK2i-NPs significantly reduced the number of macrophages and the degree of IH in the grafts at 4 weeks post-transplant (FIG. 39).

Figure 64:
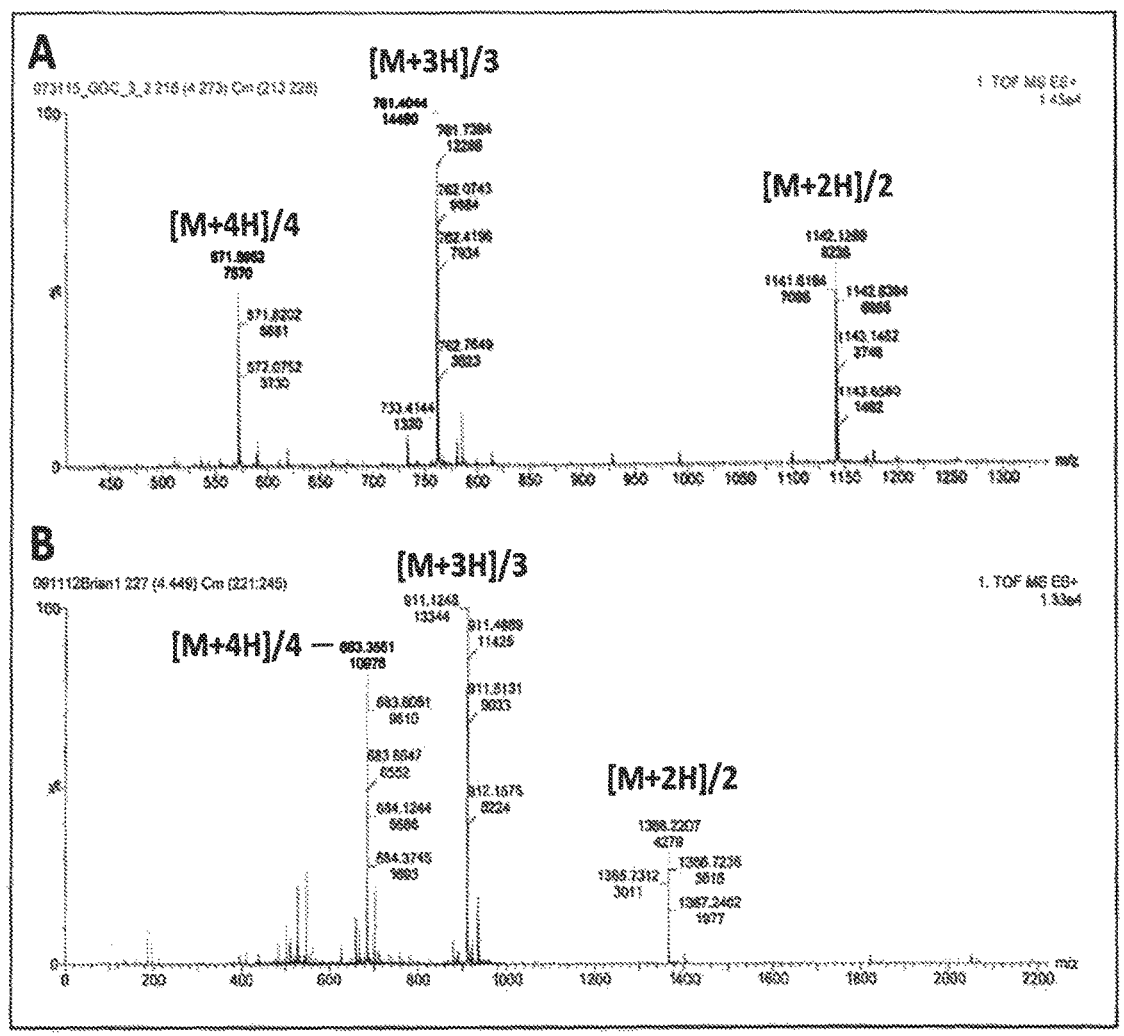
FIG. 64 shows electrospray-ionization mass spectrometry (ESI-MS) mass spectra for the HPLC-purified (A) MK2i peptide (sequence: YARAAARQARA-KALARQLGVAA, MW=2283.7 g/mol) and (B) p-HSP20 peptide (sequence: YARAAARQARA-WLRRAsAPLPGLK, MW=2731 g/mol). The mass spectra show three major peaks each corresponding to the fragmentation of the full peptide sequence.

Example 4. Synthesis, Characterization and Optimization of MK2i-NPs and p-Hsp20-NPs The MK2i peptide with the sequence YARAAARQARA-KALARQLGVAA (SEQ ID NO: 1) and the p-HSP20 peptide with the sequence YARAAARQARA-WLRRAsAP-LPGLK (SEQ ID NO: 27) were synthesized via solid phase synthesis, and purity was verified through electrospray-ionization mass spectrometry (FIG. 64). Reversible addition fragmentation chain transfer (RAFT) polymerization was utilized to synthesize poly(propylacrylic acid) (PPAA) [DP=193 (GPC), DP=190 (H¹ NMR), PDI=1.47 (GPC)]. NPs were formed by simple mixing of the PPAA homopolymer with the MK2i or p-HSP20 peptides in PBS at pH 8.0, which is between the pKa values of the primary amines present on the peptides (pKa~9-12 depending on the amino acid residue) and the carboxylic acid moieties in the PPAA polymer (pKa~6.7); this ensures optimal solubility and net charge on both molecules to facilitate electrostatic complexation.

Figure 65:
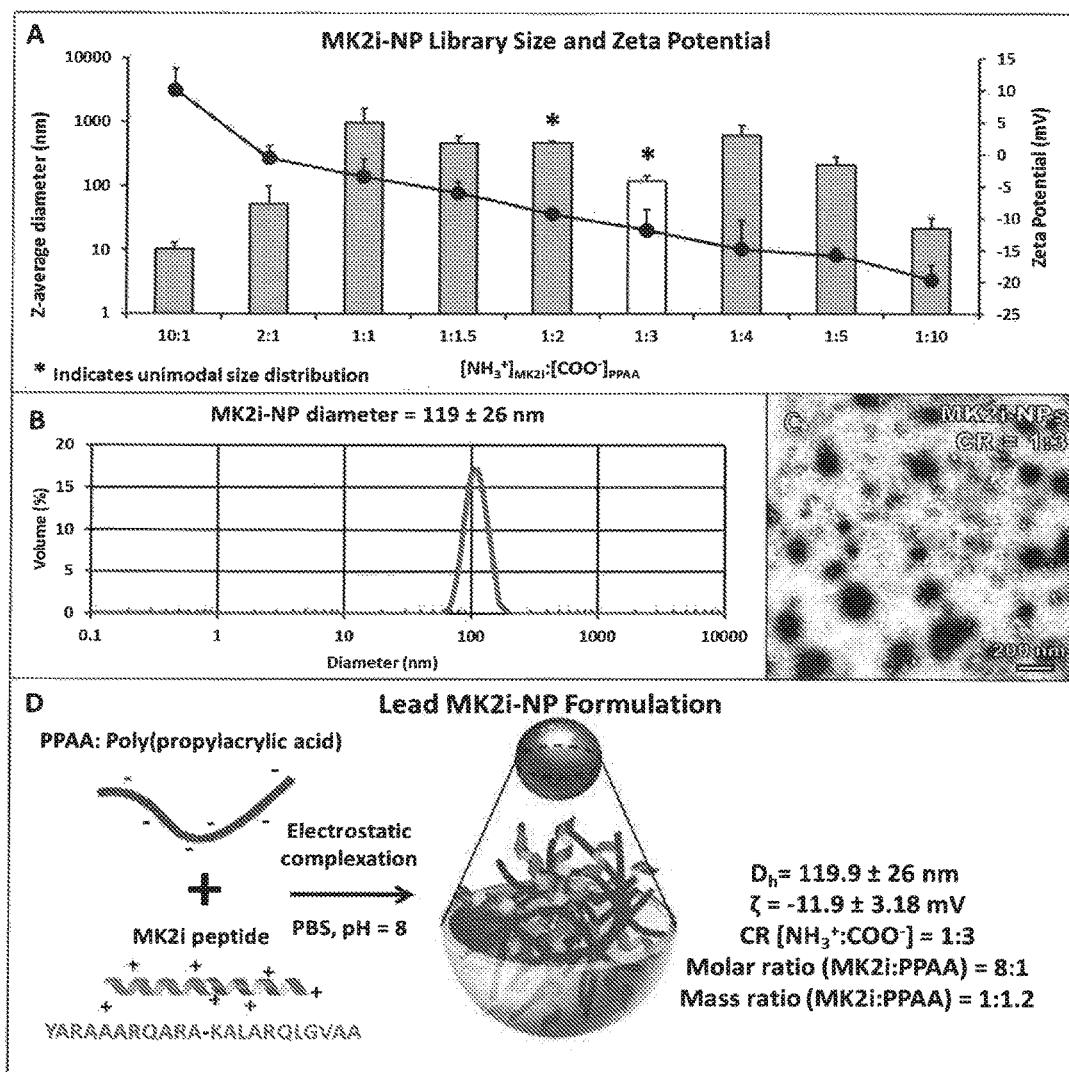
FIG. 65 shows (A) Z-average diameter (bars) and zeta potential (circles) of MK2i-NPs prepared at a different charge ratios (CR=[$NH_3^+$]$_{MK2i}$:[$COO^-$]$_{PPAA}$). Asterisks (*) denote a unimodal size distribution and the white bar represents the MK2i-NP formulation that yielded a unimodal size distribution with minimal size and polydispersity; (B) representative DLS trace of lead MK2i-NP formulation (CR=1:3); (C) representative TEM image of uranyl acetate stained MK2i-NPs, scale bar=200 nm; (D) synthesis and characterization summary for lead MK2i-NP formulation. CR=charge ratio, $D_h$=hydrodynamic diameter, ζ=zeta potential.
Figure 66:
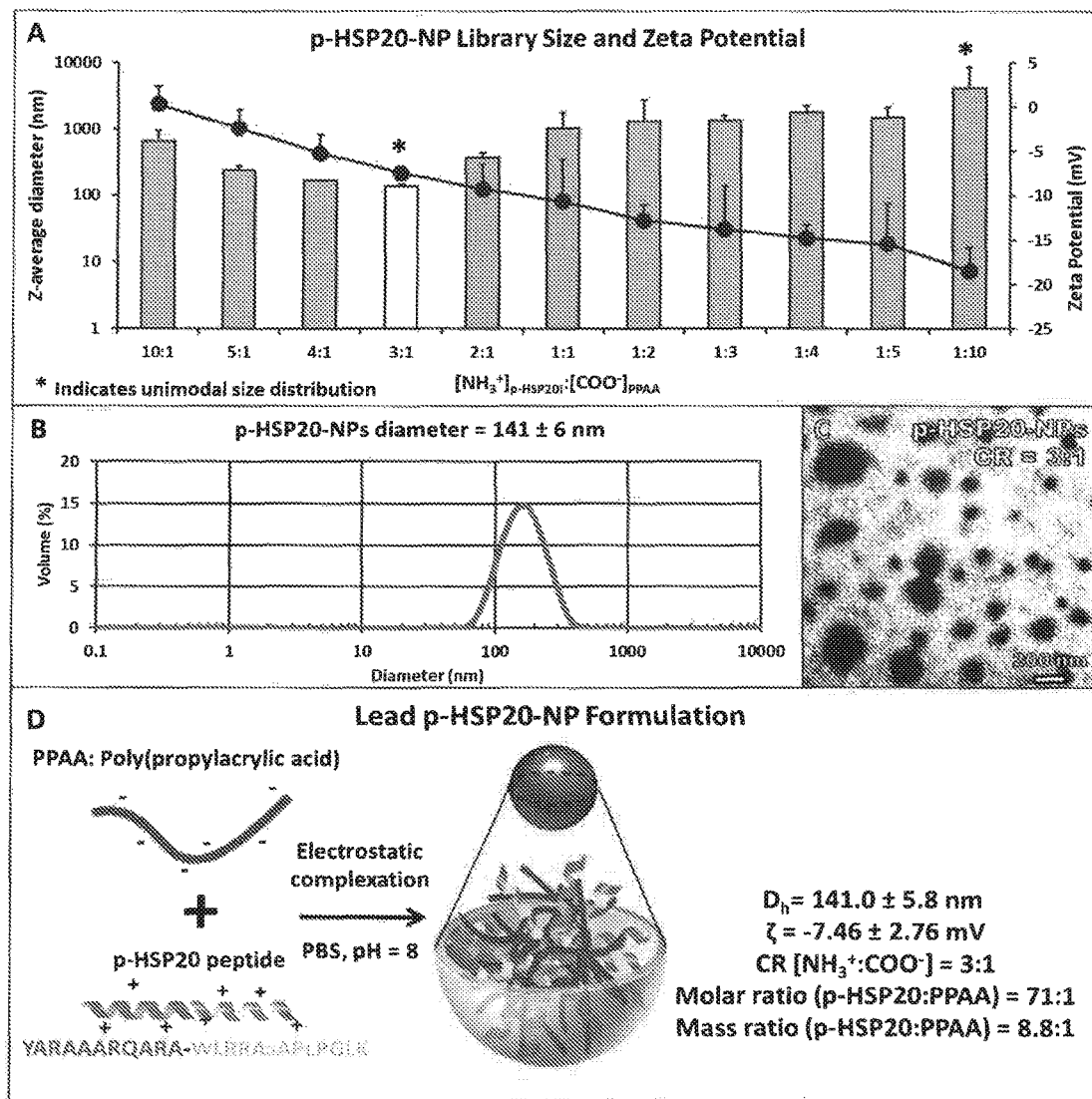
FIG. 66 shows A) Z-average diameter (bars) and zeta potential (circles) of p-HSP20-NPs prepared at a different charge ratios (CR=[$NH_3$]$_{p\text{-}HSP20}$:[$COO^-$]$_{PPAA}$). Asterisks (*) denote a unimodal size distribution, and the white bar represents the p-HSP20-NP formulation that yielded a unimodal size distribution with minimal size and polydispersity; (B) Representative DLS trace of lead p-HSP20-NP formulation (CR=3:1); (C) Representative TEM image of uranyl acetate stained p-HSP20-NPs, scale bar=200 nm (D) Synthesis and characterization summary for lead p-HSP20-NP formulation. CR=charge ratio, $D_h$=hydrodynamic diameter, $\zeta$=zeta potential.

To assess the impact of nanoparticle formulation conditions, a series of MK2i-NPs and p-HSP20-NPs were prepared at a range of charge ratios [i.e. $CR=([NH_3^+]_{MK2i/p-HSP20}:[COO^-]_{PPAA})$], and the size distribution and particle surface charge were characterized through dynamic light scattering (DLS) and ζ-potential analysis, respectively. As expected, MK2i-NP and p-HSP20 ζ-NP ζ-potential was directly proportional to the CR (FIGS. 65A, 66A). The CR also significantly affected NP size, with a narrow range of CRs yielding a unimodal size distribution (i.e. CR=1:2 and 1:3 for MK2i-NPs (Table 24) and CR=3:1 for p-HSP20-NPs, (Table 25). A CR of 1:3 was utilized in subsequent studies for the MK2i-NP formulation, and a CR of 3:1 was utilized for the p-HSP20-NP formulation; these charge ratios consistently yielded a unimodal size distribution with minimal particle size and polydispersity (MK2i-NP $d_h$=119±28 nm, ζ=−11.9±3.2 mV, FIG. 65B; p-HSP20-NP $d_h$=141±6 nm, ζ=−7.5±2.8 mV, FIG. 66B). This difference in the charge ratio that produced unimodal particles between the two peptides may be attributable to differences in peptide size, charge distribution, sequence hydrophobicity, or secondary structures, and future analysis of a broader library of peptides will be required to better understand the structure-function relationships of these formulations. Interestingly, both optimal NP formulations demonstrated a negative ζ-potential, indicating that the cationic peptides are sequestered in the core of the nanopolyplexes and the anionic PPAA polymer is more preferentially localized to the particle surface. The leading MK2i-NP and p-HSP20-NP formulations were also characterized through TEM imaging (FIGS. 65C, 66C), which confirmed the presence of nano-structures with size distributions in accordance with DLS results. For subsequent in vitro and ex vivo studies, these lead NP formulations (FIGS. 65D, 66D) were compared to the corresponding free peptide.

TABLE 24

Size summary of MK2i-NPs prepared at different charge ratios ([NH$_3^+$]/[COO$^-$]) as determined by DLS analysis

| NH$_3^+$:COO$^-$ | Z-ave diameter (nm) | PDI |
| --- | --- | --- |
| 10:1 | 10.32 ± 2.63* | 0.314 |
| 2:1 | 52.1 ± 46.86* | 0.297 |
| 1:1 | 970.6 ± 662.4* | 0.41 |
| 1:1.5 | 465.1 ± 138.4* | 0.5465 |
| 1:2 | 474.2 ± 32.59 | 0.239 |
| 1:3 | 118.8 ± 26.76 | 0.271 |
| 1:4 | 607.4 ± 285.2* | 0.662 |
| 1:5 | 213.0 ± 67.95* | 0.407 |
| 1:10 | 21.57 ± 9.89* | 0.355 |

Asterisks (*) indicate multimodal size distributions (multiple peaks present). A CR of 1:3 was chosen as the lead MK2i-NP formulation.

TABLE 25

Size summary of p-HSP20-NPs prepared at different charge ratios ([NH$_3^+$]/[COO$^-$]) as determined by DLS analysis

| NH$_3^+$:COO$^-$ | Z-ave diameter (nm) | PDI |
| --- | --- | --- |
| 10:1 | 659.4 ± 293.7* | 0.594 |
| 5:1 | 238.3 ± 38.13* | 0.574 |
| 4:1 | 169.1 ± 2.501* | 0.591 |
| 3:1 | 141.0 ± 5.783 | 0.207 |
| 2:1 | 369.3 ± 69.83* | 0.554 |
| 1:1 | 1018 ± 786.6* | 0.903 |
| 1:2 | 1321 ± 1430* | 0.662 |
| 1:3 | 1369 ± 255.9* | 0.750 |
| 1:4 | 1772 ± 513* | 0.470 |
| 1:5 | 1496 ± 602.9* | 0.429 |
| 1:10 | 4246 ± 4428 | 0.741 |

Asterisks (*) indicate multimodal size distributions (multiple peaks present). A CR of 3:1 was chosen as the lead p-HSP20-NP formulation.

Figure 67:
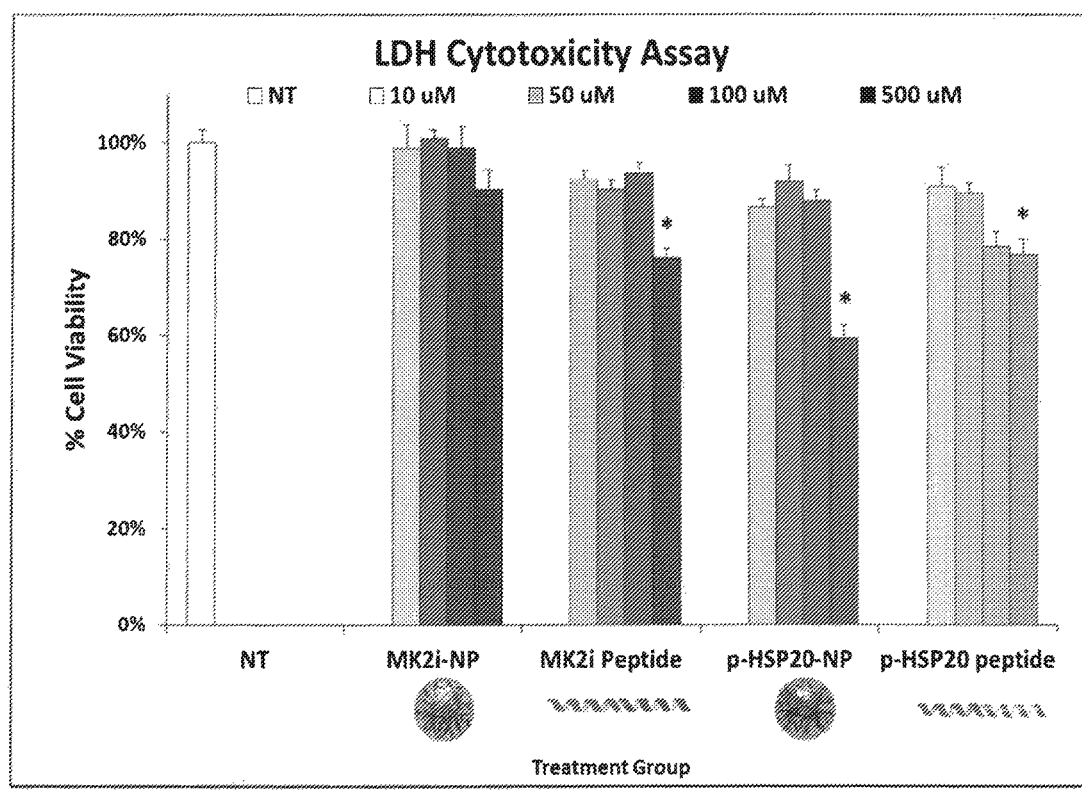
FIG. 67 shows a bar graph representing NP cytocompatibility. The cytotoxicity of MK2i-NPs and p-HSP20-NPs was compared to the corresponding dose of free peptide in HCAVSMCs. Cells were treated for 2 hours and then allowed to incubate in fresh medium for 24 hours prior to running the cytotoxicity assay. *p<0.05 vs. NT, n=4 mean±SEM.

Example 5. NP In Vitro Biocompatibility, Uptake, Retention, Trafficking and Bioactivity The biocompatibility of the lead candidate MK2i-NP and HSP20-NP formulations was compared to the corresponding free peptide at a range of doses (10-500 µM peptide) in human coronary artery vascular smooth muscle cells (HCAVSMCs) in vitro. HCAVSMCs were treated for 2 hours and then incubated in fresh medium for 24 hours prior to running the cytotoxicity assay. No significant cytotoxicity was evident for MK2i-NPs at all concentrations tested, whereas the free MK2i peptide demonstrated mild toxicity at the highest dose tested (76% cell viability at 500 µM, FIG. 67). HSP20-NPs and the HSP20 peptide were found to be biocompatible with the exception of mild cytotoxicity detected at 500 µM (60% and 77% viability for p-HSP20-NPs and the free p-HSP20 peptide, respectively).

Figure 4:
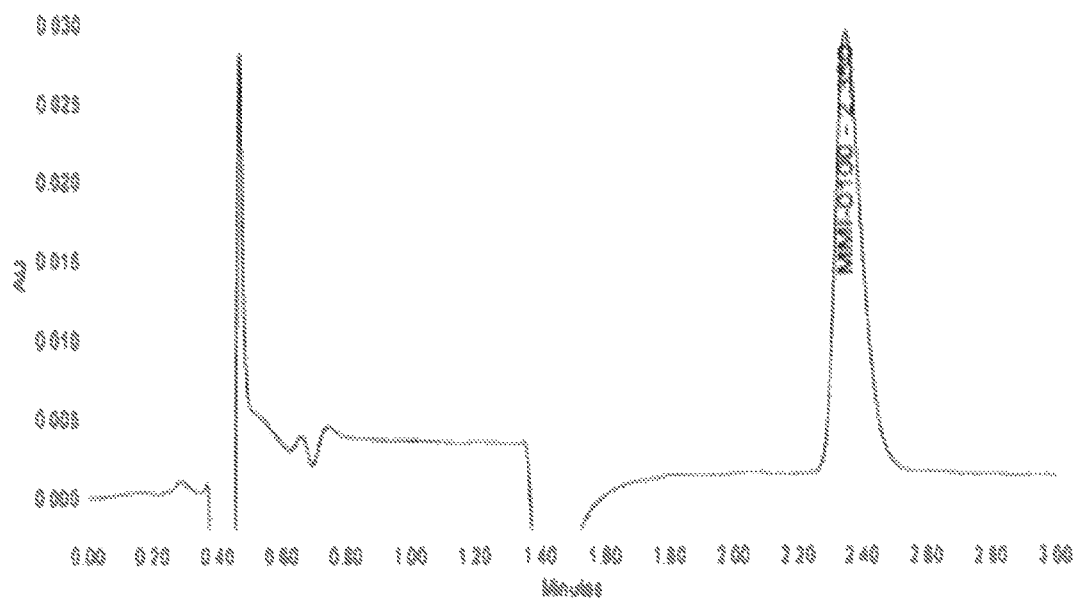
FIG. 4 shows a chromatogram of an MMI-0100 working standard.
Figure 5:
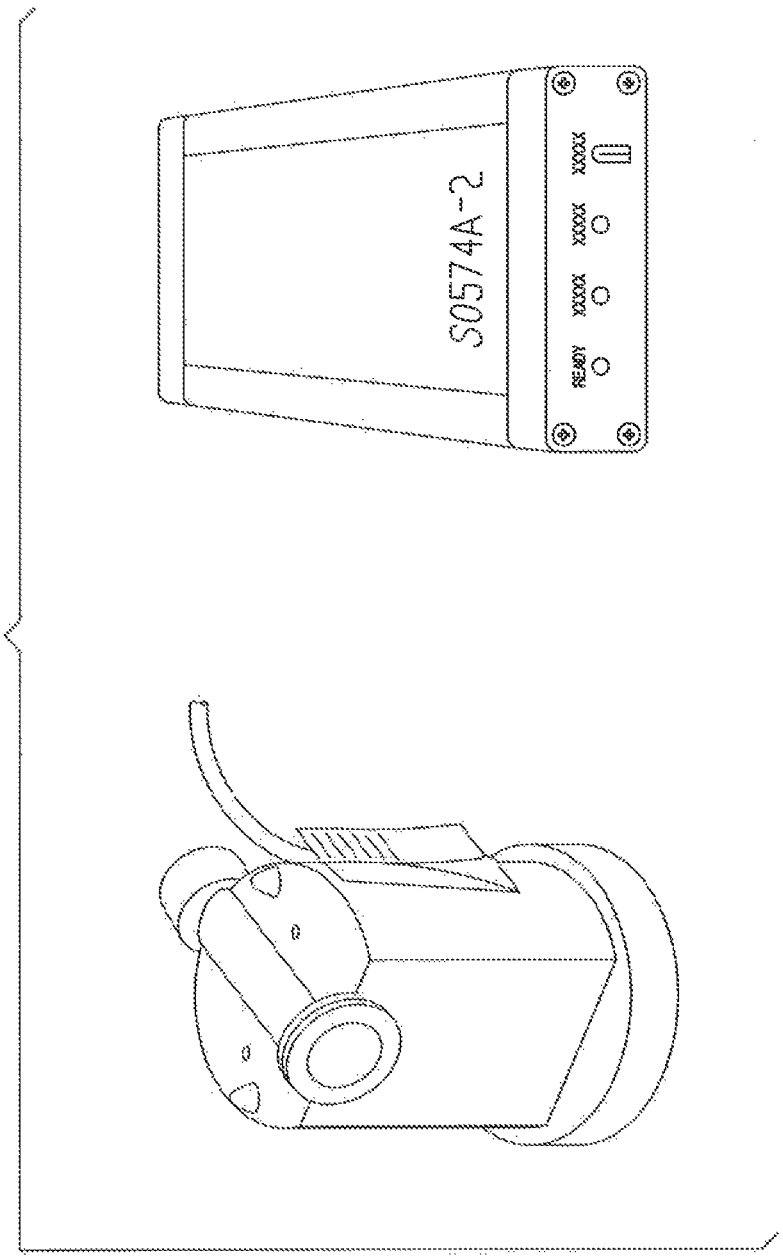
FIG. 5 shows an EPIC inhaler device. On the left is an assembled device (base unit with attached flow channel). The inhaler is tethered to an external drive box (pictured on the right) which contains the electronics.
Figure 6:
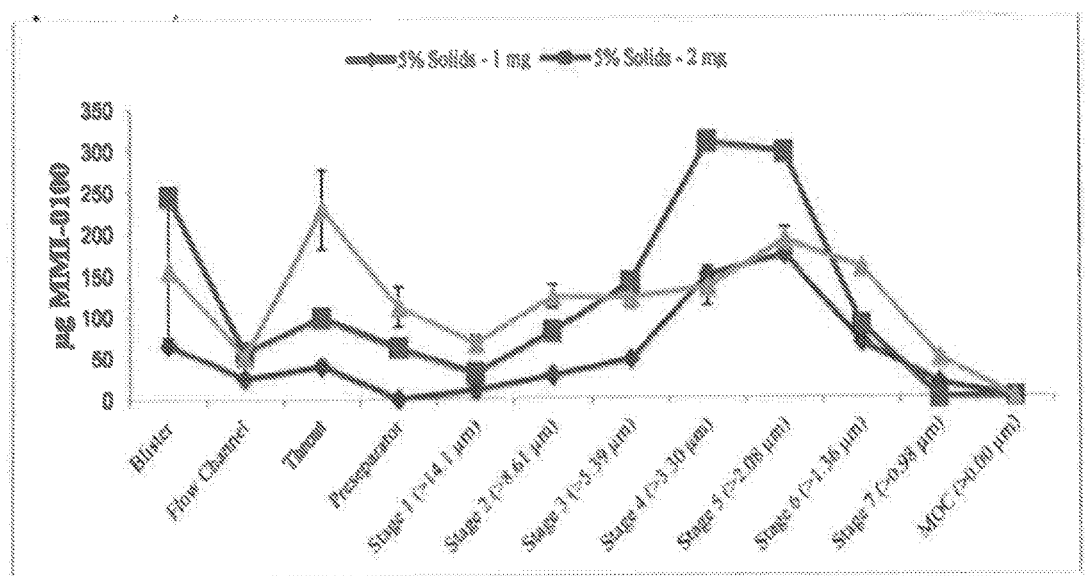
FIG. 6 shows a particle size distribution plot of initial aerosol performance results for a MMI-0100 5% formulation at 1 mg and 2 mg.
Figure 68:
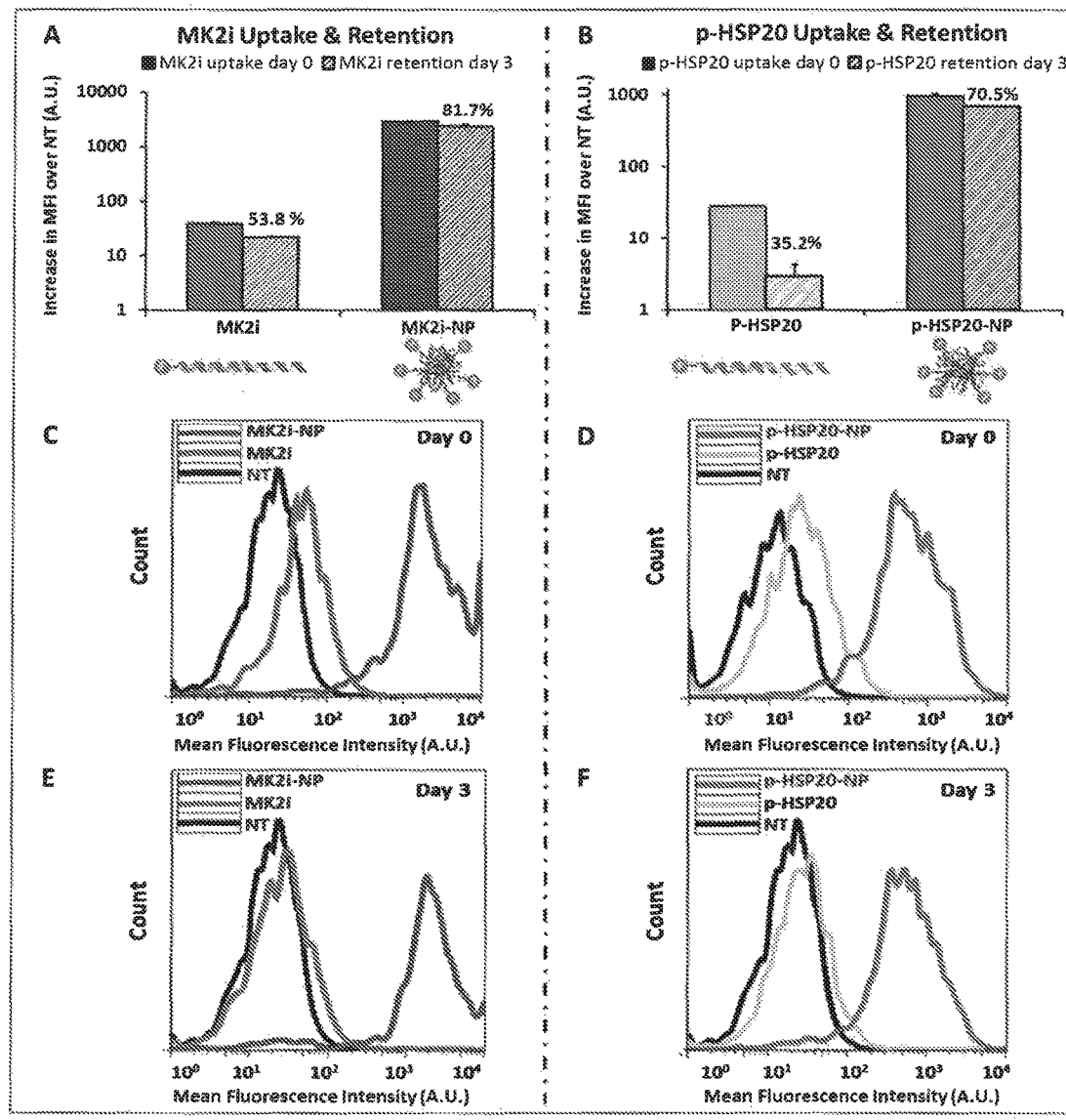
FIG. 68 shows NP uptake and retention. Flow cytometric quantification of peptide uptake and retention of (A) MK2i-NPs vs. MK2i and (B) p-HSP20-NPs vs. HSP20 at a 10 μM dose of peptide after 30 minutes of treatment. MK2i-NPs achieved ~70 fold increase in peptide uptake at the same concentration whereas p-HSP20-NPs achieved a ~35 fold increase in uptake; (C,D) representative flow histograms of HCAVSMCs immediately after treatment and (E,F) representative flow histograms demonstrating that formulation into NPs increased peptide cellular retention after 3 days of culture in fresh medium post-treatment. The percentages overwritten on A-B represent the % retention at 3 days relative to 0 days post-treatment.

Quantity of MK2i-NP and p-HSP20-NP uptake and intracellular retention over time were assessed through flow cytometric analysis of HCAVSMCs treated for 30 minutes, washed, and maintained in fresh medium for 0 or 3 days. More than an order of magnitude increase in uptake (~70-fold increase in MK2i uptake and ~35-fold increase in p-HSP20 uptake) was detected for both peptides when incorporated into NPs (FIG. 68). Since the negative ζ-potential of both NP formulations indicates that the PPAA polymer is primarily exposed at the NP surface, this increase in uptake is likely facilitated by the pH-responsive polymer. More specifically, the α-alkyl substitution of the propyl moiety imparts PPAA with lipophilic/hydrophobic character, suggesting that the observed differences in uptake may be the result of increased hydrophobic interactions of NPs with the cell membrane. In addition to increased uptake, HCAVSMCs treated with MK2i-NPs or p-HSP20-NPs demonstrated increased intracellular peptide retention 3 days after treatment removal compared to the free MK2i or p-HSP20 peptide (82% vs. 54% of initial uptake remaining for MK2i-NPs vs. free MK2i, FIG. 4A,E; 70% vs. 35% retention of p-HSP20-NPs vs. free p-HSP20, FIG. 68B,F). Intracellular retention of bioactive cargo can be improved by reducing exocytosis of the intact peptide and/or reducing degradation of the peptide in acidic endo-lysosomal compartments 18, 35. These optimized NP formulations are intentionally designed to respond to the decreased pH encountered in the endo-lysosomal trafficking pathway to facilitate cytosolic peptide delivery, as the PPAA polymer has well-defined pH-dependent endosomolytic activity 36, 37, has previously demonstrated biocompatibility in animal models38, and has been applied for intracellular delivery of a pro-apoptotic anti-cancer peptide via a multi-step bioconjugation of the PPAA polymer to the peptide through a streptavidin linker39. Thus, a simplified electrostatic complexation approach was utilized incorporating the PPAA polymer to facilitate therapeutic endosome escape and retention in these studies: PPAA undergoes a transition from an ionized, expanded conformation at physiologic pH to a collapsed, hydrophobic globular conformation in acidic/endosomal conditions. This transition results in hydrophobic interactions with lipids in the endosomal membrane and ultimately in endosomal escape and improved intracellular retention and bioactivity of the therapeutic peptide cargo.

Figure 69:
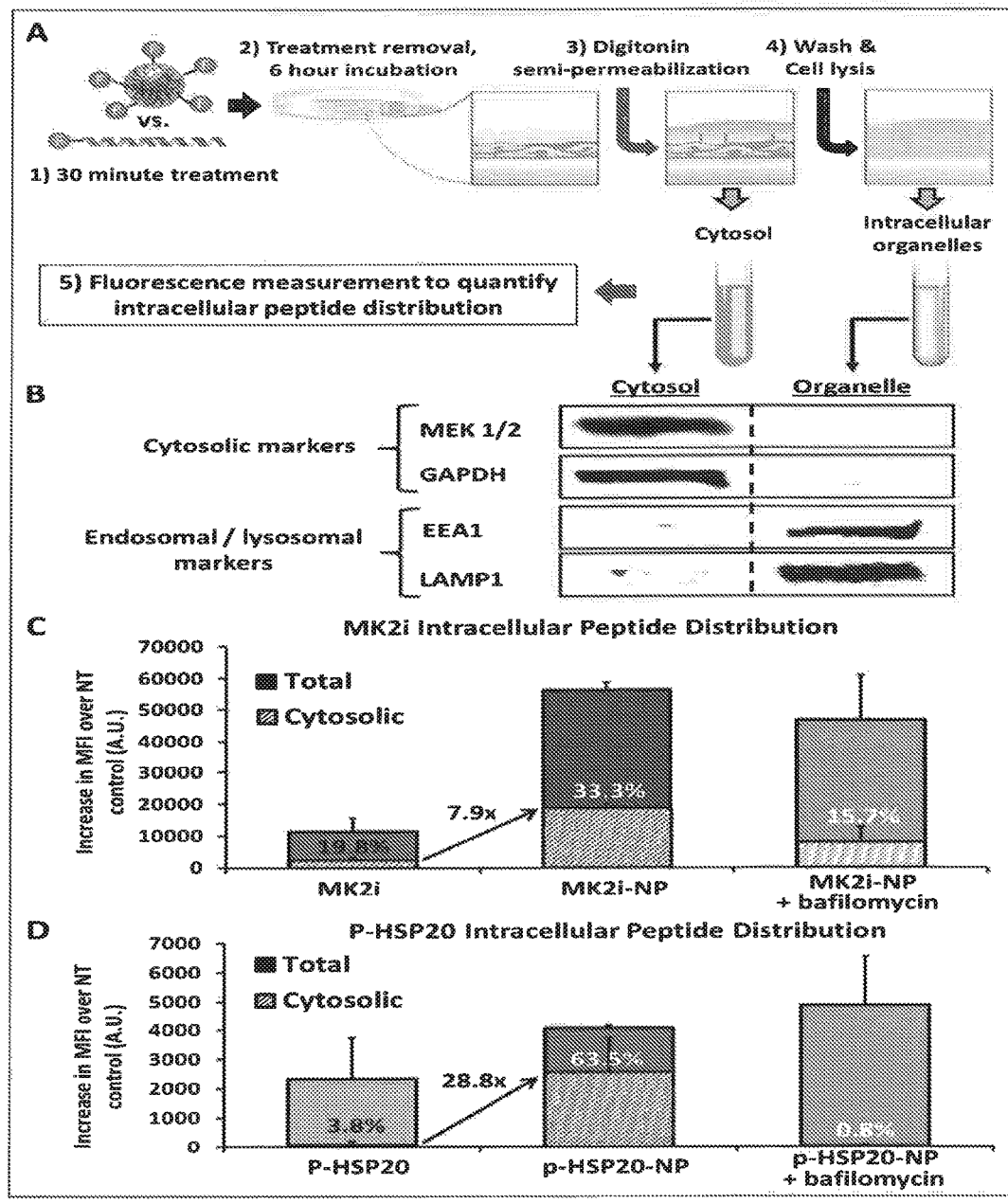
FIG. 69 shows NP Endosomal Escape and Cytosolic Peptide Delivery. (A) Experimental design for separation of vascular smooth muscle cell cytosol and intracellular organelles using digitonin semi-permeabilization. Conditions for semi-permeabilization were optimized as shown in FIG. 70; (B) Western blot validation of the optimized digitonin semi-permeabilization procedure confirmed separation of the cytosolic proteins mitogen-activated protein kinase 1/2 (MEK1/2) and glyceraldehyde 3-phosphate dehydrogenase (GAPDH) from the endo-lysosomal markers early endosomal antigen 1 (EEA1) and lysosomal-associated protein 1 (LAMP1); (C and D) comparison of the intracellular distribution of (C) MK2i and (D) p-HSP20 peptides when delivered alone or formulated into nano-polyplexes demonstrating increased cytosolic delivery of the NP formulations. Significant inhibition of NP mediated cytosolic peptide delivery when the endosomal acidification inhibitor bafilomycin was added verified the pH-dependent endosomal escape mechanism of the NPs.
Figure 70:
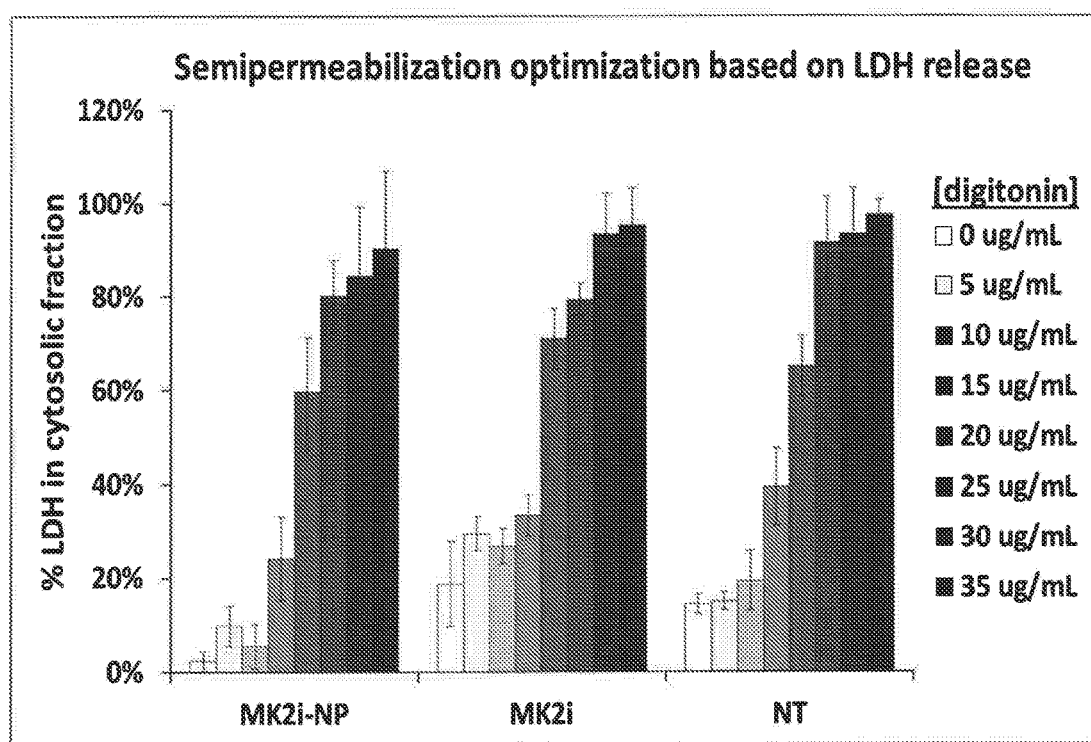
FIG. 70 shows a bar graph representing Digitonin semi-permeabilization optimization. The conditions for the digitonin semi-permeabilization procedure to separate cytosolic components from intracellular organelles (i.e., endo-lysosomal compartments) were optimized based upon LDH release following 10 minutes of incubation with various concentrations of digitonin at 0° C. on rotary shaker operating at 100 RPM. 25 ug/mL digitonin was chosen as the optimal condition as no significant increase in release of cytosolic LDH was seen at higher concentrations.

To investigate the connection between increased peptide intracellular retention and endosomal escape of peptides delivered via the NP formulation, a digitonin-based, semi-permeabilization technique40 was adapted and optimized for measuring the relative quantity of cytosolic and vesicle-bound peptide for NP and free peptide treated HCAVSMCs (FIG. 69A). Digitonin is a non-ionic detergent that, under optimized conditions, results in the selective semi-permeabilization of the cell membrane while leaving intracellular organelles (e.g., endosomes and lysosomes) intact. An optimized semi-permeabilization procedure was determined by measuring the LDH (which is known to be localized to the cytosol) quantity in the "cytosolic" and "organelle" fractions from HCAVSMCs incubated with a range of concentrations of digitonin for 10 minutes on ice. (FIG. 70). Western blot analysis of the cytosolic and organelle fractions collected using the optimized semi-permeabilization protocol verified effective separation of the cytosolic proteins mitogen-activated protein kinase kinase 1/2 (MEK1/2) and glyceraldehyde 3-phosphate dehydrogenase (GAPDH) from the endo-lysosomal markers early endosomal antigen 1 (EEA1) and lysosomal-associated protein 1 (LAMP1, FIG. 69B). Utilizing fluorescently labeled MK2i and p-HSP20 peptides allowed for quantification of the intracellular distribution of both peptides following delivery in their free form versus via NP formulations. This analysis verified that formulation into NPs not only increased peptide uptake but also significantly increased the fraction of internalized peptide in the cytosol; the net effect was an approximately 8-fold increase in cytosolic MK2i delivery and ~29-fold increase in cytosolic p-HSP20 delivery (FIG. 69C, D). In order to confirm that the increased cytosolic peptide delivery is facilitated by the pH-dependent membrane disruptive activity of PPAA in the NP formulations, cells were treated with NPs in the presence of the vacuolar-type H+ ATPase inhibitor Bafilomycin A1 to prevent endo-lysosomal acidification. Preventing endosomal acidification markedly reduced the fraction of internalized peptide in the cytosol for both NP formulations, confirming that the mechanism of NP escape from endosomes is pH-dependent (FIG. 69C, D). Bafilomycin treatment was found to have negligible effects on the cytosolic fraction of internalized free MK2i or p-HSP20 peptide (Data not shown: MK2i: 9.64%±8.17% cytosolic, p-HSP20: 7.36%±8.28% cytosolic).

Figure 71:
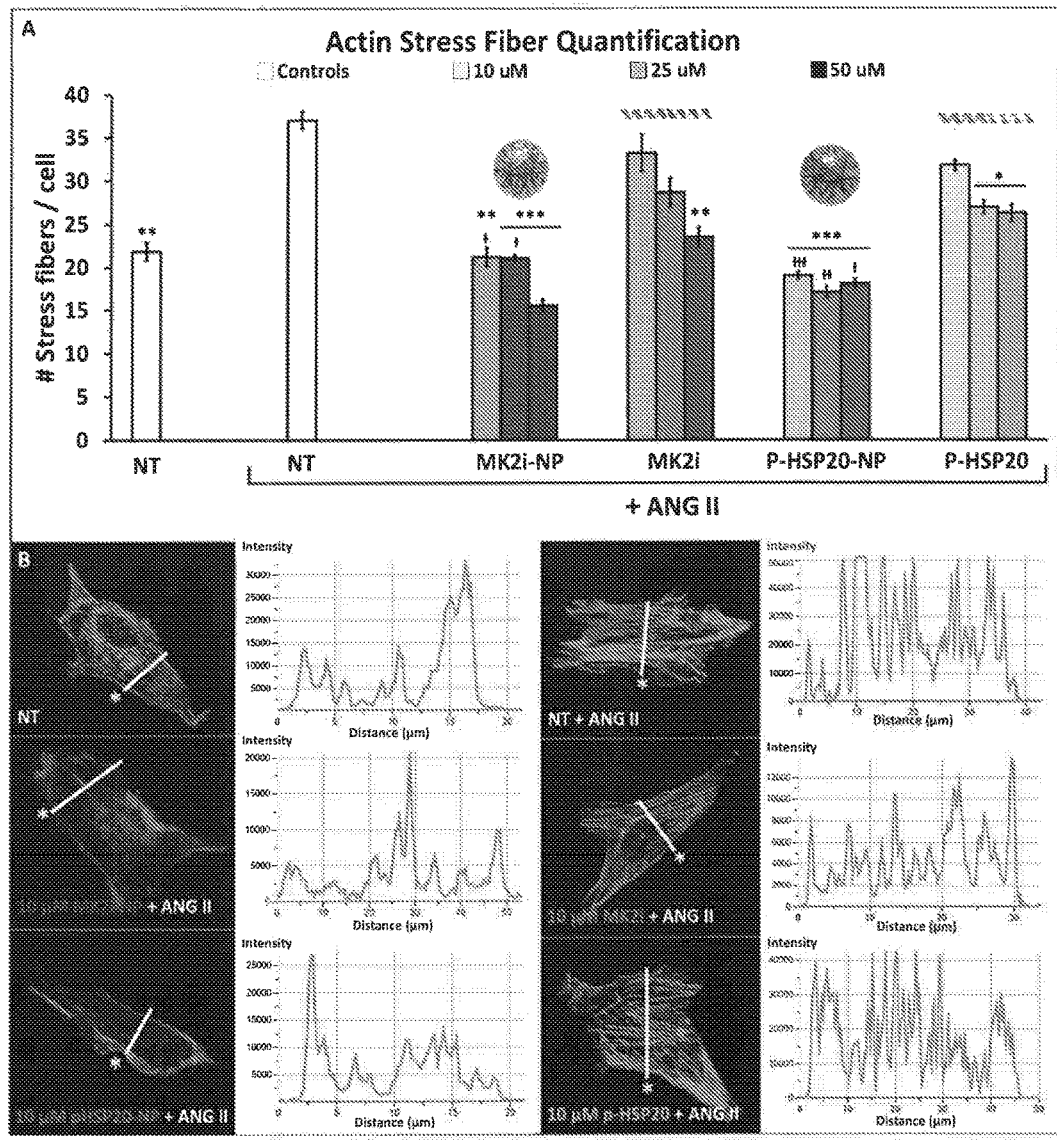
FIG. 71 shows inhibition of F-actin stress fiber formation in vascular smooth muscle cells. (A) F-actin stress fiber quantification in HCAVSMCs pre-treated with p-HSP20-NPs, free p-HSP20 peptide, MK2i-NPs or free MK2i for 1 hour and then stimulated with ANG II for 2 hours. The number of stress fibers per cell was calculated from three intensity profiles taken from the axis transverse to the cellular polarity from n≥36 ROIs from n≥12 different cells for each treatment group, *p<0.05, p<0.01, *p<0.001 vs. NT+ANG II; Ɨ p<0.1, ƗƗ p<0.01, ƗƗƗ p<0.001 vs. the free peptide at the same concentration; (B) representative fluorescence microscopy images of F-actin stress fiber formation in ANG II-stimulated HCAVSMCs and the corresponding intensity profile derived from the line shown in the image. The asterisk denotes the left side of the intensity profile shown. Gain settings were kept constant for all images obtained.
Figure 72:
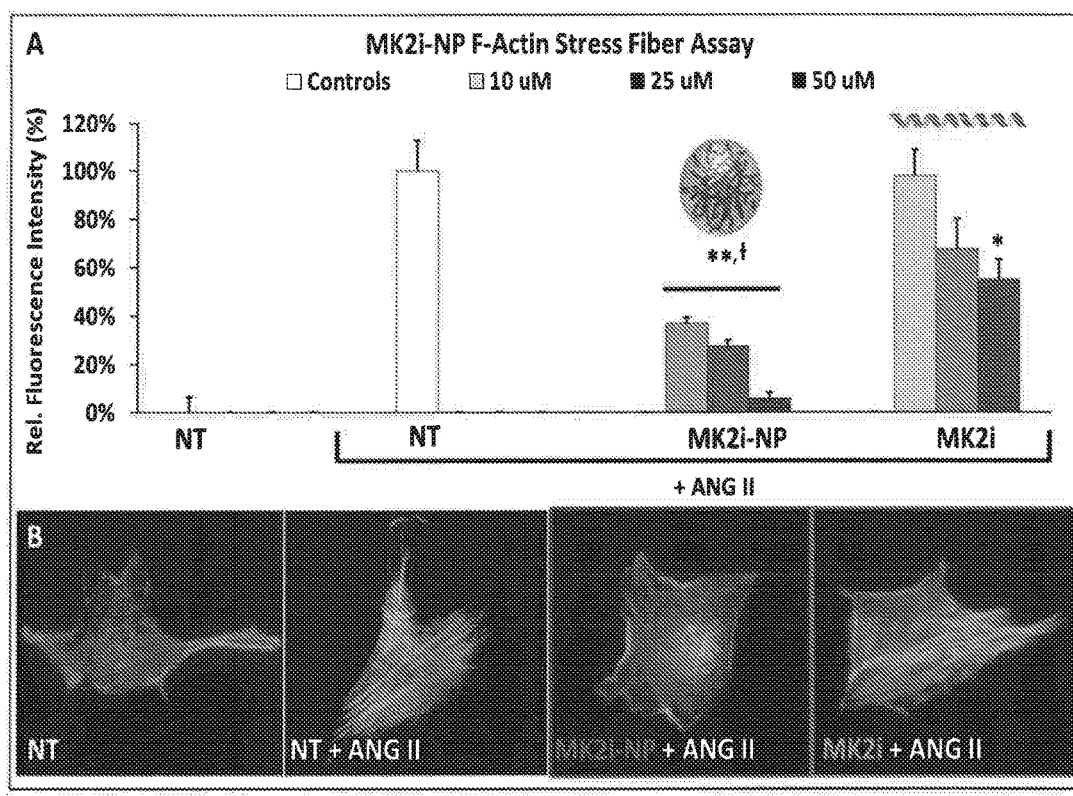
FIG. 72 shows inhibition of F-actin stress fiber formation by MK2i-NPs. (A) F-actin stress fiber quantification in HCAVSMCs pre-treated with MK2i-NPs or free MK2i for 1 hour and then stimulated with ANG II for 2 hours. Data represents n≥12 cells from 2 separate experiments: *p<0.05 vs. NT+ANG II**p<0.001 vs. NT+ANG II, Ɨ p<0.05 vs. MK2i at same concentration; (B) representative fluorescence microscopy images of F-actin stress fiber formation in ANG II-stimulated HCAVSMCs after 1 hour treatment with free MK2i or MK2i-NPs.
Figure 73:
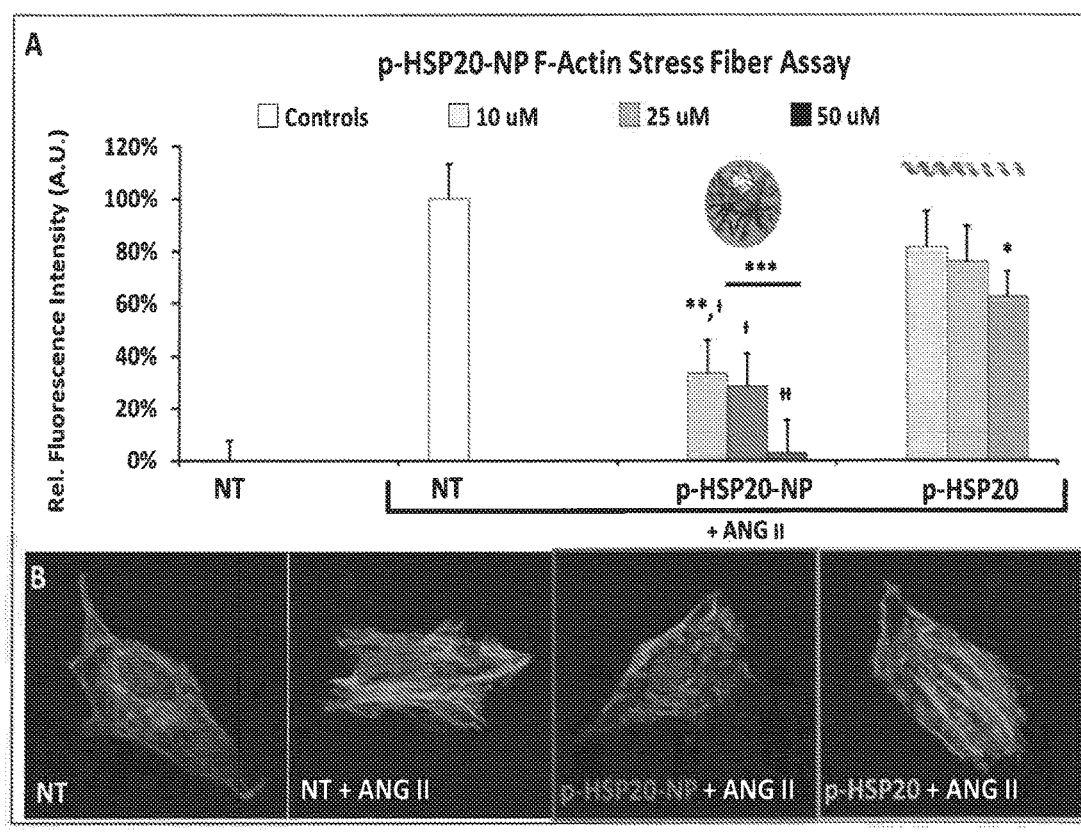
FIG. 73 shows inhibition of F-actin stress fiber formation by p-HSP20-NPs. (A) F-actin stress fiber quantification in HCAVSMCs pre-treated with p-HSP20-NPs or free p-HSP20 for 1 hour and then stimulated with ANG II for 2 hours. Data represents n≥12 cells from 2 separate experiments: *p<0.05, p<0.01, *p<0.001 vs. NT+ANG II, Ɨ p<0.05, ƗƗ p<0.001 vs p-HSP20 at same concentration; (B) representative fluorescence microscopy images of F-actin stress fiber formation in ANG II-stimulated HCAVSMCs after 1 hour treatment with free p-HSP20 or p-HSP-20-NPs.

The efficacy of MK2i-NP and p-HSP20-NP mediated inhibition of F-actin stress fiber formation was quantified in angiotensin-II (ANG II) stimulated HCAVSMCs. Both NP formulations enhanced peptide functional bioactivity as measured by a significant decrease in the average number of stress fibers per cell (FIG. 71A). Qualitatively, HCAVSMCs treated with the NP formulations and ANG II displayed cell morphology and staining consistent with unstimulated control cells, whereas HCAVSMCs treated with the free peptide demonstrated stress fiber formation similar to ANG II-stimulated control cells (FIG. 71B). The total amount of F-actin per cell was also quantified using Alexa-488 phalloidin, a stain that selectively binds to filamentous but not globular, actin (FIGS. 72 and 73). This analysis was consistent with the quantification of number of stress fibers per cell and revealed that formulation into NPs significantly enhanced stress fiber inhibitory activity of both peptides.

Example 6. NP Effect on Smooth Muscle Physiology in Human Vascular Tissue

Figure 74:
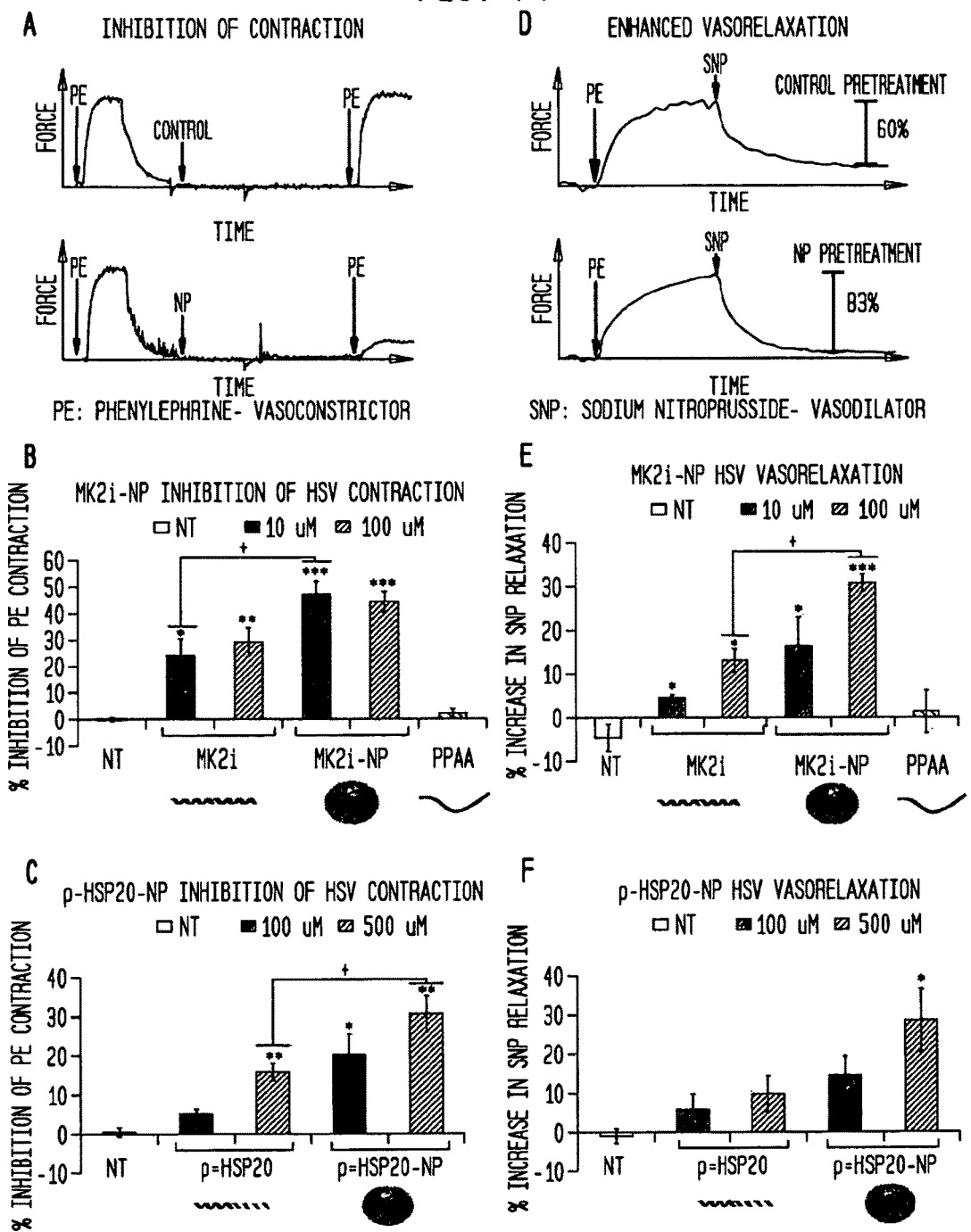
FIG. 74 shows MK2i-NP & p-HSP20-NP treatment inhibits vasoconstriction and enhances vasorelaxation. (A) Experimental design for inhibition of contraction studies: HSV rings are initially contracted with PE and then relaxed. After 2 hours of treatment with NPs, free peptide, or control, post treatment contraction is measured; (B) quantification of MK2i and MK2i-NP mediated inhibition of contraction. PPAA polymer equivalent to the highest dose of MK2i-NPs was included as a vehicle control; (C) quantification of p-HSP20 and p-HSP20-NP mediated inhibition of contraction; (D) experimental design for vasorelaxation studies: HSV rings are initially contracted with PE and subsequently relaxed with SNP. HSV rings are then treated for two hours with NPs, free peptide, or control and then contracted and relaxed under the same conditions to compare post-treatment to pre-treatment relaxation; (E) quantification of MK2i and MK2i-NP enhanced vasorelaxation. PPAA polymer equivalent to the highest dose of MK2i-NPs was included as a vehicle control; (F) quantification of p-HSP20 and p-HSP20-NP enhanced vasorelaxation. For B,C,E,F: Ɨ p<0.05; *p<0.05, p<0.01, *p<0.01 vs. NT, n≥3 separate donors; (G) F-actin visualization in Alexa-488 phalloidin stained cryosections of human saphenous vein explants obtained from a single donor (n=1) pretreated with 100 μM MK2i or MK2i-NPs, 500 μM p-HSP20 or p-HSP20-NPs and subsequently stimulated with ANG-II enabling visualization of decreased F-actin in samples treated with the NP formulations.
Figure 74:
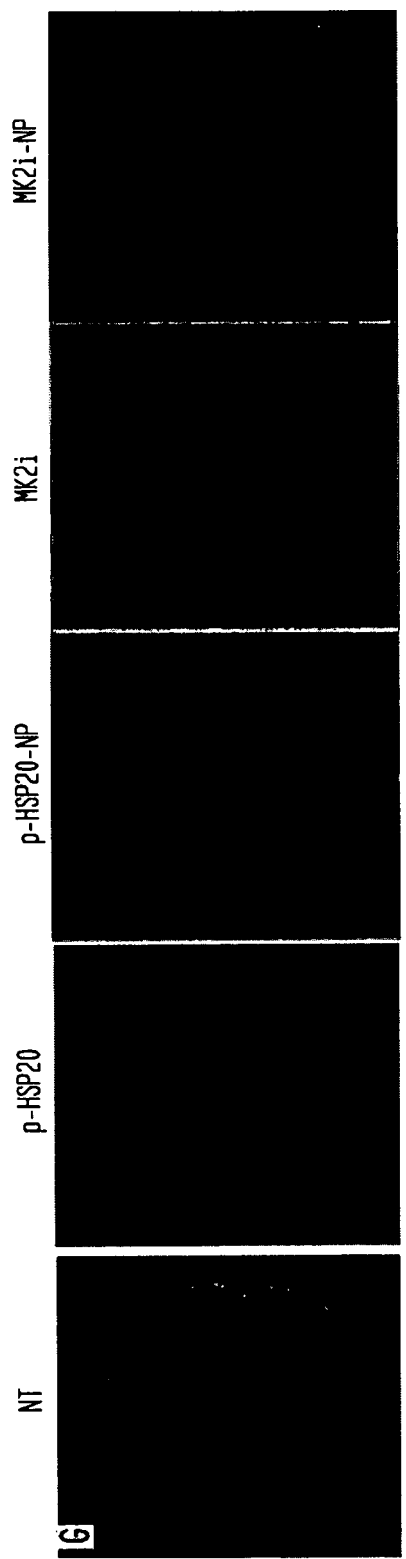
Figure 75:
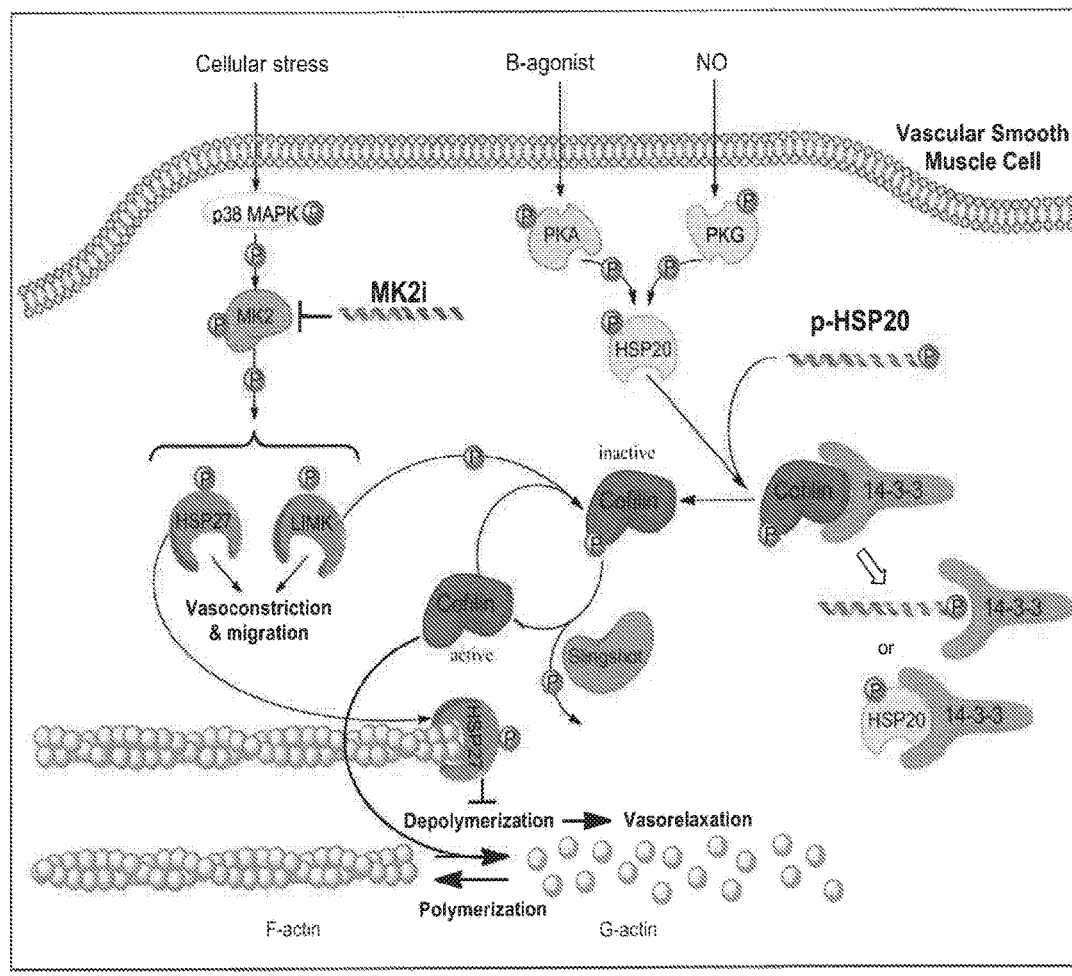
FIG. 75 shows a schematic of the Mechanisms of action of MAPKAP Kinase 2 (MK2) and Heat Shock Protein 20 (HSP20) in actin mediated vasconstriction and vasorelaxation. MK2 is activated by cellular stress (e.g. mechanical trauma, cytokines, oxidative stress, etc.) through p38 MAPK. Phosphorylated MK2 activates a number of downstream effectors: 1) phosphorylation of heat shock protein 27 (HSP27) results in capping of filamentous actin thereby inhibiting actin depolymerization and vasorelaxation. 2) phosphorylation of Lim Kinase (LIMK) results in phosphorylation and deactivation of cofilin which prevents actin degradation and inhibits vasorelaxation. The MK2 inhibitory peptide (MK2i) binds to MK2 preventing the activation of these downstream effectors and promoting vasorelaxation. HSP20 is phosphorylated by cyclic nucleotide-dependent protein kinases (PKA and PKG) resulting in binding to and displacement of phosphorylated coflin from the 14-3-3 protein. This displacement allows for cofilin to be dephosphorylated by phosphatases such as slingshot, resulting in the activation of cofilin and concomitant cofilin-mediated depolymerization of filamentous actin. The phospho-HSP20 peptide mimetic (p-HSP20) recapitulates the activity of phosphorylated HSP20, ultimately leading to vasorelaxation.
Figure 76:
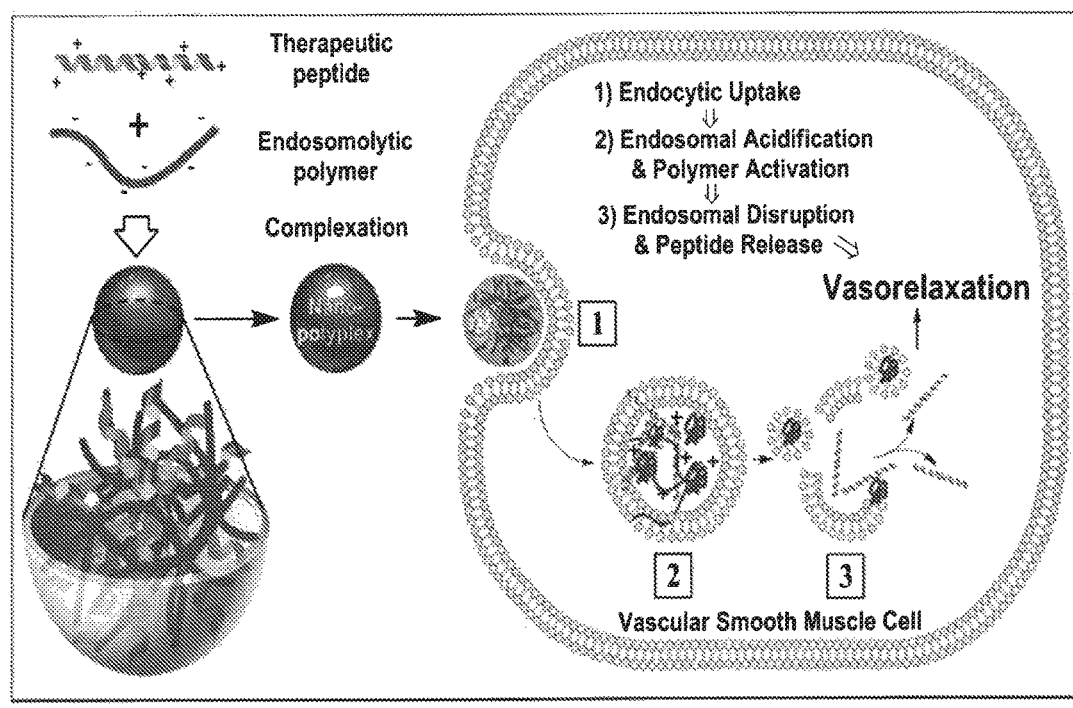
FIG. 76 shows a schematic of the mechanism of endosomolytic nano-polyplex cytosolic peptide delivery.

The effect of the MK2i-NP and p-HSP20-NP formulations on smooth muscle physiology in human vascular tissue was assessed in order to evaluate these formulations as potential treatments for vasospasm. For these studies, human saphenous vein (HSV) was collected from consented patients undergoing bypass grafting surgery and sectioned into rings. After verifying viability through KCL challenge in a muscle bath, the ability of each NP formulation to inhibit phenylephrine (PE) induced vasoconstriction was measured in HSV rings using an organ bath system outfitted with a force transducer. In an experimental design where vessels were contracted, relaxed, treated, and then contracted again, untreated control HSV rings displayed no changes in the second round of PE induced contraction relative to the initial contraction. However, intermediate treatment with the MK2i or p-HSP20 peptides significantly inhibited the second PE-induced HSV contraction (FIG. 74A-C). Consistent with in vitro F-actin stress fiber results, equivalent doses of peptide delivered via NP formulations demonstrated significantly enhanced peptide-mediated inhibition of contraction compared to the free peptide (FIG. 74C). Notably, treatment with a dose of free PPAA polymer equivalent to the highest NP dose administered showed negligible effects on PE-induced HSV contraction (FIG. 74B) indicating that the enhanced inhibitory activity is mediated through enhancement of peptide bioactivity and is not a non-specific effect of the endosomolytic polymer carrier. This ability of the peptide-NPs to potently inhibit vasoconstriction demonstrates the translational potential of these formulations as a prophylactic approach to prevent vasospasm in applications such as coronary or peripheral bypass grafting.

In addition to testing the efficacy of these NP formulations as a prophylactic therapy, the ability of the MK2i- and p-HSP20-NPs to enhance sodium nitroprusside (SNP) induced vasorelaxation was evaluated as a potential salutary therapeutic intervention (e.g., to treat SAH induced vasospasm) in viable HSV explants (FIG. 74D). Again, both NP formulations demonstrated an enhanced ability to promote SNP-induced vasorelaxation at all concentrations tested (FIG. 74E, F) whereas untreated HSV or HSV treated with the PPAA polymer alone showed negligible differences in vasorelaxation (FIG. 74E). Because MK2i-NP and p-HSP20-NP formulations trigger vasorelaxation through separate molecular mechanisms, combining both peptides into a NP formulation represents a promising approach for future studies because it may achieve a synergistic effect that produces a therapeutic benefit at lower peptide doses.

In order to qualitatively assess the correlation of F-actin stress fiber formation with the smooth muscle physiology results in human tissue, HSV rings were pretreated with free peptide or the NP formulations and then subsequently stimulated with ANG II prior to F-actin staining with Alexa-488 phalloidin (FIG. 74G). In concordance with the smooth muscle physiology results, HSV rings treated with NP formulations showed diminished phalloidin staining compared to HSV treated with the free peptide. Altogether, these results indicate that MK2i- and p-HSP20-NPs significantly enhance the ability of the MK2i and p-HSP20 peptide to inhibit vasoconstriction and promote vasorelaxation by modulating actin dynamics in human smooth muscle tissue.

The results of the experiments set forth above establish the potential use of nanotechnology to enhance cell and tissue delivery, bioactivity, and intracellular pharmacokinetics of therapeutic peptides such as MMI-0100 (MK2i). In general, CPPs are highly cationic, and thus, complexation with PPAA can potentially serve as a generalized platform biotechnology to facilitate intracellular delivery of therapeutic peptides.

Example 7. HPLC Method for Assay and Purity Determination of MMI-0100 in Solution The purpose of this study was to evaluate and optimize an HPLC method for assay and purity determination of MMI-0100 in solution by evaluating, among others, column wash steps, elution gradient, precision (injection repeatability) and linearity.

The HPLC method conditions used are listed in Table 26.

TABLE 26

| HPLC method conditions | |
| --- | --- |
| Column | Grace, Vydec C18, 5 µm, 300 A, 4.6 × 250 mm, polymeric, PN: 218TP54 with pre-column filter |
| Mobile Phase (MP) | MP A: 0.1% TFA in DI water<br>MP B: 0.1% TFA in 1:1 methanol: acetonitrile (v/v)<br>(MP A filtered through 0.8 µm membrane) |

| | Time (minutes) | % MP A | % MP B |
| --- | --- | --- | --- |
| Gradient | 0 | 85 | 15 |
| | 5.5 | 78 | 22 |
| | 35 | 57 | 43 |
| | 40 | 57 | 43 |
| | 42 | 10 | 90 |
| | 45 | 10 | 90 |
| | 47 | 85 | 15 |
| | 55 | 85 | 15 |

| | |
| --- | --- |
| Flow Rate | 1.0 mL/min |
| Detection Wavelength | Ultraviolet (UV): 215 nm |
| Column Temperature | 25° C. |
| Sample Temperature | 5° C. |
| Injection Volume | 20 µL |
| Run Time | 64 min |
| HPLC Standard and Sample Diluent ("Diluent") | Tween 20, 0.02% (v/v) in water |

In order to maintain a clean column with a large number of formulations, the column wash step (from 42-45 min) was extended by 7 min (from 42 to 52 min). Accordingly, the column equilibration step was increased by 2 min (from 47-55 min to 54-64 min). The elution condition under which the MMI-0100 elutes was not changed (e.g. 0-40 min). The optimized gradient is listed Table 27.

TABLE 27

| Optimized HPLC gradient | | | |
| --- | --- | --- | --- |
| | Time (minutes) | % MP A | % MP B |
| Optimized Gradient | 0 | 85 | 15 |
| | 5.5 | 78 | 22 |
| | 35 | 57 | 43 |
| | 40 | 57 | 43 |
| | 42 | 10 | 90 |
| | 52 | 10 | 90 |
| | 54 | 85 | 15 |
| | 64 | 85 | 15 |

Figure 77:
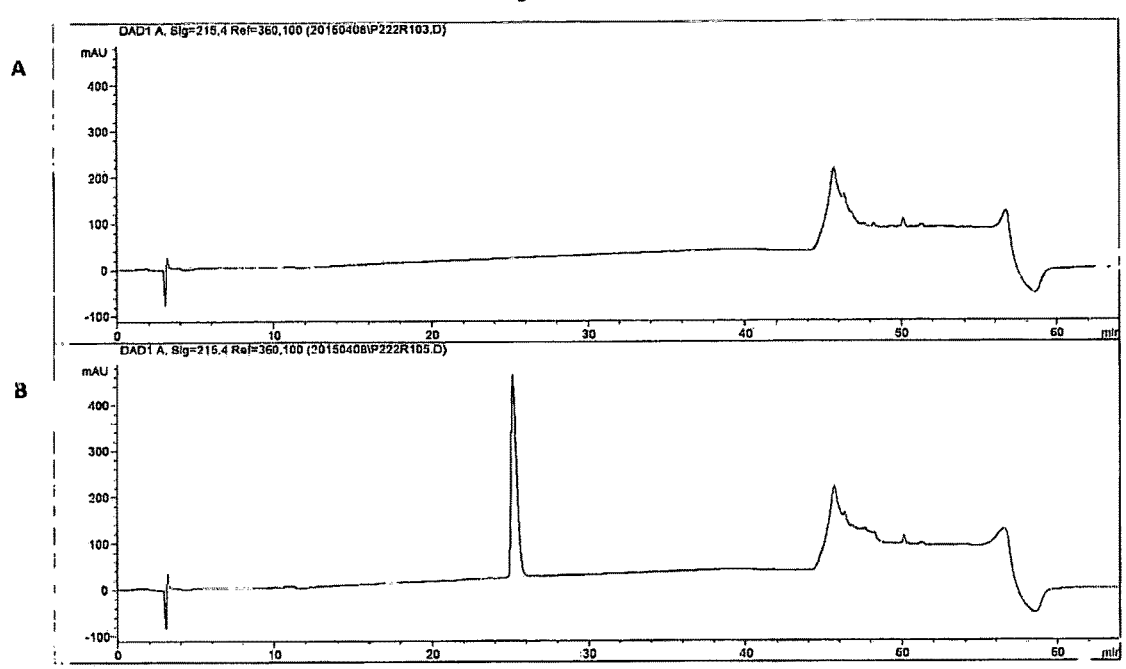
FIG. 77 shows HPLC chromatograms of diluent (A) and MMI-0100 standard at 1 mg/mL (B).

Representative HPLC chromatograms of diluent and MMI-0100 standard at 1 mg/mL are shown in FIGS. 77A and B respectively.

Precision

Precision (or injection repeatability) was evaluated by injecting a solution containing 1.1 mg/mL MMI-0100 in 0.02% Tween 20 onto the HPLC for a total of six consecutive injections. The retention time (RT), peak area, tailing factor and theoretical plate for the MMI-0100 peak were recorded for each injection and their respective relative standard deviations (RSDs) were calculated. Precision test results are shown in Table 28. The RSD for the RT and response factor from the six injections were less than 2%, indicating that the method meets precision/injection repeatability test criteria.

TABLE 28

| Precision (injection repeatability) test results | | | | | |
| --- | --- | --- | --- | --- | --- |
| Inj # | RT | PA | RF | Tailing (USP) | Theor. Plates (½ Width method) |
| 1 | 25.21 | 12296 | 11032 | 2.588 | 21997 |
| 2 | 25.21 | 12283 | 11020 | 2.617 | 22756 |
| 3 | 25.19 | 12262 | 11002 | 2.584 | 21606 |
| 4 | 25.17 | 12228 | 10971 | 2.602 | 22301 |
| 5 | 25.16 | 12190 | 10937 | 2.625 | 22287 |
| 6 | 25.15 | 12191 | 10938 | 2.582 | 22272 |
| AVG | 25.18 | 12242 | 10983 | 2.600 | 22203 |
| RSD (%) | 0.1 | 0.4 | 0.4 | 0.7 | 1.7 |

Linearity

Linearity test solutions were prepared using a stock solution of MMI-0100 with a series of dilutions. The stock solution of MMI-0100 was prepared at 1.9 mg/mL (167% of the nominal concentration of 1.1 mg/mL).

Actual Stock Preparation:

(24.0 mg of MMI-0100)*(Peptide Content from CoA 0.774)/(10 mL Volumetric Flask).

Figure 78:
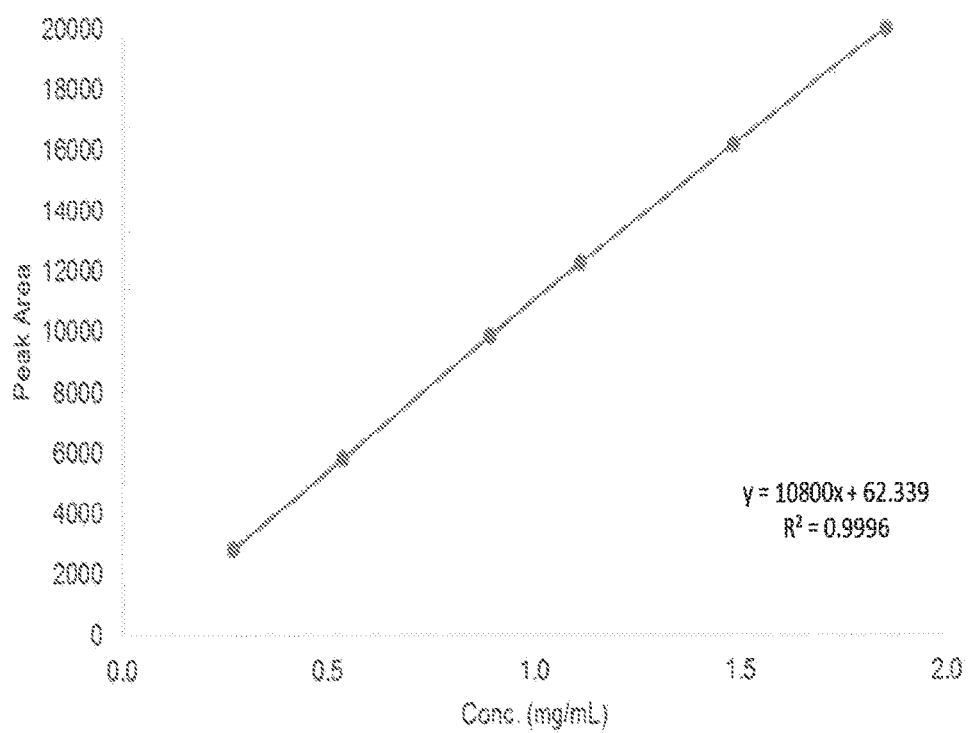
FIG. 78 shows a linearity plot of MMI-0100 concentration (mg/mL) versus Peak Area.

Linearity solution preparation is detailed in Table 29. Linearity test results are shown in Table 30 and FIG. 78. FIG. 78 shows a linearity plot of MMI-0100 concentration versus peak area. The Y-intercept bias was calculated to be 0.5% using the formula (y-int)/(Average Peak Area for 100% Nominal Concentration)*100 (62.339/12242*100=0.5%). For linearity, an acceptable correlation coefficient ($R^2$) value is >0.995 in a defined range and the y-intercept bias must be ≤5% of the peak area obtained at the nominal concentration. The linearity test results obtained meet the $R^2$ and y-intercept test criteria (Table 30 and FIG. 78).

TABLE 29

| Linearity solution preparation | | | | | |
| --- | --- | --- | --- | --- | --- |
| ID # | Solution Transferred | Sol. Vol. (mL) | Total Vol. (mL) | Conc. (mg/mL) | % Nominal |
| STOCK | | | | 1.86 | 167 |
| Linearity #1 | Stock | 4 | 5 | 1.49 | 133 |
| Linearity #2 | Stock | 3 | 5 | 1.11 | 100 |
| Linearity #3 | Linearity #1 | 3 | 5 | 0.89 | 80 |
| Linearity #4 | Linearity #3 | 3 | 5 | 0.53 | 48 |
| Linearity #5 | Linearity #4 | 1 | 2 | 0.27 | 24 |

TABLE 30

| CONC (mg/mL) | % Nominal | RT | PA | Response Factor | RF Diff from Nominal Conc (%) |
|---|---|---|---|---|---|
| 0.27 | 24 | 25.59 | 2822 | 10550 | 96 |
| 0.53 | 48 | 25.45 | 5795 | 10983 | 100 |
| 0.89 | 80 | 25.30 | 9837 | 11032 | 100 |
| 1.11 | 100 | 25.18 | 12242 | 10983 | 100 |
| 1.49 | 133 | 25.06 | 16167 | 10879 | 99 |
| 1.86 | 167 | 24.95 | 19958 | 10744 | 98 |

Example 8. Heat-Accelerated Stability Study of MMI-0100 in Various Buffers with a pH Range from 4-8

The purpose of this study was to generate a pH-stability profile MMI-0100, to determine solubility of MMI-0100 at 5.5. mg/mL in select buffers, to determine the $pH_{max}$ (pH where MMI-0100 is most stable), to generate an impurity profile at $pH_{max}$, to determine the long-term prognosis at room temperature and 2-8° C. or whether lyophilization is needed to maintain stability, to compare DI water to buffered solutions in order to determine which provides better solubility and stability for MMI-0100 and to observe any apparent viscosity change or gelation of MMI-0100 at 5.5 mg/mL.

MMI-0100 formulations prepared and tested are listed in Table 31.

TABLE 31

MMI-0100 formulations

| ID | Buffer Stock Used | Target pH | MMI-0100 (% w/w) | Final Buffer Conc (% w/w) | Buffer IIL Limit* (% w/w) |
|---|---|---|---|---|---|
| T-1 | 100 mM citric acid | 4 | 0.55 | 0.11 | 0.44 |
| T-2 | 100 mM citric acid | 5 | 0.55 | 0.11 | 0.44 |
| T-3 | 100 mM citric acid | 6 | 0.55 | 0.11 | 0.44 |
| T-4 | 100 mM citric acid | 6.5 | 0.55 | 0.11 | 0.44 |
| T-5 | DI water + NaOH/HCl for pH adjustment | 7 | 0.55 | NA | NA |
| T-6 | 50 mM phosphoric acid + NaOH for pH adjustment | 7 | 0.55 | 0.05 | NA |
| T-7 | 0.9% NaCl + NaOH/HCl for pH adjustment | 7 | 0.55 | NA | NA |
| T-8 | L-lysine monohydrate | 8 | 0.55 | 0.08 | 5.25 |

0.4 mL of each MMI-0100 formulation was filled into a HPLC vial (total 5 vials per each composition) and placed on stability as described in Table 32.

TABLE 32

Stability conditions

| Condition | Vial # | Test Schedule |
|---|---|---|
| 2-8° C. | 1 | Test as "Initial" |
| 2-8° C. (0.22 μm filtered) | 2 | Store at 2-8° C. for 24 hours; Filter using 0.22 μm SpinX; filtrate tested by HPLC |
| 25° C. | 3 | 7 and 14 days |
| 40° C. | 4 | 1, 2, 7 and 14 days |
| 60° C. | 5 | 1, 2 and 7 days |

Testing of stability samples included pH (initial only), appearance, HPLC assay and impurities. Results are shown in Tables 33-49. CC=clear and colorless.

TABLE 33

Initial pH and appearance

| | | Appearance | | | |
|---|---|---|---|---|---|
| Formulation ID | Initial pH | Initial | 2-8° C. (filtered), 24 hr | 25° C. × 7 d | 25° C. × 14 d |
| T-1 | 4.1 | CC liquid | No change | No change | No change |
| T-2 | 5.0 | CC liquid | No change | No change | No change |
| T-3 | 6.0 | CC liquid | No change | No change | No change |
| T-4 | 6.6 | CC liquid | No change | No change | No change |
| T-5 | 7.0 | CC liquid | No change | No change | No change |
| T-6 | 6.9 | CC liquid | No change | No change | No change |
| T-7 | 7.1 | CC liquid | No change | Slightly cloudy | Slightly cloudy |
| T-8 | 7.9 | CC liquid | No change | No change | No change |

TABLE 34

Appearance

| | Appearance | | | |
|---|---|---|---|---|
| Formulation ID | Initial | 40° C. × 1 d | 40° C. × 2 d | 40° C. × 7 d | 40° C. × 14 d |
| T-1 | CC liquid | No change | No change | No change | No change |
| T-2 | CC liquid | No change | No change | No change | No change |
| T-3 | CC liquid | No change | No change | No change | No change |

TABLE 34-continued

Appearance

| | Appearance | | | |
|---|---|---|---|---|
| Formulation ID | Initial | 40° C. × 1 d | 40° C. × 2 d | 40° C. × 7 d | 40° C. × 14 d |
| T-4 | CC liquid | No change | No change | Slightly cloudy | Slightly cloudy |
| T-5 | CC liquid | No change | No change | No change | No change |
| T-6 | CC liquid | No change | No change | Slightly brown | Slightly brown |
| T-7 | CC liquid | No change | No change | Slightly cloudy | Slightly cloudy |
| T-8 | CC liquid | No change | No change | No change | No change |

TABLE 35

Appearance

| Formulation ID | Initial | 60° C. × 1 d | 60° C. × 2 d | 60° C. × 7 d |
|---|---|---|---|---|
| T-1 | CC liquid | No change | No change | No change |
| T-2 | CC liquid | No change | No change | No change |
| T-3 | CC liquid | No change | No change | No change |
| T-4 | CC liquid | No change | No change | No change |
| T-5 | CC liquid | No change | No change | No change |
| T-6 | CC liquid | No change | No change | No change |
| T-7 | CC liquid | No change | No change | Slightly cloudy |
| T-8 | CC liquid | No change | No change | No change |

TABLE 36

Assay concentration

| Formulation ID | Initial | 2-8° C. Filtered | 25° C. 7 d | 25° C. 14 d |
|---|---|---|---|---|
| T-1 | 5.45 | 5.42 | 5.41 | 5.39 |
| T-2 | 5.64 | 5.66 | 5.49 | 5.55 |
| T-3 | 5.57 | 5.57 | 5.48 | 5.50 |
| T-4 | 5.48 | 5.42 | 5.32 | 5.25 |
| T-5 | 6.05 | 6.07 | 5.98 | 5.92 |
| T-6 | 5.72 | 5.66 | 5.49 | 4.93 |
| T-7 | 5.38 | 5.27 | 0.98 | 0 |
| T-8 | 5.50 | 5.44 | 5.36 | 5.04 |

TABLE 37

Assay concentration

Assay (Concentration (mg/mL))

| Formulation ID | Initial | 40° C. 1 d | 40° C. 2 d | 40° C. 7 d | 40° C. 14 d |
|---|---|---|---|---|---|
| T-1 | 5.45 | 5.48 | 5.45 | 5.23 | 5.14 |
| T-2 | 5.64 | 5.76 | 5.55 | 5.48 | 5.48 |
| T-3 | 5.57 | 5.56 | 5.58 | 5.33 | 5.35 |
| T-4 | 5.48 | 5.49 | 5.38 | 4.49 | 3.64 |
| T-5 | 6.05 | 6.04 | 6.08 | 6.12 | 6.00 |
| T-6 | 5.72 | 5.70 | 5.72 | 0 | 0 |
| T-7 | 5.38 | 5.21 | 5.21 | 5.04 | 5.00 |
| T-8 | 5.50 | 5.26 | 5.46 | 5.13 | 5.03 |

TABLE 38

Assay concentration

Assay (Concentration (mg/mL))

| Formulation ID | Initial | 60° C. 1 d | 60° C. 2 d | 60° C. 7 d |
|---|---|---|---|---|
| T-1 | 5.45 | 5.42 | 5.35 | 4.73 |
| T-2 | 5.64 | 5.69 | 5.55 | 5.08 |
| T-3 | 5.57 | 5.53 | 5.47 | 5.06 |
| T-4 | 5.48 | 5.36 | 5.28 | 4.98 |
| T-5 | 6.05 | 6.02 | 5.91 | 5.64 |
| T-6 | 5.72 | 5.38 | 5.55 | 5.18 |
| T-7 | 5.38 | 5.37 | 5.19 | 4.68 |
| T-8 | 5.50 | 5.14 | 5.12 | 3.79 |

TABLE 39

Assay recovery

Assay Recovery (% conc. over initial conc.)

| Formulation ID | Initial | 2-8° C. Filtered | 25° C. 7 d | 25° C. 14 d |
|---|---|---|---|---|
| T-1 | 100 | 99 | 99 | 99 |
| T-2 | 100 | 100 | 97 | 99 |
| T-3 | 100 | 100 | 98 | 99 |
| T-4 | 100 | 99 | 97 | 96 |
| T-5 | 100 | 100 | 99 | 98 |
| T-6 | 100 | 99 | 96 | 87 |
| T-7 | 100 | 98 | 18 | 0 |
| T-8 | 100 | 99 | 97 | 92 |

TABLE 40

Assay recovery

Assay Recovery (% conc. over initial conc.)

| Formulation ID | Initial | 40° C. 1 d | 40° C. 2 d | 40° C. 7 d | 40° C. 14 d |
|---|---|---|---|---|---|
| T-1 | 100 | 100 | 100 | 96 | 95 |
| T-2 | 100 | 102 | 98 | 97 | 98 |
| T-3 | 100 | 100 | 100 | 96 | 96 |
| T-4 | 100 | 100 | 98 | 82 | 67 |
| T-5 | 100 | 100 | 101 | 101 | 100 |
| T-6 | 100 | 100 | 100 | 0 | 0 |
| T-7 | 100 | 97 | 97 | 94 | 93 |
| T-8 | 100 | 96 | 99 | 93 | 91 |

TABLE 41

Assay recovery

Assay Recovery (% conc. over initial conc.)

| Formulation ID | Initial | 60° C. 1 d | 60° C. 2 d | 60° C. 7 d |
|---|---|---|---|---|
| T-1 | 100 | 100 | 98 | 87 |
| T-2 | 100 | 101 | 98 | 90 |
| T-3 | 100 | 99 | 98 | 91 |
| T-4 | 100 | 98 | 96 | 91 |
| T-5 | 100 | 99 | 98 | 93 |
| T-6 | 100 | 97 | 97 | 91 |
| T-7 | 100 | 100 | 96 | 87 |
| T-8 | 100 | 94 | 93 | 69 |

TABLE 42

Impurity profile for pH 4

| RT (min) | RRT | T = 0 | Filtrate | T = 1 d 40° C. | T = 1 d 60° C. | T = 2 d 40° C. | T = 2 d 60° C. | T = 7 d 25° C. | T = 7 d 40° C. | T = 7 d 60° C. | T = 14 d 25° C. | T = 14 d 40° C. |
|---|---|---|---|---|---|---|---|---|---|---|---|---|
| 25.14 | 1.00 | 99.07 | 99.06 | 98.66 | 97.47 | 98.17 | 96.40 | 98.63 | 96.44 | 91.31 | 98.00 | 94.84 |
| 18.36 | 0.69 | ND | ND | ND | ND | 0.31 | ND | 0.35 | 1.63 | ND | 0.77 | 2.20 |

TABLE 42-continued

| | | | | T = 1 d | | T = 2 d | | T = 7 d | | | T = 14 d | |
|---|---|---|---|---|---|---|---|---|---|---|---|---|
| RT (min) | RRT | T = 0 | Filtrate | 40° C. | 60° C. | 40° C. | 60° C. | 25° C. | 40° C. | 60° C. | 25° C. | 40° C. |
| 21.61 | 0.83 | ND | ND | 0.35 | 0.29 | 0.32 | ND | ND | ND | ND | ND | ND |
| 22.78 | 0.90 | ND | ND | ND | ND | ND | ND | ND | ND | 0.23 | ND | ND |
| 23.76 | 0.94 | 0.23 | 0.34 | 0.34 | 0.37 | 0.24 | 0.27 | 0.27 | 0.32 | 0.32 | 0.28 | 0.25 |
| 26.44 | 1.06 | 0.04 | ND | ND | ND | ND | ND | ND | ND | ND | ND | ND |
| 26.74 | 1.07 | 0.16 | 0.16 | ND | 0.18 | 0.10 | 0.14 | 0.18 | 0.19 | ND | 0.16 | 0.10 |
| 27.34 | 1.10 | 0.17 | 0.21 | 0.16 | 0.19 | 0.17 | 0.23 | 0.13 | 0.15 | 0.18 | 0.16 | 0.18 |
| 28.21 | 1.14 | 0.14 | 0.12 | 0.23 | 0.23 | 0.14 | 0.45 | 0.23 | 0.15 | 0.77 | 0.17 | 0.38 |
| 28.52 | 1.15 | 0.20 | 0.11 | ND | ND | 0.17 | 0.37 | ND | 0.15 | 0.37 | ND | 0.29 |
| 28.78 | 1.16 | ND | ND | 0.26 | 0.26 | ND | ND | 0.21 | ND | ND | 0.21 | ND |
| 29.99 | 1.21 | ND | ND | ND | 0.19 | ND | 0.53 | ND | ND | ND | ND | ND |
| 30.23 | 1.22 | ND | ND | ND | 0.81 | 0.36 | 1.61 | ND | 0.97 | 6.82 | 0.25 | 1.76 |
| Total Imp | | 0.93 | 0.94 | 1.34 | 2.53 | 1.83 | 3.60 | 1.37 | 3.56 | 8.69 | 2.00 | 5.16 |

TABLE 43

Impurity profile for pH 5

| | | | | T = 1 d | | T = 2 d | | T = 7 d | | | T = 14 d | |
|---|---|---|---|---|---|---|---|---|---|---|---|---|
| RT (min) | RRT | T = 0 | Filtrate | 40° C. | 60° C. | 40° C. | 60° C. | 25° C. | 40° C. | 60° C. | 25° C. | 40° C. |
| 25.20 | 1.00 | 99.09 | 98.86 | 98.86 | 98.22 | 98.44 | 97.68 | 98.84 | 97.71 | 94.25 | 98.01 | 96.63 |
| 18.41 | 0.70 | ND | ND | ND | ND | 0.24 | ND | 0.20 | 0.37 | ND | 0.41 | 0.95 |
| 21.63 | 0.84 | ND | ND | ND | 0.39 | 0.20 | ND | ND | ND | ND | ND | ND |
| 22.79 | 0.90 | ND | ND | ND | ND | ND | ND | ND | ND | 0.35 | ND | ND |
| 23.83 | 0.95 | 0.29 | 0.32 | 0.34 | 0.38 | 0.28 | 0.31 | 0.28 | 0.29 | 0.37 | 0.28 | 0.30 |
| 26.80 | 1.06 | 0.14 | 0.20 | 0.19 | ND | 0.19 | 0.19 | 0.10 | 0.26 | 0.11 | 0.16 | 0.11 |
| 27.40 | 1.09 | 0.19 | 0.22 | 0.16 | 0.15 | 0.16 | 0.22 | 0.17 | 0.18 | 0.21 | 0.20 | 0.18 |
| 28.25 | 1.12 | ND | 0.18 | 0.24 | ND | ND | ND | ND | 0.27 | ND | ND | ND |
| 28.59 | 1.13 | 0.12 | 0.22 | 0.21 | 0.13 | 0.23 | 0.28 | 0.16 | 0.29 | 0.31 | 0.27 | 036 |
| 28.69 | 1.16 | 0.16 | ND | ND | 0.17 | 0.25 | 0.18 | 0.24 | ND | 0.15 | 0.33 | 0.22 |
| 29.89 | 1.21 | ND | ND | ND | 0.12 | ND | ND | ND | ND | ND | ND | ND |
| 30.15 | 1.22 | ND | ND | ND | 0.44 | ND | 1.14 | ND | 0.63 | 4.24 | 0.35 | 1.25 |
| Total Imp | | 0.94 | 1.14 | 1.14 | 1.78 | 1.56 | 2.32 | 1.16 | 2.29 | 5.75 | 1.99 | 3.37 |

TABLE 44

Impurity profile for pH 6

| | | | | T = 1 d | | T = 2 d | | T = 7 d | | | T = 14 d | |
|---|---|---|---|---|---|---|---|---|---|---|---|---|
| RT (min) | RRT | T = 0 | Filtrate | 40° C. | 60° C. | 40° C. | 60° C. | 25° C. | 40° C. | 60° C. | 25° C. | 40° C. |
| 25.26 | 1.00 | 99.05 | 98.88 | 98.67 | 98.44 | 98.46 | 97.99 | 98.81 | 97.90 | 96.72 | 98.94 | 96.73 |
| 18.28 | 0.69 | ND | ND | ND | ND | ND | ND | ND | 0.57 | ND | ND | 1.19 |
| 21.65 | 0.83 | ND | ND | 0.34 | 0.35 | 0.46 | 0.30 | ND | ND | ND | ND | 0.29 |
| 22.84 | 0.90 | ND | ND | ND | 0.27 | ND | 0.42 | ND | ND | 0.69 | ND | 0.31 |
| 23.85 | 0.94 | 0.33 | 0.24 | 0.32 | 0.33 | 0.24 | 0.41 | 0.50 | 0.47 | 0.63 | 0.23 | 0.40 |
| 26.90 | 1.07 | 0.16 | 0.18 | 0.20 | ND | 0.20 | 0.18 | 0.15 | 0.16 | 0.08 | ND | 0.15 |
| 27.43 | 1.10 | 0.21 | 0.26 | 0.11 | 0.31 | 0.24 | 0.37 | 0.17 | 0.25 | 0.59 | 0.24 | 0.21 |
| 28.32 | 1.14 | 0.12 | 0.22 | 0.15 | ND | 0.22 | 0.20 | 0.20 | 0.39 | 0.32 | 0.26 | 0.38 |
| 28.63 | 1.15 | 0.13 | 0.22 | 0.21 | 0.31 | 0.17 | 0.13 | 0.17 | 0.25 | 0.24 | ND | 0.34 |
| 28.30 | 1.18 | ND | ND | ND | ND | ND | ND | ND | ND | 0.33 | ND | ND |
| 29.83 | 1.23 | ND | ND | ND | ND | ND | ND | ND | ND | 0.74 | ND | ND |
| Total Imp | | 0.95 | 1.12 | 1.33 | 1.56 | 1.54 | 2.01 | 1.19 | 2.10 | 3.28 | 1.06 | 3.27 |

TABLE 45

| | | | | T = 1 d | | T = 2 d | | T = 7 d | | | T = 14 d | |
|---|---|---|---|---|---|---|---|---|---|---|---|---|
| RT (min) | RRT | T = 0 | Filtrate | 40° C. | 60° C. | 40° C. | 60° C. | 25° C. | 40° C. | 60° C. | 25° C. | 40° C. |
| 25.10 | 1.00 | 98.94 | 98.96 | 98.62 | 98.77 | 98.11 | 98.08 | 99.04 | 90.73 | 96.80 | 98.44 | 85.07 |
| 9.19 | 0.27 | ND | ND | ND | ND | ND | ND | ND | 0.45 | ND | ND | ND |
| 9.97 | 0.31 | ND | ND | ND | ND | ND | ND | ND | 1.92 | ND | ND | 4.79 |
| 14.93 | 0.54 | ND | ND | ND | ND | ND | ND | ND | ND | ND | ND | 0.76 |
| 15.63 | 0.57 | ND | ND | ND | ND | ND | ND | ND | 0.63 | ND | ND | 0.78 |
| 16.74 | 0.62 | ND | ND | ND | ND | ND | ND | ND | 0.34 | ND | ND | 0.64 |
| 17.36 | 0.65 | ND | ND | ND | ND | ND | ND | ND | 0.16 | ND | ND | 0.77 |
| 18.42 | 0.69 | ND | ND | ND | ND | ND | ND | ND | 0.27 | ND | 0.53 | ND |
| 20.54 | 0.79 | ND | ND | ND | ND | 0.22 | ND | ND | 0.45 | ND | ND | ND |
| 21.66 | 0.83 | ND | ND | 0.34 | ND | 0.22 | 0.26 | ND | ND | ND | ND | ND |
| 22.82 | 0.90 | ND | ND | ND | ND | ND | 0.32 | ND | 0.58 | 0.76 | ND | 1.21 |
| 23.80 | 0.94 | 0.29 | 0.32 | 0.32 | 0.34 | 0.63 | 0.40 | 0.41 | 2.83 | 0.73 | 0.29 | 3.72 |
| 26.14 | 1.06 | ND | ND | ND | ND | ND | ND | ND | ND | 0.12 | ND | ND |
| 26.70 | 1.07 | 0.11 | 0.17 | 0.13 | 0.14 | 0.17 | 0.17 | 0.15 | 0.26 | 0.06 | 0.12 | ND |
| 27.29 | 1.10 | 0.34 | 0.11 | 0.26 | 0.33 | 0.21 | 0.50 | 0.17 | 0.09 | 1.03 | 0.13 | 0.44 |
| 28.09 | 1.14 | 0.23 | 0.23 | 0.17 | 0.19 | 0.22 | 0.12 | 0.11 | 1.13 | 0.28 | 0.27 | 1.82 |
| 28.50 | 1.16 | 0.09 | 0.22 | 0.16 | 0.23 | 0.20 | 0.15 | 0.12 | 0.16 | 0.23 | 0.22 | ND |
| Total Imp | | 1.06 | 1.04 | 1.38 | 1.23 | 1.89 | 1.92 | 0.96 | 9.27 | 3.20 | 1.56 | 14.93 |

TABLE 46

Impurity profile for pH 7 in $H_2O$

| | | | | T = 1 d | | T = 2 d | | T = 7 d | | | T = 14 d | |
|---|---|---|---|---|---|---|---|---|---|---|---|---|
| RT (min) | RRT | T = 0 | Filtrate | 40° C. | 60° C. | 40° C. | 60° C. | 25° C. | 40° C. | 60° C. | 25° C. | 40° C. |
| 25.04 | 1.00 | 98.79 | 98.40 | 98.80 | 98.93 | 98.91 | 98.96 | 99.02 | 98.90 | 97.88 | 98.91 | 98.23 |
| 18.48 | 0.70 | ND | ND | ND | ND | ND | ND | ND | 0.17 | 0.16 | 0.12 | 0.44 |
| 21.80 | 0.83 | ND | 0.53 | 0.18 | ND | ND | ND | ND | ND | ND | ND | ND |
| 23.72 | 0.94 | 0.39 | 0.33 | 0.33 | 0.28 | 0.29 | 0.31 | 0.24 | 0.33 | 0.19 | 0.26 | 0.39 |
| 24.08 | 0.96 | ND | ND | ND | ND | ND | 0.08 | ND | ND | ND | ND | ND |
| 25.97 | 1.05 | ND | ND | ND | ND | ND | ND | ND | ND | 0.07 | ND | ND |
| 26.67 | 1.07 | 0.19 | 0.16 | 0.14 | 0.16 | 0.17 | 0.20 | 0.16 | 0.13 | 0.06 | 0.14 | 0.12 |
| 27.24 | 1.10 | 0.18 | 0.21 | 0.25 | 0.30 | 0.26 | 0.21 | 0.15 | 0.25 | 0.59 | 0.15 | 0.25 |
| 28.09 | 1.14 | 0.20 | 0.17 | 0.18 | 0.17 | 0.16 | 0.10 | 0.20 | 0.12 | 0.28 | 0.22 | 0.30 |
| 28.48 | 1.16 | 0.26 | 0.21 | 0.13 | 0.15 | 0.21 | 0.15 | 0.23 | 0.11 | 0.27 | 0.20 | 0.26 |
| Total Imp | | 1.21 | 1.60 | 1.20 | 1.07 | 1.09 | 1.04 | 0.98 | 1.10 | 2.12 | 1.09 | 1.77 |

TABLE 47

Impurity profile for pH 7 in $H_3PO_4$

| | | | | T = 1 d | | T = 2 d | | T = 7 d* | | T = 14 d | |
|---|---|---|---|---|---|---|---|---|---|---|---|
| RT (min) | RRT | T = 0 | Filtrate | 40° C. | 60° C. | 40° C. | 60° C. | 25° C. | 60° C. | 25° C. | 40° C. |
| 25.13 | 1.00 | 98.76 | 98.48 | 98.53 | 98.82 | 98.91 | 98.96 | 98.68 | 94.79 | 95.95 | No Peak* |
| 18.23 | 0.69 | ND | ND | ND | ND | ND | ND | ND | ND | 0.44 | |
| 21.85 | 0.83 | ND | 0.40 | 0.39 | ND | ND | ND | ND | ND | ND | |
| 22.61 | 0.90 | ND | ND | ND | ND | ND | ND | ND | 1.07 | 0.40 | |
| 23.82 | 0.94 | 0.33 | 0.34 | 0.34 | 0.34 | 0.29 | 0.31 | 0.40 | 0.96 | 2.23 | |
| 24.08 | 0.96 | ND | ND | ND | ND | ND | 0.08 | ND | ND | ND | |
| 25.91 | 1.05 | ND | ND | ND | ND | ND | ND | ND | 0.44 | ND | |
| 26.73 | 1.07 | 0.14 | 0.18 | 0.16 | 0.15 | 0.17 | 0.20 | 0.13 | 0.07 | 0.11 | |
| 27.26 | 1.10 | 0.19 | 0.18 | 0.27 | 0.37 | 0.26 | 0.21 | 0.20 | 1.45 | 0.20 | |
| 28.16 | 1.14 | 0.23 | 0.20 | 0.15 | 0.17 | 0.16 | 0.10 | 0.33 | 0.56 | 0.38 | |
| 28.47 | 1.15 | 0.36 | 0.22 | 0.16 | 0.14 | 0.21 | 0.15 | 0.27 | 0.66 | 0.30 | |
| Total Imp | | 1.24 | 1.52 | 1.47 | 1.18 | 1.09 | 1.04 | 1.32 | 5.21 | 4.05 | |

*No peak was observed for the pH 7 solutions in $H_3PO_4$ at 40° C. at 7 and 14 days

TABLE 48

Impurity profile for pH 7 in 0.9% NaCl

| RT (min) | RRT | T = 0 | Filtrate | T = 1 d 40° C. | T = 1 d 60° C. | T = 2 d 40° C. | T = 2 d 60° C. | T = 7 d 25° C. | T = 7 d 40° C. | T = 7 d 60° C. | T = 14 d 25° C. | T = 14 d 40° C. |
|---|---|---|---|---|---|---|---|---|---|---|---|---|
| 25.10 | 1.00 | 98.78 | 98.39 | 98.52 | 98.76 | 98.79 | 98.51 | 38.60 | 97.96 | 96.44 | No Peak | 97.37 |
| 18.36 | 0.69 | ND | ND | ND | ND | ND | ND | ND | 0.26 | ND | | 0.59 |
| 20.49 | 0.79 | ND | ND | ND | ND | ND | ND | ND | 0.18 | ND | | ND |
| 21.73 | 0.83 | ND | 0.34 | 0.33 | ND | ND | ND | 57.88 | ND | ND | | ND |
| 22.75 | 0.88 | ND | ND | ND | ND | ND | ND | 0.49 | ND | 0.54 | | ND |
| 23.75 | 0.94 | 0.27 | 0.31 | 0.38 | 0.39 | 0.42 | 0.31 | 2.90 | 0.66 | 1.46 | | 0.79 |
| 26.22 | 1.05 | ND | ND | ND | ND | ND | ND | 0.14 | ND | 0.72 | | ND |
| 26.70 | 1.07 | 0.17 | 0.22 | 0.15 | 0.19 | 0.12 | 0.11 | ND | 0.07 | 0.05 | | 0.10 |
| 27.27 | 1.10 | 0.29 | 0.18 | 0.20 | 0.27 | 0.24 | 0.51 | ND | 0.40 | 1.51 | | 0.56 |
| 28.18 | 1.14 | 0.25 | 0.22 | 0.20 | 0.18 | 0.23 | 0.26 | ND | 0.25 | 0.39 | | 0.23 |
| 28.41 | 1.15 | 0.24 | 0.34 | 0.22 | 0.21 | 0.20 | 0.30 | ND | 0.22 | 0.89 | | 0.35 |
| Total Imp | | 1.22 | 1.61 | 1.48 | 1.24 | 1.21 | 1.49 | 61.40 | 2.04 | 5.56 | | 2.63 |

*No peak was observed for the pH 7 solutions in 0.9% NaCl at 25° C. at 14 days

TABLE 49

Impurity profile for pH 8

| RT (min) | RRT | T = 0 | Filtrate | T = 1 d 40° C. | T = 1 d 60° C. | T = 2 d 40° C. | T = 2 d 60° C. | T = 7 d 25° C. | T = 7 d 40° C. | T = 7 d 60° C. | T = 14 d 25° C. | T = 14 d 40° C. |
|---|---|---|---|---|---|---|---|---|---|---|---|---|
| 25.14 | 1.00 | 98.35 | 98.26 | 98.75 | 97.80 | 98.45 | 93.68 | 99.34 | 97.50 | 81.21 | 98.65 | 95.09 |
| 19.89 | 0.77 | ND | ND | ND | ND | ND | 0.45 | ND | ND | 1.16 | ND | 0.25 |
| 20.40 | 0.79 | ND | ND | ND | ND | ND | 0.26 | ND | ND | 0.86 | ND | 0.25 |
| 20.84 | 0.81 | ND | ND | ND | ND | ND | 0.08 | ND | ND | 0.31 | ND | ND |
| 21.74 | 0.83 | ND | 0.53 | ND | ND | ND | ND | ND | ND | ND | ND | ND |
| 21.61 | 0.85 | ND | ND | ND | ND | ND | 0.24 | ND | ND | 0.68 | ND | ND |
| 23.04 | 0.91 | ND | ND | ND | 0.24 | ND | 0.68 | ND | 0.50 | 2.43 | ND | 0.79 |
| 23.79 | 0.94 | 0.32 | 0.43 | 0.26 | 0.48 | 0.40 | 0.61 | ND | 0.61 | 1.49 | 0.57 | 1.05 |
| 23.91 | 0.95 | ND | ND | ND | 0.23 | ND | 0.69 | ND | ND | 3.22 | ND | ND |
| 24.62 | 0.99 | ND | ND | ND | ND | ND | 0.23 | ND | ND | 0.77 | ND | ND |
| 25.92 | 1.05 | ND | ND | ND | ND | ND | 0.92 | ND | ND | 2.57 | ND | 0.47 |
| 26.75 | 1.07 | 0.14 | 0.19 | 0.13 | 0.13 | 0.19 | 0.10 | 0.12 | 0.13 | ND | 0.13 | ND |
| 27.31 | 1.10 | 0.24 | 0.16 | 0.26 | 0.34 | 0.28 | 0.53 | 0.22 | 0.35 | 1.39 | 0.21 | 0.59 |
| 28.23 | 1.14 | 0.25 | 0.21 | 0.31 | 0.28 | 0.32 | 0.43 | 0.15 | 0.38 | 1.03 | 0.22 | 0.51 |
| 28.49 | 1.15 | 0.21 | 0.21 | 0.27 | 0.50 | 0.37 | 0.92 | 0.18 | 0.53 | 2.85 | 0.23 | 1.01 |
| Total Imp | | 1.15 | 1.74 | 1.25 | 2.20 | 1.55 | 6.14 | 0.66 | 2.50 | 18.79 | 1.35 | 3.39 |

MMI-0100 formulation solutions pH 6.5 with citrate, pH 7 with phosphate, pH 7 with 0.9% NaCl and pH 8 with L-lysine showed haziness, indicating the presence of precipitates.

Figure 79:
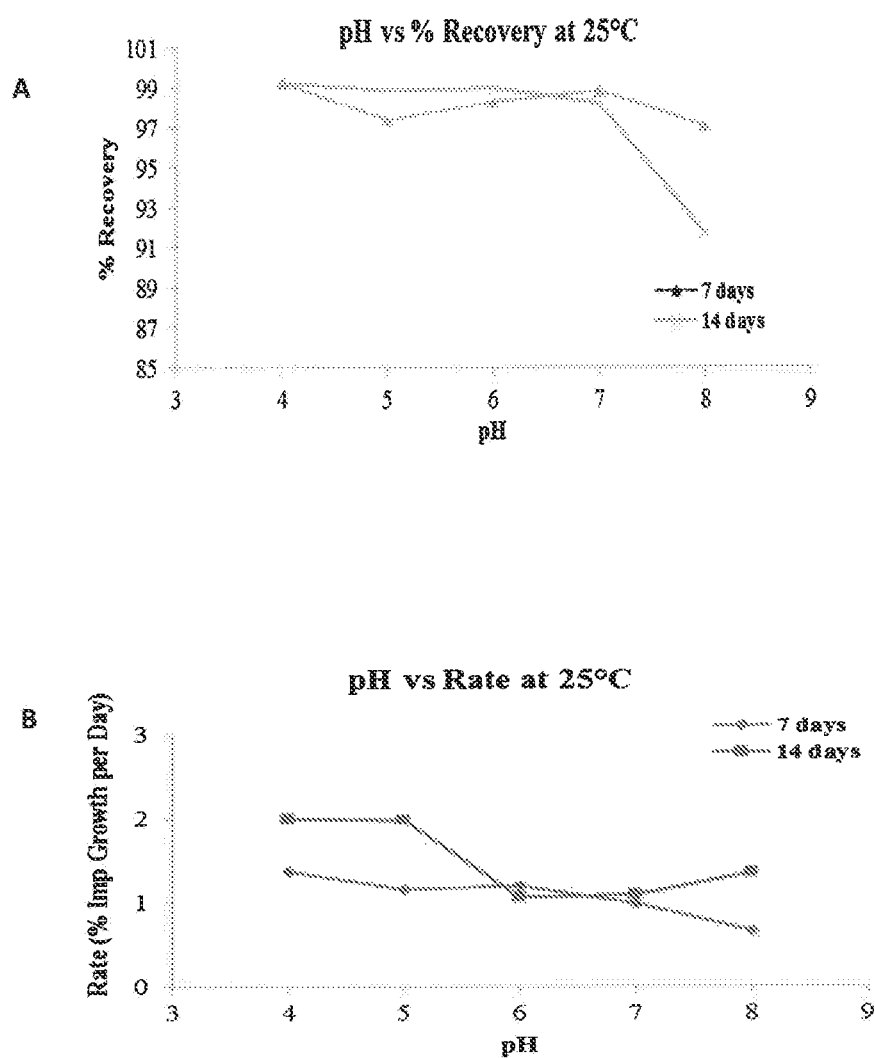
FIG. 79 is summary of MMI-0100 assay recovery and impurity growth at 25° C. (A) pH versus percent (%) recovery at 7 days and 14 days; (B) pH versus rate (percent (%) impurity growth per day) at 7 days and 14 days.
Figure 80:
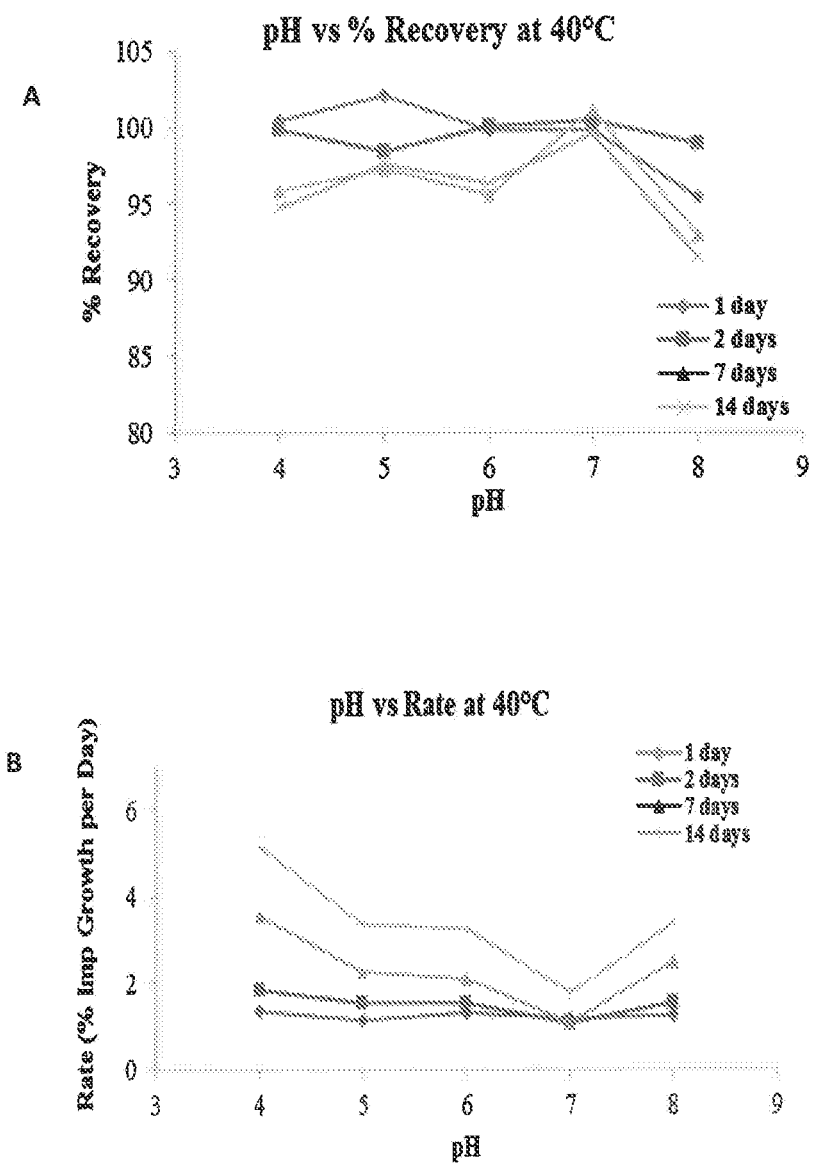
FIG. 80 is summary of MMI-0100 assay recovery and impurity growth at 40° C. (A) pH versus percent (%) recovery at 1 day, 2 days, 7 days and 14 days; (B) pH versus rate (percent (%) impurity growth per day) at 1 day, 2 days, 7 days and 14 days.
Figure 81:
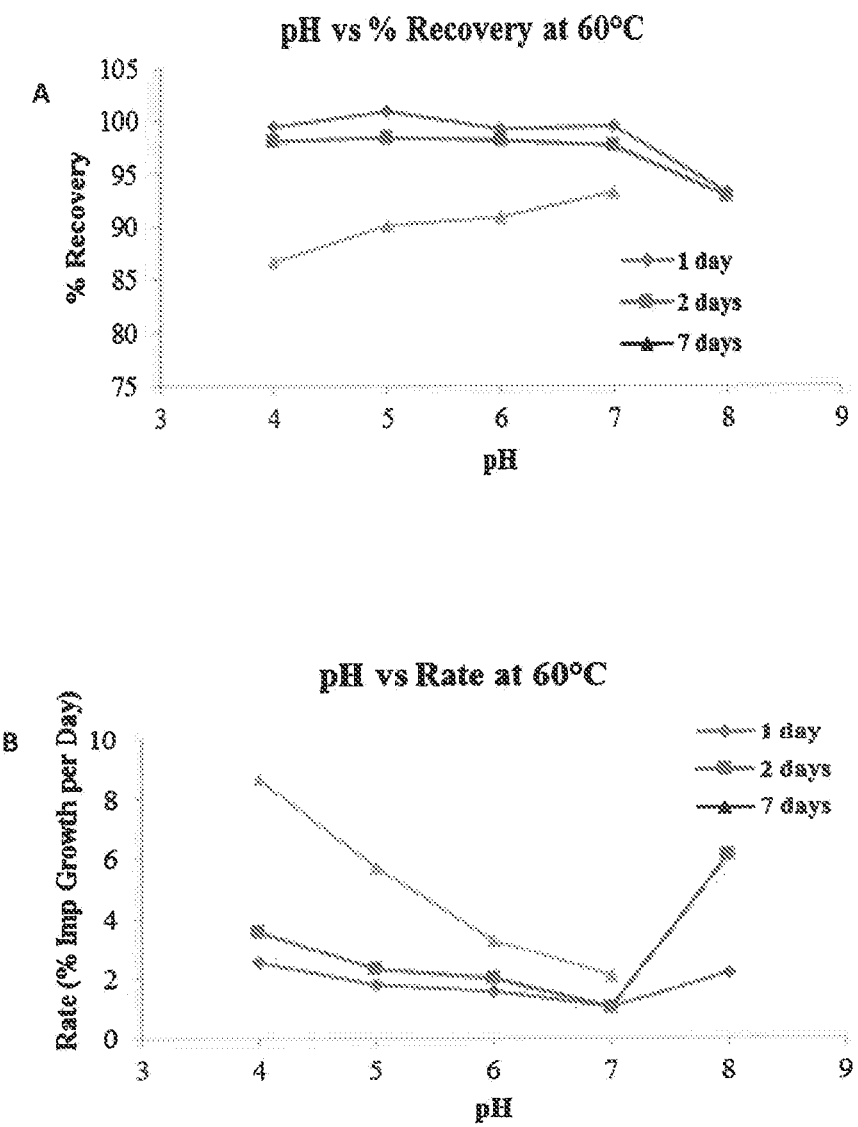
FIG. 81 is summary of MMI-0100 assay recovery and impurity growth at 60° C. (A) pH versus percent (%) recovery at 1 day, 2 days and 7 days; (B) pH versus rate (percent (%) impurity growth per day) at 1 day, 2 days and 7 days.

FIGS. 79 A and B summarize the assay recovery and impurity growth at 25° C. FIGS. 80 A and B summarize the assay recovery and impurity growth at 40° C. FIGS. 81 A and B summarize the assay recovery and impurity growth at 60° C.

The results of this study indicated that:
i. MMI-0100 is most stable at pH 7;
ii. phosphate and NaCl induced precipitation of MMI-0100 at pH 7;
iii. citrate induced precipitation of MMI-0100 at pH 6.5;
iv. in citrate, MMI-0100 is most stable at pH 6;
v. $pH_{max}$ for MMI-0100 is pH 7 and DI water (i.e. no buffer) was the best solution;
vi. in T-5, there were 5 impurities exceeding 0.2% detected at the initial (T=0) testing;
vii. in T-5 (pH 7 without a buffer), the assay recovery was near 100% after 14 days at 40° C. and 93% after 7 days at 60° C., indicating the shelf life (defined by $T_{90}$) is likely to be 2 years at 25° C. or 2 years at 5° C.;
viii. when T-5 reaches the $T_{90}$ (e.g. 10% assay loss), 7 impurities may grow to exceed 0.1% (the top three impurities were RRT=1.14, RRT=0.94 and RRT=0.70);
ix. after 7 days at 60° C. in T-5, the assay loss was 7% and total impurity was 2.12%, indicating that the impurities may have a lower extinction coefficient at the detection wavelength of 215 nm; and
x. without being limited by theory, it is suspected that the RRT=1.14, RRT=0.94 impurities are the deamination products ($Gln^8$ and $Gln^{17}$) and RRT=0.70 impurity is a hydrolysis product.

Example 9. Evaluation of Stability of Several MMI-0100 Formulation Solutions at pH 7 in DI Water Containing Various Osmotic Agents and/or Lyoprotectants The purpose of this study was to determine osmotic pressure of non-buffered 0.7 mg/mL and 7 mg/mL solutions in water at pH 7, select an osmotic agent(s) based on stability, calculate the concentration of osmotic agent(s) needed to reach the iso-osmotic pressure (e.g., Glycerin IIL limit for inhalation is 7.3%; Lactose IIL limit for inhalation is 9%).

MMI-0100 formulation solutions were prepared as described in Table 50.

TABLE 50

MMI-0100 formulation solutions

| Component | F-1 | F-2 | F-3 | F-4 |
|---|---|---|---|---|
| MMI | 0.7 | 7 | 7 | 7 |
| Glycerin | 0 | 0 | Amount needed for isotonicity | 0 |
| Lactose | 0 | 0 | 0 | Amount needed for isotonicity |
| DI-water, qs | qs | qs | qs | qs |
| Adjust pH to 7 with NaOH/HCl | 7 ± 0.1 | 7 ± 0.1 | 7 ± 0.1 | 7 ± 0.1 |

5 g of each MMI-0100 formulation solution was prepared. 0.7 mL of each formulation solution was added to an HPLC glass vial (5 vials each). One HPLC vial was used as T=0. The remaining 4 HPLC vials were stored at 60° C. and tested at 0, 1, 2 and 4 weeks. Results are shown in Tables 51-59.

TABLE 51

Appearance

| Formulation ID | Initial | 1 week at 60° C. | 2 weeks at 60° C. | 4 weeks at 60° C. |
|---|---|---|---|---|
| F-1 | Clear, colorless liquid | No change | No change | |
| F-2 | Clear, colorless liquid | No change | No change | |
| F-3 | Clear, colorless liquid | No change | No change | |
| F-4 | Clear, colorless liquid | No change | No change | |

TABLE 52

Osmotic pressure adjustment

| Formulation ID | Osmotic Pressure Modifier | Initial Osmotic Pressure (mOsm) | Amount of Modifier Added (% w/w) | Final Osmotic Pressure (mOsm) |
|---|---|---|---|---|
| F-1 | None | 13 | 0 | 13 |
| F-2 | None | 24 | 0 | 24 |
| F-3 | Glycerin | 35 (before adding glycerin) | 2.2% | 286 |
| F-4 | Lactose | 31 (before adding lactose) | 7.6% | 299 |

TABLE 53 pH

| Formulation ID | Initial | 1 week at 60° C. | 2 weeks at 60° C. | 4 weeks at 60° C. |
|---|---|---|---|---|
| F-1 | 7.0 | 8.3 | 8.1 | |
| F-2 | 7.1 | 6.9 | 7.1 | |
| F-3 | 7.1 | 7.0 | 7.1 | |
| F-4 | 7.0 | 6.6 | 6.3 | |

TABLE 54

Concentration

MMI-001 Concentration (mg/mL)

| Formulation ID | Initial | 1 week at 60° C. | 2 weeks at 60° C. | 4 weeks at 60° C. |
|---|---|---|---|---|
| F-1 | 0.65 | 0.49 | 0.35 | |
| F-2 | 6.65 | 6.84 | 6.47 | |
| F-3 | 6.45 | 6.59 | 6.17 | |
| F-4 | 6.04 | 5.03 | 4.02 | |

TABLE 55

Assay concentration (percent concentration over initial concentration)

Assay (% conc. over initial conc.)

| Formulation ID | Initial | 1 week at 60° C. | 2 weeks at 60° C. | 4 weeks at 60° C. |
|---|---|---|---|---|
| F-1 | 100 | 75 | 54 | |
| F-2 | 100 | 103 | 97 | |
| F-3 | 100 | 102 | 96 | |
| F-4 | 100 | 83 | 67 | |

TABLE 56

Impurity profile for F-1 (peak area %)

| RT (min) | RRT | T = 0 | T = 1 wk at 60° C. | T = 2 wk at 60° C. |
|---|---|---|---|---|
| 24.364 | 1.00 | 97.21 | 76.65 | 53.59 |
| 6.791 | 0.28 | 2.44 | 2.82 | 2.75 |
| 19.706 | 0.79 | ND | 1.15 | 2.16 |
| 20.246 | 0.81 | ND | 0.96 | 2.04 |
| 20.644 | 0.83 | ND | 0.42 | 1.18 |
| 21.836 | 0.88 | ND | 0.84 | 4.56 |
| 22.432 | 0.90 | ND | 1.53 | 1.39 |
| 22.749 | 0.91 | ND | 2.47 | 5.09 |
| 22.955 | 0.94 | 0.34 | 1.49 | 3.62 |
| 23.633 | 0.95 | ND | 3.48 | 6.92 |
| 24.451 | 0.98 | ND | 0.77 | 2.18 |
| 25.784 | 1.04 | ND | 2.42 | 5.25 |
| 26.763 | 1.07 | ND | 1.26 | 2.66 |
| 27.767 | 1.12 | ND | 1.04 | 2.00 |
| 28.102 | 1.13 | ND | 2.70 | 4.61 |
| Total Imp | | 2.79 | 23.35 | 46.41 |

ND = Not Detected

TABLE 57

Ipurity profile for F-2 (peak area %)

| RT (min) | RRT | T = 0 | T = 1 wk 60° C. | T = 2 wk 60° C. | T = 4 wk 60° C. |
|---|---|---|---|---|---|
| 24.40 | 1.00 | 99.56 | 98.17 | 96.29 | |
| 23.00 | 0.94 | 0.44 | 0.62 | 1.11 | |
| 26.77 | 1.08 | ND | 1.21 | 2.60 | |
| Total Imp | | 0.44 | 1.83 | 3.71 | |

ND = Not Detected

TABLE 58

Impurity profile for F-3 (peak area %)

| RT (min) | RRT | T = 0 | T = 1 wk 60° C. | T = 2 wk 60° C. | T = 4 wk 60° C. |
|---|---|---|---|---|---|
| 24.41 | 1.00 | 100 | 98.07 | 93.95 | |
| 23.38 | 0.94 | ND | 0.50 | 1.12 | |
| 26.05 | 1.04 | ND | ND | 1.47 | |
| 26.80 | 1.08 | ND | 1.43 | 3.05 | |
| 28.25 | 1.13 | ND | ND | 0.41 | |
| Total Imp | | 0 | 1.93 | 6.05 | |

ND = Not Detected

TABLE 59

Impurity profile for F-4 (peak area %)

| RT (min) | RRT | T = 0 | T = 1 wk 60° C. | T = 2 wk 60° C. | T = 4 wk 60° C. |
|---|---|---|---|---|---|
| 24.47 | 1.00 | 97.60 | 84.26 | 72.31 | |
| 23.04 | 0.94 | 0.26 | ND | 0.85 | |
| 23.94 | 0.95 | ND | ND | 0.60 | |
| 24.39 | 0.98 | ND | 11.11 | 19.45 | |
| 25.42 | 1.04 | 2.14 | 3.81 | 4.88 | |
| 26.78 | 1.07 | ND | 0.81 | 1.91 | |
| Total Imp | | 2.40 | 15.74 | 27.69 | |

ND = Not Detected

The results of this study indicated that:
i. MMI-0100 formulation solution at pH 7 without a buffer was capable of maintaining its pH at 7 at the high concentration (7 mg/mL), whereas the pH drifted up to about 8 at the lower concentration (0.7 mg/mL), indicating that at 7 mg/mL strength, no pH buffer is needed;
ii. the addition of lactose resulted in pH drift (down to about 6) and appeared to cause more degradation of MMI-0100;
iii. the addition of glycerin did not cause pH drift in the high concentration formulation, thus, glycerin is preferred over lactose;
iv. the addition of glycerin to the MMI-0100 formulation solution also caused slightly more degradation of MMI-0100 (F-3) than the formulation solution without an osmotic agent (F-2), thus, if an isosmotic formulation is not necessary, the F-2 formulation solution would be preferred.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A pharmaceutical formulation for delivery by inhalation comprising a therapeutic amount of an MK2i polypeptide of amino acid sequence YARAAARQARAKALARQLGVAA (SEQ ID NO: 1) or a functional equivalent thereof, up to 5% solids before drying, 7.5% w/w and 20% w/w trehalose, and a pharmaceutically acceptable carrier, wherein the formulation is effective to preserve at least about 96% of physical, chemical, microbiological, therapeutic, and toxicological specifications of the MK2i polypeptide for at least 4 weeks at 25 C and bioavailability of the MK2i polypeptide.

2. The pharmaceutical formulation according to claim 1, wherein the pharmaceutical formulation is a particulate pharmaceutical formulation.

3. The pharmaceutical formulation according to claim 1, wherein the pharmaceutical formulation is an aerosolized pharmaceutical formulation.

4. The pharmaceutical formulation according to claim 1, wherein the formulation is prepared by a process of spray drying.

5. The pharmaceutical formulation according to claim 2, wherein the pharmaceutical formulation comprises 1% w/w solids before drying.

6. The pharmaceutical formulation according to claim 2, wherein the pharmaceutical formulation comprises 5% w/w solids before drying.

7. The pharmaceutical formulation according to claim 1, wherein the MK2i polypeptide of amino acid sequence YARAAARQARAKALARQLGVAA (SEQ ID NO: 1) or the functional equivalent thereof and trehalose are in a ratio of 80/20 (% w/w) respectively.

8. The pharmaceutical formulation according to claim 1, wherein the MK2i polypeptide of amino acid sequence YARAAARQARAKALARQLGVAA (SEQ ID NO: 1) or the functional equivalent thereof and trehalose are in a ratio of 92.5/7.5 (% w/w) respectively.

9. The pharmaceutical formulation according to claim 1, wherein the functional equivalent is made from a fusion between a first polypeptide that is a protein transduction domain (PTD) and a second polypeptide that is a therapeutic domain (TD).

10. The pharmaceutical formulation according to claim 9, wherein the protein transduction domain (PTD) is selected from the group consisting of a polypeptide of amino acid sequence YARAAARQARA (SEQ ID NO: 11), FAKLAARLYR (SEQ ID NO: 16), and KAFAKLAARLYR (SEQ ID NO: 17), and a second polypeptide that is a therapeutic domain (TD) of amino acid sequence KALARQLGVAA (SEQ ID NO: 2).

11. The pharmaceutical formulation according to claim 1, wherein the pharmaceutical formulation is delivered to a subject via a dry powder inhalation device (DPI).

12. The pharmaceutical formulation according to claim 3 further comprising saline before drying.

13. The pharmaceutical formulation according to claim 12, wherein the saline is NaCl.

14. The pharmaceutical formulation according to claim 3, wherein the functional equivalent is made from a fusion between a first polypeptide that is a protein transduction domain (PTD) and a second polypeptide that is a therapeutic domain (TD).

15. The pharmaceutical formulation according to claim 14, wherein the protein transduction domain (PTD) is selected from the group consisting of a polypeptide of amino acid sequence YARAAARQARA (SEQ ID NO: 11), FAKLAARLYR (SEQ ID NO: 16), and KAFAKLAARLYR (SEQ ID NO: 17), and a second polypeptide that is a therapeutic domain (TD) of amino acid sequence KALARQLGVAA (SEQ ID NO: 2).

16. The pharmaceutical formulation according to claim 1, comprising an ionic complex of the MK2i polypeptide of amino acid sequence YARAAARQARAKALARQLGVAA (SEQ ID NO: 1) or a functional equivalent thereof and a nano-polyplex polymer, wherein the ionic complex dissociates in intracellular compartments selected by intracellular pH conditions such that bioactivity and stability of the peptide is preserved.

17. The pharmaceutical formulation according to claim 16, wherein the nano-polyplex polymer is anionic and endosomolytic.

18. The pharmaceutical formulation according to claim 17, wherein the nano-polyplex polymer is poly(propylacrylic acid) (PPAA).

19. The pharmaceutical formulation according to claim 18, wherein the pharmaceutical formulation comprises a charge ratio (CR) of the MK2i polypeptide of amino acid sequence YARAAARQARAKALARQLGVAA (SEQ ID NO: 1) or a functional equivalent thereof to PPAA selected from the group consisting of 10:1, 9:1, 8:1, 7:1, 6:1, 5:1, 4:1, 3:1, 2:1, 1:1, 1:1.5, 1:2, 1:3, 1:4, 1:5, 1:6, 1:7, 1:8, 1:9 and 1:10.

20. The pharmaceutical formulation according to claim 19, wherein the charge ratio (CR) is 1:3.

21. The pharmaceutical formulation according to claim 17, wherein the nano-polyplex polymer is poly(acrylic acid) (PAA).

22. The pharmaceutical formulation according to claim 16, wherein the functional equivalent is made from a fusion between a first polypeptide that is a protein transduction domain (PTD) and a second polypeptide that is a therapeutic domain (TD).

23. The pharmaceutical formulation according to claim 22, wherein the protein transduction domain (PTD) is selected from the group consisting of a polypeptide of amino acid sequence YARAAARQARA (SEQ ID NO: 11), FAKLAARLYR (SEQ ID NO: 16), and KAFAKLAARLYR (SEQ ID NO: 17), and a second polypeptide that is a therapeutic domain (TD) of amino acid sequence KALARQLGVAA (SEQ ID NO: 2).

24. The pharmaceutical formulation according to claim 16, wherein the pharmaceutical formulation is delivered to a subject via an implantation device.

25. The pharmaceutical formulation according to claim 16, wherein the pharmaceutical formulation is delivered to a subject topically.

26. The pharmaceutical formulation according to claim 16, wherein the pharmaceutical formulation is delivered to a subject parenterally.

27. A method for treating a vascular graft-induced intimal hyperplasia in a subject in need of such treatment, the method comprising administering the pharmaceutical formulation of claim 20 comprising a therapeutic amount of a polypeptide of amino sequence YARAAARQARAKALARQLGVAA (SEQ ID NO: 1) or a functional equivalent thereof, and a nano-polyplex polymer, wherein the therapeutic amount is effective to inhibit MK2; and to treat a vascular graft-induced intimal hyperplasia.

28. The method according to claim 27, wherein the nano-polyplex polymer is anionic and endosomolytic.

29. The method according to claim 28, wherein the nano-polyplex polymer is poly(propylacrylic acid) (PPAA).

30. The method according to claim 27, wherein the pharmaceutical formulation comprises a charge ratio (CR) of the polypeptide of amino acid sequence YARAAARQARAKALARQLGVAA; SEQ ID NO: 1 or a functional equivalent thereof to PPAA selected from the group consisting of 10:1, 9:1, 8:1, 7:1, 6:1, 5:1, 4:1, 3:1, 2:1, 1:1, 1:1.5, 1:2, 1:3, 1:4, 1:5, 1:6, 1:7, 1:8, 1:9 and 1:10.

31. The method according to claim 30, wherein the charge ratio (CR) is 1:3.

32. The method according to claim 28, wherein the nano-polyplex polymer is poly(acrylic acid) (PAA).

33. The method according to claim 27, wherein the functional equivalent is made from a fusion between a first polypeptide that is a protein transduction domain (PTD) and a second polypeptide that is a therapeutic domain (TD).

34. The method according to claim 33, wherein the protein transduction domain (PTD) is selected from the group consisting of a polypeptide of amino acid sequence YARAAARQARA (SEQ ID NO: 11), FAKLAARLYR (SEQ ID NO: 16), and KAFAKLAARLYR (SEQ ID NO: 17), and a second polypeptide that is a therapeutic domain (TD) of amino acid sequence KALARQLGVAA (SEQ ID NO: 2).

35. The method according to claim 27, wherein the administering is by an implantation device.

36. The method according to claim 27, wherein the administering is by topical administration.

37. The method according to claim 27, wherein the administering is by parenteral administration.

* * * * *